US012486502B2

(12) United States Patent
Nicholas et al.

(10) Patent No.: US 12,486,502 B2
(45) Date of Patent: Dec. 2, 2025

(54) RNAi AGENTS FOR INHIBITING EXPRESSION OF RECEPTOR FOR ADVANCED GLYCATION END-PRODUCTS, COMPOSITIONS THEREOF, AND METHODS OF USE

(71) Applicant: Arrowhead Pharmaceuticals, Inc., Pasadena, CA (US)

(72) Inventors: Anthony Nicholas, Oregon, WI (US); Erik W. Bush, Verona, WI (US); David Itiro Kasahara, Madison, WI (US); Casi M. Schienebeck, Deerfield, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 124 days.

(21) Appl. No.: 17/715,444

(22) Filed: Apr. 7, 2022

(65) Prior Publication Data

US 2022/0396791 A1 Dec. 15, 2022

Related U.S. Application Data

(60) Provisional application No. 63/322,603, filed on Mar. 22, 2022, provisional application No. 63/172,301, filed on Apr. 8, 2021.

(51) Int. Cl.

| | |
|---|---|
| ***C12N 15/113*** | (2010.01) |
| ***A61K 9/00*** | (2006.01) |
| ***A61P 11/00*** | (2006.01) |

(52) U.S. Cl.

CPC .......... *C12N 15/113* (2013.01); *A61K 9/0073* (2013.01); *A61P 11/00* (2018.01); *C12N 2310/11* (2013.01); *C12N 2310/14* (2013.01)

(58) Field of Classification Search

CPC .............. C12N 15/113; C12N 2310/11; C12N 2310/14; C12N 2310/315; C12N 2310/344; C12N 2310/351; A61K 31/713

See application file for complete search history.

(56) References Cited

U.S. PATENT DOCUMENTS

| | | | | |
|---|---|---|---|---|
| 4,522,811 | A | 6/1985 | Eppstein et al. | |
| 5,998,203 | A | 12/1999 | Matulic-adamic et al. | |
| 6,326,403 | B1 | 12/2001 | Holzemann et al. | |
| 6,576,637 | B1 | 6/2003 | Holzemann et al. | |
| 8,507,659 | B2 | 8/2013 | Ooya et al. | |
| 2003/0171304 | A1 | 9/2003 | Holzeman | |
| 2006/0058266 | A1 | 3/2006 | Manoharan et al. | |
| 2007/0207974 | A1 | 9/2007 | Khvorova et al. | |
| 2008/0213249 | A1 | 9/2008 | Sinha et al. | |
| 2009/0156529 | A1 | 6/2009 | Van Heeke et al. | |
| 2011/0003858 | A1 | 1/2011 | Bergstrom et al. | |
| 2015/0125392 | A1 | 5/2015 | Howard et al. | |
| 2015/0179823 | A1 | 6/2015 | Kurita | |
| 2016/0009806 | A1 | 1/2016 | Ryan et al. | |
| 2016/0152973 | A1 | 6/2016 | Jadhav | |
| 2016/0272971 | A1 | 9/2016 | Almeida et al. | |
| 2016/0319361 | A1 | 11/2016 | Spetzler et al. | |
| 2016/0348107 | A1 | 12/2016 | Wong et al. | |
| 2017/0037396 | A1* | 2/2017 | Lee ...................... | C12N 15/113 |
| 2019/0345573 | A1 | 11/2019 | Khvorova et al. | |

FOREIGN PATENT DOCUMENTS

| | | | |
|---|---|---|---|
| EP | 2913064 | A1 | 2/2015 |
| JP | 2015040181 | | 2/2015 |
| WO | 2000053722 | A2 | 9/2000 |
| WO | 2001000660 | A1 | 1/2001 |
| WO | 2004016229 | A2 | 2/2004 |
| WO | 2005051995 | A2 | 6/2005 |
| WO | 2006020768 | A2 | 2/2006 |
| WO | 2007039728 | A2 | 4/2007 |
| WO | 2008022309 | A2 | 2/2008 |
| WO | 2008112004 | A2 | 9/2008 |
| WO | 2008006102 | A2 | 10/2008 |
| WO | 2008152131 | A2 | 12/2008 |
| WO | 2010126551 | A1 | 11/2010 |
| WO | 2011073340 | A1 | 6/2011 |

(Continued)

OTHER PUBLICATIONS

Chernikov et al., Current Development of siRNA Bioconjugates: From Research to the Clinic, 2019, Frontiers in Pharmacology, 10, 1-25. (Year: 2019).*

Zhao et al., The impact of RAGE inhibition in animal models of bacterial sepsis: a systematic review and meta-analysis, 2018, J. of International Medical Research, 46, 11-21. (Year: 2018).*

Achoutti et al., Receptor for Advanced Glycation End Products (RAGE) Serves a Protective Role during *Klebsiella pneumoniae*—Induced Pneumonia, 2016, Plos One, 11, p. 1-15. (Year: 2016).*

Araki, K. et al.; (2021). The heterodimer S100A8/A9 is a potent therapeutic target for idiopathic pulmonary fibrosis. Journal of molecular medicine (Berlin, Germany), 99(1), 131-145. https://doi.org/10.1007/s00109-020-02001-x.

(Continued)

*Primary Examiner* — Jennifer Dunston
*Assistant Examiner* — Keyur A Vyas
(74) *Attorney, Agent, or Firm* — Paul VanderVelde; Meibo Chen; Mitchell Porter

(57) ABSTRACT

Described are RNAi agents, compositions that include RNAi agents, and methods for inhibition of a Receptor for Advanced Glycation End-products (AGER or RAGE) gene. The RAGE RNAi agents and RNAi agent conjugates disclosed herein inhibit the expression of an AGER gene. Pharmaceutical compositions that include one or more RAGE RNAi agents, optionally with one or more additional therapeutics, are also described. Delivery of the described RAGE RNAi agents to pulmonary cells, in vivo, provides for inhibition of AGER gene expression and a reduction in membrane RAGE activity, which can provide a therapeutic benefit to subjects, including human subjects, for the treatment of various diseases including pulmonary inflammation diseases such as severe asthma.

13 Claims, 46 Drawing Sheets

Specification includes a Sequence Listing.

(56) References Cited

FOREIGN PATENT DOCUMENTS

| | | | |
|---|---|---|---|
| WO | 2011104169 | A1 | 9/2011 |
| WO | 2012083185 | A2 | 6/2012 |
| WO | 2013032829 | A1 | 3/2013 |
| WO | 2013153092 | A1 | 10/2013 |
| WO | 2013158141 | A1 | 10/2013 |
| WO | 2014203087 | A1 | 12/2014 |
| WO | 2015160770 | A1 | 10/2015 |
| WO | 2015179823 | A2 | 11/2015 |
| WO | 2017214112 | A1 | 12/2017 |
| WO | 2018027106 | A2 | 2/2018 |
| WO | 2018085415 | A1 | 5/2018 |
| WO | 2019089765 | A1 | 5/2019 |
| WO | 2019161213 | A1 | 8/2019 |
| WO | 2021029896 | A1 | 2/2021 |

OTHER PUBLICATIONS

Barden S. et al.; "Adhesion of Several Cell Lines to Helicobacter pylori CagL is Mediated by Integrin αvβ6 via an RGDLXXL Motif"; Journal of Molecular Biology; vol. 427; 1304-1315; 2015.
Bertheloot, D. et al.; (2016). RAGE Enhances TLR Responses through Binding and Internalization of RNA. Journal of immunology (Baltimore, Md. : 1950), 197(10), 4118-4126. https://doi.org/10.4049/jimmunol.1502169.
Blondonnet, R. et al.; (2017). RAGE inhibition reduces acute lung injury in mice. Scientific reports, 7(1), 7208. https://doi.org/10.1038/s41598-017-07638-2.
Bongarzone, S. et al.; (2017). Targeting the Receptor for Advanced Glycation Endproducts (RAGE): A Medicinal Chemistry Perspective. Journal of medicinal chemistry, 60(17), 7213-7232. https://doi.org/10.1021/acs.jmedchem.7b00058.
Brandt, E. B., & Lewkowich, I. P. (2019). RAGE-induced asthma: A role for the receptor for advanced glycation end-products in promoting allergic airway disease. The Journal of allergy and clinical immunology, 144(3), 651-653. https:// doi.org/10.1016/j.jaci.2019.06.012.
Buckley, S. T., & Ehrhardt, C. (2010). The receptor for advanced glycation end products (RAGE) and the lung. Journal of biomedicine & biotechnology, 2010, 917108. https://doi.org/10.1155/2010/917108.
Butler, et al.; "The Use of Maleic Anhydride for the Reversible Blocking of Amino Groups in Polypeptide Chains"; Biochem. J.; pp. 679-689; 1969.
Cai, X. G., et al.; (2014). Anti-fibrotic effects of specific-siRNA targeting of the receptor for advanced glycation end products in a rat model of experimental hepatic fibrosis. Molecular medicine reports, 10(1), 306-314. https://doi.org/10.3892/mmr.2014.2207.
Conibear, Anne C., et al; "Arginine side-chain modification that occurs during copper-catalysed azide-alkyne click reactions resembles an advanced glycation end product"; Organic & Biomolecular Chemistry; vol. 14; 2016; 6205-6211.
Czauderna, et al.; "Structural variations and stabilising modifications of synthetic siRNAs in mammalian cells"; Nucleic acids research, 31(11), 2705-2716. https://doi.org/10.1093/nar/gkg393; 2003.
Dicara D. et al.; "Structure-Function Analysis of Arg-Gly-Asp Helix Motifs in avB6 Integrin Ligands"; Journal of Biological Chemistry; vol. 282:(13); 9657-9665; 2007.
Di Leva F. et al.; "From a Helix to a Small Cycle: Metadynamics-Inspired αvβ6 Integrin Selective Ligands"; Angewandte Chemie International Edition; vol. 57; 1-6; 2018.
Dong X. et al.; "Structural determinants of integrin β-subunit specificity for latent TGF-β"; Nature Structural & Molecular Biology; vol. 21:(12); 1091-1097; 2014.
Elayadi A. et al., "A Peptide Selected by Biopanning Identifies the Integrin αvβ6 as a Prognostic Biomarker for Nonsmall Cell Lung Cancer"; Cancer Research; vol. 67:(12); 5889-5895; 2007.
Englert, J. M. et al.; (2008). A role for the receptor for advanced glycation end products in idiopathic pulmonary fibrosis. The American journal of pathology, 172(3), 583-591. https://doi.org/10.2353/ajpath.2008.070569.
Färber S. et al.; "Therapeutic Radiopharmaceuticals Targeting Integrin αvβ6"; American Chemical Society Omega; vol. 3; 2428-2436; 2018.
Goodman, et al.; "Nanomolar Small Molecule Inhibitors for αvβ6 , αvβ5, and αvβ3 Integrins"; J. Med. Chem.; 45; 1045-1051; 2002.
Goswami, R. et al.; "Chemically Programmed Antibodies Targeting Multiple Alpha(v) Integrins and Their Effects on Tumor-Related Functions in Vitro"; Bioconjugate Chemistry; vol. 22; p. 1535-1544; Jul. 20, 2011.
Gray B. et al.; "A Liposomal Drug Platform Overrides Peptide Ligand Targeting to a Cancer Biomarker, Irrespective of Ligand Affinity or Density"; PLOS One; vol. 8:(8); 1-19; 2013.
Gray B. et al.; "From Phage Display to Nanoparticle Delivery: Functionalizing Liposomes with Multivalent Peptides Improves Targeting to a Cancer Biomarker"; Bionconjugate Chemistry; vol. 24:(1); 85-96; 2013.
Guthi J. et al.; "MRI-Visible Micellar Nanomedicine for Targeted Drug Delivery to Lung Cancer Cells"; Molecular Pharmaceutics; vol. 7:(1); 32-40; 2010.
Hackel B. et al.; "18F-Fluorobenzoate-Labeled Cystine Knot Peptides for PET Imaging of Integrin αvβ6"; The Journal of Nuclear Medicine; vol. 54; 1101-1105; 2013.
Hancock, et al.; (2010). Meta-analyses of genome-wide association studies identify multiple loci associated with pulmonary function. Nature genetics, 42(1), 45-52. https://doi.org/10.1038/ng.500.
Hausner S. et al.; "Use of a Peptide Derived from Foot-and-Mouth Disease Virus for the Noninvasive Imaging of Human Cancer: Generation and Evaluation of 4-[18F]Fluorobenzoyl A20FMDV2 for In vivo Imaging of Integrin αvβ 6 Expression with Positron Emission Tomography"; Cancer Research; vol. 67:(16); 7833-7840; 2007.
Hausner S. et al.; "Targeted In vivo Imaging of Integrin avß6 with an Improved Radiotracer and Its Relevance in a Pancreatic Tumor Model"; Cancer Research; vol. 69:(14); 5843-5850; 2009.
Hausner S. et al.; "Preclinical development and first-in-human imaging of the integrin αvβ6 with [18F]αvβ6-Binding Peptide in metastatic carcinoma."; Clinical Cancer Research; vol. 25:(4); 1206-1215; 2018.
Hu L. et al.; "Characterization and Evaluation of 64Cu-Labeled A20FMDV2 Conjugates for Imaging the Integrin αvβ6"; Molecular Imaging Biology; vol. 16:(4); 567-577; 2014.
John A. et al.; "Preclinical SPECT/CT Imaging of αvβ6 Integrins for Molecular Stratification of Idiopathic Pulmonary Fibrosis"; The Journal of Nuclear Medicine; vol. 54:(12); 2146-2152; 2013.
Kamola, et al.; "The siRNA Non-seed Region and Its Target Sequences Are Auxiliary Determinants of Off-Target Effects"; PLoS computational biology, 11(12), e1004656. https://doi.org/10.1371/journal.pcbi.1004656; 2015.
Kapp T. et al.; "A Comprehensive Evaluation of the Activity and Selectivity Profile of Ligands for RGD-binding Integrins"; Nature Scientific Reports; vol. 7; 1-13; 2017.
Kimura R. et al.; "Pharmacokinetically Stabilized Cystine Knot Peptides That Bind Alpha-v-Beta-6 Integrin with Single-Digit Nanomolar Affinities for Detection of Pancreatic Cancer"; Clinical Cancer Research; vol. 18:(3); 839-849; 2012.
Kimura R. et al.; "Evaluation of integrin αvβ6 cystine knot PET tracers to detect cancer and idiopathic pulmonary fibrosis"; Nature Communications; vol. 10:(1); 1-17; 2019.
Ko, S. Y., et al.; (2014). Cell migration is regulated by AGE-RAGE interaction in human oral cancer cells in vitro. PloS one, 9(10), e110542. https://doi.org/10.1371/journal.pone.0110542.
Kraft S. et al.; "Definition of an Unexpected Ligand Recognition Motif for αvβ6 Integrin"; The Journal of Biological Chemistry; vol. 274:(4); 1979-1988; 1999.
Leung K ; "4-[18F]Fluorobenzoyl-NAVPNLRGDLQVLAQKVART"; Molecular Imaging & Contrast Agent Database; 2008.
Li S. et al.; "Synthesis and characterization of a high-affinity αvβ6-specific ligand for in vitro and in vivo applications"; Molecular Cancer Therapy; vol. 8:(5); 1239-1249; 2009.

(56) References Cited

OTHER PUBLICATIONS

Li S. et al.; "Synthesis and biological evaluation of a peptide-paclitaxel conjugate which targets the integrin αvβ6"; Bioorganic & Medicinal Chemistry; vol. 19; 5480-5489; 2011.
Liu H. et al.; "Molecular imaging of integrin αvβ6 expression in living subjects"; American Journal of Nuclear Medicine & Molecular Imaging; vol. 4:(4); 333-345; 2014.
Lukey P. et al.; "Clinical quantification of the integrin αvβ6 by [18F]FB-A20FMDV2 positron emission tomography in healthy and fibrotic human lung (PETAL Study)"; European Journal of Nuclear Medicine and Molecular Imaging; vol. 1-13; 2019.
Maltsev O. et al.; "Stable Peptides Instead of Stapled Peptides: Highly Potent αvβ6-Selective Integrin Ligands"; Angewandte Chemie International Edition; vol. 55; 1535-1593; 2016.
Marinelli, Luciana, et al.; "Human inegrin αvβ5: Homology modeling and ligand binding."; Journal of Medicinal Chemistry; 47.17 (2004); 4166-4177.
McGuire M. et al.; "Identification and Characterization of a Suite of Tumor Targeting Peptides for Non-Small Cell Lung Cancer"; Nature Scientific Reports; vol. 4; 1-11; 2014.
Nieberler M. et al.; "Fluorescence imaging of invasive head and neck carcinoma cells with integrin _v_6-targeting RGD-peptides: an approach to a fluorescence-assisted intraoperative cytological assessment of bony resection margins"; Journal of Oral and Maxillofacial Surgery; vol. 56; 962-978; 2018.
Nothelfer E. et al.; "Identification and Characterization of a Peptide with Affinity to Head and Neck Cancer"; The Journal of Nuclear Medicine; vol. 50; 426-434; 2009.
Notni J. et al.; "In Vivo PET Imaging of the Cancer Integrin αvβ6 Using 68Ga-Labeled Cyclic RGD Nonapeptides"; The Journal of Nuclear Medicine; vol. 58:(4); 671-677; 2017.
Oczypok et al.; "All the 'Rage' in lung disease: The receptor for advanced glycation endproducts (RAGE) is a major mediator of pulmonary inflammatory responses"; Paediatr. Respir. Rev.; 2017; 23: 40-49.
Repapi et al.; "Genome-wide association study identifies five loci associated with lung function"; Nat. Genet.; 2010; 42 (1): 36-44; doi:10.1038/ng.501.
Rojas et al.; "Inhibition of RAGE Axis Signaling: A Pharmacological Challenge"; Curr. Drug Targets; 2019; 20(3): 340-346; doi:10.2174/1389450119666180820105956.
Senatus, L. et al.; (2020). RAGE impairs murine diabetic atherosclerosis regression and implicates IRF7 in macrophage inflammation and cholesterol metabolism. JCI insight, 5(13), e137289. https://doi.org/10.1172/jci.insight.137289.
GenBank NM_001136.5.
Shunzi, Li et al.; "Synthesis and biological evaluation of a peptidepaclitaxel conjugate which targets the integrin αvβ6"; Biorganic & Medicinal Chemistry; vol. 19; 2011; 5480-5489.
Singh A. et al.; "Dimerization of a Phage-Display Selected Peptide for Imaging of αvβ6-Integrin: Two Approaches to the Multivalent Effect"; Theranostics; vol. 4:(7); 745-760; 2014.
Slack R. et al.; "Pharmacological Characterization of the αvβ6 Integrin Binding and Internalization Kinetics of the Foot-and-Mouth Disease Virus Derived Peptide A20FMDV2"; Pharmacology; vol. 97; 114-125; 2015.
Sukkar, M. B. et al.; (2012). Soluble RAGE is deficient in neutrophilic asthma and COPD. The European respiratory journal, 39(3), 721-729. https://doi.org/10.1183/09031936.00022011.
Sukkar, M. B. et al.; (2012). RAGE: a new frontier in chronic airways disease. British journal of pharmacology, 167 (6), 1161-1176. https://doi.org/10.1111/j.1476-5381.2012.01984.x.
Tipping, et al.; "Relative Binding Affinities of Integrin Antagonists by Equilibrium Dialysis and Liquid Chromatography—Mass Spectrometry"; ACS Medicinal Chemistry Letters; 6, 221-224; 2015.
Uusi-Kerttula H. et al.; "Pseudotyped αvβ6 integrin-targeted adenovirus vectors for ovarian cancer therapies"; Oncotarget; vol. 7:(19); 27926-27937; 2016.
Wang et al.; "Role of Receptor for Advanced Glycation End Products in Regulating Lung Fluid Balance in Lipopolysaccharide-induced Acute Lung Injury and Infection-Related Acute Respiratory Distress Syndrome"; Shock; 2018; 50(4): 472-482.
White B. et al.; "ImmunoPET Imaging of αvβ6 Expression Using an Engineered Anti-αvβ6 Cys-diabody Site-Specifically Radiolabeled with Cu-64: Considerations for Optimal Imaging with Antibody Fragments"; Molecular Imaging and Biology; vol. 20; 103-113; 2018.
Wu, L. et al.; (2011). Advanced glycation end products and its receptor (RAGE) are increased in patients with COPD. Respiratory medicine, 105(3), 329-336. https://doi.org/10.1016/j.rmed.2010.11.001.
Xu, et al.; (2010). Advanced glycation end product (AGE)-receptor for AGE (RAGE) signaling and up-regulation of Egr-1 in hypoxic macrophages. The Journal of biological chemistry, 285(30), 23233-23240. https://doi.org/10.1074/jbc.M110.117457.
International Search Report and Written Opinion for corresponding International Application No. PCT/US2022/023813 dated Jul. 27, 2022, and with a mailing date of Aug. 17, 2022.
CAS Registry No. 442137-98-6, entered Aug. 2, 2002, American Chemical Society.
CAS Registry No. 442138-55-8, entered Aug. 2, 2002, American Chemical Society.
CAS Registry No. 444053-20-7, entered Aug. 16, 2002, American Chemical Society.
GenBank NM_001136.5, dated Jul. 13, 2023.
GenBank: OC325392.1; TRAN. "3_ Tce_b3v08," NCBI Genbank, Dec. 11, 2020 [retrieved on Jul. 26, 2022). Retrieved from the Internet: <URL: https://www.ncbi.nlm.nih.gov/nuccore/OC325392.1/>. entire document.

* cited by examiner

SEQUENCE LISTING

```
<160> NUMBER OF SEQ ID NOS: 891

<210> SEQ ID NO 1
<211> LENGTH: 1420
<212> TYPE: DNA
<213> ORGANISM: Homo Sapiens
<220> FEATURE:
<223> OTHER INFORMATION: Homo sapiens advanced glycosylation end-product
      specific receptor (AGER), transcript variant 1, GenBank
      NM_001136.5

<400> SEQUENCE: 1

agacagagcc aggaccctgg aaggaagcag gatggctgcc ggaacagcag ttggagcctg     60

ggtgctggtc ctcagtctgt ggggggcagt agtaggtgct caaaacatca cagcccggat    120

tggcgagcca ctggtgctga agtgtaaggg ggcccccaag aaaccacccc agcggctgga    180

atggaaactg aacacaggcc ggacagaagc ttggaaggtc ctgtctcccc agggaggagg    240

cccctgggac agtgtggctc gtgtccttcc caacggctcc ctcttccttc cggctgtcgg    300

gatccaggat gaggggattt tccggtgcca ggcaatgaac aggaatggaa aggagaccaa    360

gtccaactac cgagtccgtg tctaccagat tcctgggaag ccagaaattg tagattctgc    420

ctctgaactc acggctggtg ttcccaataa ggtggggaca tgtgtgtcag agggaagcta    480

ccctgcaggg actcttagct ggcacttgga tgggaagccc ctggtgccta atgagaaggg    540

agtatctgtg aaggaacaga ccaggagaca ccctgagaca gggctcttca cactgcagtc    600

ggagctaatg gtgaccccag cccggggagg agatccccgt cccaccttct cctgtagctt    660

cagcccaggc cttccccgac accgggcctt gcgcacagcc cccatccagc cccgtgtctg    720

ggagcctgtg cctctggagg aggtccaatt ggtggtggag ccagaaggtg gagcagtagc    780

tcctggtgga accgtaaccc tgacctgtga agtccctgcc cagccctctc ctcaaatcca    840

ctggatgaag gatggtgtgc ccttgcccct tccccccagc cctgtgctga tcctccctga    900

gatagggcct caggaccagg gaacctacag ctgtgtggcc acccattcca gccacgggcc    960

ccaggaaagc cgtgctgtca gcatcagcat catcgaacca ggcgaggagg ggccaactgc   1020

aggctctgtg ggaggatcag ggctgggaac tctagccctg gccctgggga tcctgggagg   1080

cctggggaca gccgccctgc tcattggggt catcttgtgg caaaggcggc aacgccgagg   1140

agaggagagg aaggccccag aaaaccagga ggaagaggag gagcgtgcag aactgaatca   1200

gtcggaggaa cctgaggcag gcgagagtag tactggaggg ccttgagggg cccacagaca   1260

gatcccatcc atcagctccc ttttcttttt cccttgaact gttctggcct cagaccaact   1320

ctctcctgta taatctctct cctgtataac ccccaccttgc caagctttct tctacaacca  1380

gagcccccca caatgatgat taaacacctg acacatcttg                         1420

<210> SEQ ID NO 2
```

<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 2
uuguguucag uuuccauucc g 21

<210> SEQ ID NO 3
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 3
uuguguucag uuuccauucc g 21

<210> SEQ ID NO 4
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 4
uuccauuccu guucauugcc u 21

<210> SEQ ID NO 5
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 5
ugauguuuug agcaccuacu c 21

<210> SEQ ID NO 6
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 6
ugauguuuug agcaccuacu c 21

<210> SEQ ID NO 7
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 7
uuguguucag uuuccauucc g 21

<210> SEQ ID NO 8
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 8
uuccauuccu guucauugcc u 21

<210> SEQ ID NO 9
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 9
ugauguuuug agcaccuacu c 21

<210> SEQ ID NO 10
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 10
cggaauggaa acugaacaca a 21

<210> SEQ ID NO 11
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 11
gaguaggugc ucaaaacauc a 21

<210> SEQ ID NO 12
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 12
aggcaaugaa caggaaunga a 21

<210> SEQ ID NO 13
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 13
cggaauggaa acugaacaca a 21

<210> SEQ ID NO 14
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 14
gaguaggugc ucaaaacauc a 21

<210> SEQ ID NO 15
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 15
aggcaaugaa caggaaunga a 21

<210> SEQ ID NO 16
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 16
cggaauggaa acugaacaca a 21

<210> SEQ ID NO 17
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 17
gaguaggugc ucaaaacauc a 21

<210> SEQ ID NO 18
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 18
aggcaaugaa caggaaunga a 21

<210> SEQ ID NO 19
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 19
cggaauggaa acugaacaca a 21

<210> SEQ ID NO 20
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 20
gaguaggugc ucaaaacauc a 21

<210> SEQ ID NO 21
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 21
aggcaaugaa caggaaunga a 21

<210> SEQ ID NO 22
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 22
gaauggaaac ugaacacag 19

<210> SEQ ID NO 23
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 23
guaggugcuc aaaacauca 19

<210> SEQ ID NO 24
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 24
gcaaugaaca ggaauggaa 19

<210> SEQ ID NO 25
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 25
aauggaaacu gaacacagg 19

<210> SEQ ID NO 26
<211> LENGTH: 19
<212> TYPE: RNA

-continued

```
<213> ORGANISM: Artificial sequence
<220> FEATURE:
<223> OTHER INFORMATION: AGER(RAGE) 19-mer gene transcript (mRNA) target
      sequence

<400> SEQUENCE: 26

cagauuccug ggaagccag                                                19


<210> SEQ ID NO 27
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 27

cugggaagcc agaaauugu                                                19


<210> SEQ ID NO 28
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 28

cacuggugcu gaaguguaa                                                19


<210> SEQ ID NO 29
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 29

gacagaagcu uggaagguc                                                19


<210> SEQ ID NO 30
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 30

ggaugagggg auuuuccgg                                                19


<210> SEQ ID NO 31
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 31

auuccuggga agccagaaa                                                19


<210> SEQ ID NO 32
<211> LENGTH: 19
<212> TYPE: RNA
<213> ORGANISM: Artificial sequence
```

<220> FEATURE:
<223> OTHER INFORMATION: AGER(RAGE) 19-mer gene transcript (mRNA) target
      sequence

<400> SEQUENCE: 32
auucugccuc ugaacucac 19

<210> SEQ ID NO 33
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 33
cccugcaggg acucuuagc 19

<210> SEQ ID NO 34
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 34
ccugcaggga cucuuagcu 19

<210> SEQ ID NO 35
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 35
ccaccuucuc cuguagcuu 19

<210> SEQ ID NO 36
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 36
cuucuccugu agcuucagc 19

<210> SEQ ID NO 37
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
      sequence

<400> SEQUENCE: 37
ugcugguccu cagucugug 19

<210> SEQ ID NO 38
<211> LENGTH: 19
<212> TYPE: RNA
<213> ORGANISM: Artificial sequence
<220> FEATURE:

<223> OTHER INFORMATION: AGER(RAGE) 19-mer gene transcript (mRNA) target
sequence

<400> SEQUENCE: 38
gcugguccuc agucugugg 19

<210> SEQ ID NO 39
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
sequence

<400> SEQUENCE: 39
uccgugucua ccagauucc 19

<210> SEQ ID NO 40
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
sequence

<400> SEQUENCE: 40
cgugucuacc agauuccug 19

<210> SEQ ID NO 41
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
sequence

<400> SEQUENCE: 41
caccuucucc uguagcuuc 19

<210> SEQ ID NO 42
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
sequence

<400> SEQUENCE: 42
ccucaaaucc acuggauga 19

<210> SEQ ID NO 43
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target
sequence

<400> SEQUENCE: 43
uagauucugc cucugaacu 19

<210> SEQ ID NO 44
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 44
gauucugccu cugaacuca 19

<210> SEQ ID NO 45
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 45
cugguguucc caauaaggu 19

<210> SEQ ID NO 46
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 46
gguguuccca auaaggugg 19

<210> SEQ ID NO 47
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 47
uuagcuggca cuuggaugg 19

<210> SEQ ID NO 48
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 48
uaaugagaag ggaguaucu 19

<210> SEQ ID NO 49
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 49
gagaagggag uaucuguga 19

<210> SEQ ID NO 50
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 50
gcaucagcau caucgaacc 19

<210> SEQ ID NO 51
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 51
ugaacaggaa uggaaagga 19

<210> SEQ ID NO 52
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 52
cuaccgaguc cgugucuac 19

<210> SEQ ID NO 53
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 53
ugggaagcca gaaauugua 19

<210> SEQ ID NO 54
<211> LENGTH: 19
<212> TYPE: RNA
<213> ORGANISM: Artificial sequence
<220> FEATURE:
<223> OTHER INFORMATION: AGER(RAGE) 19-mer gene transcript (mRNA) target sequence

<400> SEQUENCE: 54
ccuaaugaga agggaguau 19

<210> SEQ ID NO 55
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 55
uuguguucag uuuccauuc 19

<210> SEQ ID NO 56
<211> LENGTH: 19
<212> TYPE: RNA
<213> ORGANISM: Artificial sequence
<220> FEATURE:
<223> OTHER INFORMATION: RNAi agent antisense strand 19-mer core base sequence

```
<400> SEQUENCE: 56

auguguucag uuuccauuc                                                19


<210> SEQ ID NO 57
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 57

cuguguucag uuuccauuc                                                19


<210> SEQ ID NO 58
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 58

nuguguucag uuuccauuc                                                19


<210> SEQ ID NO 59
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 59

nuguguucag uuuccauun                                                19


<210> SEQ ID NO 60
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 60

uuguguucag uuuccauuc                                                19


<210> SEQ ID NO 61
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 61

auguguucag uuuccauuc                                                19


<210> SEQ ID NO 62
```

<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 62
cuguguucag uuuccauuc 19

<210> SEQ ID NO 63
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 63
nuguguucag uuuccauuc 19

<210> SEQ ID NO 64
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 64
nuguguucag uuuccauun 19

<210> SEQ ID NO 65
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 65
ugauguuuug agcaccuac 19

<210> SEQ ID NO 66
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 66
agauguuuug agcaccuac 19

<210> SEQ ID NO 67
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 67
ngauguuuug agcaccuac 19

<210> SEQ ID NO 68
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 68
ngauguuuug agcaccuan 19

<210> SEQ ID NO 69
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 69
uuccauuccu guucauugc 19

<210> SEQ ID NO 70
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 70
auccauuccu guucauugc 19

<210> SEQ ID NO 71
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 71
nuccauuccu guucauugc 19

<210> SEQ ID NO 72
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base

```
<222> LOCATION: 1, 19
<223> OTHER INFORMATION: n = any nucleobase

<400> SEQUENCE: 72

nuccauuccu guucauugn                                                19


<210> SEQ ID NO 73
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 73

uuccauuccu guucauugc                                                19


<210> SEQ ID NO 74
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 74

auccauuccu guucauugc                                                19


<210> SEQ ID NO 75
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 75

nuccauuccu guucauugc                                                19


<210> SEQ ID NO 76
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 76

nuccauuccu guucauugn                                                19


<210> SEQ ID NO 77
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 77

ucuguguuca guuuccauu                                                19
```

<210> SEQ ID NO 78
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 78
acuguguuca guuuccauu 19

<210> SEQ ID NO 79
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 79
ccuguguuca guuuccauu 19

<210> SEQ ID NO 80
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 80
ncuguguuca guuuccauu 19

<210> SEQ ID NO 81
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 81
ncuguguuca guuuccaun 19

<210> SEQ ID NO 82
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 82
ucuguguuca guuuccauu 19

<210> SEQ ID NO 83
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 83
acuguguuca guuuccauu 19

<210> SEQ ID NO 84
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 84
ccuguguuca guuuccauu 19

<210> SEQ ID NO 85
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 85
ncuguguuca guuuccauu 19

<210> SEQ ID NO 86
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 86
ncuguguuca guuuccaun 19

<210> SEQ ID NO 87
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 87
uuggcuuccc aggaaucug 19

<210> SEQ ID NO 88
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 88
auggcuuccc aggaaucug 19

<210> SEQ ID NO 89
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 89
cuggcuuccc aggaaucug 19

<210> SEQ ID NO 90
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 90
nuggcuuccc aggaaucug 19

<210> SEQ ID NO 91
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 91
nuggcuuccc aggaaucun 19

<210> SEQ ID NO 92
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 92
uuggcuuccc aggaaucug 19

<210> SEQ ID NO 93
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 93
auggcuuccc aggaaucug 19

<210> SEQ ID NO 94
<211> LENGTH: 19
<212> TYPE: RNA

```
<213> ORGANISM: Artificial sequence
<220> FEATURE:
<223> OTHER INFORMATION: RNAi agent antisense strand 19-mer core base
      sequence

<400> SEQUENCE: 94

cuggcuuccc aggaaucug                                                    19


<210> SEQ ID NO 95
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 95

nuggcuuccc aggaaucug                                                    19


<210> SEQ ID NO 96
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 96

nuggcuuccc aggaaucun                                                    19


<210> SEQ ID NO 97
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 97

acaauuucug gcuucccag                                                    19


<210> SEQ ID NO 98
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 98

ucaauuucug gcuucccag                                                    19


<210> SEQ ID NO 99
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
```

-continued

<222> LOCATION: 1
<223> OTHER INFORMATION: n = any nucleobase

<400> SEQUENCE: 99
ncaauuucug gcuucccag 19

<210> SEQ ID NO 100
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 100
ncaauuucug gcuucccan 19

<210> SEQ ID NO 101
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 101
uuacacuuca gcaccagug 19

<210> SEQ ID NO 102
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 102
auacacuuca gcaccagug 19

<210> SEQ ID NO 103
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 103
nuacacuuca gcaccagug 19

<210> SEQ ID NO 104
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 104
nuacacuuca gcaccagun 19

<210> SEQ ID NO 105
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 105
uaccuuccaa gcuucuguc 19

<210> SEQ ID NO 106
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 106
gaccuuccaa gcuucuguc 19

<210> SEQ ID NO 107
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 107
aaccuuccaa gcuucuguc 19

<210> SEQ ID NO 108
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 108
naccuuccaa gcuucuguc 19

<210> SEQ ID NO 109
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 109
naccuuccaa gcuucugun 19

-continued

<210> SEQ ID NO 110
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 110
uaccuuccaa gcuucuguc 19

<210> SEQ ID NO 111
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 111
gaccuuccaa gcuucuguc 19

<210> SEQ ID NO 112
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 112
aaccuuccaa gcuucuguc 19

<210> SEQ ID NO 113
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 113
naccuuccaa gcuucuguc 19

<210> SEQ ID NO 114
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 114
naccuuccaa gcuucugun 19

<210> SEQ ID NO 115
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 115
ucggaaaauc cccucaucc 19

<210> SEQ ID NO 116
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 116
ccggaaaauc cccucaucc 19

<210> SEQ ID NO 117
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 117
acggaaaauc cccucaucc 19

<210> SEQ ID NO 118
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 118
ncggaaaauc cccucaucc 19

<210> SEQ ID NO 119
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 119
ncggaaaauc cccucaucn 19

<210> SEQ ID NO 120
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 120
ucggaaaauc cccucaucc 19

-continued

<210> SEQ ID NO 121
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 121
ccggaaaauc cccucaucc 19

<210> SEQ ID NO 122
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 122
acggaaaauc cccucaucc 19

<210> SEQ ID NO 123
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 123
ncggaaaauc cccucaucc 19

<210> SEQ ID NO 124
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 124
ncggaaaauc cccucaucn 19

<210> SEQ ID NO 125
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 125
uuucuggcuu cccaggaau 19

<210> SEQ ID NO 126
<211> LENGTH: 19
<212> TYPE: RNA
<213> ORGANISM: Artificial sequence
<220> FEATURE:

<223> OTHER INFORMATION: RNAi agent antisense strand 19-mer core base
      sequence

<400> SEQUENCE: 126
auucuggcuu cccaggaau                                                19

<210> SEQ ID NO 127
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 127
nuucuggcuu cccaggaau                                                19

<210> SEQ ID NO 128
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 128
nuucuggcuu cccaggaan                                                19

<210> SEQ ID NO 129
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 129
uugaguucag aggcagaau                                                19

<210> SEQ ID NO 130
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 130
gugaguucag aggcagaau                                                19

<210> SEQ ID NO 131
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 131
augaguucag aggcagaau                                                19

<210> SEQ ID NO 132
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 132
nugaguucag aggcagaau 19

<210> SEQ ID NO 133
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 133
nugaguucag aggcagaan 19

<210> SEQ ID NO 134
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 134
ucuaagaguc ccugcaggg 19

<210> SEQ ID NO 135
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 135
acuaagaguc ccugcaggg 19

<210> SEQ ID NO 136
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 136
gcuaagaguc ccugcaggg 19

<210> SEQ ID NO 137
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 137
ncuaagaguc ccugcaggg 19

<210> SEQ ID NO 138
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 138
ncuaagaguc ccugcaggn 19

<210> SEQ ID NO 139
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 139
agcuaagagu cccugcagg 19

<210> SEQ ID NO 140
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 140
ugcuaagagu cccugcagg 19

<210> SEQ ID NO 141
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 141
ngcuaagagu cccugcagg 19

<210> SEQ ID NO 142
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 142
ngcuaagagu cccugcagn 19

<210> SEQ ID NO 143
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 143
agcuaagagu cccugcagg 19

<210> SEQ ID NO 144
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 144
ugcuaagagu cccugcagg 19

<210> SEQ ID NO 145
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 145
ngcuaagagu cccugcagg 19

<210> SEQ ID NO 146
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 146
ngcuaagagu cccugcagn 19

<210> SEQ ID NO 147
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 147
aagcuacagg agaaggugg 19

<210> SEQ ID NO 148
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 148
uagcuacagg agaaggugg 19

<210> SEQ ID NO 149
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 149
nagcuacagg agaaggugg 19

<210> SEQ ID NO 150
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 150
nagcuacagg agaaggugn 19

<210> SEQ ID NO 151
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 151
aagcuacagg agaaggugg 19

<210> SEQ ID NO 152
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 152
uagcuacagg agaaggugg 19

<210> SEQ ID NO 153

<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 153
nagcuacagg agaaggugg 19

<210> SEQ ID NO 154
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 154
nagcuacagg agaaggugn 19

<210> SEQ ID NO 155
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 155
ucugaagcua caggagaag 19

<210> SEQ ID NO 156
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 156
acugaagcua caggagaag 19

<210> SEQ ID NO 157
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 157
gcugaagcua caggagaag 19

<210> SEQ ID NO 158
<211> LENGTH: 19
<212> TYPE: RNA
<213> ORGANISM: Artificial sequence
<220> FEATURE:
<223> OTHER INFORMATION: RNAi agent antisense strand 19-mer core base sequence -continued
<220> FEATURE:
<221> NAME/KEY: modified_base
<222> LOCATION: 1
<223> OTHER INFORMATION: n = any nucleobase

<400> SEQUENCE: 158
ncugaagcua caggagaag 19

<210> SEQ ID NO 159
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 159
ncugaagcua caggagaan 19

<210> SEQ ID NO 160
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 160
ucugaagcua caggagaag 19

<210> SEQ ID NO 161
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 161
acugaagcua caggagaag 19

<210> SEQ ID NO 162
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 162
gcugaagcua caggagaag 19

<210> SEQ ID NO 163
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 163
ncugaagcua caggagaag 19

<210> SEQ ID NO 164
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 164
ncugaagcua caggagaan 19

<210> SEQ ID NO 165
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 165
uacagacuga ggaccagca 19

<210> SEQ ID NO 166
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 166
aacagacuga ggaccagca 19

<210> SEQ ID NO 167
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 167
cacagacuga ggaccagca 19

<210> SEQ ID NO 168
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 168
nacagacuga ggaccagca 19

<210> SEQ ID NO 169
<211> LENGTH: 19

-continued

<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 169
nacagacuga ggaccagcn 19

<210> SEQ ID NO 170
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 170
uacagacuga ggaccagca 19

<210> SEQ ID NO 171
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 171
aacagacuga ggaccagca 19

<210> SEQ ID NO 172
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 172
cacagacuga ggaccagca 19

<210> SEQ ID NO 173
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 173
nacagacuga ggaccagca 19

<210> SEQ ID NO 174
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:

<221> NAME/KEY: modified_base
<222> LOCATION: 1, 19
<223> OTHER INFORMATION: n = any nucleobase

<400> SEQUENCE: 174
nacagacuga ggaccagcn 19

<210> SEQ ID NO 175
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 175
ucacagacug aggaccagc 19

<210> SEQ ID NO 176
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 176
acacagacug aggaccagc 19

<210> SEQ ID NO 177
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 177
ncacagacug aggaccagc 19

<210> SEQ ID NO 178
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 178
ncacagacug aggaccagn 19

<210> SEQ ID NO 179
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 179

-continued ucacagacug aggaccagc 19

<210> SEQ ID NO 180
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 180
acacagacug aggaccagc 19

<210> SEQ ID NO 181
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 181
ncacagacug aggaccagc 19

<210> SEQ ID NO 182
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 182
ncacagacug aggaccagn 19

<210> SEQ ID NO 183
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 183
ucacagacug aggaccagc 19

<210> SEQ ID NO 184
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 184
acacagacug aggaccagc 19

<210> SEQ ID NO 185
<211> LENGTH: 19
<212> TYPE: RNA

<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 185
ncacagacug aggaccagc 19

<210> SEQ ID NO 186
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 186
ncacagacug aggaccagn 19

<210> SEQ ID NO 187
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 187
ugaaucuggu agacacgga 19

<210> SEQ ID NO 188
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 188
agaaucuggu agacacgga 19

<210> SEQ ID NO 189
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 189
ggaaucuggu agacacgga 19

<210> SEQ ID NO 190
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 190
ngaaucuggu agacacgga 19

<210> SEQ ID NO 191
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 191
ngaaucuggu agacacggn 19

<210> SEQ ID NO 192
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 192
ugaaucuggu agacacgga 19

<210> SEQ ID NO 193
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 193
agaaucuggu agacacgga 19

<210> SEQ ID NO 194
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 194
ggaaucuggu agacacgga 19

<210> SEQ ID NO 195
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 195
ngaaucuggu agacacgga 19

<210> SEQ ID NO 196
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 196
ngaaucuggu agacacggn 19

<210> SEQ ID NO 197
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 197
uaggaaucug guagacacg 19

<210> SEQ ID NO 198
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 198
aaggaaucug guagacacg 19

<210> SEQ ID NO 199
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 199
caggaaucug guagacacg 19

<210> SEQ ID NO 200
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 200
naggaaucug guagacacg 19

<210> SEQ ID NO 201
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 201
naggaaucug guagacacn 19

<210> SEQ ID NO 202
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 202
uaagcuacag gagaaggug 19

<210> SEQ ID NO 203
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 203
aaagcuacag gagaaggug 19

<210> SEQ ID NO 204
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 204
gaagcuacag gagaaggug 19

<210> SEQ ID NO 205
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 205
naagcuacag gagaaggug 19

<210> SEQ ID NO 206
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19

<223> OTHER INFORMATION: n = any nucleobase

<400> SEQUENCE: 206
naagcuacag gagaaggun 19

<210> SEQ ID NO 207
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 207
uaagcuacag gagaaggug 19

<210> SEQ ID NO 208
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 208
aaagcuacag gagaaggug 19

<210> SEQ ID NO 209
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 209
gaagcuacag gagaaggug 19

<210> SEQ ID NO 210
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 210
naagcuacag gagaaggug 19

<210> SEQ ID NO 211
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 211
naagcuacag gagaaggun 19

```
<210> SEQ ID NO 212
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 212

ucauccagug gauuugagg                                                19


<210> SEQ ID NO 213
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 213

acauccagug gauuugagg                                                19


<210> SEQ ID NO 214
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1
<223> OTHER INFORMATION: n = any nucleobase

<400> SEQUENCE: 214

ncauccagug gauuugagg                                                19


<210> SEQ ID NO 215
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 215

ncauccagug gauuugagn                                                19


<210> SEQ ID NO 216
<211> LENGTH: 19
<212> TYPE: RNA
<213> ORGANISM: Artificial sequence
<220> FEATURE:
<223> OTHER INFORMATION: RNAi agent antisense strand 19-mer core base
      sequence

<400> SEQUENCE: 216

ucauccagug gauuugagg                                                19


<210> SEQ ID NO 217
<211> LENGTH: 19
<212> TYPE: RNA
<213> ORGANISM: Artificial sequence
<220> FEATURE:
```

-continued

<223> OTHER INFORMATION: RNAi agent antisense strand 19-mer core base sequence

<400> SEQUENCE: 217
acauccagug gauuugagg 19

<210> SEQ ID NO 218
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 218
ncauccagug gauuugagg 19

<210> SEQ ID NO 219
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 219
ncauccagug gauuugagn 19

<210> SEQ ID NO 220
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 220
aguucagagg cagaaucua 19

<210> SEQ ID NO 221
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 221
uguucagagg cagaaucua 19

<210> SEQ ID NO 222
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 222
nguucagagg cagaaucua 19

<210> SEQ ID NO 223
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 223
nguucagagg cagaaucun 19

<210> SEQ ID NO 224
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 224
aguucagagg cagaaucua 19

<210> SEQ ID NO 225
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 225
uguucagagg cagaaucua 19

<210> SEQ ID NO 226
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 226
nguucagagg cagaaucua 19

<210> SEQ ID NO 227
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 227

-continued nguucagagg cagaaucun 19

<210> SEQ ID NO 228
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 228
ugaguucaga ggcagaauc 19

<210> SEQ ID NO 229
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 229
agaguucaga ggcagaauc 19

<210> SEQ ID NO 230
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 230
ngaguucaga ggcagaaun 19

<210> SEQ ID NO 231
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 231
ngaguucaga ggcagaaun 19

<210> SEQ ID NO 232
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 232
accuuauugg gaacaccag 19

<210> SEQ ID NO 233
<211> LENGTH: 19

<212> TYPE: RNA
<213> ORGANISM: Artificial sequence
<220> FEATURE:
<223> OTHER INFORMATION: RNAi agent antisense strand 19-mer core base
sequence

<400> SEQUENCE: 233
uccuuauugg gaacaccag 19

<210> SEQ ID NO 234
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 234
nccuuauugg gaacaccag 19

<210> SEQ ID NO 235
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 235
nccuuauugg gaacaccan 19

<210> SEQ ID NO 236
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 236
ucaccuuauu gggaacacc 19

<210> SEQ ID NO 237
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 237
acaccuuauu gggaacacc 19

<210> SEQ ID NO 238
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 238
ccaccuuauu gggaacacc 19

<210> SEQ ID NO 239
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 239
ncaccuuauu gggaacacc 19

<210> SEQ ID NO 240
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 240
ncaccuuauu gggaacacn 19

<210> SEQ ID NO 241
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 241
ucaccuuauu gggaacacc 19

<210> SEQ ID NO 242
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 242
acaccuuauu gggaacacc 19

<210> SEQ ID NO 243
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 243
ccaccuuauu gggaacacc 19

<210> SEQ ID NO 244

-continued

<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 244
ncaccuuauu gggaacacc 19

<210> SEQ ID NO 245
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 245
ncaccuuauu gggaacacn 19

<210> SEQ ID NO 246
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 246
ucauccaagu gccagcuaa 19

<210> SEQ ID NO 247
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 247
acauccaagu gccagcuaa 19

<210> SEQ ID NO 248
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 248
ccauccaagu gccagcuaa 19

<210> SEQ ID NO 249
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 249
ncauccaagu gccagcuaa 19

<210> SEQ ID NO 250
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 250
ncauccaagu gccagcuan 19

<210> SEQ ID NO 251
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 251
ucauccaagu gccagcuaa 19

<210> SEQ ID NO 252
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 252
acauccaagu gccagcuaa 19

<210> SEQ ID NO 253
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 253
ccauccaagu gccagcuaa 19

<210> SEQ ID NO 254
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 254

-continued ncauccaagu gccagcuaa 19

<210> SEQ ID NO 255
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 255
ncauccaagu gccagcuan 19

<210> SEQ ID NO 256
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 256
agauacuccc uucucauua 19

<210> SEQ ID NO 257
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 257
ugauacuccc uucucauua 19

<210> SEQ ID NO 258
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 258
ngauacuccc uucucauua 19

<210> SEQ ID NO 259
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 259
ngauacuccc uucucauun 19

<210> SEQ ID NO 260
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 260
agauacuccc uucucauua 19

<210> SEQ ID NO 261
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 261
ugauacuccc uucucauua 19

<210> SEQ ID NO 262
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 262
ngauacuccc uucucauua 19

<210> SEQ ID NO 263
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 263
ngauacuccc uucucauun 19

<210> SEQ ID NO 264
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 264
ucacagauac ucccuucuc 19

<210> SEQ ID NO 265
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 265
acacagauac ucccuucuc 19

<210> SEQ ID NO 266
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 266
ncacagauac ucccuucuc 19

<210> SEQ ID NO 267
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 267
ncacagauac ucccuucun 19

<210> SEQ ID NO 268
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 268
ucacagauac ucccuucuc 19

<210> SEQ ID NO 269
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 269
acacagauac ucccuucuc 19

<210> SEQ ID NO 270
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1

<223> OTHER INFORMATION: n = any nucleobase

<400> SEQUENCE: 270
ncacagauac ucccuucuc 19

<210> SEQ ID NO 271
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 271
ncacagauac ucccuucun 19

<210> SEQ ID NO 272
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 272
uguucgauga ugcugaugc 19

<210> SEQ ID NO 273
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 273
aguucgauga ugcugaugc 19

<210> SEQ ID NO 274
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 274
gguucgauga ugcugaugc 19

<210> SEQ ID NO 275
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 275
nguucgauga ugcugaugc 19

<210> SEQ ID NO 276
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 276
nguucgauga ugcugaugn 19

<210> SEQ ID NO 277
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 277
uguucgauga ugcugaugc 19

<210> SEQ ID NO 278
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 278
aguucgauga ugcugaugc 19

<210> SEQ ID NO 279
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 279
gguucgauga ugcugaugc 19

<210> SEQ ID NO 280
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 280
nguucgauga ugcugaugc 19

<210> SEQ ID NO 281
<211> LENGTH: 19
<212> TYPE: RNA
<213> ORGANISM: Artificial sequence
<220> FEATURE:

<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 281
nguucgauga ugcugaugn 19

<210> SEQ ID NO 282
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 282
accuuuccau uccuguuca 19

<210> SEQ ID NO 283
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 283
uccuuuccau uccuguuca 19

<210> SEQ ID NO 284
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 284
nccuuuccau uccuguuca 19

<210> SEQ ID NO 285
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 285
nccuuuccau uccuguucn 19

<210> SEQ ID NO 286
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 286
auagacacgg acucgguag 19

<210> SEQ ID NO 287
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 287
uuagacacgg acucgguag 19

<210> SEQ ID NO 288
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1
<223> OTHER INFORMATION: n = any nucleobase

<400> SEQUENCE: 288
nuagacacgg acucgguag 19

<210> SEQ ID NO 289
<211> LENGTH: 19
<212> TYPE: RNA
<213> ORGANISM: Artificial sequence
<220> FEATURE:
<223> OTHER INFORMATION: RNAi agent antisense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 289
nuagacacgg acucgguan 19

<210> SEQ ID NO 290
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 290
aacaauuucu ggcuuccca 19

<210> SEQ ID NO 291
<211> LENGTH: 19
<212> TYPE: RNA
<213> ORGANISM: Artificial sequence
<220> FEATURE:
<223> OTHER INFORMATION: RNAi agent antisense strand 19-mer core base sequence

<400> SEQUENCE: 291
uacaauuucu ggcuuccca 19

<210> SEQ ID NO 292
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 292
nacaauuucu ggcuuccca 19

<210> SEQ ID NO 293
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 293
nacaauuucu ggcuucccn 19

<210> SEQ ID NO 294
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 294
auacucccuu cucauuagg 19

<210> SEQ ID NO 295
<211> LENGTH: 19
<212> TYPE: RNA
<213> ORGANISM: Artificial sequence
<220> FEATURE:
<223> OTHER INFORMATION: RNAi agent antisense strand 19-mer core base
sequence

<400> SEQUENCE: 295
uuacucccuu cucauuagg 19

<210> SEQ ID NO 296
<211> LENGTH: 19
<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1
<223> OTHER INFORMATION: n = any nucleobase

<400> SEQUENCE: 296
nuacucccuu cucauuagg 19

<210> SEQ ID NO 297
<211> LENGTH: 19

<212> TYPE: RNA
<213> ORGANISM: Artificial sequence
<220> FEATURE:
<223> OTHER INFORMATION: RNAi agent antisense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 297
nuacucccuu cucauuagn 19

<210> SEQ ID NO 298
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 298
gaauggaaac ugaacacaa 19

<210> SEQ ID NO 299
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 299
gaauggaaac ugaacacau 19

<210> SEQ ID NO 300
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 300
gaauggaaac ugaacacag 19

<210> SEQ ID NO 301
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 301
gaauggaaac ugaacacan 19

<210> SEQ ID NO 302
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:

<221> NAME/KEY: modified_base
<222> LOCATION: 1, 19
<223> OTHER INFORMATION: n = any nucleobase

<400> SEQUENCE: 302
naauggaaac ugaacacan 19

<210> SEQ ID NO 303
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 12
<223> OTHER INFORMATION: n = inosine (hypoxanthine)

<400> SEQUENCE: 303
gaauggaaac unaacacaa 19

<210> SEQ ID NO 304
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 12
<223> OTHER INFORMATION: n = inosine (hypoxanthine)

<400> SEQUENCE: 304
gaauggaaac unaacacau 19

<210> SEQ ID NO 305
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 12
<223> OTHER INFORMATION: n = inosine (hypoxanthine)

<400> SEQUENCE: 305
gaauggaaac unaacacag 19

<210> SEQ ID NO 306
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 12
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 306
gaauggaaac unaacacan 19

<210> SEQ ID NO 307
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 12
<223> OTHER INFORMATION: n = inosine (hypoxanthine)

<400> SEQUENCE: 307
naauggaaac unaacacan 19

<210> SEQ ID NO 308
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 308
guaggugcuc aaaacauca 19

<210> SEQ ID NO 309
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 309
guaggugcuc aaaacaucu 19

<210> SEQ ID NO 310
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 310
guaggugcuc aaaacaucn 19

<210> SEQ ID NO 311
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 311
nuaggugcuc aaaacaucn 19

<210> SEQ ID NO 312
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 312
gcaaugaaca ggaauggaa 19

<210> SEQ ID NO 313
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 313
gcaaugaaca ggaauggau 19

<210> SEQ ID NO 314
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 314
gcaaugaaca ggaauggan 19

<210> SEQ ID NO 315
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 315
ncaaugaaca ggaauggan 19

<210> SEQ ID NO 316
<211> LENGTH: 19
<212> TYPE: RNA
<213> ORGANISM: Artificial sequence
<220> FEATURE:
<221> NAME/KEY: modified_base
<222> LOCATION: 16
<223> OTHER INFORMATION: n = inosine (hypoxanthine)
<220> FEATURE:
<223> OTHER INFORMATION: RNAi agent sense strand 19-mer core base sequence

<400> SEQUENCE: 316
gcaaugaaca ggaaungaa 19

<210> SEQ ID NO 317
<211> LENGTH: 19
<212> TYPE: RNA
<213> ORGANISM: Artificial sequence
<220> FEATURE:
<221> NAME/KEY: modified_base
<222> LOCATION: 16
<223> OTHER INFORMATION: n = inosine (hypoxanthine)
<220> FEATURE:
<223> OTHER INFORMATION: RNAi agent sense strand 19-mer core base
sequence

<400> SEQUENCE: 317
gcaaugaaca ggaaungau 19

<210> SEQ ID NO 318
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 318
gcaaugaaca ggaaungan 19

<210> SEQ ID NO 319
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 1, 19
<223> OTHER INFORMATION: n = any nucleobase

<400> SEQUENCE: 319
ncaaugaaca ggaaungan 19

<210> SEQ ID NO 320
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 320
aauggaaacu gaacacaga 19

<210> SEQ ID NO 321
<211> LENGTH: 19
<212> TYPE: RNA
<213> ORGANISM: Artificial sequence
<220> FEATURE:

<223> OTHER INFORMATION: RNAi agent sense strand 19-mer core base
      sequence

<400> SEQUENCE: 321
aauggaaacu gaacacagu                                                19

<210> SEQ ID NO 322
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 322
aauggaaacu gaacacagg                                                19

<210> SEQ ID NO 323
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 323
aauggaaacu gaacacagn                                                19

<210> SEQ ID NO 324
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 324
nauggaaacu gaacacagn                                                19

<210> SEQ ID NO 325
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)

<400> SEQUENCE: 325
aauggaaacu gaacacana                                                19

<210> SEQ ID NO 326
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

```
<220> FEATURE:
<221> NAME/KEY: modified_base
<222> LOCATION: 18
<223> OTHER INFORMATION: n = inosine (hypoxanthine)

<400> SEQUENCE: 326

aauggaaacu gaacacanu                                                19


<210> SEQ ID NO 327
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)

<400> SEQUENCE: 327

aauggaaacu gaacacang                                                19


<210> SEQ ID NO 328
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 328

aauggaaacu gaacacann                                                19


<210> SEQ ID NO 329
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 329

nauggaaacu gaacacann                                                19


<210> SEQ ID NO 330
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 330
```

cagauuccug ggaagccaa 19

<210> SEQ ID NO 331
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 331
cagauuccug ggaagccau 19

<210> SEQ ID NO 332
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 332
cagauuccug ggaagccag 19

<210> SEQ ID NO 333
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 333
cagauuccug ggaagccan 19

<210> SEQ ID NO 334
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 334
nagauuccug ggaagccan 19

<210> SEQ ID NO 335
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 335
cagauuccug ggaanccaa 19

<210> SEQ ID NO 336
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 15
<223> OTHER INFORMATION: n = inosine (hypoxanthine)

<400> SEQUENCE: 336
cagauuccug ggaanccau 19

<210> SEQ ID NO 337
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 15
<223> OTHER INFORMATION: n = inosine (hypoxanthine)

<400> SEQUENCE: 337
cagauuccug ggaanccag 19

<210> SEQ ID NO 338
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 338
cagauuccug ggaanccan 19

<210> SEQ ID NO 339
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 339
nagauuccug ggaanccan 19

<210> SEQ ID NO 340
<211> LENGTH: 19

<212> TYPE: RNA
<213> ORGANISM: Artificial sequence
<220> FEATURE:
<223> OTHER INFORMATION: RNAi agent sense strand 19-mer core base sequence

<400> SEQUENCE: 340
cugggaagcc agaaauugu 19

<210> SEQ ID NO 341
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 341
cugggaagcc agaaauuga 19

<210> SEQ ID NO 342
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 342
cugggaagcc agaaauugn 19

<210> SEQ ID NO 343
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 343
nugggaagcc agaaauugn 19

<210> SEQ ID NO 344
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 344
cacuggugcu gaaguguaa 19

<210> SEQ ID NO 345
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 345
cacuggugcu gaaguguau 19

<210> SEQ ID NO 346
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 346
cacuggugcu gaaguguan 19

<210> SEQ ID NO 347
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 347
nacuggugcu gaaguguan 19

<210> SEQ ID NO 348
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 348
gacagaagcu uggaaggua 19

<210> SEQ ID NO 349
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 349
gacagaagcu uggaagguc 19

<210> SEQ ID NO 350
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 350
gacagaagcu uggaagguu 19

<210> SEQ ID NO 351

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 351
gacagaagcu uggaaggun 19

<210> SEQ ID NO 352
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 352
nacagaagcu uggaaggun 19

<210> SEQ ID NO 353
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

<400> SEQUENCE: 353
gacagaagcu uggaagnua 19

<210> SEQ ID NO 354
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

<400> SEQUENCE: 354
gacagaagcu uggaagnuc 19

<210> SEQ ID NO 355
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

```
<400> SEQUENCE: 355

gacagaagcu uggaagnuu                                                    19


<210> SEQ ID NO 356
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 356

gacagaagcu uggaagnun                                                    19


<210> SEQ ID NO 357
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = inosine (hypoxanthine)

<400> SEQUENCE: 357

nacagaagcu uggaagnun                                                    19


<210> SEQ ID NO 358
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 358

ggaugagggg auuuuccga                                                    19


<210> SEQ ID NO 359
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 359

ggaugagggg auuuuccgg                                                    19


<210> SEQ ID NO 360
<211> LENGTH: 19
<212> TYPE: RNA
<213> ORGANISM: Artificial sequence
<220> FEATURE:
<223> OTHER INFORMATION: RNAi agent sense strand 19-mer core base
```

sequence

<400> SEQUENCE: 360
ggaugagggg auuuuccgu 19

<210> SEQ ID NO 361
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 361
ggaugagggg auuuuccgn 19

<210> SEQ ID NO 362
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 362
ngaugagggg auuuuccgn 19

<210> SEQ ID NO 363
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)

<400> SEQUENCE: 363
ggaugagggg auuuuccna 19

<210> SEQ ID NO 364
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)

<400> SEQUENCE: 364
ggaugagggg auuuuccng 19

<210> SEQ ID NO 365
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)

<400> SEQUENCE: 365
ggaugagggg auuuuccnu 19

<210> SEQ ID NO 366
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 366
ggaugagggg auuuuccnn 19

<210> SEQ ID NO 367
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 367
ngaugagggg auuuuccnn 19

<210> SEQ ID NO 368
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 368
auuccuggga agcuagaaa 19

<210> SEQ ID NO 369
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 369
auuccuggga agcuagaau 19

<210> SEQ ID NO 370
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 370
auuccuggga agcuagaan 19

<210> SEQ ID NO 371
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 371
nuuccuggga agcuagaan 19

<210> SEQ ID NO 372
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 372
auucugccuc ugaacucac 19

<210> SEQ ID NO 373
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 373
auucugccuc ugaacucac 19

<210> SEQ ID NO 374
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 374
auucugccuc ugaacucau 19

<210> SEQ ID NO 375
<211> LENGTH: 19
<212> TYPE: RNA
<213> ORGANISM: Artificial sequence -continued
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 375
auucugccuc ugaacucan 19

<210> SEQ ID NO 376
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 376
nuucugccuc ugaacucan 19

<210> SEQ ID NO 377
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 377
cccugcaggg acucuuaga 19

<210> SEQ ID NO 378
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 378
cccugcaggg acucuuagu 19

<210> SEQ ID NO 379
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 379
cccugcaggg acucuuagc 19

<210> SEQ ID NO 380
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19

<223> OTHER INFORMATION: n = any nucleobase

<400> SEQUENCE: 380
cccugcaggg acucuuagn 19

<210> SEQ ID NO 381
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 381
nccugcaggg acucuuagn 19

<210> SEQ ID NO 382
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 382
ccugcaggga cucuuagcu 19

<210> SEQ ID NO 383
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 383
ccugcaggga cucuuagca 19

<210> SEQ ID NO 384
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 384
ccugcaggga cucuuagcn 19

<210> SEQ ID NO 385
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 385
ncugcaggga cucuuagcn 19

<210> SEQ ID NO 386
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

<400> SEQUENCE: 386
ccugcaggga cucuuancu 19

<210> SEQ ID NO 387
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

<400> SEQUENCE: 387
ccugcaggga cucuuanca 19

<210> SEQ ID NO 388
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 388
ccugcaggga cucuuancn 19

<210> SEQ ID NO 389
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 17
<223> OTHER INFORMATION: n = inosine (hypoxanthine)

<400> SEQUENCE: 389
ncugcaggga cucuuancn 19

<210> SEQ ID NO 390
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 390
ccaccuucuc cuguagcuu 19

<210> SEQ ID NO 391
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 391
ccaccuucuc cuguagcua 19

<210> SEQ ID NO 392
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 392
ccaccuucuc cuguagcun 19

<210> SEQ ID NO 393
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 393
ncaccuucuc cuguagcun 19

<210> SEQ ID NO 394
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)

<400> SEQUENCE: 394
ccaccuucuc cuguancuu 19

<210> SEQ ID NO 395
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)

<400> SEQUENCE: 395
ccaccuucuc cuguancua 19

<210> SEQ ID NO 396
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 396
ccaccuucuc cuguancun 19

<210> SEQ ID NO 397
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 397
ncaccuucuc cuguancun 19

<210> SEQ ID NO 398
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 398
cuucuccugu agcuucaga 19

<210> SEQ ID NO 399
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 399
cuucuccugu agcuucagu 19

<210> SEQ ID NO 400
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 400
cuucuccugu agcuucagc 19

<210> SEQ ID NO 401
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 401
cuucuccugu agcuucagn 19

<210> SEQ ID NO 402
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 402
nuucuccugu agcuucagn 19

<210> SEQ ID NO 403
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 18
<223> OTHER INFORMATION: n = inosine (hypoxanthine)

<400> SEQUENCE: 403
cuucuccugu agcuucana 19

<210> SEQ ID NO 404
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 18
<223> OTHER INFORMATION: n = inosine (hypoxanthine)

<400> SEQUENCE: 404
cuucuccugu agcuucanu 19

<210> SEQ ID NO 405
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)

<400> SEQUENCE: 405
cuucuccugu agcuucanc 19

<210> SEQ ID NO 406
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 406
cuucuccugu agcuucann 19

<210> SEQ ID NO 407
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 407
nuucuccugu agcuucann 19

<210> SEQ ID NO 408
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 408
ugcugguccu cagucugua 19

<210> SEQ ID NO 409
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 409
ugcugguccu cagucuguu 19

<210> SEQ ID NO 410
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 410
ugcugguccu cagucugug 19

<210> SEQ ID NO 411
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 411
ugcugguccu cagucugun 19

<210> SEQ ID NO 412
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 412
ugcugguccu cagucugun 19

<210> SEQ ID NO 413
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 17
<223> OTHER INFORMATION: n = inosine (hypoxanthine)

<400> SEQUENCE: 413
ugcugguccu cagucunua 19

<210> SEQ ID NO 414

<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

<400> SEQUENCE: 414
ugcugguccu cagucunuu 19

<210> SEQ ID NO 415
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)

<400> SEQUENCE: 415
ugcugguccu cagucunug 19

<210> SEQ ID NO 416
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 416
ugcugguccu cagucunun 19

<210> SEQ ID NO 417
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 17
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 417
ugcugguccu cagucunun 19

<210> SEQ ID NO 418
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 418 gcuggucuc agucuguga 19

<210> SEQ ID NO 419
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 419 gcuggucuc agucugugu 19

<210> SEQ ID NO 420
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 420 gcuggucuc agucugugn 19

<210> SEQ ID NO 421
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 421 ncuggucuc agucugugn 19

<210> SEQ ID NO 422
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)

<400> SEQUENCE: 422 gcuggucuc agucuguna 19

<210> SEQ ID NO 423
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 18
<223> OTHER INFORMATION: n = inosine (hypoxanthine)

<400> SEQUENCE: 423
gcugguccuc agucugunu 19

<210> SEQ ID NO 424
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 424
gcugguccuc agucugunn 19

<210> SEQ ID NO 425
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 18
<223> OTHER INFORMATION: n = inosine (hypoxanthine)

<400> SEQUENCE: 425
ncugguccuc agucugunn 19

<210> SEQ ID NO 426
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = inosine (hypoxanthine)

<400> SEQUENCE: 426
gcugguccuc agucunuga 19

<210> SEQ ID NO 427
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = inosine (hypoxanthine)

<400> SEQUENCE: 427 gcuggucuc agucunugu 19

<210> SEQ ID NO 428
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 428 gcuggucuc agucunugn 19

<210> SEQ ID NO 429
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 429 ncuggucuc agucunugn 19

<210> SEQ ID NO 430
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 430
uccgugucua ccagauuca 19

<210> SEQ ID NO 431
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 431
uccgugucua ccagauucu 19

<210> SEQ ID NO 432
<211> LENGTH: 19
<212> TYPE: RNA

<213> ORGANISM: Artificial sequence
<220> FEATURE:
<223> OTHER INFORMATION: RNAi agent sense strand 19-mer core base
      sequence

<400> SEQUENCE: 432
uccgugucua ccagauucc                                                19

<210> SEQ ID NO 433
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 433
uccgugucua ccagauucn                                                19

<210> SEQ ID NO 434
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 434
nccgugucua ccagauucn                                                19

<210> SEQ ID NO 435
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)

<400> SEQUENCE: 435
uccgugucua ccanauuca                                                19

<210> SEQ ID NO 436
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)

<400> SEQUENCE: 436
uccgugucua ccanauucu                                                19

<210> SEQ ID NO 437

<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = inosine (hypoxanthine)

<400> SEQUENCE: 437
uccgugucua ccanauucc 19

<210> SEQ ID NO 438
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 438
uccgugucua ccanauucn 19

<210> SEQ ID NO 439
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = inosine (hypoxanthine)

<400> SEQUENCE: 439
nccgugucua ccanauucn 19

<210> SEQ ID NO 440
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 440
cgugucuacc agauuccua 19

<210> SEQ ID NO 441
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 441
cgugucuacc agauuccuu 19

<210> SEQ ID NO 442
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 442
cgugucuacc agauuccug 19

<210> SEQ ID NO 443
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 443
cgugucuacc agauuccun 19

<210> SEQ ID NO 444
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 444
ngugucuacc agauuccun 19

<210> SEQ ID NO 445
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 445
caccuucucc uguagcuua 19

<210> SEQ ID NO 446
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 446
caccuucucc uguagcuuu 19

<210> SEQ ID NO 447

<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 447
caccuucucc uguagcuuc 19

<210> SEQ ID NO 448
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 448
caccuucucc uguagcuun 19

<210> SEQ ID NO 449
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 449
naccuucucc uguagcuun 19

<210> SEQ ID NO 450
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 450
caccuucucc uguancuua 19

<210> SEQ ID NO 451
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 451
caccuucucc uguancuuu 19

```
<210> SEQ ID NO 452
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)

<400> SEQUENCE: 452

caccuucucc uguancuuc                                                19


<210> SEQ ID NO 453
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 453

caccuucucc uguancuun                                                19


<210> SEQ ID NO 454
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 1, 19
<223> OTHER INFORMATION: n = any nucleobase

<400> SEQUENCE: 454

naccuucucc uguancuun                                                19


<210> SEQ ID NO 455
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 455

ccucaaaucc acuggauga                                                19


<210> SEQ ID NO 456
<211> LENGTH: 19
<212> TYPE: RNA
<213> ORGANISM: Artificial sequence
<220> FEATURE:
<223> OTHER INFORMATION: RNAi agent sense strand 19-mer core base
```

sequence

<400> SEQUENCE: 456
ccucaaaucc acuggaugu 19

<210> SEQ ID NO 457
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 457
ccucaaaucc acuggaugn 19

<210> SEQ ID NO 458
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 458
ncucaaaucc acuggaugn 19

<210> SEQ ID NO 459
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = inosine (hypoxanthine)

<400> SEQUENCE: 459
ccucaaaucc acungauga 19

<210> SEQ ID NO 460
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = inosine (hypoxanthine)

<400> SEQUENCE: 460
ccucaaaucc acungaugu 19

<210> SEQ ID NO 461
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 461
ccucaaaucc acungaugn 19

<210> SEQ ID NO 462
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = inosine (hypoxanthine)

<400> SEQUENCE: 462
ncucaaaucc acungaugn 19

<210> SEQ ID NO 463
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 463
uagauucugc cucugaacu 19

<210> SEQ ID NO 464
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 464
uagauucugc cucugaaca 19

<210> SEQ ID NO 465
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 465
uagauucugc cucugaacn 19

<210> SEQ ID NO 466
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 466
nagauucugc cucugaacn 19

<210> SEQ ID NO 467
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 467
uagauucugc cucunaacu 19

<210> SEQ ID NO 468
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 468
uagauucugc cucunaaca 19

<210> SEQ ID NO 469
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 469
uagauucugc cucunaacn 19

<210> SEQ ID NO 470
<211> LENGTH: 19
<212> TYPE: RNA
<213> ORGANISM: Artificial sequence
<220> FEATURE:

<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 1, 19
<223> OTHER INFORMATION: n = any nucleobase

<400> SEQUENCE: 470
nagauucugc cucunaacn 19

<210> SEQ ID NO 471
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 471
gauucugccu cugaacuca 19

<210> SEQ ID NO 472
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 472
gauucugccu cugaacucu 19

<210> SEQ ID NO 473
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 473
gauucugccu cugaacucn 19

<210> SEQ ID NO 474
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 474
nauucugccu cugaacucn 19

<210> SEQ ID NO 475
<211> LENGTH: 19
<212> TYPE: RNA

```
<213> ORGANISM: Artificial sequence
<220> FEATURE:
<223> OTHER INFORMATION: RNAi agent sense strand 19-mer core base
      sequence

<400> SEQUENCE: 475

cuggguguucc caauaaggu                                              19


<210> SEQ ID NO 476
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 476

cugguguucc caauaagga                                               19


<210> SEQ ID NO 477
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 477

cugguguucc caauaaggn                                               19


<210> SEQ ID NO 478
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase

<400> SEQUENCE: 478

nugguguucc caauaaggn                                               19


<210> SEQ ID NO 479
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 479

gguguuccca auaagguga                                               19


<210> SEQ ID NO 480
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 480
```

ggugiuuccca auaaggugu 19

<210> SEQ ID NO 481
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 481
gguguuccca auaaggugg 19

<210> SEQ ID NO 482
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 482
gguguuccca auaaggugn 19

<210> SEQ ID NO 483
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 483
nguguuccca auaaggugn 19

<210> SEQ ID NO 484
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 484
gguguuccca auaanguga 19

<210> SEQ ID NO 485
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 485
gguguuccca auaangugu 19

<210> SEQ ID NO 486
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 15
<223> OTHER INFORMATION: n = inosine (hypoxanthine)

<400> SEQUENCE: 486
gguguuccca auaangugg 19

<210> SEQ ID NO 487
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 487
gguguuccca auaangugn 19

<210> SEQ ID NO 488
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 15
<223> OTHER INFORMATION: n = inosine (hypoxanthine)

<400> SEQUENCE: 488
nguguuccca auaangugn 19

<210> SEQ ID NO 489
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 489
uuagcuggca cuuggauga 19

<210> SEQ ID NO 490

<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 490
uuagcuggca cuuggaugu 19

<210> SEQ ID NO 491
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 491
uuagcuggca cuuggaugg 19

<210> SEQ ID NO 492
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 492
uuagcuggca cuuggaugn 19

<210> SEQ ID NO 493
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 493
nuagcuggca cuuggaugn 19

<210> SEQ ID NO 494
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = inosine (hypoxanthine)

<400> SEQUENCE: 494
uuagcuggca cuungauga 19

<210> SEQ ID NO 495
<211> LENGTH: 19
<212> TYPE: RNA

-continued

<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)

<400> SEQUENCE: 495
uuagcuggca cuungaugu 19

<210> SEQ ID NO 496
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)

<400> SEQUENCE: 496
uuagcuggca cuungaugg 19

<210> SEQ ID NO 497
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 497
uuagcuggca cuungaugn 19

<210> SEQ ID NO 498
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 14
<223> OTHER INFORMATION: n = inosine (hypoxanthine)

<400> SEQUENCE: 498
nuagcuggca cuungaugn 19

<210> SEQ ID NO 499
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 499
uaaugagaag ggaguaucu 19

<210> SEQ ID NO 500
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 500
uaaugagaag ggaguauca 19

<210> SEQ ID NO 501
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 501
uaaugagaag ggaguaucn 19

<210> SEQ ID NO 502
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 502
naaugagaag ggaguaucn 19

<210> SEQ ID NO 503
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 14
<223> OTHER INFORMATION: n = inosine (hypoxanthine)

<400> SEQUENCE: 503
uaaugagaag gganuaucu 19

<210> SEQ ID NO 504
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:

<221> NAME/KEY: modified_base
<222> LOCATION: 14
<223> OTHER INFORMATION: n = inosine (hypoxanthine)

<400> SEQUENCE: 504
uaaugagaag gganuauca 19

<210> SEQ ID NO 505
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 505
uaaugagaag gganuaucn 19

<210> SEQ ID NO 506
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 14
<223> OTHER INFORMATION: n = inosine (hypoxanthine)
<220> FEATURE:
<221> NAME/KEY: modified_base
<222> LOCATION: 1, 19
<223> OTHER INFORMATION: n = any nucleobase

<400> SEQUENCE: 506
naaugagaag gganuaucn 19

<210> SEQ ID NO 507
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 507
gagaagggag uaucuguga 19

<210> SEQ ID NO 508
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 508
gagaagggag uaucugugu 19

<210> SEQ ID NO 509
<211> LENGTH: 19

<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 509
gagaagggag uaucugugn 19

<210> SEQ ID NO 510
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 510
nagaagggag uaucugugn 19

<210> SEQ ID NO 511
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)

<400> SEQUENCE: 511
gagaagggag uaucunuga 19

<210> SEQ ID NO 512
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)

<400> SEQUENCE: 512
gagaagggag uaucunugu 19

<210> SEQ ID NO 513
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 16
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 513
gagaagggag uaucunugn 19

<210> SEQ ID NO 514
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase
<220> FEATURE:
<221> NAME/KEY: modified_base
<222> LOCATION: 16
<223> OTHER INFORMATION: n = inosine (hypoxanthine)

<400> SEQUENCE: 514
nagaagggag uaucunugn 19

<210> SEQ ID NO 515
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 515
gcaucagcau caucgaaca 19

<210> SEQ ID NO 516
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 516
gcaucagcau caucgaacu 19

<210> SEQ ID NO 517
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 517
gcaucagcau caucgaacc 19

<210> SEQ ID NO 518
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 518
gcaucagcau caucgaacn 19

<210> SEQ ID NO 519
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 519
ncaucagcau caucgaacn 19

<210> SEQ ID NO 520
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 520
gcaucagcau caucnaaca 19

<210> SEQ ID NO 521
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 521
gcaucagcau caucnaacu 19

<210> SEQ ID NO 522
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 15
<223> OTHER INFORMATION: n = inosine (hypoxanthine)

<400> SEQUENCE: 522
gcaucagcau caucnaacc 19

<210> SEQ ID NO 523
<211> LENGTH: 19
<212> TYPE: RNA
<213> ORGANISM: Artificial sequence
<220> FEATURE:

-continued

<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 19
<223> OTHER INFORMATION: n = any nucleobase

<400> SEQUENCE: 523
gcaucagcau caucnaacn 19

<210> SEQ ID NO 524
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 15
<223> OTHER INFORMATION: n = inosine (hypoxanthine)
<220> FEATURE:
<221> NAME/KEY: modified_base
<222> LOCATION: 1, 19
<223> OTHER INFORMATION: n = any nucleobase

<400> SEQUENCE: 524
ncaucagcau caucnaacn 19

<210> SEQ ID NO 525
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 525
ugaacaggaa uggaaaggu 19

<210> SEQ ID NO 526
<211> LENGTH: 19
<212> TYPE: RNA
<213> ORGANISM: Artificial sequence
<220> FEATURE:
<223> OTHER INFORMATION: RNAi agent sense strand 19-mer core base
      sequence

<400> SEQUENCE: 526
ugaacaggaa uggaaagga 19

<210> SEQ ID NO 527
<211> LENGTH: 19
<212> TYPE: RNA
<213> ORGANISM: Artificial sequence
<220> FEATURE:
<223> OTHER INFORMATION: RNAi agent sense strand 19-mer core base
      sequence
<220> FEATURE:
<221> NAME/KEY: modified_base
<222> LOCATION: 19
<223> OTHER INFORMATION: n = any nucleobase

<400> SEQUENCE: 527
ugaacaggaa uggaaaggn 19

<210> SEQ ID NO 528
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 528
ngaacaggaa uggaaaggn 19

<210> SEQ ID NO 529
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 529
cuaccgaguc cgugucuaa 19

<210> SEQ ID NO 530
<211> LENGTH: 19
<212> TYPE: RNA
<213> ORGANISM: Artificial sequence
<220> FEATURE:
<223> OTHER INFORMATION: RNAi agent sense strand 19-mer core base
sequence

<400> SEQUENCE: 530
cuaccgaguc cgugucuau 19

<210> SEQ ID NO 531
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 19
<223> OTHER INFORMATION: n = any nucleobase

<400> SEQUENCE: 531
cuaccgaguc cgugucuan 19

<210> SEQ ID NO 532
<211> LENGTH: 19
<212> TYPE: RNA
<213> ORGANISM: Artificial sequence
<220> FEATURE:
<223> OTHER INFORMATION: RNAi agent sense strand 19-mer core base
sequence
<220> FEATURE:
<221> NAME/KEY: modified_base
<222> LOCATION: 1, 19
<223> OTHER INFORMATION: n = any nucleobase

<400> SEQUENCE: 532
nuaccgaguc cgugucuan 19

<210> SEQ ID NO 533

<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 533
ugggaagcca gaaauugua 19

<210> SEQ ID NO 534
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 534
ugggaagcca gaaauuguu 19

<210> SEQ ID NO 535
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 535
ugggaagcca gaaauugun 19

<210> SEQ ID NO 536
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 536
ngggaagcca gaaauugun 19

<210> SEQ ID NO 537
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 537
ccuaaugaga agggaguaa 19

<210> SEQ ID NO 538
<211> LENGTH: 19
<212> TYPE: RNA
<213> ORGANISM: Artificial sequence
<220> FEATURE:
<223> OTHER INFORMATION: RNAi agent sense strand 19-mer core base sequence

<400> SEQUENCE: 538
ccuaaugaga agggaguau 19

<210> SEQ ID NO 539
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 19
<223> OTHER INFORMATION: n = any nucleobase

<400> SEQUENCE: 539
ccuaaugaga agggaguan 19

<210> SEQ ID NO 540
<211> LENGTH: 19
<212> TYPE: RNA
<213> ORGANISM: Artificial sequence
<220> FEATURE:
<223> OTHER INFORMATION: RNAi agent sense strand 19-mer core base sequence
<220> FEATURE:
<221> NAME/KEY: modified_base
<222> LOCATION: 1, 19
<223> OTHER INFORMATION: n = any nucleobase

<400> SEQUENCE: 540
ncuaaugaga agggaguan 19

<210> SEQ ID NO 541
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 541
uuguguucag uuuccauucc g 21

<210> SEQ ID NO 542
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 542
uuguguucag uuuccauucc g 21

<210> SEQ ID NO 543
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 543
ucuguguuca guuuccauuc c 21

<210> SEQ ID NO 544
<211> LENGTH: 21
<212> TYPE: RNA

<213> ORGANISM: Artificial sequence
<220> FEATURE:
<223> OTHER INFORMATION: RNAi agent antisense strand modified sequence

<400> SEQUENCE: 544
ucuguguuca guuuccauuc c 21

<210> SEQ ID NO 545
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 545
uuggcuuccc aggaaucugg u 21

<210> SEQ ID NO 546
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 546
uuggcuuccc aggaaucugg u 21

<210> SEQ ID NO 547
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 547
acaauuucug gcuucccagg a 21

<210> SEQ ID NO 548
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 548
acaauuucug gcuucccagg a 21

<210> SEQ ID NO 549
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 549
uuacacuuca gcaccagugg c 21

<210> SEQ ID NO 550
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 550
uaccuuccaa gcuucugucc g 21

<210> SEQ ID NO 551
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 551
ucggaaaauc cccucauccu g 21

<210> SEQ ID NO 552
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 552
uuucuggcuu cccaggaauc u 21

<210> SEQ ID NO 553
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 553
uugaguucag aggcagaauc u 21

<210> SEQ ID NO 554
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 554
ucuaagaguc ccugcagggu a 21

<210> SEQ ID NO 555
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 555
agcuaagagu cccugcaggg u 21

<210> SEQ ID NO 556
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 556
aagcuacagg agaagguggg a 21

<210> SEQ ID NO 557
<211> LENGTH: 21
<212> TYPE: RNA
<213> ORGANISM: Artificial sequence
<220> FEATURE:

<223> OTHER INFORMATION: RNAi agent antisense strand modified sequence

<400> SEQUENCE: 557
ucugaagcua caggagaagg u 21

<210> SEQ ID NO 558
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 558
uacagacuga ggaccagcac c 21

<210> SEQ ID NO 559
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 559
uacagacuga ggaccagcac c 21

<210> SEQ ID NO 560
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 560
ucacagacug aggaccagca c 21

<210> SEQ ID NO 561
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 561
uuguguucag uuuccauucc c 21

<210> SEQ ID NO 562
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 562
uuguguucag uuuccauucc g 21

<210> SEQ ID NO 563
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 563
uuguguucag uuuccauucc g 21

<210> SEQ ID NO 564
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 564
uuguguucag uuuccauucc g 21

<210> SEQ ID NO 565
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 565
uuguguucag uuuccauucc g 21

<210> SEQ ID NO 566
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 566
ugauguuuug agcaccuacu c 21

<210> SEQ ID NO 567
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 567
uuccauuccu guucauugcc u 21

<210> SEQ ID NO 568
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 568
ugaaucuggu agacacggac u 21

<210> SEQ ID NO 569
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 569
uaggaaucug guagacacgg a 21

<210> SEQ ID NO 570
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 570
uaagcuacag gagaaggugg g 21

<210> SEQ ID NO 571
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 571
ucauccagug gauuugagga g 21

<210> SEQ ID NO 572
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 572
aguucagagg cagaaucuac c 21

<210> SEQ ID NO 573
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 573
ugaguucaga ggcagaaucu a 21

<210> SEQ ID NO 574
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 574
accuuauugg gaacaccagc c 21

<210> SEQ ID NO 575
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 575
ucaccuuauu gggaacacca g 21

<210> SEQ ID NO 576
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 576
ucauccaagu gccagcuaag c 21

<210> SEQ ID NO 577
<211> LENGTH: 21

<212> TYPE: RNA
<213> ORGANISM: Artificial sequence
<220> FEATURE:
<223> OTHER INFORMATION: RNAi agent antisense strand modified sequence

<400> SEQUENCE: 577
agauacuccc uucucauuag g 21

<210> SEQ ID NO 578
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 578
ucacagauac ucccuucuca c 21

<210> SEQ ID NO 579
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 579
uguucgauga ugcugaugcu g 21

<210> SEQ ID NO 580
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 580
uuguguucag uuuccauucc g 21

<210> SEQ ID NO 581
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 581
uuguguucag uuuccauucc g 21

<210> SEQ ID NO 582
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 582
uuguguucag uuuccauucc g 21

<210> SEQ ID NO 583
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 583
uuguguucag uuuccauucc g 21

<210> SEQ ID NO 584
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 584
uuguguucag uuuccauucc g 21

<210> SEQ ID NO 585
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 585
uuguguucag uuuccauucc g 21

<210> SEQ ID NO 586
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 586
uuguguucag uuuccauucc c 21

<210> SEQ ID NO 587
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 587
uuguguucag uuuccauucc a 21

<210> SEQ ID NO 588
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 588
uuguguucag uuuccauucc g 21

<210> SEQ ID NO 589
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 589
uuguguucag uuuccauucc g 21

<210> SEQ ID NO 590
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 590
uuguguucag uuuccauucc c 21

<210> SEQ ID NO 591
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 591
uuguguucag uuuccauucc c 21

<210> SEQ ID NO 592
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 592
uuguguucag uuuccauucc c 21

<210> SEQ ID NO 593
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 593
uuguguucag uuuccauucc g 21

<210> SEQ ID NO 594
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 594
uuguguucag uuuccauucc c 21

<210> SEQ ID NO 595
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 595
uuguguucag uuuccauucc c 21

<210> SEQ ID NO 596
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 596
uccuuuccau uccuguucau c 21

<210> SEQ ID NO 597
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 597
uuagacacgg acucgguagu c 21

<210> SEQ ID NO 598
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 598
auacucccuu cucauuaggc a 21

<210> SEQ ID NO 599
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 599
ugauguuuug agcaccuacu c 21

<210> SEQ ID NO 600
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 600
ugauguuuug agcaccuacu c 21

<210> SEQ ID NO 601
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 601
ugauguuuug agcaccuacu c 21

<210> SEQ ID NO 602
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 602
uuccauuccu guucauugcc u 21

<210> SEQ ID NO 603
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 603
uuccauuccu guucauugcc u 21

<210> SEQ ID NO 604
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 604
uuccauuccu guucauugcc u 21

<210> SEQ ID NO 605
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 605
uuccauuccu guucauugcc u 21

<210> SEQ ID NO 606
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 606
uuccauuccu guucauugcc u 21

<210> SEQ ID NO 607
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 607
uuccauuccu guucauugcc c 21

<210> SEQ ID NO 608
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 608
ugauguuuug agcaccuacu g 21

<210> SEQ ID NO 609
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 609
ugauguuuug agcaccuacu c 21

<210> SEQ ID NO 610

<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 610
ugauguuuug agcaccuacu a 21

<210> SEQ ID NO 611
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 611
uuccauuccu guucauugcc u 21

<210> SEQ ID NO 612
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 612
uuccauuccu guucauugcc u 21

<210> SEQ ID NO 613
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 613
uuccauuccu guucauugcc u 21

<210> SEQ ID NO 614
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 614
uuguguucag uuuccauucc g 21

<210> SEQ ID NO 615
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 615
uuguguucag uuuccauucc g 21

<210> SEQ ID NO 616
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 616
ugauguuuug agcaccuacu c 21

<210> SEQ ID NO 617
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 617
ugauguuuug agcaccuacu c 21

<210> SEQ ID NO 618
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 618
ugauguuuug agcaccuacu c 21

<210> SEQ ID NO 619
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 619
uuguguucag uuuccauucc a 21

<210> SEQ ID NO 620
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 620
uacaauuucu ggcuucccag g 21

<210> SEQ ID NO 621
<211> LENGTH: 21
<212> TYPE: RNA
<213> ORGANISM: Artificial sequence
<220> FEATURE:
<223> OTHER INFORMATION: RNAi agent antisense strand modified sequence

<400> SEQUENCE: 621
ucuguguuca guuuccauuc c 21

<210> SEQ ID NO 622
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 622
cggaauggaa acugaacaca a 21

<210> SEQ ID NO 623
<211> LENGTH: 21
<212> TYPE: RNA

<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 623
ggaauggaaa cugaacacan a 21

<210> SEQ ID NO 624
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 624
accagauucc ugggaancca a 21

<210> SEQ ID NO 625
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 625
uccugggaag ccagaaauug u 21

<210> SEQ ID NO 626
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 626
gccacuggug cugaagugua a 21

<210> SEQ ID NO 627
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 627
cggacagaag cuuggaagnu a 21

<210> SEQ ID NO 628
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 628
caggaugagg ggauuuuccn a 21

<210> SEQ ID NO 629
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 629
agauuccugg gaagcuagaa a 21

<210> SEQ ID NO 630
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 1
<223> OTHER INFORMATION: n = 2'-O-methyl-2-aminoadenosine-3'-phosphate

<400> SEQUENCE: 630
ngauucugcc ucugaacuca a 21

<210> SEQ ID NO 631
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 631
uacccugcag ggacucuuag a 21

<210> SEQ ID NO 632
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 632
acccugcagg gacucuuanc u 21

<210> SEQ ID NO 633
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 633
ucccaccuuc uccuguancu u 21

<210> SEQ ID NO 634

<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 634
accuucuccu guagcuucan a 21

<210> SEQ ID NO 635
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 635
ggugcugguc cucagucunu a 21

<210> SEQ ID NO 636
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 636
ggugcugguc cucagucugu a 21

<210> SEQ ID NO 637
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 637
gugcuggucc ucagucugun a 21

<210> SEQ ID NO 638
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 638
gugcuggucc ucagucunug a 21

<210> SEQ ID NO 639
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 639
cggaauggaa acugaacaca a 21

<210> SEQ ID NO 640
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 640
gggaauggaa acugaacaca a 21

<210> SEQ ID NO 641
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 641
cggaauggaa acunaacaca a 21

<210> SEQ ID NO 642
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate
<220> FEATURE:
<221> NAME/KEY: modified_base
<222> LOCATION: 14
<223> OTHER INFORMATION: n = 2'-O-methylinosine-3'-phosphate

<400> SEQUENCE: 642
cggaauggan acunaacaca a 21

<210> SEQ ID NO 643
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 643
cggaauggaa acugaauaca a 21

<210> SEQ ID NO 644
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 644
cggaauggaa acugaacaca a 21

<210> SEQ ID NO 645
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 645
uccugggaag ccagaaauug u 21

<210> SEQ ID NO 646
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 646
gaguaggugc ucaaaacauc a 21

<210> SEQ ID NO 647
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 647
aggcaaugaa caggaaunga a 21

<210> SEQ ID NO 648
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 648
aguccguguc uaccanauuc a 21

<210> SEQ ID NO 649
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 649
uccgugucua ccagauuccu a 21

<210> SEQ ID NO 650
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 650
cccaccuucu ccuguancuu a 21

<210> SEQ ID NO 651
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 651
cuccucaaau ccacungaug a 21

<210> SEQ ID NO 652
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 652
gguagauucu gccucunaac u 21

<210> SEQ ID NO 653
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 653
uagauucugc cucugaacuc a 21

<210> SEQ ID NO 654
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 654
ggcugguguu cccaauaagg u 21

<210> SEQ ID NO 655
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 655 cuggguguucc caauaagnug a 21

<210> SEQ ID NO 656

```
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 656

gcuuagcugg cacuungaug a                                              21


<210> SEQ ID NO 657
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 657

ccuaaugaga aggganuauc u                                              21


<210> SEQ ID NO 658
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 658

gugagaaggg aguaucunug a                                              21


<210> SEQ ID NO 659
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 659

cagcaucagc aucaucnaac a                                              21


<210> SEQ ID NO 660
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 660

cggaauggaa acugaacaca a                                              21


<210> SEQ ID NO 661
<211> LENGTH: 21
<212> TYPE: RNA
<213> ORGANISM: Artificial sequence
```

<220> FEATURE:
<223> OTHER INFORMATION: RNAi agent sense strand modified sequence

<400> SEQUENCE: 661
cggaauggaa acugaacaca a 21

<210> SEQ ID NO 662
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 662
cggaauggaa acugaacaca a 21

<210> SEQ ID NO 663
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 663
cggaauggaa acugaauaca a 21

<210> SEQ ID NO 664
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 664
gggaauggaa acugaacaca a 21

<210> SEQ ID NO 665
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 665
uggaauggaa acugaacaca a 21

<210> SEQ ID NO 666
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate

<400> SEQUENCE: 666
cggaauggan acugaacaca a 21

<210> SEQ ID NO 667
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 667
cggaauggaa acugaacaca a 21

<210> SEQ ID NO 668
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 668
cggaauggaa acugaacaca a 21

<210> SEQ ID NO 669
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 669
cggaauggaa acugaacaca a 21

<210> SEQ ID NO 670
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 670
cggaauggaa acugaacaca a 21

<210> SEQ ID NO 671
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 671
cggaauggaa acugaacaca a 21

<210> SEQ ID NO 672
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 672
cggaauggaa acugaacaca a 21

<210> SEQ ID NO 673
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 673
gaugaacagg aauggaaagg a 21

<210> SEQ ID NO 674
<211> LENGTH: 21

<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 674
gaugaacagg aauggaaagn a 21

<210> SEQ ID NO 675
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 675
gacuaccgag uccgugucua a 21

<210> SEQ ID NO 676
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 676
ugccuaauga gaagggagua u 21

<210> SEQ ID NO 677
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 677
gaguaggugc ucaaaacauc a 21

<210> SEQ ID NO 678
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 7
<223> OTHER INFORMATION: n = 2'-O-methylinosine-3'-phosphate

<400> SEQUENCE: 678
gaguagnugc ucaaaacauc a 21

<210> SEQ ID NO 679
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 679
gaguaggugc ucaaaacauc a 21

<210> SEQ ID NO 680

<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 680
gaguaggugc ucaaaacauc a 21

<210> SEQ ID NO 681
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 681
aggcaaugaa caggaaunga a 21

<210> SEQ ID NO 682
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 682
aggcaaugaa caggaaugga a 21

<210> SEQ ID NO 683
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 683
aggcaaugaa caggaaugna a 21

<210> SEQ ID NO 684
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 684
aggcaaugaa cagnaaugga a 21

<210> SEQ ID NO 685
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 685
aggcaaugaa cangaaugga a 21

<210> SEQ ID NO 686
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 686
gggcaaugaa caggaaunga a 21

<210> SEQ ID NO 687
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 687
caguaggugc ucaaaacauc a 21

<210> SEQ ID NO 688
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 688
unguaggugc ucaaaacauc a 21

<210> SEQ ID NO 689
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 689
gaguaggugc ucaaaacauc a 21

<210> SEQ ID NO 690
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 690
aggcaaugaa caggaaugga a 21

<210> SEQ ID NO 691
<211> LENGTH: 21
<212> TYPE: RNA

<213> ORGANISM: Artificial sequence
<220> FEATURE:
<223> OTHER INFORMATION: RNAi agent sense strand modified sequence

<400> SEQUENCE: 691
gaguaggugc ucaaaacauc a 21

<210> SEQ ID NO 692
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 692
aggcaaugaa caggaaunga a 21

<210> SEQ ID NO 693
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 693
cggaauggaa acugaacaca a 21

<210> SEQ ID NO 694
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 694
cggaauggaa acugaacaca a 21

<210> SEQ ID NO 695
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 695
ccugggaagc cagaaauugu a 21

<210> SEQ ID NO 696
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 696
cggaauggaa acugaacaca a 21

<210> SEQ ID NO 697
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 697
cggaauggaa acugaacaca a 21

<210> SEQ ID NO 698
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 698
ggaauggaaa cugaacacan a 21

<210> SEQ ID NO 699
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 699
accagauucc ugggaancca a 21

<210> SEQ ID NO 700
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 700
uccugggaag ccagaaauug u 21

<210> SEQ ID NO 701
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 701
gccacuggug cugaagugua a 21

<210> SEQ ID NO 702
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 702
cggacagaag cuuggaagnu a 21

<210> SEQ ID NO 703

```
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 703

caggaugagg ggauuuuccn a                                              21


<210> SEQ ID NO 704
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 704

agauuccugg gaagcuagaa a                                              21


<210> SEQ ID NO 705
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 1
<223> OTHER INFORMATION: n = 2'-O-methyl-2-aminoadenosine-3'-phosphate

<400> SEQUENCE: 705

ngauucugcc ucugaacuca a                                              21


<210> SEQ ID NO 706
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 706

uacccugcag ggacucuuag a                                              21


<210> SEQ ID NO 707
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 707

acccugcagg gacucuuanc u                                              21


<210> SEQ ID NO 708
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
```

<222> LOCATION: 18
<223> OTHER INFORMATION: n = 2'-O-methylinosine-3'-phosphate

<400> SEQUENCE: 708
ucccaccuuc uccuguancu u 21

<210> SEQ ID NO 709
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 709
accuucuccu guagcuucan a 21

<210> SEQ ID NO 710
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 710
ggugcugguc cucagucunu a 21

<210> SEQ ID NO 711
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 711
ggugcugguc cucagucugu a 21

<210> SEQ ID NO 712
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 712
gugcuggucc ucagucugun a 21

<210> SEQ ID NO 713
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 713
gugcuggucc ucagucunug a 21

<210> SEQ ID NO 714
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 714
cggaauggaa acugaacaca a 21

<210> SEQ ID NO 715
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 715
gggaauggaa acugaacaca a 21

<210> SEQ ID NO 716
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 716
cggaauggaa acunaacaca a 21

<210> SEQ ID NO 717
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate
<220> FEATURE:
<221> NAME/KEY: modified_base
<222> LOCATION: 14
<223> OTHER INFORMATION: n = 2'-O-methylinosine-3'-phosphate

<400> SEQUENCE: 717
cggaauggan acunaacaca a 21

<210> SEQ ID NO 718
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 718
cggaauggaa acugaauaca a 21

<210> SEQ ID NO 719
<211> LENGTH: 21

<212> TYPE: RNA
<213> ORGANISM: Artificial sequence
<220> FEATURE:
<223> OTHER INFORMATION: RNAi agent sense strand modified sequence

<400> SEQUENCE: 719
cggaauggaa acugaacaca a 21

<210> SEQ ID NO 720
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 720
uccugggaag ccagaaauug u 21

<210> SEQ ID NO 721
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 721
gaguaggugc ucaaaacauc a 21

<210> SEQ ID NO 722
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 722
aggcaaugaa caggaaunga a 21

<210> SEQ ID NO 723
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 723
aguccguguc uaccanauuc a 21

<210> SEQ ID NO 724
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 724
uccgugucua ccagauuccu a 21

<210> SEQ ID NO 725

<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 725
cccaccuucu ccuguancuu a 21

<210> SEQ ID NO 726
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 726
cuccucaaau ccacungaug a 21

<210> SEQ ID NO 727
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 727
gguagauucu gccucunaac u 21

<210> SEQ ID NO 728
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 728
uagauucugc cucugaacuc a 21

<210> SEQ ID NO 729
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 729
ggcugguguu cccaauaagg u 21

<210> SEQ ID NO 730
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 730
cugguguucc caauaagnug a 21

<210> SEQ ID NO 731
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 731
gcuuagcugg cacuungaug a 21

<210> SEQ ID NO 732
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 16
<223> OTHER INFORMATION: n = 2'-O-methylinosine-3'-phosphate

<400> SEQUENCE: 732
ccuaaugaga aggganuauc u 21

<210> SEQ ID NO 733
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 733
gugagaaggg aguaucunug a 21

<210> SEQ ID NO 734
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 734
cagcaucagc aucaucnaac a 21

<210> SEQ ID NO 735
<211> LENGTH: 21
<212> TYPE: RNA
<213> ORGANISM: Artificial sequence
<220> FEATURE:
<223> OTHER INFORMATION: RNAi agent sense strand modified sequence -continued

<400> SEQUENCE: 735
cggaauggaa acugaacaca a 21

<210> SEQ ID NO 736
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 736
cggaauggaa acugaacaca a 21

<210> SEQ ID NO 737
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 737
cggaauggaa acugaacaca a 21

<210> SEQ ID NO 738
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 738
cggaauggaa acugaauaca a 21

<210> SEQ ID NO 739
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 739
gggaauggaa acugaacaca a 21

<210> SEQ ID NO 740
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 740
uggaauggaa acugaacaca a 21

<210> SEQ ID NO 741
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate

<400> SEQUENCE: 741
cggaauggan acugaacaca a 21

<210> SEQ ID NO 742
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 742
cggaauggaa acugaacaca a 21

<210> SEQ ID NO 743
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 743
cggaauggaa acugaacaca a 21

<210> SEQ ID NO 744
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 744
cggaauggaa acugaacaca a 21

<210> SEQ ID NO 745
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 745
cggaauggaa acugaacaca a 21

<210> SEQ ID NO 746
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 746
cggaauggaa acugaacaca a 21

<210> SEQ ID NO 747
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 747
cggaauggaa acugaacaca a 21

<210> SEQ ID NO 748
<211> LENGTH: 21
<212> TYPE: RNA
<213> ORGANISM: Artificial sequence
<220> FEATURE:

<223> OTHER INFORMATION: RNAi agent sense strand modified sequence

<400> SEQUENCE: 748
gaugaacagg aauggaaagg a 21

<210> SEQ ID NO 749
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 749
gaugaacagg aauggaaagn a 21

<210> SEQ ID NO 750
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 750
gacuaccgag uccgugucua a 21

<210> SEQ ID NO 751
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 751
ugccuaauga gaagggagua u 21

<210> SEQ ID NO 752
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 752
gaguaggugc ucaaaacauc a 21

<210> SEQ ID NO 753
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 7
<223> OTHER INFORMATION: n = 2'-O-methylinosine-3'-phosphate

<400> SEQUENCE: 753
gaguagnugc ucaaaacauc a 21

<210> SEQ ID NO 754
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 754
gaguaggugc ucaaaacauc a 21

<210> SEQ ID NO 755
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 755
gaguaggugc ucaaaacauc a 21

<210> SEQ ID NO 756
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 756
aggcaaugaa caggaaunga a 21

<210> SEQ ID NO 757
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 757
aggcaaugaa caggaaugga a 21

<210> SEQ ID NO 758
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 19
<223> OTHER INFORMATION: n = 2'-O-methylinosine-3'-phosphate

<400> SEQUENCE: 758
aggcaaugaa caggaaugna a 21

<210> SEQ ID NO 759
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 759
aggcaaugaa cagnaaugga a 21

<210> SEQ ID NO 760
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 13
<223> OTHER INFORMATION: n = 2'-O-methylinosine-3'-phosphate

<400> SEQUENCE: 760
aggcaaugaa cangaaugga a 21

<210> SEQ ID NO 761
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 761
gggcaaugaa caggaaunga a 21

<210> SEQ ID NO 762
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 762
caguaggugc ucaaaacauc a 21

<210> SEQ ID NO 763
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 2
<223> OTHER INFORMATION: n = 2'-O-methyl-2-aminoadenosine-3'-phosphate

<400> SEQUENCE: 763
unguaggugc ucaaaacauc a 21

<210> SEQ ID NO 764
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 764
gaguaggugc ucaaaacauc a 21

<210> SEQ ID NO 765
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 765
aggcaaugaa caggaaugga a 21

<210> SEQ ID NO 766
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 766
gaguaggugc ucaaaacauc a 21

<210> SEQ ID NO 767
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 767
aggcaaugaa caggaaunga a 21

<210> SEQ ID NO 768
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 768
cggaauggaa acugaacaca a 21

<210> SEQ ID NO 769
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 769
cggaauggaa acugaacaca a 21

<210> SEQ ID NO 770
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 770
ccugggaagc cagaaauugu a 21

<210> SEQ ID NO 771
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 771
cggaauggaa acugaacaca a 21

<210> SEQ ID NO 772
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 772
cggaauggaa acugaacaca a 21

<210> SEQ ID NO 773
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 773
cggaauggaa acugaacaca a 21

<210> SEQ ID NO 774
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 774
cggaauggaa acugaacaca a 21

<210> SEQ ID NO 775
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 775
cggaauggaa acugaacaca a 21

<210> SEQ ID NO 776
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 776
cggaauggaa acugaauaca a 21

<210> SEQ ID NO 777
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 777
cggaauggaa acugaacaca a 21

<210> SEQ ID NO 778
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 778
gggaauggaa acugaacaca a 21

<210> SEQ ID NO 779
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 779
uggaauggaa acugaacaca a 21

<210> SEQ ID NO 780
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate

<400> SEQUENCE: 780
cggaauggan acugaacaca a 21

<210> SEQ ID NO 781
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 781
cggaauggaa acugaauaca a 21

<210> SEQ ID NO 782
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 782
cggaauggaa acugaacaca a 21

<210> SEQ ID NO 783
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 783
cggaauggaa acugaacaca a 21

<210> SEQ ID NO 784
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 784
cggaauggaa acugaacaca a 21

<210> SEQ ID NO 785
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 785
cggaauggaa acugaacaca a 21

<210> SEQ ID NO 786
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 786
cggaauggaa acugaacaca a 21

<210> SEQ ID NO 787
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 787
cggaauggaa acugaacaca a 21

<210> SEQ ID NO 788
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 788
gggaauggaa acugaacaca a 21

<210> SEQ ID NO 789
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 14
<223> OTHER INFORMATION: n = 2'-O-methylinosine-3'-phosphate

<400> SEQUENCE: 789
cggaauggaa acunaacaca a 21

<210> SEQ ID NO 790
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 10
<223> OTHER INFORMATION: n = 2'-O-methyl-2-aminoadenosine-3'-phosphate
<220> FEATURE:
<221> NAME/KEY: modified_base
<222> LOCATION: 14
<223> OTHER INFORMATION: n = 2'-O-methylinosine-3'-phosphate

<400> SEQUENCE: 790
cggaauggan acunaacaca a 21

<210> SEQ ID NO 791
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 20
<223> OTHER INFORMATION: n = 2'-O-methylinosine-3'-phosphate

<400> SEQUENCE: 791
ggaauggaaa cugaacacan a 21

<210> SEQ ID NO 792
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 792
accagauucc ugggaancca a 21

<210> SEQ ID NO 793
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 793
uccugggaag ccagaaauug u 21

<210> SEQ ID NO 794
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 794
gaguaggugc ucaaaacauc a 21

<210> SEQ ID NO 795
<211> LENGTH: 21
<212> TYPE: RNA
<213> ORGANISM: Artificial sequence
<220> FEATURE:
<223> OTHER INFORMATION: RNAi agent sense strand modified sequence
<220> FEATURE:
<221> NAME/KEY: modified_base
<222> LOCATION: 18
<223> OTHER INFORMATION: n = 2'-O-methylinosine-3'-phosphate

<400> SEQUENCE: 795
aggcaaugaa caggaaunga a 21

<210> SEQ ID NO 796
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 796
cggaauggaa acugaacaca a 21

<210> SEQ ID NO 797
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 797
gaguaggugc ucaaaacauc a 21

<210> SEQ ID NO 798
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 798
ccugggaagc cagaaauugu a 21

<210> SEQ ID NO 799
<211> LENGTH: 21
<212> TYPE: RNA
<213> ORGANISM: Artificial sequence
<220> FEATURE:
<223> OTHER INFORMATION: RNAi agent sense strand modified sequence

<400> SEQUENCE: 799
cggaauggaa acugaacaca a 21

<210> SEQ ID NO 800
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 800
uuguguucag uuuccauucc g 21

<210> SEQ ID NO 801
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 801
ucuguguuca guuuccauuc c 21

<210> SEQ ID NO 802
<211> LENGTH: 21

<212> TYPE: RNA
<213> ORGANISM: Artificial sequence
<220> FEATURE:
<223> OTHER INFORMATION: RNAi agent antisense strand underlying base sequence

<400> SEQUENCE: 802
uuggcuuccc aggaaucugg u 21

<210> SEQ ID NO 803
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 803
acaauuucug gcuucccagg a 21

<210> SEQ ID NO 804
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 804
uuacacuuca gcaccagugg c 21

<210> SEQ ID NO 805
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 805
uaccuuccaa gcuucugucc g 21

<210> SEQ ID NO 806
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 806
ucggaaaauc cccucauccu g 21

<210> SEQ ID NO 807
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 807
uuucuggcuu cccaggaauc u 21

<210> SEQ ID NO 808
<211> LENGTH: 21
<212> TYPE: RNA

<213> ORGANISM: Artificial sequence
<220> FEATURE:
<223> OTHER INFORMATION: RNAi agent antisense strand underlying base
sequence

<400> SEQUENCE: 808
uugaguucag aggcagaauc u 21

<210> SEQ ID NO 809
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 809
ucuaagaguc ccugcagggu a 21

<210> SEQ ID NO 810
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 810
agcuaagagu cccugcaggg u 21

<210> SEQ ID NO 811
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 811
aagcuacagg agaagguggg a 21

<210> SEQ ID NO 812
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 812
ucugaagcua caggagaagg u 21

<210> SEQ ID NO 813
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 813
uacagacuga ggaccagcac c 21

<210> SEQ ID NO 814
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 814
ucacagacug aggaccagca c 21

<210> SEQ ID NO 815
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 815
uuguguucag uuuccauucc c 21

<210> SEQ ID NO 816
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 816
ugauguuuug agcaccuacu c 21

<210> SEQ ID NO 817
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 817
uuccauuccu guucauugcc u 21

<210> SEQ ID NO 818
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 818
ugaaucuggu agacacggac u 21

<210> SEQ ID NO 819
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 819
uaggaaucug guagacacgg a 21

<210> SEQ ID NO 820
<211> LENGTH: 21
<212> TYPE: RNA
<213> ORGANISM: Artificial sequence
<220> FEATURE:

<223> OTHER INFORMATION: RNAi agent antisense strand underlying base sequence

<400> SEQUENCE: 820
uaagcuacag gagaaggugg g 21

<210> SEQ ID NO 821
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 821
ucauccagug gauuugagga g 21

<210> SEQ ID NO 822
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 822
aguucagagg cagaaucuac c 21

<210> SEQ ID NO 823
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 823
ugaguucaga ggcagaaucu a 21

<210> SEQ ID NO 824
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 824
accuuauugg gaacaccagc c 21

<210> SEQ ID NO 825
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 825
ucaccuuauu gggaacacca g 21

<210> SEQ ID NO 826
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 826
ucauccaagu gccagcuaag c 21

<210> SEQ ID NO 827
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 827
agauacuccc uucucauuag g 21

<210> SEQ ID NO 828
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 828
ucacagauac ucccuucuca c 21

<210> SEQ ID NO 829
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 829
uguucgauga ugcugaugcu g 21

<210> SEQ ID NO 830
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 830
uuguguucag uuuccauucc a 21

<210> SEQ ID NO 831
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 831
uccuuuccau uccuguucau c 21

<210> SEQ ID NO 832
<211> LENGTH: 21
<212> TYPE: RNA
<213> ORGANISM: Artificial sequence
<220> FEATURE:
<223> OTHER INFORMATION: RNAi agent antisense strand underlying base sequence

<400> SEQUENCE: 832
uuagacacgg acucgguagu c 21

<210> SEQ ID NO 833
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 833
auacucccuu cucauuaggc a 21

<210> SEQ ID NO 834
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 834
uuccauuccu guucauugcc c 21

<210> SEQ ID NO 835
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 835
ugauguuuug agcaccuacu g 21

<210> SEQ ID NO 836
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 836
ugauguuuug agcaccuacu a 21

<210> SEQ ID NO 837
<211> LENGTH: 21
<212> TYPE: RNA
<213> ORGANISM: Artificial sequence
<220> FEATURE:
<223> OTHER INFORMATION: RNAi agent antisense strand underlying base
sequence

<400> SEQUENCE: 837
uacaauuucu ggcuucccag g 21

<210> SEQ ID NO 838
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 838
cggaauggaa acugaacaca a 21

<210> SEQ ID NO 839
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 839
ggaauggaaa cugaacacan a 21

<210> SEQ ID NO 840
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = inosine (hypoxanthine)

<400> SEQUENCE: 840
accagauucc ugggaancca a 21

<210> SEQ ID NO 841
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 841
uccugggaag ccagaaauug u 21

<210> SEQ ID NO 842
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 842
gccacuggug cugaagugua a 21

<210> SEQ ID NO 843
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 19
<223> OTHER INFORMATION: n = inosine (hypoxanthine)

<400> SEQUENCE: 843
cggacagaag cuuggaagnu a 21

<210> SEQ ID NO 844
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 844
caggaugagg ggauuuuccn a 21

<210> SEQ ID NO 845
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 845
agauuccugg gaagcuagaa a 21

<210> SEQ ID NO 846
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 1
<223> OTHER INFORMATION: n = 2-aminoadenosine (2-aminoadenine)

<400> SEQUENCE: 846
ngauucugcc ucugaacuca a 21

<210> SEQ ID NO 847
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 847
uacccugcag ggacucuuag a 21

<210> SEQ ID NO 848
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 19
<223> OTHER INFORMATION: n = inosine (hypoxanthine)

<400> SEQUENCE: 848
acccugcagg gacucuuanc u 21

<210> SEQ ID NO 849
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 849
ucccaccuuc uccuguancu u 21

<210> SEQ ID NO 850
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 850
accuucuccu guagcuucan a 21

<210> SEQ ID NO 851
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 19
<223> OTHER INFORMATION: n = inosine (hypoxanthine)

<400> SEQUENCE: 851
ggugcugguc cucagucunu a 21

<210> SEQ ID NO 852
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 852
ggugcugguc cucagucugu a 21

<210> SEQ ID NO 853
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 853
gugcuggucc ucagucugun a 21

<210> SEQ ID NO 854
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 854
gugcuggucc ucagucunug a 21

<210> SEQ ID NO 855
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 855
gggaauggaa acugaacaca a 21

<210> SEQ ID NO 856
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 14
<223> OTHER INFORMATION: n = inosine (hypoxanthine)

<400> SEQUENCE: 856
cggaauggaa acunaacaca a 21

<210> SEQ ID NO 857
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 10
<223> OTHER INFORMATION: n = 2-aminoadenosine (2-aminoadenine)
<220> FEATURE:
<221> NAME/KEY: modified_base
<222> LOCATION: 14
<223> OTHER INFORMATION: n = inosine (hypoxanthine)

<400> SEQUENCE: 857
cggaauggan acunaacaca a 21

<210> SEQ ID NO 858
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 858
cggaauggaa acugaauaca a 21

<210> SEQ ID NO 859
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 859
gaguaggugc ucaaaacauc a 21

<210> SEQ ID NO 860
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 18
<223> OTHER INFORMATION: n = inosine (hypoxanthine)

<400> SEQUENCE: 860
aggcaaugaa caggaaunga a 21

<210> SEQ ID NO 861
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 16
<223> OTHER INFORMATION: n = inosine (hypoxanthine)

<400> SEQUENCE: 861
aguccguguc uaccanauuc a 21

<210> SEQ ID NO 862
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 862
uccgugucua ccagauuccu a 21

<210> SEQ ID NO 863
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 17
<223> OTHER INFORMATION: n = inosine (hypoxanthine)

<400> SEQUENCE: 863

-continued cccaccuucu ccuguancuu a 21

<210> SEQ ID NO 864
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 16
<223> OTHER INFORMATION: n = inosine (hypoxanthine)

<400> SEQUENCE: 864
cuccucaaau ccacungaug a 21

<210> SEQ ID NO 865
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 17
<223> OTHER INFORMATION: n = inosine (hypoxanthine)

<400> SEQUENCE: 865
gguagauucu gccucunaac u 21

<210> SEQ ID NO 866
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 866
uagauucugc cucugaacuc a 21

<210> SEQ ID NO 867
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 867
ggcugguguu cccaauaagg u 21

<210> SEQ ID NO 868
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 18
<223> OTHER INFORMATION: n = inosine (hypoxanthine)

<400> SEQUENCE: 868
cugguguucc caauaagnug a 21

<210> SEQ ID NO 869
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 16
<223> OTHER INFORMATION: n = inosine (hypoxanthine)

<400> SEQUENCE: 869
gcuuagcugg cacuungaug a 21

<210> SEQ ID NO 870
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 16
<223> OTHER INFORMATION: n = inosine (hypoxanthine)

<400> SEQUENCE: 870
ccuaaugaga aggganuauc u 21

<210> SEQ ID NO 871
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 18
<223> OTHER INFORMATION: n = inosine (hypoxanthine)

<400> SEQUENCE: 871
gugagaaggg aguaucunug a 21

<210> SEQ ID NO 872
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 17
<223> OTHER INFORMATION: n = inosine (hypoxanthine)

<400> SEQUENCE: 872
cagcaucagc aucaucnaac a 21

<210> SEQ ID NO 873
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 873
uggaauggaa acugaacaca a 21

<210> SEQ ID NO 874
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 10
<223> OTHER INFORMATION: n = 2-aminoadenosine (2-aminoadenine)

<400> SEQUENCE: 874
cggaauggan acugaacaca a 21

<210> SEQ ID NO 875
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 875
gaugaacagg aauggaaagg a 21

<210> SEQ ID NO 876
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 20
<223> OTHER INFORMATION: n = inosine (hypoxanthine)

<400> SEQUENCE: 876
gaugaacagg aauggaaagn a 21

<210> SEQ ID NO 877
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 877
gacuaccgag uccgugucua a 21

<210> SEQ ID NO 878
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 878
ugccuaauga gaagggagua u 21

<210> SEQ ID NO 879
<211> LENGTH: 21
<212> TYPE: RNA

<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 7
<223> OTHER INFORMATION: n = inosine (hypoxanthine)

<400> SEQUENCE: 879
gaguagnugc ucaaaacauc a 21

<210> SEQ ID NO 880
<211> LENGTH: 21
<212> TYPE: RNA
<213> ORGANISM: Artificial sequence
<220> FEATURE:
<223> OTHER INFORMATION: RNAi agent sense strand underlying base sequence

<400> SEQUENCE: 880
aggcaaugaa caggaaugga a 21

<210> SEQ ID NO 881
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 19
<223> OTHER INFORMATION: n = inosine (hypoxanthine)

<400> SEQUENCE: 881
aggcaaugaa caggaaugna a 21

<210> SEQ ID NO 882
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 14
<223> OTHER INFORMATION: n = inosine (hypoxanthine)

<400> SEQUENCE: 882
aggcaaugaa cagnaaugga a 21

<210> SEQ ID NO 883
<211> LENGTH: 21
<212> TYPE: RNA
<213> ORGANISM: Artificial sequence
<220> FEATURE:
<223> OTHER INFORMATION: RNAi agent sense strand underlying base sequence
<220> FEATURE:
<221> NAME/KEY: modified_base
<222> LOCATION: 13
<223> OTHER INFORMATION: n = inosine (hypoxanthine)

<400> SEQUENCE: 883
aggcaaugaa cangaaugga a 21

<210> SEQ ID NO 884

<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 18
<223> OTHER INFORMATION: n = inosine (hypoxanthine)

<400> SEQUENCE: 884
gggcaaugaa caggaaunga a 21

<210> SEQ ID NO 885
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 885
caguaggugc ucaaaacauc a 21

<210> SEQ ID NO 886
<211> LENGTH: 21
<212> TYPE: RNA
<213> ORGANISM: Artificial sequence
<220> FEATURE:
<223> OTHER INFORMATION: RNAi agent sense strand underlying base
sequence
<220> FEATURE:
<221> NAME/KEY: modified_base
<222> LOCATION: 2
<223> OTHER INFORMATION: n = 2-aminoadenosine (2-aminoadenine)

<400> SEQUENCE: 886
unguaggugc ucaaaacauc a 21

<210> SEQ ID NO 887
<211> LENGTH: 21
<212> TYPE: RNA
<213> ORGANISM: Artificial sequence
<220> FEATURE:
<223> OTHER INFORMATION: RNAi agent sense strand underlying base
sequence

<400> SEQUENCE: 887
ccugggaagc cagaaauugu a 21

<210> SEQ ID NO 888
<211> LENGTH: 21
<212> TYPE: RNA
<213> ORGANISM: Artificial sequence
<220> FEATURE:
<223> OTHER INFORMATION: Rodent-specific RNAi agent modified sense
strand sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 888
ccacaugauc caugcunagu a 21

<210> SEQ ID NO 889
<211> LENGTH: 21
<212> TYPE: RNA

-continued

```
<213> ORGANISM: Artificial sequence
<220> FEATURE:
<223> OTHER INFORMATION: Rodent-specific RNAi agent modified antisense
      strand sequence

<400> SEQUENCE: 889

uacucagcau ggaucaugug g                                              21


<210> SEQ ID NO 890
<211> LENGTH: 21
<212> TYPE: RNA
<213> ORGANISM: Artificial sequence
<220> FEATURE:
<223> OTHER INFORMATION: Rodent-specific RNAi agent modified sense
      strand sequence
<220> FEATURE:
<221> NAME/KEY: modified_base
<222> LOCATION: 17
<223> OTHER INFORMATION: n = 2'-O-methylinosine-3'-phosphate

<400> SEQUENCE: 890

ccacaugauc caugcunagu a                                              21


<210> SEQ ID NO 891
<211> LENGTH: 21
<212> TYPE: RNA
<213> ORGANISM: Artificial sequence
<220> FEATURE:
<223> OTHER INFORMATION: Rodent-specific RNAi agent modified antisense
      strand sequence

<400> SEQUENCE: 891

uacucagcau ggaucaugug g                                              21
```

RNAi AGENTS FOR INHIBITING EXPRESSION OF RECEPTOR FOR ADVANCED GLYCATION END-PRODUCTS, COMPOSITIONS THEREOF, AND METHODS OF USE

CROSS REFERENCE TO RELATED APPLICATIONS

This application claims priority from U.S. Provisional Patent Application Ser. No. 63/172,301, filed on Apr. 8, 2021, and U.S. Provisional Patent Application Ser. No. 63/322,603, filed on Mar. 22, 2022, the contents of each of which are incorporated herein by reference in their entirety.

SEQUENCE LISTING

This application contains a Sequence Listing which has been submitted in ASCII format and is hereby incorporated by reference in its entirety. The ASCII copy is named SEQLIST_30691.txt and is 223 kb in size.

FIELD OF THE INVENTION

The present disclosure relates to RNA interference (RNAi) agents, e.g., double stranded RNAi agents, for inhibition of Receptor for Advanced Glycation End-products ("RAGE" or "AGER") gene expression, compositions that include RAGE RNAi agents, and methods of use thereof.

BACKGROUND

The Receptor for Advanced Glycation End-products ("RAGE" or "AGER") is a 35 kilodalton transmembrane protein of the immunoglobulin superfamily which functions as a pro-inflammatory pattern recognition receptor. In its full-length, membrane-bound form, the receptor has three functional domains: an extracellular ligand-binding domain, a hydrophobic transmembrane domain, and a cytoplasmic domain that mediates ligand-dependent signal transduction. A second, non-membrane bound soluble form of the receptor (sRAGE) contains only the extracellular ligand-binding domain; formed by proteolytic cleavage of full-length membrane-bound RAGE (or by alternative splicing), sRAGE antagonizes RAGE function since it binds ligands but lacks a cytoplasmic signaling domain.

RAGE is expressed at constitutively high levels in the lung, primarily localized to type 1 alveolar epithelial cells. Other tissues in the body normally express RAGE at low levels, but expression is upregulated in the presence of RAGE ligands and chronic inflammation. As a pattern recognition receptor, RAGE binds a wide variety of endogenous ligands, including advanced glycation end-products (sugar-modified proteins or lipids), high mobility group box 1 (HMGB1) and S100 proteins. Different intermediate signaling pathways can be activated by different RAGE ligands (e.g. ERKI/2, p38 and JAK/STAT) culminating in the production of reactive oxygen species, sustained activation of NF-κB and the transcription of pro-inflammatory genes (e.g. interleukins, interferon, TNF alpha). Transcription of the gene encoding RAGE itself is promoted by NF-xB, creating a positive feedback loop that perpetuates chronic inflammation.

RAGE has been linked to the chronic, pathological inflammation that contributes to many diseases, including: pulmonary disease (asthma, acute respiratory distress syndrome, idiopathic pulmonary fibrosis, chronic obstructive pulmonary disease, cystic fibrosis, pneumonia, lung cancer, bronchopulmonary dysplasia), cardiovascular disease (atherosclerosis, myocardial infarction, heart failure, peripheral vascular disease), cancer, diabetes, chronic kidney disease, neurodegenerative disease, rheumatoid arthritis, non-alcoholic steatohepatitis, injury caused by certain viral infections including SARS-CoV-2, certain ocular inflammatory conditions, and skeletal muscle wasting.

In the pulmonary disease space, RAGE knockout (KO) mice are completely protected, physiologically and histologically, from allergic asthma produced by challenge with house dust mite allergen or ovalbumin. Similarly, RAGE knockout mice are protected from hyperoxia or lipopolysaccharide-induced acute lung injury and inflammation. (See, e.g., Oczypok et al., Paediatr Respir Rev., 23: 40-49 (2017); Wang et al., Shock, 50: 472-482 (2018)). Genome-wide association studies (GWAS) have linked a variant gain-of-function RAGE allele (G82S) to increased inflammation, decreased pulmonary function, and risk of asthma (see, e.g., Hancock et al., Nat Genet., 42: 45-52 (2010); Repapi et al., Nat Genet., 42: 36-44 (2010)).

Despite its potential attractiveness as a drug target, development of potent and selective RAGE inhibitors has proven extremely challenging. Rather than binding to a discrete domain, a wide range of RAGE ligands interact with multiple binding sites within the antibody-like extracellular domain (see, e.g., Rojas et al., Current Drug Targets, 20: 340-346 (2019)). While certain RNAi agents capable of inhibiting the expression of a RAGE in vitro have been previously identified and reported in various studies, or are otherwise commercially available, the known RNAi agent constructs are neither sufficiently potent nor sufficiently specific to be viable as a therapeutic drug candidate. Thus, there exists a need for RAGE RNAi agents suitable for use as a therapeutic in the treatment of RAGE-associated diseases and disorders.

SUMMARY

There continues to exist a need for novel RNA interference (RNAi) agents (termed RNAi agents, RNAi triggers, or triggers), e.g., double stranded RNAi agents, that are able to selectively and efficiently inhibit the expression of a RAGE (AGER) gene, including for use as a therapeutic or medicament. Further, there exists a need for compositions of novel RAGE-specific RNAi agents for the treatment of diseases or disorders associated with pathological inflammation and/or disorders that can be mediated at least in part by a reduction in AGER gene expression and/or RAGE receptor levels.

The nucleotide sequences and chemical modifications of the RAGE RNAi agents disclosed herein, as well as their combination with certain specific targeting ligands suitable for selectively and efficiently delivering the RAGE RNAi agents in vivo, differ from those previously disclosed or known in the art. As shown in, for example, the various Examples herein, the disclosed RAGE RNAi agents provide for highly potent and efficient inhibition of the expression of an AGER (RAGE) gene.

In general, the present disclosure features RAGE gene-specific RNAi agents, compositions that include RAGE RNAi agents, and methods for inhibiting expression of an AGER (RAGE) gene in vitro and/or in vivo using the RAGE RNAi agents and compositions that include RAGE RNAi agents described herein. The RAGE RNAi agents described herein are able to selectively and efficiently decrease or inhibit expression of an AGER gene, and thereby reduce the expression of the RAGE receptor and decrease activation of RAGE receptor signaling, including NF-xB, which ultimately results in reduced inflammation.

The described RAGE RNAi agents can be used in methods for therapeutic treatment (including preventative or prophylactic treatment) of symptoms and diseases including, but not limited to various pulmonary disease (asthma, acute respiratory distress syndrome, idiopathic pulmonary fibrosis, chronic obstructive pulmonary disease, cystic fibrosis, pneumonia, lung cancer, bronchopulmonary dysplasia), cardiovascular disease (atherosclerosis, myocardial infarction, heart failure, peripheral vascular disease), cancer, diabetes, chronic kidney disease, neurodegenerative disease, rheumatoid arthritis, non-alcoholic steatohepatitis, the inflammatory injury caused by certain viral infections including SARS-CoV-2, certain ocular inflammatory conditions, and skeletal muscle wasting.

In one aspect, the disclosure features RNAi agents for inhibiting expression of a RAGE (AGER) gene, wherein the RNAi agent includes a sense strand (also referred to as a passenger strand) and an antisense strand (also referred to as a guide strand). The sense strand and the antisense strand can be partially, substantially, or fully complementary to each other. The length of the RNAi agent sense strands described herein each can be 15 to 49 nucleotides in length. The length of the RNAi agent antisense strands described herein each can be 18 to 49 nucleotides in length. In some embodiments, the sense and antisense strands are independently 18 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the antisense strands are independently 18, 19, 20, 21, 22, 23, 24, 25, 26, 27, 28, 29, or 30 nucleotides in length. In some embodiments, the sense strands are independently 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The RNAi agents described herein, upon delivery to a cell expressing RAGE such as a pulmonary cell (including, more specifically, type 1 alveolar epithelial cell), inhibit the expression of one or more AGER gene variants in vivo and/or in vitro.

The RAGE RNAi agents disclosed herein target a human AGER gene (see, e.g., SEQ ID NO:1). In some embodiments, the RAGE RNAi agents disclosed herein target a portion of an AGER gene having the sequence of any of the sequences disclosed in Table 1.

In another aspect, the disclosure features compositions, including pharmaceutical compositions, that include one or more of the disclosed RAGE RNAi agents that are able to selectively and efficiently decrease expression of an AGER gene. The compositions that include one or more RAGE RNAi agents described herein can be administered to a subject, such as a human or animal subject, for the treatment (including prophylactic treatment or inhibition) of symptoms and diseases associated with RAGE receptor activity.

Examples of RAGE RNAi agent sense strands and antisense strands that can be used in a RAGE RNAi agent are provided in Tables 3, 4, 5, and 6. Examples of RAGE RNAi agent duplexes are provided in Tables 7A, 7B, 8, 9A, 9B, and 10. Examples of 19-nucleotide core stretch sequences that may consist of or may be included in the sense strands and antisense strands of certain RAGE RNAi agents disclosed herein, are provided in Table 2.

In another aspect, the disclosure features methods for delivering RAGE RNAi agents to pulmonary epithelial cells in a subject, such as a mammal, in vivo. Also described herein are compositions for use in such methods. In some embodiments, disclosed herein are methods for delivering RAGE RNAi agents to pulmonary cells (including epithelial cells, macrophages, smooth muscle, endothelial cells, and preferably type 1 alveolar epithelial cells) to a subject in vivo. In some embodiments, the subject is a human subject.

The methods disclosed herein include the administration of one or more RAGE RNAi agents to a subject, e.g., a human or animal subject, by any suitable means known in the art. The pharmaceutical compositions disclosed herein that include one or more RAGE RNAi agents can be administered in a number of ways depending upon whether local or systemic treatment is desired. Administration can be, but is not limited to, for example, intravenous, intraarterial, subcutaneous, intraperitoneal, subdermal (e.g., via an implanted device), and intraparenchymal administration. In some embodiments, the pharmaceutical compositions described herein are administered by inhalation (such as dry powder inhalation or aerosol inhalation), intranasal administration, intratracheal administration, or oropharyngeal aspiration administration.

In some embodiments, it is desired that the RAGE RNAi agents described herein inhibit the expression of an AGER gene in the pulmonary epithelium, for which the administration is by inhalation (e.g., by an inhaler device, such as a metered-dose inhaler, or a nebulizer such as a jet or vibrating mesh nebulizer, or a soft mist inhaler).

The one or more RAGE RNAi agents can be delivered to target cells or tissues using any oligonucleotide delivery technology known in the art. In some embodiments, a RAGE RNAi agent is delivered to cells or tissues by covalently linking the RNAi agent to a targeting group. In some embodiments, the targeting group can include a cell receptor ligand, such as an integrin targeting ligand. Integrins are a family of transmembrane receptors that facilitate cell-extracellular matrix (ECM) adhesion. In particular, integrin alpha-v-beta-6 ($\alpha v\beta 6$) is an epithelial-specific integrin that is known to be a receptor for ECM proteins and the TGF-beta latency-associated peptide (LAP), and is expressed in various cells and tissues. Integrin $\alpha v\beta 6$ is known to be highly upregulated in injured pulmonary epithelium. In some embodiments, the RAGE RNAi agents described herein are linked to an integrin targeting ligand that has affinity for integrin $\alpha v\beta 6$. As referred to herein, an "$\alpha v\beta 6$ integrin targeting ligand" is a compound that has affinity for integrin $\alpha v\beta 6$, which can be utilized as a ligand to facilitate the targeting and delivery of an RNAi agent to which it is attached to the desired cells and/or tissues (i.e., to cells expressing integrin $\alpha v\beta 6$). In some embodiments, multiple $\alpha v\beta 6$ integrin targeting ligands or clusters of $\alpha v\beta 6$ integrin targeting ligands are linked to a RAGE RNAi agent. In some embodiments, the RAGE RNAi agent-$\alpha v\beta 6$ integrin targeting ligand conjugates are selectively internalized by lung epithelial cells, either through receptor-mediated endocytosis or by other means.

Examples of targeting groups useful for delivering RAGE RNAi agents that include $\alpha v\beta 6$ integrin targeting ligands are disclosed, for example, in International Patent Application Publication No. WO 2018/085415 and International Patent Application Publication No. WO 2019/089765, the contents of each of which are incorporated by reference herein in their entirety.

A targeting group can be linked to the 3' or 5' end of a sense strand or an antisense strand of a RAGE RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker.

In another aspect, the disclosure features compositions that include one or more RAGE RNAi agents that have the duplex structures disclosed in Tables 7A, 7B, 8, 9A, 9B, and 10.

The use of RAGE RNAi agents provides methods for therapeutic (including prophylactic) treatment of diseases or disorders for which a reduction in RAGE receptor activity can provide a therapeutic benefit. The RAGE RNAi agents disclosed herein can be used to treat various respiratory diseases, including pulmonary disease (asthma, acute respiratory distress syndrome, idiopathic pulmonary fibrosis, chronic obstructive pulmonary disease, cystic fibrosis, pneumonia, lung cancer, bronchopulmonary dysplasia), cardiovascular disease (atherosclerosis, myocardial infarction, heart failure, peripheral vascular disease), cancer, diabetes, chronic kidney disease, neurodegenerative disease, rheumatoid arthritis, non-alcoholic steatohepatitis, injury caused by certain viral infections including SARS-CoV-2, certain ocular inflammatory conditions, and skeletal muscle wasting. In some embodiments, the RAGE RNAi agents disclosed herein can be used to treat a pulmonary inflammatory disease or condition. RAGE RNAi agents can further be used to treat, for example, various ocular inflammatory diseases and disorders. Such methods of treatment include administration of a RAGE RNAi agent to a human being or animal having elevated or enhanced RAGE receptor levels or RAGE receptor activity beyond desirable levels.

One aspect described herein is an RNAi agent for inhibiting expression of a receptor for advanced glycation end-products gene, comprising:

(i) an antisense strand comprising at least 17 contiguous nucleotides differing by 0 or 1 nucleotides from any one of the sequences provided in Table 3;
(ii) a sense strand comprising a nucleotide sequence that is at least partially complementary to the antisense strand; and
(iii) one or more targeting ligands.

In another aspect described is an RNAi agent capable of inhibiting expression of a receptor for advanced glycation end-products gene comprising:

(i) an antisense strand that is between 18 and 49 nucleotides in length that is at least partially complementary to a receptor for advanced glycation end-products gene (SEQ ID NO:1);
(ii) a sense strand that is at least partially complementary to the antisense strand; and
(iii) a targeting ligand linked to the sense strand.

In some embodiments, a RAGE RNAi agent disclosed herein includes an antisense strand that consists of, consists essentially of, or comprises a nucleobase sequence differing by 0 or 1 nucleobases from the nucleotide sequence (5'→3') UUGUGUUCAGUUUCCAUUCCG (SEQ ID NO: 7). In some embodiments, a RAGE RNAi agent disclosed herein includes an antisense strand that consists of, consists essentially of, or comprises a nucleotide sequence differing by no more than 1 nucleotide from the nucleotide sequence (5'→3') UUGUGUUCAGUUUCCAUUCCG (SEQ ID NO: 7), wherein all or substantially all of the nucleotides are modified nucleotides. In some embodiments, a RAGE RNAi agent disclosed herein includes an antisense strand that consists of, consists essentially of, or comprises a nucleobase sequence differing by 0 or 1 nucleobases from the nucleotide sequence (5'→3') UUGUGUUCAGUUUCCAUUCCG (SEQ ID NO: 7), wherein SEQ ID NO: 7 is located at positions 1-21 (5'→3') of the antisense strand.

In some embodiments, a RAGE RNAi agent disclosed herein includes an antisense strand that consists of, consists essentially of, or comprises a modified nucleotide sequence differing by no more than 1 nucleotide from the nucleotide sequence (5'→3') usUfsgsUfgUfuCfaGfuUfuCfcAfuUfcCfsg (SEQ ID NO: 2), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11J showing all internucleoside linkages). In some embodiments, a RAGE RNAi agent disclosed herein includes an antisense strand that consists of, consists essentially of, or comprises the nucleotide sequence (5'→3') usUfsgsUfgUfuCfaGfuUfuCfcAfuUfcCfsg (SEQ ID NO: 2), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a RAGE RNAi agent disclosed herein includes an antisense strand that consists of, consists essentially of, or comprises a modified nucleotide sequence differing by no more than 1 nucleotide from the nucleotide sequence (5'→3') cPrpusUfsgsUfgUfuCfaGfuUfuCfcAfuUfcCfsg (SEQ ID NO: 3), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand. In some embodiments, a RAGE RNAi agent disclosed herein includes an antisense strand that consists of, consists essentially of, or comprises the nucleotide sequence (5'→3') cPrpusUfsgsUfgUfuCfaGfuUfuCfcAfuUfcCfsg (SEQ ID NO: 3), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand.

In some embodiments, a RAGE RNAi agent disclosed herein includes an antisense strand that consists of, consists essentially of, or comprises a nucleobase sequence differing by 0 or 1 nucleobases from the nucleotide sequence (5'→3') UUCCAUUCCUGUUCAUUGCCU (SEQ ID NO: 8). In some embodiments, a RAGE RNAi agent disclosed herein includes an antisense strand that consists of, consists essentially of, or comprises a nucleotide sequence differing by no more than 1 nucleotide from the nucleotide sequence (5'→3') UUCCAUUCCUGUUCAUUGCCU (SEQ ID NO: 8), wherein all or substantially all of the nucleotides are modified nucleotides. In some embodiments, a RAGE RNAi agent disclosed herein includes an antisense strand that consists of, consists essentially of, or comprises a nucleobase sequence differing by 0 or 1 nucleobases from the nucleotide sequence (5'→3') UUCCAUUCCUGUUCAUUGCCU (SEQ ID NO: 8), wherein SEQ ID NO: 8 is located at positions 1-21 (5'→3') of the antisense strand.

In some embodiments, a RAGE RNAi agent disclosed herein includes an antisense strand that consists of, consists essentially of, or comprises a modified nucleotide sequence differing by no more than 1 nucleotide from the nucleotide sequence (5'→3') usUfscsCfaUfuCfcUfgUfuCfaUfuGfcCfsu (SEQ ID NO: 4), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11J showing all intemucleoside linkages). In some embodiments, a RAGE RNAi agent disclosed herein includes an antisense strand that consists of, consists essentially of, or comprises the nucleotide sequence (5'→3') usUfscsCfaUfuCfcUfgUfuCfaUfuGfcCfsu (SEQ ID NO: 4), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a RAGE RNAi agent disclosed herein includes an antisense strand that consists of, consists essentially of, or comprises a nucleobase sequence differing by 0 or 1 nucleobases from the nucleotide sequence (5'→3') UGAUGUUUUGAGCACCUACUC (SEQ ID NO: 9). In some embodiments, a RAGE RNAi agent disclosed herein includes an antisense strand that consists of, consists essentially of, or comprises a nucleotide sequence differing by no more than 1 nucleotide from the nucleotide sequence (5' →3') UGAUGUUUUGAGCACCUACUC (SEQ ID NO: 9), wherein all or substantially all of the nucleotides are modified nucleotides. In some embodiments, a RAGE RNAi agent disclosed herein includes an antisense strand that consists of, consists essentially of, or comprises a nucleobase sequence differing by 0 or 1 nucleobases from the nucleotide sequence (5'→3') UGAUGUUUUGAGCACCUACUC (SEQ ID NO: 9), wherein SEQ ID NO: 7 is located at positions 1-21 (5'→3') of the antisense strand.

In some embodiments, a RAGE RNAi agent disclosed herein includes an antisense strand that consists of, consists essentially of, or comprises a modified nucleotide sequence differing by no more than 1 nucleotide from the nucleotide sequence (5'→3') usGfsasuguuuugaGfcAfcCfuacusc (SEQ ID NO: 5), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides (see, e.g., FIGS. 11A through 11J showing all intemucleoside linkages). In some embodiments, a RAGE RNAi agent disclosed herein includes an antisense strand that consists of, consists essentially of, or comprises the nucleotide sequence (5'→3') usGfsasuguuuugaGfcAfcCfuacusc (SEQ ID NO: 5), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; and s represents a phosphorothioate linkage, and wherein the sense strand is at least substantially complementary to the antisense strand.

In some embodiments, a RAGE RNAi agent disclosed herein includes an antisense strand that consists of, consists essentially of, or comprises a modified nucleotide sequence differing by no more than 1 nucleotide from the nucleotide sequence (5'→3') cPrpusGfsasuguuuugaGfcAfcCfuacusc (SEQ ID NO: 6), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand. In some embodiments, a RAGE RNAi agent disclosed herein includes an antisense strand that consists of, consists essentially of, or comprises the nucleotide sequence (5'→3') cPrpusGfsasuguuuugaGfcAfcCfuacusc (SEQ ID NO: 6), wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; and s represents a phosphorothioate linkage, and wherein the sense strand is at least substantially complementary to the antisense strand.

In some embodiments, a RAGE RNAi agent disclosed herein includes an antisense strand that consists of, consists essentially of, or comprises a nucleotide sequence that differs by 0 or 1 nucleotides from one of the following nucleotide sequences (5'→3'):

```
                                        (SEQ ID NO:7)
UUGUGUUCAGUUUCCAUUCCG;

                                        (SEQ ID NO:8)
UUCCAUUCCUGUUCAUUGCCU;

or

                                       (SEQ ID NO: 9)
UGAUGUUUUGAGCACCUACUC;
```

wherein the RAGE RNAi agent further includes a sense strand that is at least partially complementary to the antisense strand; and wherein all or substantially all of the nucleotides on both the antisense strand and the sense strand are modified nucleotides.

In some embodiments, a RAGE RNAi agent disclosed herein includes an antisense strand that consists of, consists essentially of, or comprises a nucleotide sequence that differs by 0 or 1 nucleotides from one of the following nucleotide sequences (5'→3'):

(SEQ ID NO:7)
UUGUGUUCAGUUUCCAUUCCG;

(SEQ ID NO:8)
UUCCAUUCCUGUUCAUUGCCU;

or (SEQ ID NO: 9)
UGAUGUUUUGAGCACCUACUC;

wherein the RAGE RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound having affinity for an integrin receptor.

In some embodiments, a RAGE RNAi agent disclosed herein includes an antisense strand that consists of, consists essentially of, or comprises a nucleotide sequence that differs by 0 or 1 nucleotides from one of the following nucleotide sequences (5'→3'):

(SEQ ID NO: 7)
UUGUGUUCAGUUUCCAUUCCG;

(SEQ ID NO: 8)
UUCCAUUCCUGUUCAUUGCCU;
or
(SEQ ID NO: 9)
UGAUGUUUUGAGCACCUACUC;

wherein the RAGE RNAi agent further includes a sense strand that is at least partially complementary to the antisense strand; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound having affinity for an integrin receptor; and wherein the respective antisense strand sequence is located at positions 1-21 of the antisense strand.

In some embodiments, a RAGE RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

(SEQ ID NO: 7)
UUGUGUUCAGUUUCCAUUCCG
and (SEQ ID NO: 19)
CGGAAUGGAAACUGAACACAA;

(SEQ ID NO: 8)
UUCCAUUCCUGUUCAUUGCCU
and (SEQ ID NO: 21)
AGGCAAUGAACAGGAAUIGAA;
or -continued (SEQ ID NO: 9)
UGAUGUUUUGAGCACCUACUC
and (SEQ ID NO: 20)
GAGUAGGUGCUCAAAACAUCA;

wherein all or substantially all of the nucleotides on both the antisense strand and the sense strand are modified nucleotides.

In some embodiments, a RAGE RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences (5'→3') pairs:

(SEQ ID NO: 7)
UUGUGUUCAGUUUCCAUUCCG
and (SEQ ID NO: 19)
CGGAAUGGAAACUGAACACAA;

(SEQ ID NO: 8)
UUCCAUUCCUGUUCAUUGCCU
and (SEQ ID NO: 21)
AGGCAAUGAACAGGAAUIGAA;
or (SEQ ID NO: 9)
UGAUGUUUUGAGCACCUACUC
and (SEQ ID NO: 20)
GAGUAGGUGCUCAAAACAUCA;

wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a RAGE RNAi agent disclosed herein includes an antisense strand that consists of, consists essentially of, or comprises a modified nucleotide sequence that differs by 0 or 1 nucleotides from one of the following nucleotide sequences (5'→3'):

(SEQ ID NO: 2)
usUfsgsUfgUfuCfaGfuUfuCfcAfuUfcCfsg;

(SEQ ID NO: 3)
cPrpusUfsgsUfgUfuCfaGfuUfuCfcAfuUfcCfsg;

(SEQ ID NO: 5)
usGfsasuguuuugaGfcAfcCfuacusc;

(SEQ ID NO: 6)
cPrpusGfsasuguuuugaGfcAfcCfuacusc;

(SEQ ID NO: 4)
usUfscsCfaUfuCfcUfgUfuCfaUfuGfcCfsu;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; s represents a phosphorothioate linkage; and wherein the RAGE RNAi agent further includes the sense strand that is at least partially complementary to the antisense strand; and wherein all or substantially all of the nucleotides of the sense strand are modified nucleotides.

In some embodiments, a RAGE RNAi agent disclosed herein includes an antisense strand that consists of, consists essentially of, or comprises a modified nucleotide sequence that differs by 0 or 1 nucleotides from one of the following nucleotide sequences (5'→3'):

```
                                    (SEQ ID NO: 2)
usUfsgsUfgUfuCfaGfuUfuCfcAfuUfcCfsg;

                                    (SEQ ID NO: 3)
cPrpusUfsgsUfgUfuCfaGfuUfuCfcAfuUfcCfsg;

                                    (SEQ ID NO: 5)
usGfsasuguuuugaGfcAfcCfuacusc;

                                    (SEQ ID NO: 6)
cPrpusGfsasuguuuugaGfcAfcCfuacusc;

                                    (SEQ ID NO: 4)
usUfscsCfaUfuCfcUfgUfuCfaUfuGfcCfsu;
```

wherein the RAGE RNAi agent further includes the sense strand that is at least partially complementary to the antisense strand; wherein all or substantially all of the nucleotides of the sense strand are modified nucleotides; wherein all or substantially all of the nucleotides on both the antisense strand and the sense strand are modified nucleotides; and wherein the sense strand further includes inverted abasic residues at the 3' terminal end and at the 5' end of the nucleotide sequence, and the sense strand also includes a targeting ligand that is covalently linked to the 5' terminal end, wherein the targeting ligand includes a compound with affinity for an integrin receptor.

In some embodiments, a RAGE RNAi agent disclosed herein includes an antisense strand and a sense strand that consists of, consists essentially of, or comprises one of the following nucleotide sequence pairs (5'→3'):

```
                                    (SEQ ID NO: 2)
usUfsgsUfgUfuCfaGfuUfuCfcAfuUfcCfsg
and

                                   (SEQ ID NO: 13)
csggaauggAfAfAfcugaacacaa;

                                    (SEQ ID NO: 3)
cPrpusUfsgsUfgUfuCfaGfuUfuCfcAfuUfcCfsg
and

                                   (SEQ ID NO: 13)
csggaauggAfAfAfcugaacacaa;

                                    (SEQ ID NO: 5)
usGfsasuguuuugaGfcAfcCfuacusc
and

                                   (SEQ ID NO: 14)
gsaguagGfuGfcUfcaaaacauca;

                                    (SEQ ID NO: 6)
cPrpusGfsasuguuuugaGfcAfcCfuacusc
and

                                   (SEQ ID NO: 14)
gsaguagGfuGfcUfcaaaacauca;
and
```

-continued

```
                                    (SEQ ID NO: 4)
usUfscsCfaUfuCfcUfgUfuCfaUfuGfcCfsu
and

                                   (SEQ ID NO: 15)
asggcaaugAfAfCfaggaauigaa;
```

wherein a, c, g, i, and u represent 2'-O-methyl adenosine, cytidine, guanosine, inosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; Tri-SM6.1-αvβ6-(TA14) represents the tridentate αvβ6 epithelial cell targeting ligand with the chemical structure as shown in FIG. 1; and s represents a phosphorothioate linkage; and wherein the sense strand also includes a targeting ligand having affinity for an integrin receptor, wherein the targeting ligand is optionally linked at the 5'-end of the sense strand.

In some embodiments, a RAGE RNAi agent disclosed herein includes an antisense strand and a sense strand that consists of, consists essentially of, or comprises modified nucleotide sequences that differs by 0 or 1 nucleotides from one of the following sequence pairs (5'→3'):

```
                                    (SEQ ID NO: 2)
usUfsgsUfgUfuCfaGfuUfuCfcAfuUfcCfsg
and

Tri-SM6.1-αvβ6-(TA14)
                                   (SEQ ID NO: 10)
csggaauggAf

AfAfcugaacacaas(invAb);

                                    (SEQ ID NO: 3)
cPrpusUfsgsUfgUfuCfaGfuUfuCfcAfuUfcCfsg
and

Tri-SM6.1-αvβ6-(TA14)
                                   (SEQ ID NO: 10)
csggaauggAfAfAf

cugaacacaas(invAb);

                                    (SEQ ID NO: 5)
usGfsasuguuuugaGfcAfcCfuacusc
and

Tri-SM6.1-αvβ6-(TA14)
                                   (SEQ ID NO: 11)
gsaguagGfuG

fcUfcaaaacaucas(invAb);

                                    (SEQ ID NO: 6)
cPrpusGfsasuguuuugaGfcAfcCfuacusc
and

Tri-SM6.1-αvβ6-(TA14)
                                   (SEQ ID NO: 11)
gsaguagGfuGf

cUfcaaaacaucas(invAb);
and

                                    (SEQ ID NO: 4)
usUfscsCfaUfuCfcUfgUfuCfaUfuGfcCfsu
and

Tri-SM6.1-αvβ6-(TA14)
                                   (SEQ ID NO: 12)
asggcaaugAfAfC

faggaauigaas(invAb);
```

wherein a, c, g, i, and u represent 2'-O-methyl adenosine, cytidine, guanosine, inosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyluridine; Tri-SM6.1-αvβ6-(TA14) represents the tridentate αvβ6 epithelial cell targeting ligand with the chemical structure as shown in FIG. 1; (invAb) represents an inverted abasic deoxyribonucleotide (see also Table 11), and s represents a phosphorothioate linkage.

In some embodiments, a RAGE RNAi agent disclosed herein includes an antisense strand that includes a nucleobase sequence that differs by 0 or 1 nucleobases from the nucleotide sequences selected from the group consisting of (5'→3'):

```
                                 (SEQ ID NO: 55)
UUGUGUUCAGUUUCCAUUC;

                                 (SEQ ID NO: 69)
UUCCAUUCCUGUUCAUUGC;
and

                                 (SEQ ID NO: 65)
UGAUGUUUUGAGCACCUAC.
```

In some embodiments, a RAGE RNAi agent disclosed herein includes an antisense strand that includes a nucleobase sequence that differs by 0 or 1 nucleobases from the nucleotide sequences selected from the group consisting of (5'→3'):

```
                                 (SEQ ID NO: 55)
UUGUGUUCAGUUUCCAUUC;

                                 (SEQ ID NO: 69)
UUCCAUUCCUGUUCAUUGC;
and

                                 (SEQ ID NO: 65)
UGAUGUUUUGAGCACCUAC.
```

wherein all or substantially all of the nucleotides are modified nucleotides.

In some embodiments, a RAGE RNAi agent disclosed herein includes an antisense strand that includes a nucleobase sequence that differs by 0 or 1 nucleobases from the nucleotide sequences selected from the group consisting of (5'→3'):

```
                                 (SEQ ID NO: 55)
UUGUGUUCAGUUUCCAUUC;

                                 (SEQ ID NO: 69)
UUCCAUUCCUGUUCAUUGC;
and

                                 (SEQ ID NO: 65)
UGAUGUUUUGAGCACCUAC.
```

wherein all or substantially all of the nucleotides are modified nucleotides, and wherein SEQ ID NO:55, SEQ ID NO: 69 and SEQ ID NO: 65, respectively, is located at nucleotide positions 1-19 (5'→3') of the antisense strand.

In some embodiments, a RAGE RNAi agent disclosed herein includes an antisense strand and a sense strand that each include a nucleobase sequences that differs by 0 or 1 nucleobases from the nucleotide sequence pairs selected from the group consisting of (5'→3'):

```
                                 (SEQ ID NO: 55)
UUGUGUUCAGUUUCCAUUC
and

                                (SEQ ID NO: 298)
GAAUGGAAACUGAACACAA;

                                 (SEQ ID NO: 69)
UUCCAUUCCUGUUCAUUGC;
and

                                (SEQ ID NO: 316)
GCAAUGAACAGGAAUIGAA;
or

                                 (SEQ ID NO: 65)
UGAUGUUUUGAGCACCUAC
and

                                (SEQ ID NO: 308)
GUAGGUGCUCAAAACAUCA.
```

In some embodiments, a RAGE RNAi agent disclosed herein includes an antisense strand and a sense strand that each include a nucleobase sequences that differs by 0 or 1 nucleobases from the nucleotide sequence pairs selected from the group consisting of (5'→3'):

```
                                 (SEQ ID NO: 55)
UUGUGUUCAGUUUCCAUUC
and

                                (SEQ ID NO: 298)
GAAUGGAAACUGAACACAA;

                                 (SEQ ID NO: 69)
UUCCAUUCCUGUUCAUUGC;
and

                                (SEQ ID NO: 316)
GCAAUGAACAGGAAUIGAA;
or

                                 (SEQ ID NO: 65)
UGAUGUUUUGAGCACCUAC
and

                                (SEQ ID NO: 308)
GUAGGUGCUCAAAACAUCA
```

wherein all or substantially all of the nucleotides are modified nucleotides.

DEFINITIONS

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target gene in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action.

RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e., AGER mRNA). RNAi agents can include one or more modified nucleotides and/or one or more non-phosphodiester linkages.

As used herein, the terms “silence,” “reduce,” “inhibit,” “down-regulate,” or “knockdown” when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms “sequence” and “nucleotide sequence” mean a succession or order of nucleobases or nucleotides, described with a succession of letters using standard nomenclature.

As used herein, a “base,” “nucleotide base,” or “nucleobase,” is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, and unless otherwise indicated, the term “complementary,” when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, “perfectly complementary” or “fully complementary” means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, “partially complementary” means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, “substantially complementary” means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms “complementary,” “fully complementary,” “partially complementary,” and “substantially complementary” are used with respect to the nucleobase or nucleotide matching between the sense strand and the antisense strand of an RNAi agent, or between the antisense strand of an RNAi agent and a sequence of an AGER mRNA.

As used herein, the term “substantially identical” or “substantial identity,” as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms “treat,” “treatment,” and the like, mean the methods or steps taken to provide relief from or alleviation of the number, severity, and/or frequency of one or more symptoms of a disease in a subject. As used herein, “treat” and “treatment” may include the prevention, management, prophylactic treatment, and/or inhibition or reduction of the number, severity, and/or frequency of one or more symptoms of a disease in a subject.

As used herein, the phrase “introducing into a cell,” when referring to an RNAi agent, means functionally delivering the RNAi agent into a cell. The phrase “functional delivery,” means delivering the RNAi agent to the cell in a manner that enables the RNAi agent to have the expected biological activity, e.g., sequence-specific inhibition of gene expression.

Unless stated otherwise, use of the symbol as used herein means that any group or groups may be linked thereto that is in accordance with the scope of the inventions described herein.

As used herein, the term “isomers” refers to compounds that have identical molecular formulae, but that differ in the nature or the sequence of bonding of their atoms or in the arrangement of their atoms in space. Isomers that differ in the arrangement of their atoms in space are termed “stereoisomers.” Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other objects, features, aspects, and advantages of the invention will be apparent from the following detailed description, accompanying figures, and from the claims.

DETAILED DESCRIPTION

RNAi Agents

Figure 1:
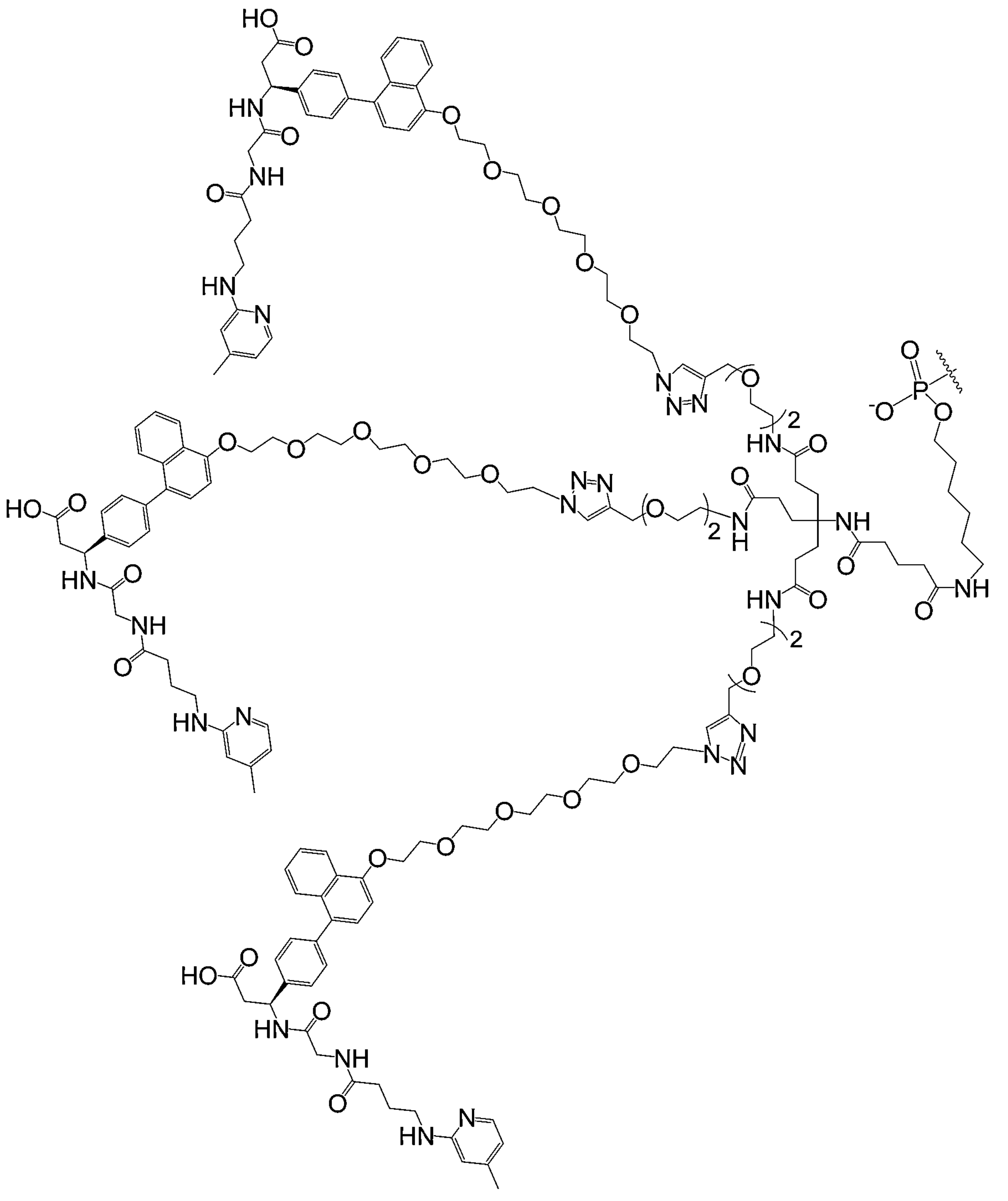
FIG. 1. Chemical structure representation of the tridentate αvβ6 epithelial cell targeting ligand referred to herein as Tri-SM6.1-αvβ6-(TA14).

Described herein are RNAi agents for inhibiting expression of the AGER (or RAGE) gene (referred to herein as RAGE RNAi agents or RAGE RNAi triggers). Each RAGE RNAi agent disclosed herein comprises a sense strand and an antisense strand. The length of the RNAi agent sense strands described herein each can be 15 to 49 nucleotides in length. The length of the RNAi agent antisense strands described herein each can be 18 to 49 nucleotides in length. In some embodiments, the sense and antisense strands are independently 18 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the antisense strands are independently 18, 19, 20, 21, 22, 23, 24, 25, 26, 27, 28, 29, or 30 nucleotides in length. In some embodiments, the sense strands are independently 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. In some embodiments, a double-stranded RNAi agent has a duplex length of about 16, 17, 18, 19, 20, 21, 22, 23 or 24 nucleotides.

Examples of nucleotide sequences used in forming RAGE RNAi agents are provided in Tables 2, 3, 4, 5, 6, and 10. Examples of RNAi agent duplexes, that include the sense strand and antisense strand sequences in Tables 2, 3, 4, 5, 6, are shown in Tables 7A, 7B, 8, 9A, 9B, and 10.

In some embodiments, the region of perfect, substantial, or partial complementarity between the sense strand and the antisense strand is 15-26 (e.g., 15, 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the RAGE RNAi agents described herein includes at least 15 consecutive nucleotides that have at least 85% identity to a core stretch sequence (also referred to herein as a "core stretch" or "core sequence") of the same number of nucleotides in an AGER mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the AGER mRNA target. In some embodiments, this sense strand core stretch is 15, 16, 17, 18, 19, 20, 21, 22, or 23 nucleotides in length. In some embodiments, this sense strand core stretch is 17 nucleotides in length. In some embodiments, this sense strand core stretch is 19 nucleotides in length.

An antisense strand of a RAGE RNAi agent described herein includes at least 15 consecutive nucleotides that have at least 85% complementarity to a core stretch of the same number of nucleotides in an AGER mRNA and to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the AGER mRNA target. In some embodiments, this antisense strand core stretch is 15, 16, 17, 18, 19, 20, 21, 22, 23, 24, 25, or 26 nucleotides in length. In some embodiments, this antisense strand core stretch is 19 nucleotides in length. In some embodiments, this antisense strand core stretch is 17 nucleotides in length. A sense strand core stretch sequence can be the same length as a corresponding antisense core sequence or it can be a different length.

The RAGE RNAi agent sense and antisense strands anneal to form a duplex. A sense strand and an antisense strand of a RAGE RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 15, at least 16, at least 17, at least 18, at least 19, at least 20, at least 21, at least 22, or at least 23 nucleotides that is at least 85% or 100% complementary to a corresponding 15, 16, 17, 18, 19, 20, 21, 22, or 23 nucleotide sequence of the antisense strand core stretch sequence (i.e., the sense and antisense core stretch sequences of a RAGE RNAi agent have a region of at least 15, at least 16, at least 17, at least 18, at least 19, at least 20, at least 21, at least 22, or at least 23 nucleotides that is at least 85% base paired or 100% base paired.)

In some embodiments, the antisense strand of a RAGE RNAi agent disclosed herein differs by 0, 1, 2, or 3 nucleotides from any of the antisense strand sequences in Table 2 or Table 3. In some embodiments, the sense strand of a RAGE RNAi agent disclosed herein differs by 0, 1, 2, or 3 nucleotides from any of the sense strand sequences in Table 2, Table 4, Table 5. Table 6, or Table 10.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the AGER mRNA. The sense strand additional nucleotides, if present, may or may not be identical to the corresponding sequence in the AGER mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a RAGE RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, a RAGE RNAi agent comprises an antisense strand having a 3' extension of 1, 2, 3, 4, 5, or 6 nucleotides in length. In other embodiments, a RAGE RNAi agent comprises an antisense strand having a 3' extension of 1, 2, or 3 nucleotides in length. In some embodiments, one or more of the antisense strand extension nucleotides comprise nucleotides that are complementary to the corresponding AGER mRNA sequence. In some embodiments, one or more of the antisense strand extension nucleotides comprise nucleotides that are not complementary to the corresponding AGER mRNA sequence.

In some embodiments, a RAGE RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the AGER mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, a RAGE RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the AGER mRNA sequence.

Examples of sequences used in forming RAGE RNAi agents are provided in Tables 2, 3, 4, 5, 6, and 10. In some embodiments, a RAGE RNAi agent antisense strand includes a sequence of any of the sequences in Tables 2, 3, or 10. In certain embodiments, a RAGE RNAi agent antisense strand comprises or consists of any one of the modified sequences in Table 3. In some embodiments, a RAGE RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2 or 3. In some embodiments, a RAGE RNAi agent sense strand includes the sequence of any of the sequences in Tables 2, 4, 5, or 6. In some embodiments, a RAGE RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2, 4, 5, or 6. In certain embodiments, a RAGE RNAi agent sense strand comprises or consists of a modified sequence of any one of the modified sequences in Table 4, 5, 6, or 10.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands form a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The RAGE RNAi agents disclosed herein may also be comprised of one or more modified nucleotides. In some embodiments, substantially all of the nucleotides of the sense strand and substantially all of the nucleotides of the antisense strand of the RAGE RNAi agent are modified nucleotides. The RAGE RNAi agents disclosed herein may further be comprised of one or more modified intemucleoside linkages, e.g., one or more phosphorothioate linkages. In some embodiments, a RAGE RNAi agent contains one or more modified nucleotides and one or more modified intemucleoside linkages. In some embodiments, a 2'-modified nucleotide is combined with modified intemucleoside linkage.

In some embodiments, a RAGE RNAi agent is prepared or provided as a salt, mixed salt, or a free-acid. In some embodiments, a RAGE RNAi agent is prepared as a pharmaceutically acceptable salt. In some embodiments, a RAGE RNAi agent is prepared as a pharmaceutically acceptable sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administration of the oligonucleotide construct.

In some embodiments, a RAGE RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' intemucleoside linked) nucleotides, 2'-F-Arabino nucleotides, 5'-Me, 2'-fluoro nucleotide, morpholino nucleotides, vinyl phosphonate deoxyribonucleotides, vinyl phosphonate containing nucleotides, and cyclopropyl phosphonate containing nucleotides. 2'-modified nucleotides (i.e., a nucleotide with a group other than a hydroxyl group at the 2' position of the five-membered sugar ring) include, but are not limited to, 2'-O-methyl nucleotides (also referred to as 2'-methoxy nucleotides), 2'-fluoro nucleotides (also referred to herein and in the art as 2'-deoxy-2'-fluoro nucleotides), 2'-deoxy nucleotides, 2'-methoxyethyl (2'-O-2-methoxylethyl) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single RAGE RNAi agent or even in a single nucleotide thereof. The RAGE RNAi agent sense strands and antisense strands can be synthesized and/or modified by methods known in the art. Modification at one nucleotide is independent of modification at another nucleotide.

Modified nucleobases include synthetic and natural nucleobases, such as 5-substituted pyrimidines, 6-azapyrimidines and N-2, N-6 and 0-6 substituted purines, (e.g., 2-arninopropyladenine, 5-propynyluracil, or 5-propynylcytosine), 5-methylcytosine (5-me-C), 5-hydroxymethyl cytosine, inosine, xanthine, hypoxanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thyrnine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. (See, e.g., U.S. Pat. No. 5,998,203). In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide. Chemical structures for certain modified nucleotides are set forth in Table 11 herein.

Modified Internucleoside Linkages

In some embodiments, one or more nucleotides of a RAGE RNAi agent are linked by non-standard linkages or backbones (i.e., modified intemucleoside linkages or modified backbones). Modified intemucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified intemucleoside linkage or backbone lacks a phosphorus atom. Modified intemucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified intemucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a RAGE RNAi agent can contain 1, 2, 3, 4, 5, or 6 phosphorothioate linkages, an antisense strand of a RAGE RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a RAGE RNAi agent can contain 1, 2, 3, or 4 phosphorothioate linkages, an antisense strand of a RAGE RNAi agent can contain 1, 2, 3, or 4 phosphorothioate linkages, or both the sense strand and the antisense strand independently can contain 1, 2, 3, or 4 phosphorothioate linkages.

In some embodiments, a RAGE RNAi agent sense strand contains at least two phosphorothioate intemucleoside linkages. In some embodiments, the phosphorothioate intemucleoside linkages are between the nucleotides at positions 1-3 from the 3' end of the sense strand. In some embodiments, one phosphorothioate intemucleoside linkage is at the 5' end of the sense strand nucleotide sequence, and another phosphorothioate linkage is at the 3' end of the sense strand nucleotide sequence. In some embodiments, two phosphorothioate intemucleoside linkage are located at the 5' end of the sense strand, and another phosphorothioate linkage is at the 3' end of the sense strand. In some embodiments, the sense strand does not include any phosphorothioate intemucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a RAGE RNAi agent antisense strand contains four phosphorothioate intemucleoside linkages. In some embodiments, the four phosphorothioate intemucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate intemucleoside linkages are located between positions 1-4 from the 5' end of the antisense strand, and a fourth phosphorothioate intemucleoside linkage is located between positions 20-21 from the 5' end of the antisense strand. In some embodiments, a RAGE RNAi agent contains at least three or four phosphorothioate intemucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues (see Table 11). (See, e.g., F. Czaudema, Nucleic Acids Res., 2003, 31(11), 2705-16). Capping residues are generally known in the art, and include, for example, inverted abasic residues as well as carbon chains such as a terminal C3H7 (propyl), C6H13 (hexyl), or C12H25 (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other intemucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. The chemical structures for inverted abasic deoxyribose residues are shown in Table 11 below.

RAGE RNAi Agents

The RAGE RNAi agents disclosed herein are designed to target specific positions on an AGER (RAGE) gene (e.g., SEQ ID NO:1 (NM_001136.5)). As defined herein, an antisense strand sequence is designed to target an AGER gene at a given position on the gene when the 5' terminal nucleobase of the antisense strand is aligned with a position that is 21 nucleotides downstream (towards the 3' end) from the position on the gene when base pairing to the gene. For example, as illustrated in Tables 1 and 2 herein, an antisense strand sequence designed to target an AGER gene at position 177 requires that when base pairing to the gene, the 5' terminal nucleobase of the antisense strand is aligned with position 197 of an AGER gene.

As provided herein, a RAGE RNAi agent does not require that the nucleobase at position 1 (5'→3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for a RAGE RNAi agent disclosed herein that is designed to target position 177 of an AGER gene, the 5' terminal nucleobase of the antisense strand of the of the RAGE RNAi agent must be aligned with position 197 of the gene; however, the 5' terminal nucleobase of the antisense strand may be, but is not required to be, complementary to position 197 of an AGER gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the RAGE RNAi agent (e.g., whether the RAGE RNAi agent is designed to target an AGER gene at position 177, at position 90, at position 330, or at some other position) is an important factor to the level of inhibition achieved by the RAGE RNAi agent. (See, e.g., Kamola et al., *The siRNA Non-seed Region and Its Target Sequences are Auxiliary Determinants of Off—Target Effects*, PLOS Computational Biology, 11(12), FIG. 1 (2015)).

In some embodiments, the RAGE RNAi agents disclosed herein target an AGER gene at or near the positions of the AGER sequence shown in Table 1. In some embodiments, the antisense strand of a RAGE RNAi agent disclosed herein includes a core stretch sequence that is fully, substantially, or at least partially complementary to a target RAGE 19-mer sequence disclosed in Table 1.

TABLE 1

AGER (RAGE) 19-mer mRNA Target Sequences (taken from *homo sapiens* advanced glycosylation end-product specific receptor (AGER), transcript variant 1, GenBank NM_001136.5 (SEQ ID NO: 1))

| SEQ ID No. | AGER (RAGE) 19-mer Target Sequences (5'→3') | Corresponding Positions of Sequence on SEQ ID NO: 1 | Targeted Gene Position (as referred to herein) |
|---|---|---|---|
| 22 | GAAUGGAAACUGAACACAG | 179-197 | 177 |
| 23 | GUAGGUGCUCAAAACAUCA | 92-110 | 90 |
| 24 | GCAAUGAACAGGAAUGGAA | 332-350 | 330 |
| 25 | AAUGGAAACUGAACACAGG | 180-198 | 178 |
| 26 | CAGAUUCCUGGGAAGCCAG | 386-404 | 384 |
| 27 | CUGGGAAGCCAGAAAUUGU | 393-411 | 391 |
| 28 | CACUGGUGCUGAAGUGUAA | 129-147 | 127 |
| 29 | GACAGAAGCUUGGAAGGUC | 202-220 | 200 |
| 30 | GGAUGAGGGGAUUUUCCGG | 307-325 | 305 |
| 31 | AUUCCUGGGAAGCCAGAAA | 389-407 | 387 |
| 32 | AUUCUGCCUCUGAACUCAC | 414-432 | 412 |
| 33 | CCCUGCAGGGACUCUUAGC | 481-499 | 479 |
| 34 | CCUGCAGGGACUCUUAGCU | 482-500 | 480 |
| 35 | CCACCUUCUCCUGUAGCUU | 642-660 | 640 |
| 36 | CUUCUCCUGUAGCUUCAGC | 646-664 | 644 |

TABLE 1-continued

AGER (RAGE) 19-mer mRNA Target Sequences (taken from *homo sapiens* advanced glycosylation end-product specific receptor (AGER), transcript variant 1, GenBank NM_001136.5 (SEQ ID NO: 1))

| SEQ ID No. | AGER (RAGE) 19-mer Target Sequences (5'→3') | Corresponding Positions of Sequence on SEQ ID NO: 1 | Targeted Gene Position (as referred to herein) |
|---|---|---|---|
| 37 | UGCUGGUCCUCAGUCUGUG | 63-81 | 61 |
| 38 | GCUGGUCCUCAGUCUGUGG | 64-82 | 62 |
| 39 | UCCGUGUCUACCAGAUUCC | 375-393 | 373 |
| 40 | CGUGUCUACCAGAUUCCUG | 377-395 | 375 |
| 41 | CACCUUCUCCUGUAGCUUC | 643-661 | 641 |
| 42 | CCUCAAAUCCACUGGAUGA | 830-848 | 828 |
| 43 | UAGAUUCUGCCUCUGAACU | 411-429 | 409 |
| 44 | GAUUCUGCCUCUGAACUCA | 413-431 | 411 |
| 45 | CUGGUGUUCCCAAUAAGGU | 435-453 | 433 |
| 46 | GGUGUUCCCAAUAAGGUGG | 437-455 | 435 |
| 47 | UUAGCUGGCACUUGGAUGG | 495-513 | 493 |
| 48 | UAAUGAGAAGGGAGUAUCU | 529-547 | 527 |
| 49 | GAGAAGGGAGUAUCUGUGA | 533-551 | 531 |
| 50 | GCAUCAGCAUCAUCGAACC | 981-999 | 979 |
| 51 | UGAACAGGAAUGGAAAGGA | 336-354 | 334 |
| 52 | CUACCGAGUCCGUGUCUAC | 367-385 | 365 |
| 53 | UGGGAAGCCAGAAAUUGUA | 394-412 | 392 |
| 54 | CCUAAUGAGAAGGGAGUAU | 527-545 | 525 |

*Homo sapiens* advanced glycosylation end-product specific receptor (AGER), transcript variant 1, GenBank NM_001136.5 (SEQ ID NO: 1), gene transcript (1420 bases):

```
  1 agacagagcc aggaccctgg aaggaagcag
    gatggctgcc ggaacagcag ttggagcctg
 61 ggtgctggtc ctcagtctgt ggggggcagt
    agtaggtgct caaaacatca cagcccggat
121 tggcgagcca ctggtgctga agtgtaaggg
    ggcccccaag aaaccacccc agcggctgga
181 atggaaactg aacacaggcc ggacagaagc
    ttggaaggtc ctgtctcccc agggaggagg
```

-continued

```
 241 cccctgggac agtgtggctc gtgtccttcc
     caacggctcc ctcttccttc cggctgtcgg
 301 gatccaggat gaggggattt tccggtgcca
     ggcaatgaac aggaatggaa aggagaccaa
 361 gtccaactac cgagtccgtg tctaccagat
     tcctgggaag ccagaaattg tagattctgc
 421 ctctgaactc acggctggtg ttcccaataa
     ggtggggaca tgtgtgtcag agggaagcta
 481 ccctgcaggg actcttagct ggcacttgga
     tgggaagccc ctggtgccta atgagaaggg
 541 agtatctgtg aaggaacaga ccaggagaca
     ccctgagaca gggctcttca cactgcagtc
 601 ggagctaatg gtgaccccag cccggggagg
     agatccccgt cccaccttct cctgtagctt
 661 cagcccaggc cttccccgac accgggcctt
     gcgcacagcc cccatccagc cccgtgtctg
 721 ggagcctgtg cctctggagg aggtccaatt
     ggtggtggag ccagaaggtg gagcagtagc
 781 tcctggtgga accgtaaccc tgacctgtga
     agtccctgcc cagccctctc ctcaaatcca
 841 ctggatgaag gatggtgtgc ccttgcccct
     tccccccagc cctgtgctga tcctccctga
 901 gatagggcct caggaccagg gaacctacag
     ctgtgtggcc acccattcca gccacgggcc
 961 ccaggaaagc cgtgctgtca gcatcagcat
     catcgaacca ggcgaggagg ggccaactgc
1021 aggctctgtg ggaggatcag ggctgggaac
     tctagccctg gccctggggatectgggagg
1081 cctggggaca gccgccctgc tcattggggt
     catcttgtgg caaaggcggc aacgccgagg
1141 agaggagagg aaggccccag aaaaccagga
     ggaagaggag gagcgtgcag aactgaatca
1201 gtcggaggaa cctgaggcag gcgagagtag
     tactggaggg ccttgagggg cccacagaca
```

-continued

```
1261 gatcccatcc atcagctccc ttttcttttt
     cccttgaact gttctggcct cagaccaact
1321 ctctcctgta taatctctct cctgtataac
     cccaccttgc caagctttct tctacaacca
1381 gagcccccca caatgatgat taaacacctg
     acacatcttg
```

In some embodiments, a RAGE RNAi agent includes an antisense strand wherein position 19 of the antisense strand (5'→3') is capable of forming abase pair with position 1 of a 19-mer target sequence disclosed in Table 1. In some embodiments, a RAGE RNAi agent includes an antisense strand wherein position 1 of the antisense strand (5'→3') is capable of forming a base pair with position 19 of a 19-mer target sequence disclosed in Table 1.

In some embodiments, a RAGE RNAi agent includes an antisense strand wherein position 2 of the antisense strand (5'→3') is capable of forming a base pair with position 18 of a 19-mer target sequence disclosed in Table 1. In some embodiments, a RAGE RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to an AGER gene, or can be non-complementary to an AGER gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a RAGE RNAi agent antisense strand comprises the sequence of nucleotides (from 5' end→3' end) 2-18 or 2-19 of any of the antisense strand sequences in Table 2 or Table 3. In some embodiments, a RAGE RNAi sense strand comprises the sequence of nucleotides (from 5' end→3' end) 1-17, 1-18, or 2-18 of any of the sense strand sequences in Table 2, Table 4, Table 5, or Table 6.

In some embodiments, a RAGE RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2, Table 4, Table 5, or Table 6.

In some embodiments, the RAGE RNAi agents include core 19-mer nucleotide sequences shown in the following Table 2.

TABLE 2

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corre-sponding Positions of Identified Sequence on SEQ ID NO: 1 | Targeted Gene Position |
|---|---|---|---|---|---|
| 55 | UUGUGUUCAGUUUCCAUUC | 298 | GAAUGGAAACUGAACACAA | 179-197 | 177 |
| 56 | AUGUGUUCAGUUUCCAUUC | 299 | GAAUGGAAACUGAACACAU | 179-197 | 177 |
| 57 | CUGUGUUCAGUUUCCAUUC | 300 | GAAUGGAAACUGAACACAG | 179-197 | 177 |
| 58 | NUGUGUUCAGUUUCCAUUC | 301 | GAAUGGAAACUGAACACAN | 179-197 | 177 |
| 59 | NUGUGUUCAGUUUCCAUUN | 302 | NAAUGGAAACUGAACACAN | 179-197 | 177 |
| 60 | UUGUGUUCAGUUUCCAUUC | 303 | GAAUGGAAACUIAACACAA | 179-197 | 177 |
| 61 | AUGUGUUCAGUUUCCAUUC | 304 | GAAUGGAAACUIAACACAU | 179-197 | 177 |
| 62 | CUGUGUUCAGUUUCCAUUC | 305 | GAAUGGAAACUIAACACAG | 179-197 | 177 |
| 63 | NUGUGUUCAGUUUCCAUUC | 306 | GAAUGGAAACUIAACACAN | 179-197 | 177 |
| 64 | NUGUGUUCAGUUUCCAUUN | 307 | NAAUGGAAACUIAACACAN | 179-197 | 177 |
| 65 | UGAUGUUUUGAGCACCUAC | 308 | GUAGGUGCUCAAAACAUCA | 92-110 | 90 |
| 66 | AGAUGUUUUGAGCACCUAC | 309 | GUAGGUGCUCAAAACAUCU | 92-110 | 90 |
| 67 | NGAUGUUUUGAGCACCUAC | 310 | GUAGGUGCUCAAAACAUCN | 92-110 | 90 |
| 68 | NGAUGUUUUGAGCACCUAN | 311 | NUAGGUGCUCAAAACAUCN | 92-110 | 90 |
| 69 | UUCCAUUCCUGUUCAUUGC | 312 | GCAAUGAACAGGAAUGGAA | 332-350 | 330 |
| 70 | AUCCAUUCCUGUUCAUUGC | 313 | GCAAUGAACAGGAAUGGAU | 332-350 | 330 |
| 71 | NUCCAUUCCUGUUCAUUGC | 314 | GCAAUGAACAGGAAUGGAN | 332-350 | 330 |
| 72 | NUCCAUUCCUGUUCAUUGN | 315 | NCAAUGAACAGGAAUGGAN | 332-350 | 330 |
| 73 | UUCCAUUCCUGUUCAUUGC | 316 | GCAAUGAACAGGAAUIGAA | 332-350 | 330 |
| 74 | AUCCAUUCCUGUUCAUUGC | 317 | GCAAUGAACAGGAAUIGAU | 332-350 | 330 |
| 75 | NUCCAUUCCUGUUCAUUGC | 318 | GCAAUGAACAGGAAUIGAN | 332-350 | 330 |
| 76 | NUCCAUUCCUGUUCAUUGN | 319 | NCAAUGAACAGGAAUIGAN | 332-350 | 330 |
| 77 | UCUGUGUUCAGUUUCCAUU | 320 | AAUGGAAACUGAACACAGA | 180-198 | 178 |
| 78 | ACUGUGUUCAGUUUCCAUU | 321 | AAUGGAAACUGAACACAGU | 180-198 | 178 |
| 79 | CCUGUGUUCAGUUUCCAUU | 322 | AAUGGAAACUGAACACAGG | 180-198 | 178 |
| 80 | NCUGUGUUCAGUUUCCAUU | 323 | AAUGGAAACUGAACACAGN | 180-198 | 178 |
| 81 | NCUGUGUUCAGUUUCCAUN | 324 | NAUGGAAACUGAACACAGN | 180-198 | 178 |
| 82 | UCUGUGUUCAGUUUCCAUU | 325 | AAUGGAAACUGAACACAIA | 180-198 | 178 |
| 83 | ACUGUGUUCAGUUUCCAUU | 326 | AAUGGAAACUGAACACAIU | 180-198 | 178 |
| 84 | CCUGUGUUCAGUUUCCAUU | 327 | AAUGGAAACUGAACACAIG | 180-198 | 178 |
| 85 | NCUGUGUUCAGUUUCCAUU | 328 | AAUGGAAACUGAACACAIN | 180-198 | 178 |
| 86 | NCUGUGUUCAGUUUCCAUN | 329 | NAUGGAAACUGAACACAIN | 180-198 | 178 |
| 87 | UUGGCUUCCCAGGAAUCUG | 330 | CAGAUUCCUGGGAAGCCAA | 386-404 | 384 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corre-sponding Positions of Identified Sequence on SEQ ID NO: 1 | Targeted Gene Position |
|---|---|---|---|---|---|
| 88 | AUGGCUUCCCAGGAAUCUG | 331 | CAGAUUCCUGGGAAGCCAU | 386-404 | 384 |
| 89 | CUGGCUUCCCAGGAAUCUG | 332 | CAGAUUCCUGGGAAGCCAG | 386-404 | 384 |
| 90 | NUGGCUUCCCAGGAAUCUG | 333 | CAGAUUCCUGGGAAGCCAN | 386-404 | 384 |
| 91 | NUGGCUUCCCAGGAAUCUN | 334 | NAGAUUCCUGGGAAGCCAN | 386-404 | 384 |
| 92 | UUGGCUUCCCAGGAAUCUG | 335 | CAGAUUCCUGGGAAICCAA | 386-404 | 384 |
| 93 | AUGGCUUCCCAGGAAUCUG | 336 | CAGAUUCCUGGGAAICCAU | 386-404 | 384 |
| 94 | CUGGCUUCCCAGGAAUCUG | 337 | CAGAUUCCUGGGAAICCAG | 386-404 | 384 |
| 95 | NUGGCUUCCCAGGAAUCUG | 338 | CAGAUUCCUGGGAAICCAN | 386-404 | 384 |
| 96 | NUGGCUUCCCAGGAAUCUN | 339 | NAGAUUCCUGGGAAICCAN | 386-404 | 384 |
| 97 | ACAAUUUCUGGCUUCCCAG | 340 | CUGGGAAGCCAGAAAUUGU | 393-411 | 391 |
| 98 | UCAAUUUCUGGCUUCCCAG | 341 | CUGGGAAGCCAGAAAUUGA | 393-411 | 391 |
| 99 | NCAAUUUCUGGCUUCCCAG | 342 | CUGGGAAGCCAGAAAUUGN | 393-411 | 391 |
| 100 | NCAAUUUCUGGCUUCCCAN | 343 | NUGGGAAGCCAGAAAUUGN | 393-411 | 391 |
| 101 | UUACACUUCAGCACCAGUG | 344 | CACUGGUGCUGAAGUGUAA | 129-147 | 127 |
| 102 | AUACACUUCAGCACCAGUG | 345 | CACUGGUGCUGAAGUGUAU | 129-147 | 127 |
| 103 | NUACACUUCAGCACCAGUG | 346 | CACUGGUGCUGAAGUGUAN | 129-147 | 127 |
| 104 | NUACACUUCAGCACCAGUN | 347 | NACUGGUGCUGAAGUGUAN | 129-147 | 127 |
| 105 | UACCUUCCAAGCUUCUGUC | 348 | GACAGAAGCUUGGAAGGUA | 202-220 | 200 |
| 106 | GACCUUCCAAGCUUCUGUC | 349 | GACAGAAGCUUGGAAGGUC | 202-220 | 200 |
| 107 | AACCUUCCAAGCUUCUGUC | 350 | GACAGAAGCUUGGAAGGUU | 202-220 | 200 |
| 108 | NACCUUCCAAGCUUCUGUC | 351 | GACAGAAGCUUGGAAGGUN | 202-220 | 200 |
| 109 | NACCUUCCAAGCUUCUGUN | 352 | NACAGAAGCUUGGAAGGUN | 202-220 | 200 |
| 110 | UACCUUCCAAGCUUCUGUC | 353 | GACAGAAGCUUGGAAGIUA | 202-220 | 200 |
| ill | GACCUUCCAAGCUUCUGUC | 354 | GACAGAAGCUUGGAAGIUC | 202-220 | 200 |
| 112 | AACCUUCCAAGCUUCUGUC | 355 | GACAGAAGCUUGGAAGIUU | 202-220 | 200 |
| 113 | NACCUUCCAAGCUUCUGUC | 356 | GACAGAAGCUUGGAAGIUN | 202-220 | 200 |
| 114 | NACCUUCCAAGCUUCUGUN | 357 | NACAGAAGCUUGGAAGIUN | 202-220 | 200 |
| 115 | UCGGAAAAUCCCCUCAUCC | 358 | GGAUGAGGGGAUUUUCCGA | 307-325 | 305 |
| 116 | CCGGAAAAUCCCCUCAUCC | 359 | GGAUGAGGGGAUUUUCCGG | 307-325 | 305 |
| 117 | ACGGAAAAUCCCCUCAUCC | 360 | GGAUGAGGGGAUUUUCCGU | 307-325 | 305 |
| 118 | NCGGAAAAUCCCCUCAUCC | 361 | GGAUGAGGGGAUUUUCCGN | 307-325 | 305 |
| 119 | NCGGAAAAUCCCCUCAUCN | 362 | NGAUGAGGGGAUUUUCCGN | 307-325 | 305 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corre-sponding Positions of Identified Sequence on SEQ ID NO: 1 | Targeted Gene Position |
|---|---|---|---|---|---|
| 120 | UCGGAAAAUCCCCUCAUCC | 363 | GGAUGAGGGGAUUUUCCIA | 307-325 | 305 |
| 121 | CCGGAAAAUCCCCUCAUCC | 364 | GGAUGAGGGGAUUUUCCIG | 307-325 | 305 |
| 122 | ACGGAAAAUCCCCUCAUCC | 365 | GGAUGAGGGGAUUUUCCIU | 307-325 | 305 |
| 123 | NCGGAAAAUCCCCUCAUCC | 366 | GGAUGAGGGGAUUUUCCIN | 307-325 | 305 |
| 124 | NCGGAAAAUCCCCUCAUCN | 367 | NGAUGAGGGGAUUUUCCIN | 307-325 | 305 |
| 125 | UUUCUGGCUUCCCAGGAAU | 368 | AUUCCUGGGAAGCUAGAAA | 389-407 | 387 |
| 126 | AUUCUGGCUUCCCAGGAAU | 369 | AUUCCUGGGAAGCUAGAAU | 389-407 | 387 |
| 127 | NUUCUGGCUUCCCAGGAAU | 370 | AUUCCUGGGAAGCUAGAAN | 389-407 | 387 |
| 128 | NUUCUGGCUUCCCAGGAAN | 371 | NUUCCUGGGAAGCUAGAAN | 389-407 | 387 |
| 129 | UUGAGUUCAGAGGCAGAAU | 372 | AUUCUGCCUCUGAACUCAC | 414-432 | 412 |
| 130 | GUGAGUUCAGAGGCAGAAU | 373 | AUUCUGCCUCUGAACUCAC | 414-432 | 412 |
| 131 | AUGAGUUCAGAGGCAGAAU | 374 | AUUCUGCCUCUGAACUCAU | 414-432 | 412 |
| 132 | NUGAGUUCAGAGGCAGAAU | 375 | AUUCUGCCUCUGAACUCAN | 414-432 | 412 |
| 133 | NUGAGUUCAGAGGCAGAAN | 376 | NUUCUGCCUCUGAACUCAN | 414-432 | 412 |
| 134 | UCUAAGAGUCCCUGCAGGG | 377 | CCCUGCAGGGACUCUUAGA | 481-499 | 479 |
| 135 | ACUAAGAGUCCCUGCAGGG | 378 | CCCUGCAGGGACUCUUAGU | 481-499 | 479 |
| 136 | GCUAAGAGUCCCUGCAGGG | 379 | CCCUGCAGGGACUCUUAGC | 481-499 | 479 |
| 137 | NCUAAGAGUCCCUGCAGGG | 380 | CCCUGCAGGGACUCUUAGN | 481-499 | 479 |
| 138 | NCUAAGAGUCCCUGCAGGN | 381 | NCCUGCAGGGACUCUUAGN | 481-499 | 479 |
| 139 | AGCUAAGAGUCCCUGCAGG | 382 | CCUGCAGGGACUCUUAGCU | 482-500 | 480 |
| 140 | UGCUAAGAGUCCCUGCAGG | 383 | CCUGCAGGGACUCUUAGCA | 482-500 | 480 |
| 141 | NGCUAAGAGUCCCUGCAGG | 384 | CCUGCAGGGACUCUUAGCN | 482-500 | 480 |
| 142 | NGCUAAGAGUCCCUGCAGN | 385 | NCUGCAGGGACUCUUAGCN | 482-500 | 480 |
| 143 | AGCUAAGAGUCCCUGCAGG | 386 | CCUGCAGGGACUCUUAICU | 482-500 | 480 |
| 144 | UGCUAAGAGUCCCUGCAGG | 387 | CCUGCAGGGACUCUUAICA | 482-500 | 480 |
| 145 | NGCUAAGAGUCCCUGCAGG | 388 | CCUGCAGGGACUCUUAICN | 482-500 | 480 |
| 146 | NGCUAAGAGUCCCUGCAGN | 389 | NCUGCAGGGACUCUUAICN | 482-500 | 480 |
| 147 | AAGCUACAGGAGAAGGUGG | 390 | CCACCUUCUCCUGUAGCUU | 642-660 | 640 |
| 148 | UAGCUACAGGAGAAGGUGG | 391 | CCACCUUCUCCUGUAGCUA | 642-660 | 640 |
| 149 | NAGCUACAGGAGAAGGUGG | 392 | CCACCUUCUCCUGUAGCUN | 642-660 | 640 |
| 150 | NAGCUACAGGAGAAGGUGN | 393 | NCACCUUCUCCUGUAGCUN | 642-660 | 640 |
| 151 | AAGCUACAGGAGAAGGUGG | 394 | CCACCUUCUCCUGUAICUU | 642-660 | 640 |
| 152 | UAGCUACAGGAGAAGGUGG | 395 | CCACCUUCUCCUGUAICUA | 642-660 | 640 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corre-sponding Positions of Identified Sequence on SEQ ID NO: 1 | Targeted Gene Position |
|---|---|---|---|---|---|
| 153 | NAGCUACAGGAGAAGGUGG | 396 | CCACCUUCUCCUGUAICUN | 642-660 | 640 |
| 154 | NAGCUACAGGAGAAGGUGN | 397 | NCACCUUCUCCUGUAICUN | 642-660 | 640 |
| 155 | UCUGAAGCUACAGGAGAAG | 398 | CUUCUCCUGUAGCUUCAGA | 646-664 | 644 |
| 156 | ACUGAAGCUACAGGAGAAG | 399 | CUUCUCCUGUAGCUUCAGU | 646-664 | 644 |
| 157 | GCUGAAGCUACAGGAGAAG | 400 | CUUCUCCUGUAGCUUCAGC | 646-664 | 644 |
| 158 | NCUGAAGCUACAGGAGAAG | 401 | CUUCUCCUGUAGCUUCAGN | 646-664 | 644 |
| 159 | NCUGAAGCUACAGGAGAAN | 402 | NUUCUCCUGUAGCUUCAGN | 646-664 | 644 |
| 160 | UCUGAAGCUACAGGAGAAG | 403 | CUUCUCCUGUAGCUUCAIA | 646-664 | 644 |
| 161 | ACUGAAGCUACAGGAGAAG | 404 | CUUCUCCUGUAGCUUCAIU | 646-664 | 644 |
| 162 | GCUGAAGCUACAGGAGAAG | 405 | CUUCUCCUGUAGCUUCAIC | 646-664 | 644 |
| 163 | NCUGAAGCUACAGGAGAAG | 406 | CUUCUCCUGUAGCUUCAIN | 646-664 | 644 |
| 164 | NCUGAAGCUACAGGAGAAN | 407 | NUUCUCCUGUAGCUUCAIN | 646-664 | 644 |
| 165 | UACAGACUGAGGACCAGCA | 408 | UGCUGGUCCUCAGUCUGUA | 63-81 | 61 |
| 166 | AACAGACUGAGGACCAGCA | 409 | UGCUGGUCCUCAGUCUGUU | 63-81 | 61 |
| 167 | CACAGACUGAGGACCAGCA | 410 | UGCUGGUCCUCAGUCUGUG | 63-81 | 61 |
| 168 | NACAGACUGAGGACCAGCA | 411 | UGCUGGUCCUCAGUCUGUN | 63-81 | 61 |
| 169 | NACAGACUGAGGACCAGCN | 412 | UGCUGGUCCUCAGUCUGUN | 63-81 | 61 |
| 170 | UACAGACUGAGGACCAGCA | 413 | UGCUGGUCCUCAGUCUIUA | 63-81 | 61 |
| 171 | AACAGACUGAGGACCAGCA | 414 | UGCUGGUCCUCAGUCUIUU | 63-81 | 61 |
| 172 | CACAGACUGAGGACCAGCA | 415 | UGCUGGUCCUCAGUCUIUG | 63-81 | 61 |
| 173 | NACAGACUGAGGACCAGCA | 416 | UGCUGGUCCUCAGUCUIUN | 63-81 | 61 |
| 174 | NACAGACUGAGGACCAGCN | 417 | UGCUGGUCCUCAGUCUIUN | 63-81 | 61 |
| 175 | UCACAGACUGAGGACCAGC | 418 | GCUGGUCCUCAGUCUGUGA | 64-82 | 62 |
| 176 | ACACAGACUGAGGACCAGC | 419 | GCUGGUCCUCAGUCUGUGU | 64-82 | 62 |
| 177 | NCACAGACUGAGGACCAGC | 420 | GCUGGUCCUCAGUCUGUGN | 64-82 | 62 |
| 178 | NCACAGACUGAGGACCAGN | 421 | NCUGGUCCUCAGUCUGUGN | 64-82 | 62 |
| 179 | UCACAGACUGAGGACCAGC | 422 | GCUGGUCCUCAGUCUGUIA | 64-82 | 62 |
| 180 | ACACAGACUGAGGACCAGC | 423 | GCUGGUCCUCAGUCUGUIU | 64-82 | 62 |
| 181 | NCACAGACUGAGGACCAGC | 424 | GCUGGUCCUCAGUCUGUIN | 64-82 | 62 |
| 182 | NCACAGACUGAGGACCAGN | 425 | NCUGGUCCUCAGUCUGUIN | 64-82 | 62 |
| 183 | UCACAGACUGAGGACCAGC | 426 | GCUGGUCCUCAGUCUIUGA | 64-82 | 62 |
| 184 | ACACAGACUGAGGACCAGC | 427 | GCUGGUCCUCAGUCUIUGU | 64-82 | 62 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corresponding Positions of Identified Sequence on SEQ ID NO: 1 | Targeted Gene Position |
|---|---|---|---|---|---|
| 185 | NCACAGACUGAGGACCAGC | 428 | GCUGGUCCUCAGUCUIUGN | 64-82 | 62 |
| 186 | NCACAGACUGAGGACCAGN | 429 | NCUGGUCCUCAGUCUIUGN | 64-82 | 62 |
| 187 | UGAAUCUGGUAGACACGGA | 430 | UCCGUGUCUACCAGAUUCA | 375-393 | 373 |
| 188 | AGAAUCUGGUAGACACGGA | 431 | UCCGUGUCUACCAGAUUCU | 375-393 | 373 |
| 189 | GGAAUCUGGUAGACACGGA | 432 | UCCGUGUCUACCAGAUUCC | 375-393 | 373 |
| 190 | NGAAUCUGGUAGACACGGA | 433 | UCCGUGUCUACCAGAUUCN | 375-393 | 373 |
| 191 | NGAAUCUGGUAGACACGGN | 434 | NCCGUGUCUACCAGAUUCN | 375-393 | 373 |
| 192 | UGAAUCUGGUAGACACGGA | 435 | UCCGUGUCUACCAIAUUCA | 375-393 | 373 |
| 193 | AGAAUCUGGUAGACACGGA | 436 | UCCGUGUCUACCAIAUUCU | 375-393 | 373 |
| 194 | GGAAUCUGGUAGACACGGA | 437 | UCCGUGUCUACCAIAUUCC | 375-393 | 373 |
| 195 | NGAAUCUGGUAGACACGGA | 438 | UCCGUGUCUACCAIAUUCN | 375-393 | 373 |
| 196 | NGAAUCUGGUAGACACGGN | 439 | NCCGUGUCUACCAIAUUCN | 375-393 | 373 |
| 197 | UAGGAAUCUGGUAGACACG | 440 | CGUGUCUACCAGAUUCCUA | 377-395 | 375 |
| 198 | AAGGAAUCUGGUAGACACG | 441 | CGUGUCUACCAGAUUCCUU | 377-395 | 375 |
| 199 | CAGGAAUCUGGUAGACACG | 442 | CGUGUCUACCAGAUUCCUG | 377-395 | 375 |
| 200 | NAGGAAUCUGGUAGACACG | 443 | CGUGUCUACCAGAUUCCUN | 377-395 | 375 |
| 201 | NAGGAAUCUGGUAGACACN | 444 | NGUGUCUACCAGAUUCCUN | 377-395 | 375 |
| 202 | UAAGCUACAGGAGAAGGUG | 445 | CACCUUCUCCUGUAGCUUA | 643-661 | 641 |
| 203 | AAAGCUACAGGAGAAGGUG | 446 | CACCUUCUCCUGUAGCUUU | 643-661 | 641 |
| 204 | GAAGCUACAGGAGAAGGUG | 447 | CACCUUCUCCUGUAGCUUC | 643-661 | 641 |
| 205 | NAAGCUACAGGAGAAGGUG | 448 | CACCUUCUCCUGUAGCUUN | 643-661 | 641 |
| 206 | NAAGCUACAGGAGAAGGUN | 449 | NACCUUCUCCUGUAGCUUN | 643-661 | 641 |
| 207 | UAAGCUACAGGAGAAGGUG | 450 | CACCUUCUCCUGUAICUUA | 643-661 | 641 |
| 208 | AAAGCUACAGGAGAAGGUG | 451 | CACCUUCUCCUGUAICUUU | 643-661 | 641 |
| 209 | GAAGCUACAGGAGAAGGUG | 452 | CACCUUCUCCUGUAICUUC | 643-661 | 641 |
| 210 | NAAGCUACAGGAGAAGGUG | 453 | CACCUUCUCCUGUAICUUN | 643-661 | 641 |
| 211 | NAAGCUACAGGAGAAGGUN | 454 | NACCUUCUCCUGUAICUUN | 643-661 | 641 |
| 212 | UCAUCCAGUGGAUUUGAGG | 455 | CCUCAAAUCCACUGGAUGA | 830-848 | 828 |
| 213 | ACAUCCAGUGGAUUUGAGG | 456 | CCUCAAAUCCACUGGAUGU | 830-848 | 828 |
| 214 | NCAUCCAGUGGAUUUGAGG | 457 | CCUCAAAUCCACUGGAUGN | 830-848 | 828 |
| 215 | NCAUCCAGUGGAUUUGAGN | 458 | NCUCAAAUCCACUGGAUGN | 830-848 | 828 |
| 216 | UCAUCCAGUGGAUUUGAGG | 459 | CCUCAAAUCCACUIGAUGA | 830-848 | 828 |
| 217 | ACAUCCAGUGGAUUUGAGG | 460 | CCUCAAAUCCACUIGAUGU | 830-848 | 828 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corre-sponding Positions of Identified Sequence on SEQ ID NO: 1 | Targeted Gene Position |
|---|---|---|---|---|---|
| 218 | NCAUCCAGUGGAUUUGAGG | 461 | CCUCAAAUCCACUIGAUGN | 830-848 | 828 |
| 219 | NCAUCCAGUGGAUUUGAGN | 462 | NCUCAAAUCCACUIGAUGN | 830-848 | 828 |
| 220 | AGUUCAGAGGCAGAAUCUA | 463 | UAGAUUCUGCCUCUGAACU | 411-429 | 409 |
| 221 | UGUUCAGAGGCAGAAUCUA | 464 | UAGAUUCUGCCUCUGAACA | 411-429 | 409 |
| 222 | NGUUCAGAGGCAGAAUCUA | 465 | UAGAUUCUGCCUCUGAACN | 411-429 | 409 |
| 223 | NGUUCAGAGGCAGAAUCUN | 466 | NAGAUUCUGCCUCUGAACN | 411-429 | 409 |
| 224 | AGUUCAGAGGCAGAAUCUA | 467 | UAGAUUCUGCCUCUIAACU | 411-429 | 409 |
| 225 | UGUUCAGAGGCAGAAUCUA | 468 | UAGAUUCUGCCUCUIAACA | 411-429 | 409 |
| 226 | NGUUCAGAGGCAGAAUCUA | 469 | UAGAUUCUGCCUCUIAACN | 411-429 | 409 |
| 227 | NGUUCAGAGGCAGAAUCUN | 470 | NAGAUUCUGCCUCUIAACN | 411-429 | 409 |
| 228 | UGAGUUCAGAGGCAGAAUC | 471 | GAUUCUGCCUCUGAACUCA | 413-431 | 411 |
| 229 | AGAGUUCAGAGGCAGAAUC | 472 | GAUUCUGCCUCUGAACUCU | 413-431 | 411 |
| 230 | NGAGUUCAGAGGCAGAAUN | 473 | GAUUCUGCCUCUGAACUCN | 413-431 | 411 |
| 231 | NGAGUUCAGAGGCAGAAUN | 474 | NAUUCUGCCUCUGAACUCN | 413-431 | 411 |
| 232 | ACCUUAUUGGGAACACCAG | 475 | CUGGUGUUCCCAAUAAGGU | 435-453 | 433 |
| 233 | UCCUUAUUGGGAACACCAG | 476 | CUGGUGUUCCCAAUAAGGA | 435-453 | 433 |
| 234 | NCCUUAUUGGGAACACCAG | 477 | CUGGUGUUCCCAAUAAGGN | 435-453 | 433 |
| 235 | NCCUUAUUGGGAACACCAN | 478 | NUGGUGUUCCCAAUAAGGN | 435-453 | 433 |
| 236 | UCACCUUAUUGGGAACACC | 479 | GGUGUUCCCAAUAAGGUGA | 437-455 | 435 |
| 237 | ACACCUUAUUGGGAACACC | 480 | GGUGUUCCCAAUAAGGUGU | 437-455 | 435 |
| 238 | CCACCUUAUUGGGAACACC | 481 | GGUGUUCCCAAUAAGGUGG | 437-455 | 435 |
| 239 | NCACCUUAUUGGGAACACC | 482 | GGUGUUCCCAAUAAGGUGN | 437-455 | 435 |
| 240 | NCACCUUAUUGGGAACACN | 483 | NGUGUUCCCAAUAAGGUGN | 437-455 | 435 |
| 241 | UCACCUUAUUGGGAACACC | 484 | GGUGUUCCCAAUAAIGUGA | 437-455 | 435 |
| 242 | ACACCUUAUUGGGAACACC | 485 | GGUGUUCCCAAUAAIGUGU | 437-455 | 435 |
| 243 | CCACCUUAUUGGGAACACC | 486 | GGUGUUCCCAAUAAIGUGG | 437-455 | 435 |
| 244 | NCACCUUAUUGGGAACACC | 487 | GGUGUUCCCAAUAAIGUGN | 437-455 | 435 |
| 245 | NCACCUUAUUGGGAACACN | 488 | NGUGUUCCCAAUAAIGUGN | 437-455 | 435 |
| 246 | UCAUCCAAGUGCCAGCUAA | 489 | UUAGCUGGCACUUGGAUGA | 495-513 | 493 |
| 247 | ACAUCCAAGUGCCAGCUAA | 490 | UUAGCUGGCACUUGGAUGU | 495-513 | 493 |
| 248 | CCAUCCAAGUGCCAGCUAA | 491 | UUAGCUGGCACUUGGAUGG | 495-513 | 493 |
| 249 | NCAUCCAAGUGCCAGCUAA | 492 | UUAGCUGGCACUUGGAUGN | 495-513 | 493 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corresponding Positions of Identified Sequence on SEQ ID NO: 1 | Targeted Gene Position |
|---|---|---|---|---|---|
| 250 | NCAUCCAAGUGCCAGCUAN | 493 | NUAGCUGGCACUUGGAUGN | 495-513 | 493 |
| 251 | UCAUCCAAGUGCCAGCUAA | 494 | UUAGCUGGCACUUIGAUGA | 495-513 | 493 |
| 252 | ACAUCCAAGUGCCAGCUAA | 495 | UUAGCUGGCACUUIGAUGU | 495-513 | 493 |
| 253 | CCAUCCAAGUGCCAGCUAA | 496 | UUAGCUGGCACUUIGAUGG | 495-513 | 493 |
| 254 | NCAUCCAAGUGCCAGCUAA | 497 | UUAGCUGGCACUUIGAUGN | 495-513 | 493 |
| 255 | NCAUCCAAGUGCCAGCUAN | 498 | NUAGCUGGCACUUIGAUGN | 495-513 | 493 |
| 256 | AGAUACUCCCUUCUCAUUA | 499 | UAAUGAGAAGGGAGUAUCU | 529-547 | 527 |
| 257 | UGAUACUCCCUUCUCAUUA | 500 | UAAUGAGAAGGGAGUAUCA | 529-547 | 527 |
| 258 | NGAUACUCCCUUCUCAUUA | 501 | UAAUGAGAAGGGAGUAUCN | 529-547 | 527 |
| 259 | NGAUACUCCCUUCUCAUUN | 502 | NAAUGAGAAGGGAGUAUCN | 529-547 | 527 |
| 260 | AGAUACUCCCUUCUCAUUA | 503 | UAAUGAGAAGGGAIUAUCU | 529-547 | 527 |
| 261 | UGAUACUCCCUUCUCAUUA | 504 | UAAUGAGAAGGGAIUAUCA | 529-547 | 527 |
| 262 | NGAUACUCCCUUCUCAUUA | 505 | UAAUGAGAAGGGAIUAUCN | 529-547 | 527 |
| 263 | NGAUACUCCCUUCUCAUUN | 506 | NAAUGAGAAGGGAIUAUCN | 529-547 | 527 |
| 264 | UCACAGAUACUCCCUUCUC | 507 | GAGAAGGGAGUAUCUGUGA | 533-551 | 531 |
| 265 | ACACAGAUACUCCCUUCUC | 508 | GAGAAGGGAGUAUCUGUGU | 533-551 | 531 |
| 266 | NCACAGAUACUCCCUUCUC | 509 | GAGAAGGGAGUAUCUGUGN | 533-551 | 531 |
| 267 | NCACAGAUACUCCCUUCUN | 510 | NAGAAGGGAGUAUCUGUGN | 533-551 | 531 |
| 268 | UCACAGAUACUCCCUUCUC | 511 | GAGAAGGGAGUAUCUIUGA | 533-551 | 531 |
| 269 | ACACAGAUACUCCCUUCUC | 512 | GAGAAGGGAGUAUCUIUGU | 533-551 | 531 |
| 270 | NCACAGAUACUCCCUUCUC | 513 | GAGAAGGGAGUAUCUIUGN | 533-551 | 531 |
| 271 | NCACAGAUACUCCCUUCUN | 514 | NAGAAGGGAGUAUCUIUGN | 533-551 | 531 |
| 272 | UGUUCGAUGAUGCUGAUGC | 515 | GCAUCAGCAUCAUCGAACA | 981-999 | 979 |
| 273 | AGUUCGAUGAUGCUGAUGC | 516 | GCAUCAGCAUCAUCGAACU | 981-999 | 979 |
| 274 | GGUUCGAUGAUGCUGAUGC | 517 | GCAUCAGCAUCAUCGAACC | 981-999 | 979 |
| 275 | NGUUCGAUGAUGCUGAUGC | 518 | GCAUCAGCAUCAUCGAACN | 981-999 | 979 |
| 276 | NGUUCGAUGAUGCUGAUGN | 519 | NCAUCAGCAUCAUCGAACN | 981-999 | 979 |
| 277 | UGUUCGAUGAUGCUGAUGC | 520 | GCAUCAGCAUCAUCIAACA | 981-999 | 979 |
| 278 | AGUUCGAUGAUGCUGAUGC | 521 | GCAUCAGCAUCAUCIAACU | 981-999 | 979 |
| 279 | GGUUCGAUGAUGCUGAUGC | 522 | GCAUCAGCAUCAUCIAACC | 981-999 | 979 |
| 280 | NGUUCGAUGAUGCUGAUGC | 523 | GCAUCAGCAUCAUCIAACN | 981-999 | 979 |
| 281 | NGUUCGAUGAUGCUGAUGN | 524 | NCAUCAGCAUCAUCIAACN | 981-999 | 979 |
| 282 | ACCUUUCCAUUCCUGUUCA | 525 | UGAACAGGAAUGGAAAGGU | 336-354 | 334 |

TABLE 2-continued

RAGE RNAi Agent Antisense Strand and Sense Strand Core Stretch Base Sequences (N = any nucleobase; I = inosine (hypoxanthine) nucleobase)

| SEQ ID NO:. | Antisense Strand Base Sequence (5'→3') (Shown as an Unmodified Nucleotide Sequence) | SEQ ID NO:. | Sense Strand Base Sequence (5'→3') (Shown as an Unmodified Nucleotide Sequence) | Corre-sponding Positions of Identified Sequence on SEQ ID NO: 1 | Targeted Gene Position |
|---|---|---|---|---|---|
| 283 | UCCUUUCCAUUCCUGUUCA | 526 | UGAACAGGAAUGGAAAGGA | 336-354 | 334 |
| 284 | NCCUUUCCAUUCCUGUUCA | 527 | UGAACAGGAAUGGAAAGGN | 336-354 | 334 |
| 285 | NCCUUUCCAUUCCUGUUCN | 528 | NGAACAGGAAUGGAAAGGN | 336-354 | 334 |
| 286 | AUAGACACGGACUCGGUAG | 529 | CUACCGAGUCCGUGUCUAA | 367-385 | 365 |
| 287 | UUAGACACGGACUCGGUAG | 530 | CUACCGAGUCCGUGUCUAU | 367-385 | 365 |
| 288 | NUAGACACGGACUCGGUAG | 531 | CUACCGAGUCCGUGUCUAN | 367-385 | 365 |
| 289 | NUAGACACGGACUCGGUAN | 532 | NUACCGAGUCCGUGUCUAN | 367-385 | 365 |
| 290 | AACAAUUUCUGGCUUCCCA | 533 | UGGGAAGCCAGAAAUUGUA | 394-412 | 392 |
| 291 | UACAAUUUCUGGCUUCCCA | 534 | UGGGAAGCCAGAAAUUGUU | 394-412 | 392 |
| 292 | NACAAUUUCUGGCUUCCCA | 535 | UGGGAAGCCAGAAAUUGUN | 394-412 | 392 |
| 293 | NACAAUUUCUGGCUUCCCN | 536 | NGGGAAGCCAGAAAUUGUN | 394-412 | 392 |
| 294 | AUACUCCCUUCUCAUUAGG | 537 | CCUAAUGAGAAGGGAGUAA | 527-545 | 525 |
| 295 | UUACUCCCUUCUCAUUAGG | 538 | CCUAAUGAGAAGGGAGUAU | 527-545 | 525 |
| 296 | NUACUCCCUUCUCAUUAGG | 539 | CCUAAUGAGAAGGGAGUAN | 527-545 | 525 |
| 297 | NUACUCCCUUCUCAUUAGN | 540 | NCUAAUGAGAAGGGAGUAN | 527-545 | 525 |

The RAGE RNAi agent sense strands and antisense strands that comprise or consist of the nucleotide sequences in Table 2 can be modified nucleotides or unmodified nucleotides. In some embodiments, the RAGE RNAi agents having the sense and antisense strand sequences that comprise or consist of any of the nucleotide sequences in Table 2 are all or substantially all modified nucleotides.

In some embodiments, the antisense strand of a RAGE RNAi agent disclosed herein differs by 0, 1, 2, or 3 nucleotides from any of the antisense strand sequences in Table 2. In some embodiments, the sense strand of a RAGE RNAi agent disclosed herein differs by 0, 1, 2, or 3 nucleotides from any of the sense strand sequences in Table 2.

In some embodiments, the antisense strand of a RAGE RNAi agent disclosed comprises at least 15 contiguous nucleotides differing by 0, 1, 2, or 3 nucleotides from any of the antisense strand sequences in Table 2. In some embodiments, the sense strand of a RAGE RNAi agent disclosed herein comprises at least 15 contiguous nucleotides differing by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified RAGE RNAi agent sense and antisense strands are provided in Table 3. Table 4. Table 5. Table 6, and Table 10. Certain modified RAGE RNAi agent antisense strands, as well as their underlying unmodified nucleobase sequences, are provided in Table 3. Certain modified RAGE RNAi agent sense strands, as well as their underlying unmodified nucleobase sequences, are provided in Tables 4, 5, and 6. In forming RAGE RNAi agents, each of the nucleotides in each of the underlying base sequences listed in Tables 3, 4, 5, and 6, as well as in Table 2, above, can be a modified nucleotide.

The RAGE RNAi agents described herein are formed by annealing an antisense strand with a sense strand. A sense strand containing a sequence listed in Table 2, Table 4, Table 5, or Table 6 can be hybridized to any antisense strand containing a sequence listed in Table 2 or Table 3, provided the two sequences have a region of at least 85% complementarity over a contiguous 16, 17, 18, 19, 20, or 21 nucleotide sequence.

In some embodiments, a RAGE RNAi agent antisense strand comprises a nucleotide sequence of any of the sequences in Table 2 or Table 3.

In some embodiments, a RAGE RNAi agent comprises or consists of a duplex having the nucleobase sequences of the sense strand and the antisense strand of any of the sequences in Table 2, Table 3, Table 4, Table 5, Table 6, or Table 10.

Examples of antisense strands containing modified nucleotides are provided in Table 3. Examples of sense strands containing modified nucleotides are provided in Tables 4, 5 and 6.

As used in Tables 3, 4, 5, 6, and 10, the following notations are used to indicate modified nucleotides, targeting groups, and linking groups:

A=adenosine-3'-phosphate
C=cytidine-3'-phosphate
G=guanosine-3'-phosphate
U=uridine-3'-phosphate
I=inosine-3'-phosphate
a=2'-O-methyladenosine-3'-phosphate
as =2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
i=2'-O-methylinosine-3'-phosphate
is=2'-O-methylinosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dT=2'-deoxythymidine-3'-phosphate
$A_{UNA}$=2',3'-seco-adenosine-3'-phosphate
$A_{UNAS}$=2',3'-seco-adenosine-3'-phosphorothioate
$C_{UNA}$=2',3'-seco-cytidine-3'-phosphate
$C_{UNAS}$=2',3'-seco-cytidine-3'-phosphorothioate
$G_{UNA}$=2',3'-seco-guanosine-3'-phosphate
$G_{UNAs}$=2',3'-seco-guanosine-3'-phosphorothioate
$U_{UNA}$=2',3'-seco-uridine-3'-phosphate
$U_{UNAS}$=2',3'-seco-uridine-3'-phosphorothioate
a_2N=see Table 11
a_2Ns=see Table 11
(invAb)=inverted abasic deoxyribonucleotide-5'-phosphate, see Table 11
(invAb)s=inverted abasic deoxyribonucleotide-5'-phosphorothioate, see Table 11
s=phosphorothioate linkage
p=terminal phosphate (as synthesized)
vpdN=vinyl phosphonate deoxyribonucleotide
cPrpa=5'-cyclopropyl phosphonate-2'-O-methyladenosine-3'-phosphate (see Table 11)
cPrpas=5'-cyclopropyl phosphonate-2'-O-methyladenosine-3'-phosphorothioate (see Table 11)
cPrpu=5'-cyclopropyl phosphonate-2'-O-methyluridine-3'-phosphate (see Table 11)
cPrpus=5'-cyclopropyl phosphonate-2'-O-methyluridine-3'-phosphorothioate (see Table 11)
(Alk-SS-C6)=see Table 11
(C6-SS-Alk)=see Table 11
(C6-SS-C6)=see Table 11
(6-SS-6)=see Table 11
(C6-SS-Alk-Me)=see Table 11
(NH2-C6)=see Table 11
(TriAlk14)=see Table 11
(TriAlk14)s=see Table 11
-C6-=see Table 11
-C6s-=see Table 11
-L6-C6-=see Table 11
-L6-C6s-=see Table 11
-Alk-cyHex-=see Table 11
-Alk-cyHexs-=see Table 11
(TA14)=see Table 11 (structure of (TriAlk14)s after conjugation)
(TA14)s=see Table 11 (structure of (TriAlk14)s after conjugation)

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3' position of the given monomer instead of a phosphate moiety ex vivo. Additionally, for the embodiments disclosed herein, when viewing the respective strand 5'→3', the inverted abasic residues are inserted such that the 3' position of the deoxyribose is linked at the 3' end of the preceding monomer on the respective strand (see, e.g., Table 11). Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the RAGE RNAi agents and compositions of RAGE RNAi agents disclosed herein.

Certain examples of targeting groups and linking groups used with the RAGE RNAi agents disclosed herein are included in the chemical structures provided below in Table 11. Each sense strand and/or antisense strand can have any targeting groups or linking groups listed herein, as well as other targeting or linking groups, conjugated to the 5' and/or 3' end of the sequence.

TABLE 3

| RAGE RNAi Agent Antisense Strand Sequences | | | | |
|---|---|---|---|---|
| AS Strand ID | Modified Antisense Strand (5'→3') | SEQ ID NO. | Underlying Base Sequence (5'→3') (Shown as an Unmodified Nucleotide Sequence) | SEQ ID NO. |
| AM10308-AS | usUfsgsUfgUfuCfaGfuUfuCfcAfuUfeCfsg | 2 | UUGUGUUCAGUUUCCAUUCCG | 7 |
| AM10309-AS | cPrpusUfsgsUfgUfuCfaGfuUfuCfcAfuUfcCfsg | 3 | UUGUGUUCAGUUUCCAUUCCG | 7 |
| AMI0311-AS | usCfsusGfuGfuUfcAfgUfuUfcCfaUfuCfsc | 543 | UCUGUGUUCAGUUUCCAUUCC | 801 |
| AM10312-AS | cPrpusCfsusGfuGfuUfcAfgUfuUfcCfaUfuCfsc | 544 | UCUGUGUUCAGUUUCCAUUCC | 801 |
| AM10314-AS | usUfsgsGfcUfuCfcCfaGfgAfaUfcUfgGfsu | 545 | UUGGCUUCCCAGGAAUCUGGU | 802 |
| AM10315-AS | cPrpusUfsgsGfcUfuCfcCfaGfgAfaUfcUfgGfsu | 546 | UUGGCUUCCCAGGAAUCUGGU | 802 |
| AM10317-AS | asCfsasAfuUfuCfuGfgCfuUfcCfcAfgGfsa | 547 | ACAAUUUCUGGCUUCCCAGGA | 803 |
| AM10318-AS | cPrpasCfsasAfuUfuCfuGfgCfuUfcCfcAfgGfsa | 548 | ACAAUUUCUGGCUUCCCAGGA | 803 |
| AM10467-AS | usUfsasCfaCfuUfcAfgCfaCfcAfgUfgGfsc | 549 | UUACACUUCAGCACCAGUGGC | 804 |
| AM10469-AS | usAfscsCfuUfcCfaAfgCfuUfcUfgUfcCfsg | 550 | UACCUUCCAAGCUUCUGUCCG | 805 |
| AM10471-AS | usCfsgsGfaAfaAfuCfcCfcUfcAfuCfcUfsg | 551 | UCGGAAAAUCCCCUCAUCCUG | 806 |
| AM10473-AS | usUfsusCfuGfgCfuUfcCfcAfgGfaAfuCfsu | 552 | UUUCUGGCUUCCCAGGAAUCU | 807 |
| AM10475-AS | usUfsgsAfgUfuCfaGfaGfgCfaGfaAfuCfsu | 553 | UUGAGUUCAGAGGCAGAAUCU | 808 |
| AM10477-AS | usCfsusAfaGfaGfuCfcCfuGfcAfgGfgUfsa | 554 | UCUAAGAGUCCCUGCAGGGUA | 809 |
| AM10479-AS | asGfscsUfaAfgAfgUfcCfcUfgCfaGfgGfsu | 555 | AGCUAAGAGUCCCUGCAGGGU | 810 |
| AM10481-AS | asAfsgsCfuAfcAfgGfaGfaAfgGfuGfgGfsa | 556 | AAGCUACAGGAGAAGGUGGGA | 811 |
| AM10483-AS | usCfsusGfaAfgCfuAfcAfgGfaGfaAfgGfsu | 557 | UCUGAAGCUACAGGAGAAGGU | 812 |
| AM10571-AS | usAfscsAfgAfcUfgAfgGfaCfcAfgCfaCfsc | 558 | UACAGACUGAGGACCAGCACC | 813 |
| AM10573-AS | usAfscsAfgAf$C_{UNA}$UfgAfgGfaCfcAfgCfaCfsc | 559 | UACAGACUGAGGACCAGCACC | 813 |
| AM10575-AS | usCfsasCfaGfaCfuGfaGfgAfcCfaGfcAfsc | 560 | UCACAGACUGAGGACCAGCAC | 814 |
| AM10717-AS | usUfsgsUfgUfuCfaGfuUfuCfcAfuUfcCfsc | 561 | UUGUGUUCAGUUUCCAUUCCG | 815 |
| AM10720-AS | usUfsgsUfgUf$U_{UNA}$CfaGfuUfuCfcAfuUfcCfsg | 562 | UUGUGUUCAGUUUCCAUUCCG | 7 |
| AM10722-AS | usUfsgsUfgUfucaguUfuCfcAfuUfcCfsg | 563 | UUGUGUUCAGUUUCCAUUCCG | 7 |
| AM10723-AS | usUfsgsuguucaguUfuCfcAfuuccsg | 564 | UUGUGUUCAGUUUCCAUUCCG | 7 |
| AM10724-AS | usUfsgsuguucaGfuUfuCfcAfuuccsg | 565 | UUGUGUUCAGUUUCCAUUCCG | 7 |
| AM10752-AS | usGfsasUfgUfuUfuGfaGfcAfcCfuAfcUfsc | 566 | UGAUGUUUUGAGCACCUACUC | 9 |
| AM10754-AS | usUfscsCfaUfuCfcUfgUfuCfaUfuGfcCfsu | 4 | UUCCAUUCCUGUUCAUUGCCU | 8 |
| AM10756-AS | usGfsasAfuCfuGfgUfaGfaCfaCfgGfaCfsu | 568 | UGAAUCUGGUAGACACGGACU | 818 |
| AM10758-AS | usAfsgsGfaAfuCfuGfgUfaGfaCfaCfgGfsa | 569 | UAGGAAUCUGGUAGACACGGA | 819 |
| AM10760-AS | usAfsasGfcUfaCfaGfgAfgAfaGfgUfgGfsg | 570 | UAAGCUACAGGAGAAGGUGGG | 820 |
| AM10762-AS | usCfsasUfcCfaGfuGfgAfuUfuGfaGfgAfsg | 571 | UCAUCCAGUGGAUUUGAGGAG | 821 |
| AM10774-AS | asGfsusUfcAfgAfgGfcAfgAfaUfcUfaCfsc | 572 | AGUUCAGAGGCAGAAUCUACC | 822 |
| AM10776-AS | usGfsasGfuUfuC$_{UNA}$AfgAfgGfcAfgAfaUfcUfsa | 573 | UGAGUUCAGAGGCAGAAUCUA | 823 |
| AM10778-AS | asCfscsUfuAfuUfgGfgAfaCfaCfcAfgCfsc | 574 | ACCUUAUUGGGAACACCAGCC | 824 |
| AM10780-AS | usCfsasCfcUfuAfuUfgGfgAfaCfaCfcAfsg | 575 | UCACCUUAUUGGGAACACCAG | 825 |
| AM10782-AS | usCfsasUfcCfaAfgUfgCfcAfgCfuAfaGfsc | 576 | UCAUCCAAGUGCCAGCUAAGC | 826 |
| AM10784-AS | asGfsasUfaCfuCfcCfuUfcUfcAfuUfaGfsg | 577 | AGAUACUCCCUUCUCAUUAGG | 827 |

TABLE 3-continued

RAGE RNAi Agent Antisense Strand Sequences

| AS Strand ID | Modified Antisense Strand (5'→3') | SEQ ID NO. | Underlying Base Sequence (5'→3') (Shown as an Unmodified Nucleotide Sequence) | SEQ ID NO. |
|---|---|---|---|---|
| AM10786-AS | usCfsasCfaGfaUfaCfuCfcCfuUfcUfcAfsc | 578 | UCACAGAUACUCCCUUCUCAC | 828 |
| AM10788-AS | usGfsusUfcGfaUfgAfuGfcUfgAfuGfcUfsg | 579 | UGUUCGAUGAUGCUGAUGCUG | 829 |
| AM11103-AS | cPrpusUfgUfgUfuCfaGfuUfuCfcAfuUfcCfsg | 580 | UUGUGUUCAGUUUCCAUUCCG | 7 |
| AM11104-AS | cPrpuUfgUfgUfuCfaGfuUfuCfcAfuUfcCfsg | 581 | UUGUGUUCAGUUUCCAUUCCG | 7 |
| AM11188-AS | cPrpusUfsgsuguucaguUfuCfcAfuuccsg | 582 | UUGUGUUCAGUUUCCAUUCCG | 7 |
| AM11190-AS | usUfsgsuguuC$_{UNA}$aguUfuCfcAfuuccsg | 583 | UUGUGUUCAGUUUCCAUUCCG | 7 |
| AMI1191-AS | usUfsgsuguU$_{UNA}$caguUfuCfcAfuuccsg | 584 | UUGUGUUCAGUUUCCAUUCCG | 7 |
| AM11192-AS | usUfsgsugU$_{UNA}$UcaguUfuCfcAfuuccsg | 585 | UUGUGUUCAGUUUCCAUUCCG | 7 |
| AM11194-AS | usUfsgsuguucaguUfuCfcAfuuccsc | 586 | UUGUGUUCAGUUUCCAUUCCG | 815 |
| AM11196-AS | usUfsgsuguucaguUfuCfcAfuuccsa | 587 | UUGUGUUCAGUUUCCAUUCCA | 830 |
| AM11757-AS | cPrpuUfguguucaguUfuCfcAfuuccsg | 588 | UUGUGUUCAGUUUCCAUUCCG | 7 |
| AM11758-AS | cPrpuUfguguU$_{UNA}$caguUfuCfcAfuuccsg | 589 | UUGUGUUCAGUUUCCAUUCCG | 7 |
| AM11759-AS | cPrpuUfguguucaguUfuCfcAfuuccsc | 590 | UUGUGUUCAGUUUCCAUUCCG | 815 |
| AM11760-AS | cPrpuUfguguU$_{UNA}$caguUfuCfcAfuuccsc | 591 | UUGUGUUCAGUUUCCAUUCCG | 815 |
| AM11761-AS | usUfsgsuguU$_{UNA}$caguUfuCfcAfuuccsc | 592 | UUGUGUUCAGUUUCCAUUCCG | 815 |
| AM11762-AS | cPrpusUfsgsuguU$_{UNA}$caguUfuCfcAfuuccsg | 593 | UUGUGUUCAGUUUCCAUUCCG | 7 |
| AM11763-AS | cPrpusUfsgsuguucaguUfuCfcAfuuccsc | 594 | UUGUGUUCAGUUUCCAUUCCC | 815 |
| AM11764-AS | cPrpusUfsgsuguU$_{UNA}$caguUfuCfcAfuuccsc | 595 | UUGUGUUCAGUUUCCAUUCCG | 815 |
| AM11889-AS | usCfscsUfuUfcCfaUfuCfcUfgUfuCfaUfsc | 596 | UCCUUUCCAUUCCUGUUCAUC | 831 |
| AMI1892-AS | usUfsasGfaCfaCfgGfaCfuCfgGfuAfgUfsc | 597 | UUAGACACGGACUCGGUAGUC | 832 |
| AM11894-AS | asUfsasCfuCfcCfuUfcUfcAfuUfaGfgCfsa | 598 | AUACUCCCUUCUCAUUAGGCA | 833 |
| AM11895-AS | cPrpusGfsasUfgUfuUfuGfaGfcAfcCfuAfcUfsc | 599 | UGAUGUUUUGAGCACCUACUC | 9 |
| AM11897-AS | usGfsasuguuuugaGfcAfcCfuacusc | 5 | UGAUGUUUUGAGCACCUACUC | 9 |
| AM11898-AS | cPrpusGfsasuguuuugaGfcAfcCfuacusc | 6 | UGAUGUUUUGAGCACCUACUC | 9 |
| AM12234-AS | cPrpusUfscsCfaUfuCfcUfgUfuCfaUfuGfcCfsu | 602 | UUCCAUUCCUGUUCAUUGCCU | 8 |
| AM12236-AS | usUfscscauuccugUfuCfaUfugccsu | 603 | UUCCAUUCCUGUUCAUUGCCU | 8 |
| AM12237-AS | cPrpusUfscscauuccugUfuCfaUfugccsu | 604 | UUCCAUUCCUGUUCAUUGCCU | 8 |
| AM12240-AS | usUfscscauU$_{UNA}$CCugUfuCfaUfugccsu | 605 | UUCCAUUCCUGUUCAUUGCCU | 8 |
| AM12241-AS | usUfscscaU$_{UNA}$UccugUfuCfaUfugccsu | 606 | UUCCAUUCCUGUUCAUUGCCU | 8 |
| AM12245-AS | usUfscscauuccugUfuCfaUfugccsc | 607 | UUCCAUUCCUGUUCAUUGCCC | 834 |
| AM12593-AS | usGfsasuguuuugaGfcAfcCfuacusg | 608 | UGAUGUUUUGAGCACCUACUG | 835 |
| AM12594-AS | usGfsasuguU$_{UNA}$UugaGfcAfcCfuacusc | 609 | UGAUGUUUUGAGCACCUACUC | 9 |
| AM12596-AS | usGfsasuguuuugaGfcAfcCfuacusa | 610 | UGAUGUUUUGAGCACCUACUA | 836 |
| AM12755-AS | usUfscsCfaUfuccugUfuCfaUfuGfccsu | 611 | UUCCAUUCCUGUUCAUUGCCU | 8 |
| AM12756-AS | cPrpusUfscsCfaUfuccugUfuCfaUfuGfccsu | 612 | UUCCAUUCCUGUUCAUUGCCU | 8 |
| AM12757-AS | cPrpuUfcCfaUfuccugUfuCfaUfuGfccsu | 613 | UUCCAUUCCUGUUCAUUGCCU | 8 |

TABLE 3-continued

| RAGE RNAi Agent Antisense Strand Sequences | | | | |
|---|---|---|---|---|
| AS Strand ID | Modified Antisense Strand (5'→3') | SEQ ID NO. | Underlying Base Sequence (5'→3') (Shown as an Unmodified Nucleotide Sequence) | SEQ ID NO. |
| AM14090-AS | usUfsgsUfguucaguUfuCfcAfuuccsg | 614 | UUGUGUUCAGUUUCCAUUCCG | 7 |
| AM14091-AS | usUfsgsuguUfcaguUfuCfcAfuuccsg | 615 | UUGUGUUCAGUUUCCAUUCCG | 7 |
| AM14093-AS | usGfsasUfguuuugaGfcAfcCfuacusc | 616 | UGAUGUUUUGAGCACCUACUC | 9 |
| AM14094-AS | usGfsasuguuuugaGfcAfcCfuAfcusc | 617 | UGAUGUUUUGAGCACCUACUC | 9 |
| AM14095-AS | usGfsasuguUfuugaGfcAfcCfuacusc | 618 | UGAUGUUUUGAGCACCUACUC | 9 |
| AMI5021-AS | cPrpusUfsgsuguucaguUfuCfcAfuuccsa | 619 | UUGUGUUCAGUUUCCAUUCCA | 830 |
| AM15767-AS | cPrpusAfscsAfaUfuucugGfcUfuCfcCfagsg | 620 | UACAAUUUCUGGCUUCCCAGG | 837 |
| AM15770-AS | cPrpusCfsusGfuGfuucagUfuUfcCfaUfucsc | 621 | UCUGUGUUCAGUUUCCAUUCC | 801 |

TABLE 4

| RAGE RNAi Agent Sense Strand Sequences (Shown Without Linkers, Conjugated Targeting Ligands, or Capping Moieties) | | | | |
|---|---|---|---|---|
| Strand ID | Modified Sense Strand (5'→3') | SEQ ID NO. | Underlying Base Sequence (5'→3') (Shown as an Unmodified Nucleotide Sequence) | SEQ ID NO. |
| AM10307-SS-NL | csggaauggAfAfAfcugaacacaa | 13 | CGGAAUGGAAACUGAACACAA | 19 |
| AM10310-SS-NL | gsgaauggaAfAfCfugaacacaia | 623 | GGAAUGGAAACUGAACACAIA | 839 |
| AM10313-SS-NL | asccagauuCfCfUfgggaaiccaa | 624 | ACCAGAUUCCUGGGAAICCAA | 840 |
| AM10316-SS-NL | usccugggaAfGfCfcagaaauugu | 625 | UCCUGGGAAGCCAGAAAUUGU | 841 |
| AM10466-SS-NL | gsccacuggUfGfCfugaaguguaa | 626 | GCCACUGGUGCUGAAGUGUAA | 842 |
| AM10468-SS-NL | csggacagaAfGfCfuuggaagiua | 627 | CGGACAGAAGCUUGGAAGIUA | 843 |
| AM10470-SS-NL | csaggaugaGfGfGfgauuuuccia | 628 | CAGGAUGAGGGGAUUUUCCIA | 844 |
| AM10472-SS-NL | asgauuccuGfGfGfaagcuagaaa | 629 | AGAUUCCUGGGAAGCUAGAAA | 845 |
| AM10474-SS-NL | a_2NsgauucugCfCfUfcugaacucaa | 630 | $(A^{2N})$ GAUUCUGCCUCUGAACUCAA | 846 |
| AM10476-SS-NL | usacccugcAfGfGfgacucuuaga | 631 | UACCCUGCAGGGACUCUUAGA | 847 |
| AM10478-SS-NL | ascccugcaGfGfGfacucuuaicu | 632 | ACCCUGCAGGGACUCUUAICU | 848 |
| AM10480-SS-NL | uscccaccuUfCfUfccuguaicuu | 633 | UCCCACCUUCUCCUGUAICUU | 849 |
| AM10482-SS-NL | asccuucucCfUfGfuagcuucaia | 634 | ACCUUCUCCUGUAGCUUCAIA | 850 |
| AM10570-SS-NL | gsgugcuggUfCfCfucagucuiua | 635 | GGUGCUGGUCCUCAGUCUIUA | 851 |
| AM10572-SS-NL | gsgugcuggUfCfCfucagucugua | 636 | GGUGCUGGUCCUCAGUCUGUA | 852 |
| AM10574-SS-NL | gsugcugguCfCfUfcagucuguia | 637 | GUGCUGGUCCUCAGUCUGUIA | 853 |
| AM10576-SS-NL | gsugcugguCfCfUfcagucuiuga | 638 | GUGCUGGUCCUCAGUCUIUGA | 854 |
| AM10644-SS-NL | csggaauggAfAfAfcugaacacaa | 13 | CGGAAUGGAAACUGAACACAA | 19 |
| AM10716-SS-NL | gsggaauggAfAfAfcugaacacaa | 640 | GGGAAUGGAAACUGAACACAA | 855 |
| AM10718-SS-NL | csggaauggAfAfAfcuiaacacaa | 641 | CGGAAUGGAAACUIAACACAA | 856 |
| AM10719-SS-NL | csggaauggAfa_2NAfcuiaacacaa | 642 | CGGAAUGGA$(A^{2N})$ACUIAACACAA | 857 |
| AM10721-SS-NL | csggaauggAfAfAfcugaauacaa | 643 | CGGAAUGGAAACUGAACACAA | 858 |
| AM10725-SS-NL | csggaauGfgAfaAfcugaacacaa | 644 | CGGAAUGGAAACUGAACACAA | 19 |

TABLE 4-continued

RAGE RNAi Agent Sense Strand Sequences (Shown Without Linkers, Conjugated Targeting Ligands, or Capping Moieties)

| Strand ID | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM10737-SS-NL | usccugggaAfGfCfcagaaauugu | 645 | UCCUGGGAAGCCAGAAAUUGU | 841 |
| AM10751-SS-NL | gsaguagguGfCfUfcaaaacauca | 646 | GAGUAGGUGCUCAAAACAUCA | 20 |
| AM10753-SS-NL | asggcaaugAfAfCfaggaauigaa | 15 | AGGCAAUGAACAGGAAUIGAA | 21 |
| AM10755-SS-NL | asguccgugUfCfUfaccaiauuca | 648 | AGUCCGUGUCUACCAIAUUCA | 861 |
| AM10757-SS-NL | usccgugucUfAfCfcagauuccua | 649 | UCCGUGUCUACCAGAUUCCUA | 862 |
| AM10759-SS-NL | csccaccuuCfUfCfcuguaicuua | 650 | CCCACCUUCUCCUGUAICUUA | 863 |
| AM10761-SS-NL | csuccucaaAfUfCfcacuigauga | 651 | CUCCUCAAAUCCACUIGAUGA | 864 |
| AM10773-SS-NL | gsguagauuCfUfGfccucuiaacu | 652 | GGUAGAUUCUGCCUCUIAACU | 865 |
| AM10775-SS-NL | usagauucuGfCfCfucugaacuca | 653 | UAGAUUCUGCCUCUGAACUCA | 866 |
| AM10777-SS-NL | gsgcuggugUfUfCfccaauaaggu | 654 | GGCUGGUGUUCCCAAUAAGGU | 867 |
| AM10779-SS-NL | csugguguuCfCfCfaauaagiuga | 655 | CUGGUGUUCCCAAUAAGIUGA | 868 |
| AM10781-SS-NL | gscuuagcuGfGfCfacuuigauga | 656 | GCUUAGCUGGCACUUIGAUGA | 869 |
| AM10783-SS-NL | cscuaaugaGfAfAfgggaiuaucu | 657 | CCUAAUGAGAAGGGAIUAUCU | 870 |
| AM10785-SS-NL | gsugagaagGfGfAfguaucuiuga | 658 | GUGAGAAGGGAGUAUCUIUGA | 871 |
| AM10787-SS-NL | csagcaucaGfCfAfucauciaaca | 659 | CAGCAUCAGCAUCAUCIAACA | 872 |
| AM11105-SS-NL | cggaauggAfAfAfcugaacacaa | 660 | CGGAAUGGAAACUGAACACAA | 19 |
| AM11106-SS-NL | csggaauggAfAfAfcugaacacaa | 13 | CGGAAUGGAAACUGAACACAA | 19 |
| AM11107-SS-NL | cggaauggAfAfAfcugaacacaa | 662 | CGGAAUGGAAACUGAACACAA | 19 |
| AM11189-SS-NL | csggaauGfgAfaAfcugaauacaa | 663 | CGGAAUGGAAACUGAACACAA | 858 |
| AM11193-SS-NL | gsggaauGfgAfaAfcugaacacaa | 664 | GGGAACGGAAACCGAACACAA | 855 |
| AM11195-SS_NL | usggaauGfgAfaAfcugaacacaa | 665 | CGGAAUGGAAACUGAACACAA | 873 |
| AM11197-SS-NL | csggaauGfgAfa_2NAfcugaacacaa | 666 | CGGAAUGGA(A$^{2N}$)ACUGAACACAA | 874 |
| AM11512-SS-NL | cggaauggAfAfAfcugaacacaa | 667 | CGGAAUGGAAACUGAACACAA | 19 |
| AM11513-SS-NL | csggaauggAfAfAfcugaacacaa | 13 | CGGAAUGGAAACUGAACACAA | 19 |
| AM11514-SS-NL | csggaauggAfAfAfcugaacacaa | 13 | CGGAAUGGAAACUGAACACAA | 19 |
| AM11515-SS-NL | cggaauggAfAfAfcugaacacaa | 670 | CGGAAUGGAAACUGAACACAA | 19 |
| AM11516-SS-NL | csggaauggAfAfAfcugaacacaa | 13 | CGGAAUGGAAACUGAACACAA | 19 |
| AM11517-SS-NL | cggaauggAfAfAfcugaacacaa | 672 | CGGAAUGGAAACUGAACACAA | 19 |
| AM11888-SS-NL | gsaugaacaGfGfAfauggaaagga | 673 | GAUGAACAGGAAUGGAAAGGA | 875 |
| AM11890-SS-NL | gsaugaacaGfGfAfauggaaagia | 674 | GAUGAACAGGAAUGGAAAGIA | 876 |
| AM11891-SS-NL | gsacuaccgAfGfUfccgugucuaa | 675 | GACUACCGAGUCCGUGUCUAA | 877 |
| AM11893-SS-NL | usgccuaauGfAfGfaagggaguau | 676 | UGCCUAAUGAGAAGGGAGUAU | 878 |
| AM11896-SS-NL | gsaguagguGfcUfcAfaaacauca | 677 | GAGUAGGUGCUCAAAACAUCA | 20 |
| AM11899-SS-NL | gsaguagiuGfcUfcAfaaacauca | 678 | GAGUAGIUGCUCAAAACAUCA | 879 |
| AM11900-SS-NL | gsaguagGfuGfcUfcaaaacauca | 14 | GAGUAGGUGCUCAAAACAUCA | 20 |
| AM11901-SS-NL | gsaguagguGfcUfcaaaacauca | 680 | GAGUAGGUGCUCAAAACAUCA | 20 |

TABLE 4-continued

RAGE RNAi Agent Sense Strand Sequences (Shown Without Linkers, Conjugated Targeting Ligands, or Capping Moieties)

| Strand ID | Modified Sense Strand (5'→3') | SEQ ID NO. | Underlying Base Sequence (5'→3') (Shown as an Unmodified Nucleotide Sequence) | SEQ ID NO. |
|---|---|---|---|---|
| AM12235-SS-NL | asggcaaUfgAfaCfaggaauigaa | 681 | AGGCAAUGAACAGGAAUIGAA | 21 |
| AM12238-SS-NL | asggcaaUfgAfaCfaggaauggaa | 682 | AGGCAAUGAACAGGAAUGGAA | 880 |
| AM12239-SS-NL | asggcaaUfgAfaCfaggaaugiaa | 683 | AGGCAAUGAACAGGAAUGIAA | 881 |
| AM12242-SS-NL | asggcaaUfgAfaCfagiaauggaa | 684 | AGGCAAUGAACAGIAAUGGAA | 882 |
| AM12243-SS-NL | asggcaaUfgAfaCfaigaauggaa | 685 | AGGCAAUGAACAIGAAUGGAA | 883 |
| AM12244-SS-NL | gsggcaaUfgAfaCfaggaauigaa | 686 | GGGCAAUGAACAGGAAUIGAA | 884 |
| AM12592-SS-NL | csaguagGfuGfcUfcaaaacauca | 687 | GAGUAGGUGCUCAAAACAUCA | 885 |
| AM12595-SS-NL | usa_2NguagGfuGfcUfcaaaacauca | 688 | U($A^{2N}$)GUAGGUGCUCAAAACAUCA | 886 |
| AM12597-SS-NL | gsaguagguGfcUfCfaaaacauca | 689 | GAGUAGGUGCUCAAAACAUCA | 20 |
| AM12754-SS-NL | asggcaaugAfAfCfaggaauggaa | 690 | AGGCAAUGAACAGGAAUGGAA | 880 |
| AM12910-SS-NL | gsaguagGfuGfcUfcaaaacauca | 14 | GAGUAGGUGCUCAAAACAUCA | 20 |
| AM12911-SS-NL | asggcaaugAfAfCfaggaauigaa | 15 | AGGCAAUGAACAGGAAUIGAA | 21 |
| AM13987-SS-NL | csggaauggAfAfAfcugaacacaa | 13 | CGGAAUGGAAACUGAACACAA | 19 |
| AM14092-SS-NL | csggaauggAfaAfcUfgaacacaa | 694 | CGGAAUGGAAACUGAACACAA | 19 |
| AM15766-SS-NL | cscugggaaGfCfCfagaaauugua | 695 | CCUGGGAAGCCAGAAAUUGUA | 887 |
| AM16133-SS-NL | csggaauggAfAfAfcugaacacaa | 13 | CGGAAUGGAAACUGAACACAA | 19 |

($A^{2N}$) = 2-aminoadenine-containing nucleotide; 1 = hypoxanthine (inosine) nucleotide}

TABLE 5

RAGE RNAi Agent Sense Strand Sequences (Shown With TriAlk14 Linker (see Table 11 for structure information)).

| Strand ID | Modified Sense Strand (5'→3') | SEQ ID NO. | Underlying Base Sequence TriAlk14 (Shown as an Unmodified Nucleotide Sequence) | SEQ ID NO. |
|---|---|---|---|---|
| AM10307-SS | (TriAlk14)csggaauggAfAfAfcugaacacaas(invAb) | 16 | CGGAAUGGAAACUGAACACAA | 19 |
| AM10310-SS | (TriAlk14)gsgaauggaAfAfCfugaacacaias(invAb) | 698 | GGAAUGGAAACUGAACACAIA | 839 |
| AM10313-SS | (TriAlk14)asccagauuCfCfUfgggaaiccaas(invAb) | 699 | ACCAGAUUCCUGGGAAICCAA | 840 |
| AM10316-SS | (TriAik14)usccugggaAfGfCfcagaaauugus(invAb) | 700 | UCCUGGGAAGCCAGAAAUUGU | 841 |
| AM10466-SS | (TriAlk14)gsccacuggUfGfCfugaaguguaas(invAb) | 701 | GCCACUGGUGCUGAAGUGUAA | 842 |
| AM10468-SS | (TriAik14)csggacagaAfGfCfuuggaagiuas(invAb) | 702 | CGGACAGAAGCUUGGAAGIUA | 843 |
| AM10470-SS | (TriAik14)csaggaugaGfGfGfgauuuuccias(invAb) | 703 | CAGGAUGAGGGGAUUUUCCIA | 844 |
| AM10472-SS | (TriAlk14)asgauuccuGfGfGfaagcuagaaas(invAb) | 704 | AGAUUCCUGGGAAGCUAGAAA | 845 |
| AM10474-SS | (TriAlk14)a_2NsgauucugCfCfUfcugaacucaas(invAb) | 705 | ($A^{2N}$)GAUUCUGCCUCUGAACUCAA | 846 |
| AM10476-SS | (TriAlk14)usacccugcAfGfGfgacucuuagas(invAb) | 706 | UACCCUGCAGGGACUCUUAGA | 847 |
| AM10478-SS | (TriAik14)ascccugcaGfGfGfacucuuaicus(invAb) | 707 | ACCCUGCAGGGACUCUUAICU | 848 |
| AM10480-SS | (TriAlk14)uscccaccuUfCfUfccuguaicuus(invAb) | 708 | UCCCACCUUCUCCUGUAICUU | 849 |
| AM10482-SS | (TriAlk14)asccuucucCfUfGfuagcuucaias(invAb) | 709 | ACCUUCUCCUGUAGCUUCAIA | 850 |
| AM10570-SS | (TriAlk14)gsgugcuggUfCfCfucagucuiuas(invAb) | 710 | GGUGCUGGUCCUCAGUCUIUA | 851 |
| AM10572-SS | (TriAlk14)gsgugcuggUfCfCfucagucuguas(invAb) | 711 | GGUGCUGGUCCUCAGUCUGUA | 852 |
| AM10574-SS | (TriAlk14)gsugcugguCfCfUfcagucuguias(invAb) | 712 | GUGCUGGUCCUCAGUCUGUIA | 853 |
| AM10576-SS | (TriAlk14)gsugcugguCfCfUfcagucuiugas(invAb) | 713 | GUGCUGGUCCUCAGUCUIUGA | 854 |
| AM10644-SS | (TriAlk14)csggaauggAfAfAfcugaacacaas(invAb) | 16 | CGGAAUGGAAACUGAACACAA | 19 |
| AM10716-SS | (TriAik14)gsggaauggAfAfAfcugaacacaas(invAb) | 715 | GGGAAUGGAAACUGAACACAA | 855 |
| AM10718-SS | (TriAlk14)csggaauggAfAfAfcuiaacacaas(invAb) | 716 | CGGAAUGGAAACUIAACACAA | 856 |
| AM10719-SS | (TriAlk14)csggaauggAfa_2NAfcuiaacacaas(invAb) | 717 | CGGAAUGGA($A^{2N}$)ACUIAACACAA | 857 |
| AM10721-SS | (TriAlk14)csggaauggAfAfAfcugaauacaas(invAb) | 718 | CGGAAUGGAAACUGAAUACAA | 858 |

TABLE 5-continued

RAGE RNAi Agent Sense Strand Sequences (Shown With TriAlk14 Linker (see Table 11 for structure information)).

| Strand ID | Modified Sense Strand (5'→3') | SEQ ID NO. | Underlying Base Sequence TriAlk14 (Shown as an Unmodified Nucleotide Sequence) | SEQ ID NO. |
|---|---|---|---|---|
| AM10725-SS | (TriAik14)csggaauGfgAfaAfcugaacacaas(invAb) | 719 | CGGAAUGGAAACUGAACACAA | 19 |
| AM10737-SS | (TriAik14)usccugggaAfGfCfcagaaauugus(invAb) | 720 | UCCUGGGAAGCCAGAAAUUGU | 841 |
| AM10751-SS | (TriAlk14)gsaguagguGfCfUfcaaaacaucas(invAb) | 721 | GAGUAGGUGCUCAAAACAUCA | 20 |
| AM10753-SS | (TriAlk14)asggcaaugAfAfCfaggaauigaas(invAb) | 18 | AGGCAAUGAACAGGAAUIGAA | 21 |
| AM10755-SS | (TriAlk14)asguccgugUfCfUfaccaiauucas(invAb) | 723 | AGUCCGUGUCUACCAIAUUCA | 861 |
| AM10757-SS | (TriAlk14)usccgugucUfAfCfcagauuccuas(invAb) | 724 | UCCGUGUCUACCAGAUUCCUA | 862 |
| AM10759-SS | (TriAlk14)csccaccuuCfUfCfcuguaicuuas(invAb) | 725 | CCCACCUUCUCCUGUAICUUA | 863 |
| AM10761-SS | (TriAlk14)csuccucaaAfUfCfcacuigaugas(invAb) | 726 | CUCCUCAAAUCCACUIGAUGA | 864 |
| AM10773-SS | (TriAlk14)gsguagauuCfUfGfccucuiaacus(invAb) | 727 | GGUAGAUUCUGCCUCUIAACU | 865 |
| AM10775-SS | (TriAik14)usagauucuGfCfCfucugaacucas(invAb) | 728 | UAGAUUCUGCCUCUGAACUCA | 866 |
| AM10777-SS | (TriAlk14)gsgcuggugUfUfCfccaauaaggus(invAb) | 729 | GGCUGGUGUUCCCAAUAAGGU | 867 |
| AM10779-SS | (TriAlk14)csugguguuCfCfCfaauaagiugas(invAb) | 730 | CUGGUGUUCCCAAUAAGIUGA | 868 |
| AM10781-SS | (TriAik14)gscuuagcuGfGfCfacuuigaugas(invAb) | 731 | GCUUAGCUGGCACUUIGAUGA | 869 |
| AM10783-SS | (TriAik14)cscuaaugaGfAfAfgggaiuaucus(invAb) | 732 | CCUAAUGAGAAGGGAIUAUCU | 870 |
| AM10785-SS | (TriAik14)gsugagaagGfGfAfguaucuiugas(invAb) | 733 | GUGAGAAGGGAGUAUCUIUGA | 871 |
| AM10787-SS | (TriAlk14)csagcaucaGfCfAfucauciaacas(invAb) | 734 | CAGCAUCAGCAUCAUCIAACA | 872 |
| AM11105-SS | (TriAik14)cggaauggAfAfAfcugaacacaas(invAb) | 735 | CGGAAUGGAAACUGAACACAA | 19 |
| AM11106-SS | (TriAlk14)csggaauggAfAfAfcugaacacaa(invAb) | 736 | CGGAAUGGAAACUGAACACAA | 19 |
| AM11107-SS | (TriAik14)cggaauggAfAfAfcugaacacaa(invAb) | 737 | CGGAAUGGAAACUGAACACAA | 19 |
| AM11189-SS | (TriAik14)csggaauGfgAfaAfcugaauacaas(invAb) | 738 | CGGAAUGGAAACUGAAUACAA | 858 |
| AM11193-SS | (TriAik14)gsggaauGfgAfaAfcugaacacaas(invAb) | 739 | CGGAAUGGAAACUGAACACAA | 855 |
| AM11195-SS | (TriAik14)usggaauGfgAfaAfcugaacacaas(invAb) | 740 | CGGAAUGGAAACUGAACACAA | 873 |
| AM11197-SS | (TriAlk14)csggaauGfgAfa_2NAfcugaacacaas(invAb) | 741 | CGGAAUGGA($A^{2N}$)ACUGAACACAA | 874 |

TABLE 5-continued

RAGE RNAi Agent Sense Strand Sequences (Shown With TriAlk14 Linker (see Table 11 for structure information)).

| Strand ID | Modified Sense Strand (5'→3') | SEQ ID NO. | Underlying Base Sequence TriAlk14 (Shown as an Unmodified Nucleotide Sequence) | SEQ ID NO. |
|---|---|---|---|---|
| AM11512-SS | (TriAik14)cggaauggAfAfAfcugaacacaas(invAb) | 742 | CGGAAUGGAAACUGAACACAA | 19 |
| AM11513-SS | (TriAlk14)csggaauggAfAfAfcugaacacaas(invAb) | 16 | CGGAAUGGAAACUGAACACAA | 19 |
| AM11514-SS | (TriAlk14)csggaauggAfAfAfcugaacacaas(invAb) | 16 | CGGAAUGGAAACUGAACACAA | 19 |
| AM11515-SS | (TriAlk14)cggaauggAfAfAfcugaacacaas(invAb) | 745 | CGGAAUGGAAACUGAACACAA | 19 |
| AM11516-SS | (TriAlk14)csggaauggAfAfAfcugaacacaas(invAb) | 16 | CGGAAUGGAAACUGAACACAA | 19 |
| AM11517-SS | (TriAlk14)cggaauggAfAfAfcugaacacaas(invAb) | 747 | CGGAAUGGAAACUGAACACAA | 19 |
| AM11888-SS | (TriAik14)gsaugaacaGfGfAfauggaaaggas(invAb) | 748 | GAUGAACAGGAAUGGAAAGGA | 875 |
| AM11890-SS | (TriAlk14)gsaugaacaGfGfAfauggaaagias(invAb) | 749 | GAUGAACAGGAAUGGAAAGIA | 876 |
| AM11891-SS | (TriAlk14)gsacuaccgAfGfUfccgugucuaas(invAb) | 750 | GACUACCGAGUCCGUGUCUAA | 877 |
| AM11893-SS | (TriAik14)usgccuaauGfAfGfaagggaguaus(invAb) | 751 | UGCCUAAUGAGAAGGGAGUAU | 878 |
| AM11896-SS | (TriAik14)gsaguagguGfcUfcAfaaacaucas(invAb) | 752 | GAGUAGGUGCUCAAAACAUCA | 20 |
| AM11899-SS | (TriAlk14)gsaguagiuGfcUfcAfaaacaucas(invAb) | 753 | GAGUAGIUGCUCAAAACAUCA | 879 |
| AM11900-SS | (TriAlk14)gsaguagGfuGfcUfcaaaacaucas(invAb) | 17 | GAGUAGGUGCUCAAAACAUCA | 20 |
| AM11901-SS | (TriAlk14)gsaguagguGfcUfcaaaacaucas(invAb) | 755 | GAGUAGGUGCUCAAAACAUCA | 20 |
| AM12235-SS | (TriAlk14)asggcaaUfgAfaCfaggaauigaas(invAb) | 756 | AGGCAAUGAACAGGAAUIGAA | 21 |
| AM12238-SS | (TriAik14)asggcaaUfgAfaCfaggaauggaas(invAb) | 757 | AGGCAAUGAACAGGAAUGGAA | 880 |

TABLE 5-continued

| RAGE RNAi Agent Sense Strand Sequences (Shown With TriAlk14 Linker (see Table 11 for structure information)). | | | | |
|---|---|---|---|---|
| Strand ID | Modified Sense Strand (5'→3') | SEQ ID NO. | Underlying Base Sequence TriAlk14 (Shown as an Unmodified Nucleotide Sequence) | SEQ ID NO. |
| AM12239-SS | (TriAlk14)asggcaaUfgAfaCfaggaaugiaas(invAb) | 758 | AGGCAAUGAACAGGAAUGIAA | 881 |
| AM12242-SS | (TriAlk14)asggcaaUfgAfaCfagiaauggaas(invAb) | 759 | AGGCAAUGAACAGIAAUGGAA | 882 |
| AM12243-SS | (TriAlk14)asggcaaUfgAfaCfaigaauggaas(invAb) | 760 | AGGCAAUGAACAIGAAUGGAA | 883 |
| AM12244-SS | (TriAlk14)gsggcaaUfgAfaCfaggaauigaas(invAb) | 761 | GGGCAAUGAACAGGAAUIGAA | 884 |
| AM12592-SS | (TriAlk14)csaguagGfuGfcUfcaaaacaucas(invAb) | 762 | GAGUAGGUGCUCAAAACAUCA | 885 |
| AM12595-SS | (TriAlk14)usa_2NguagGfuGfcUfcaaaacaucas(invAb) | 763 | U($A^{2N}$)GUAGGUGCUCAAAACAUCA | 886 |
| AM12597-SS | (TriAik14)gsaguagguGfcUfCfaaaacaucas(invAb) | 764 | GAGUAGGUGCUCAAAACAUCA | 20 |
| AM12754-SS | (TriAlk14)asggcaaugAfAfCfaggaauggaas(invAb) | 765 | AGGCAAUGAACAGGAAUGGAA | 880 |
| AM12910-SS | (TriAlk14)gsaguagGfuGfcUfcaaaacaucas(invAb) | 17 | GAGUAGGUGCUCAAAACAUCA | 20 |
| AM12911-SS | (TriAik14)asggcaaugAfAfCfaggaauigaas(invAb) | 18 | AGGCAAUGAACAGGAAUIGAA | 21 |
| AM13987-SS | (TriAik14)csggaauggAfAfAfcugaacacaas(invAb) | 16 | CGGAAUGGAAACUGAACACAA | 19 |
| AM14092-SS | (TriAlk14)csggaauggAfaAfcUfgaacacaas(invAb) | 769 | CGGAAUGGAAACUGAACACAA | 19 |
| AM15766-SS | (TriAlk14)cscugggaaGfCfCfagaaauuguas(invAb) | 770 | CCUGGGAAGCCAGAAAUUGUA | 887 |
| AM16133-SS | (TriAlk14)scsggaauggAfAfAfcugaacacaas(invAb) | 771 | CGGAAUGGAAACUGAACACAA | 19 |

($A^{2N}$) = 2-aminoadenine-containing nucleotide; 1 = hypoxanthine (inosine) nucleotide}

TABLE 6

RAGE RNAi Agent Sense Strand Sequences (Shown with Targeting Ligand Conjugate. The structure of avβ6-SM6.1 is shown in Table 11, and the structure of Tri-SM6.1-avβ6-(TA14) is shown in FIG. 1.)

| Strand ID | Modified Sense Strand (5'→3') | SEQ ID NO. | Corresponding Sense Strand AM Number Without Linker or Conjugate (See Table 4) |
|---|---|---|---|
| CS000363 | Tri-SM6.1-avβ6-(TA14)csggaauggAfAfAfcugaacacaas(invAb) | 10 | AM10307-SS-NL |
| CS000368 | Tri-SM6.1-avβ6-(TA14)cggaauggAfAfAfcugaacacaas(invAb) | 773 | AM11105-SS-NL |
| CS000369 | Tri-SM6.1-avβ6-(TA14)csggaauggAfAfAfcugaacacaa(invAb) | 774 | AM11106-SS-NL |
| CS000386 | Tri-SM6.1-avβ6-(TA14)cggaauggAfAfAfcugaacacaa(invAb) | 775 | AM11107-SS-NL |
| CS000497 | Tri-SM6.1-avβ6-(TA14)csggaauGfgAfaAfcugaauacaas(invAb) | 776 | AM11189-SS-NL |
| CS000499 | Tri-SM6.1-avβ6-(TA14)csggaauGfgAfaAfcugaacacaas(invAb) | 777 | AM10725-SS-NL |
| CS000503 | Tri-SM6.1-avβ6-(TA14)gsggaauGfgAfaAfcugaacacaas(invAb) | 778 | AM11193-SS-NL |
| CS000505 | Tri-SM6.1-avβ6-(TA14)usggaauGfgAfaAfcugaacacaas(invAb) | 779 | AM11195-SS-NL |
| CS000507 | Tri-SM6.1-avβ6-(TA14)csggaauGfgAfa_2NAfcugaacacaas(invAb) | 780 | AM11197-SS-NL |
| CS000531 | Tri-SM6.1-avβ6-(TA14)csggaauggAfAfAfcugaauacaas(invAb) | 781 | AM10721-SS-NL |
| CS000672 | avβ6-SM6.1-L6-C6-csggaauggAfAfAfcugaacacaas(invAb) | 782 | AM11514-SS-NL |
| CS000673 | avβ6-SM6.1-L6-C6s-(invAb)scggaauggAfAfAfcugaacacaas(invAb) | 783 | AM11515-SS-NL |
| CS000674 | avβ6-SM6.1-Alk-cyHex-csggaauggAfAfAfcugaacacaas(invAb) | 784 | AM11516-SS-NL |
| CS000675 | avβ6-SM6.1-Alk-cyHexs-(invAb)scggaauggAfAfAfcugaacacaas (invAb) | 785 | AM11517-SS-NL |
| CS000690 | avβ6-pep1-C6-csggaauggAfAfAfcugaacacaas(invAb) | 786 | AM11514-SS-NL |
| CS000691 | avβ6-pep1-C6s-(invAb)scggaauggAfAfAfcugaacacaas(invAb) | 787 | AM11515-SS-NL |
| CS000986 | Tri-SM6.1-avβ6-(TA14)gsggaauggAfAfAfcugaacacaas(invAb) | 788 | AM10716-SS-NL |
| CS000988 | Tri-SM6.1-avβ6-(TA14)csggaauggAfAfAfcuiaacacaas(invAb) | 789 | AM10718-SS-NL |
| CS000989 | Tri-SM6.1-avβ6-(TA14)csggaauggAfa_2NAfcuiaacacaas(invAb) | 790 | AM10719-SS-NL |
| CS001021 | Tri-SM6.1-avβ6-(TA14)gsgaauggaAfAfCfugaacacaias(invAb) | 791 | AM10310-SS-NL |
| CS001024 | Tri-SM6.1-avβ6-(TA14)asccagauuCfCfUfgggaaiccaas(invAb) | 792 | AM10313-SS-NL |
| CS001027 | Tri-SM6.1-avβ6-(TA14)usccugggaAfGfCfcagaaauugus(invAb) | 793 | AM10316-SS-NL |
| CS001579 | Tri-SM6.1-avβ6-(TA14)gsaguagGfuGfcUfcaaaacaucas(invAb) | 11 | AM12910-SS-NL |
| CS001582 | Tri-SM6.1-avβ6-(TA14)asggcaaugAfAfCfaggaauigaas(invAb) | 12 | AM12911-SS-NL |
| CS002138 | Tri-SM6.1-avβ6-(TA14)csggaauggAfaAfcUfgaacacaas(invAb) | 796 | AM14092-SS-NL |
| CS002399 | Tri-SM6.1-avβ6-(TA14)gsaguagGfuGfcUfcaaaacauca(invAb) | 797 | AM12910-SS-NL |
| CS002976 | Tri-SM6.1-avβ6-(TA14)cscugggaaGfCfCfagaaauuguas(invAb) | 798 | AM15766-SS-NL |
| CS003048 | Tri-SM6.1-avβ6-(TA14)scsggaauggAfAfAfcugaacacaas(invAb) | 799 | AM10307-SS-NL |

The RAGE RNAi agents disclosed herein are formed by annealing an antisense strand with a sense strand. A sense strand containing a sequence listed in Table 2, Table 4, Table 5, or Table 6 can be hybridized to any antisense strand containing a sequence listed in Table 2 or Table 3, provided the two sequences have a region of at least 85% complementarity over a contiguous 15, 16, 17, 18, 19, 20, or 21 nucleotide sequence.

As shown in Table 5 above, certain of the example RAGE RNAi agent nucleotide sequences are shown to further include reactive linking groups at one or both of the 5' terminal end and the 3' terminal end of the sense strand. For example, many of the RAGE RNAi agent sense strand sequences shown in Table 5 above have a (TriAlk14) linking group at the 5' end of the nucleotide sequence. Other linking groups, such as an (NH2-C6) linking group or a (6-SS-6) or (C6-SS-C6) linking group, may be present as well or alternatively in certain embodiments. Such reactive linking groups are positioned to facilitate the linking of targeting ligands, targeting groups, and/or PK/PD modulators to the RAGE RNAi agents disclosed herein. Linking or conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction, inverse-demand Diels-Alder cycloaddition reaction, oxime ligation, and Copper (I)— catalyzed or strain-promoted azide-alkyne cycloaddition reaction cycloaddition reaction.

In some embodiments, targeting ligands, such as the integrin targeting ligands shown in the examples and figures disclosed herein, can be synthesized as activated esters, such as tetrafluorophenyl (TFP) esters, which can be displaced by a reactive amino group (e.g., NH2-C6) to attach the targeting ligand to the RAGE RNAi agents disclosed herein. In some embodiments, targeting ligands are synthesized as azides, which can be conjugated to a propargyl (e.g., TriAlk14) or DBCO group, for example, via Copper (I)— catalyzed or strain-promoted azide-alkyne cycloaddition reaction.

Additionally, certain of the nucleotide sequences can be synthesized with a dT nucleotide at the 3' terminal end of the sense strand, followed by (3'→5') a linker (e.g., C6-SS-C6). The linker can, in some embodiments, facilitate the linkage to additional components, such as, for example, a PK/PD modulator or one or more targeting ligands. As described herein, the disulfide bond of C6-SS-C6 is first reduced, removing the dT from the molecule, which can then facilitate the conjugation of the desired PK/PD modulator. The terminal dT nucleotide therefore is not a part of the fully conjugated construct.

In some embodiments, the antisense strand of a RAGE RNAi agent disclosed herein differs by 0, 1, 2, or 3 nucleotides from any of the antisense strand sequences in Table 3 or Table 10. In some embodiments, the sense strand of a RAGE RNAi agent disclosed herein differs by 0, 1, 2, or 3 nucleotides from any of the sense strand sequences in Table 4, Table 5, Table 6, or Table 10.

In some embodiments, a RAGE RNAi agent antisense strand comprises a nucleotide sequence of any of the sequences in Table 2 or Table 3. In some embodiments, a RAGE RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2, Table 3, or Table 10. In certain embodiments, a RAGE RNAi agent antisense strand comprises or consists of a modified sequence of any one of the modified sequences in Table 3 or Table 10.

In some embodiments, a RAGE RNAi agent sense strand comprises the nucleotide sequence of any of the sequences in Table 2 or Table 4. In some embodiments, a RAGE RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24, of any of the sequences in Table 2, Table 4, Table 5, Table 6, or Table 10. In certain embodiments, a RAGE RNAi agent sense strand comprises or consists of a modified sequence of any one of the modified sequences in Table 3 or Table 10.

For the RNAi agents disclosed herein, the nucleotide at position 1 of the antisense strand (from 5' end→3' end) can be perfectly complementary to an AGER gene, or can be non-complementary to an AGER gene. In some embodiments, the nucleotide at position 1 of the antisense strand (from 5' end→3' end) is a U, A, or dT (or a modified version of U, A or dT). In some embodiments, the nucleotide at position 1 of the antisense strand (from 5' end→3' end) forms an A:U or U:A base pair with the sense strand.

In some embodiments, a RAGE RNAi agent antisense strand comprises the sequence of nucleotides (from 5' end→3' end) 2-18 or 2-19 of any of the antisense strand sequences in Table 2, Table 3, or Table 10. In some embodiments, a RAGE RNAi sense strand comprises the sequence of nucleotides (from 5' end→3' end) 1-17 or 1-18 of any of the sense strand sequences in Table 2, Table 4, Table 5, Table 6, or Table 10.

In some embodiments, a RAGE RNAi agent includes (i) an antisense strand comprising the sequence of nucleotides (from 5' end→3' end) 2-18 or 2-19 of any of the antisense strand sequences in Table 2, Table 3, or Table 10, and (ii) a sense strand comprising the sequence of nucleotides (from 5' end→3' end) 1-17 or 1-18 of any of the sense strand sequences in Table 2, Table 4, Table 5, Table 6, or Table 10.

A sense strand containing a sequence listed in Table 2 or Table 4 can be hybridized to any antisense strand containing a sequence listed in Table 2 or Table 3 provided the two sequences have a region of at least 85% complementarity over a contiguous 16, 17, 18, 19, 20, or 21 nucleotide sequence. In some embodiments, the RAGE RNAi agent has a sense strand consisting of the modified sequence of any of the modified sequences in Table 4, Table 5, Table 6, or Table 10, and an antisense strand consisting of the modified sequence of any of the modified sequences in Table 3 or Table 10. Certain representative sequence pairings are exemplified by the Duplex ID Nos. shown in Tables 7A, 73, 8, 9A and 9B.

In some embodiments, a RAGE RNAi agent comprises, consists of, or consists essentially of a duplex represented by any one of the Duplex ID Nos. presented herein. In some embodiments, a RAGE RNAi agent consists of any of the Duplex ID Nos. presented herein. In some embodiments, a RAGE RNAi agent comprises the sense strand and antisense strand nucleotide sequences of any of the Duplex ID Nos. presented herein. In some embodiments, a RAGE RNAi agent comprises the sense strand and antisense strand nucleotide sequences of any of the Duplex ID Nos. presented herein and a targeting group, linking group, and/or other non-nucleotide group wherein the targeting group, linking group, and/or other non-nucleotide group is covalently linked (i.e., conjugated) to the sense strand or the antisense strand. In some embodiments, a RAGE RNAi agent includes the sense strand and antisense strand modified nucleotide sequences of any of the Duplex ID Nos. presented herein. In some embodiments, a RAGE RNAi agent comprises the sense strand and antisense strand modified nucleotide sequences of any of the Duplex ID Nos. presented herein and a targeting group, linking group, and/or other non-nucleotide group, wherein the targeting group, linking group, and/or other non-nucleotide group is covalently linked to the sense strand or the antisense strand.

In some embodiments, a RAGE RNAi agent comprises an antisense strand and a sense strand having the nucleotide sequences of any of the antisense strand/sense strand duplexes of Tables 2, 7A, 7B, 8, 9A, 9B, or 10, and comprises a targeting group. In some embodiments, a RAGE RNAi agent comprises an antisense strand and a sense strand having the nucleotide sequences of any of the antisense strand/sense strand duplexes of Tables 2, 7A, 7B, 8, 9A, 9B, or 10, and comprises one or more αvβ6 integrin targeting ligands.

In some embodiments, a RAGE RNAi agent comprises an antisense strand and a sense strand having the nucleotide sequences of any of the antisense strand/sense strand duplexes of Tables 2, 7A, 7B, 8, 9A, 9B, or 10, and comprises a targeting group that is an integrin targeting ligand. In some embodiments, a RAGE RNAi agent comprises an antisense strand and a sense strand having the nucleotide sequences of any of the antisense strand/sense strand duplexes of Tables 2, 7A, 7B, 8, 9A, 9B, or 10, and comprises one or more αvβ6 integrin targeting ligands or clusters of αvβ6 integrin targeting ligands (e.g., a tridentate αvβ6 integrin targeting ligand).

In some embodiments, a RAGE RNAi agent comprises an antisense strand and a sense strand having the modified nucleotide sequences of any of the antisense strand/sense strand duplexes of Tables 7A, 7B, 8, 9A, 9B, and 10.

In some embodiments, a RAGE RNAi agent comprises an antisense strand and a sense strand having the modified nucleotide sequences of any of the antisense strand/sense strand duplexes of Tables 7A, 7B, 8, 9A, 9B, and 10, and comprises an integrin targeting ligand.

In some embodiments, a RAGE RNAi agent comprises, consists of, or consists essentially of any of the duplexes of Tables 7A, 7B, 8, 9A, 9B, and 10.

TABLE 7A

AGE RNAi Agent Duplexes with Corresponding Sense and Antisense Strand ID Numbers and Sequence ID numbers for the modified and unmodified nucleotide sequences. (Shown without Linking Agents or Conjugates)

| Duplex | AS ID | AS modified SEQID NO: | AS unmodified SEQ ID NO: | SS ID | SS modified SEQ ID NO: | SS unmodified SEQ ID NO: |
|---|---|---|---|---|---|---|
| AD07474 | AM10308-AS | 2 | 7 | AM10307-SS-NL | 13 | 19 |
| AD07475 | AM10309-AS | 3 | 7 | AM10307-SS-NL | 13 | 19 |
| AD07476 | AM10311-AS | 543 | 801 | AM10310-SS-NL | 623 | 839 |
| AD07477 | AM10312-AS | 544 | 801 | AM10310-SS-NL | 623 | 839 |
| AD07478 | AM10314-AS | 545 | 802 | AM10313-SS-NL | 624 | 840 |
| AD07479 | AM10315-AS | 546 | 802 | AM10313-SS-NL | 624 | 840 |
| AD07480 | AM10317-AS | 547 | 803 | AM10316-SS-NL | 625 | 841 |
| AD07481 | AM10318-AS | 548 | 803 | AM10316-SS-NL | 625 | 841 |
| AD07559 | AM10467-AS | 549 | 804 | AM10466-SS-NL | 626 | 842 |
| AD07560 | AM10469-AS | 550 | 805 | AM10468-SS-NL | 627 | 843 |
| AD07561 | AM10471-AS | 551 | 806 | AM10470-SS-NL | 628 | 844 |
| AD07562 | AM10473-AS | 552 | 807 | AM10472-SS-NL | 629 | 845 |
| AD07563 | AM10475-AS | 553 | 808 | AM10474-SS-NL | 630 | 846 |
| AD07564 | AM10477-AS | 554 | 809 | AM10476-SS-NL | 631 | 847 |
| AD07565 | AM10479-AS | 555 | 810 | AM10478-SS-NL | 632 | 848 |
| AD07566 | AM10481-AS | 556 | 811 | AM10480-SS-NL | 633 | 849 |
| AD07567 | AM10483-AS | 557 | 812 | AM10482-SS-NL | 634 | 850 |
| AD07621 | AM10571-AS | 558 | 813 | AM10570-SS-NL | 635 | 851 |
| AD07622 | AM10573-AS | 559 | 813 | AM10572-SS-NL | 636 | 852 |
| AD07623 | AM10575-AS | 560 | 814 | AM10574-SS-NL | 637 | 853 |
| AD07624 | AM10575-AS | 560 | 814 | AM10576-SS-NL | 638 | 854 |
| AD07661 | AM10308-AS | 2 | 7 | AM10644-SS-NL | 13 | 19 |
| AD07700 | AM10717-AS | 561 | 815 | AM10716-SS-NL | 640 | 855 |
| AD07701 | AM10308-AS | 2 | 7 | AM10718-SS-NL | 641 | 856 |
| AD07702 | AM10308-AS | 2 | 7 | AM10719-SS-NL | 642 | 857 |
| AD07703 | AM10720-AS | 562 | 7 | AM10307-SS-NL | 13 | 19 |
| AD07704 | AM10308-AS | 2 | 7 | AM10721-SS-NL | 643 | 858 |
| AD07705 | AM10722-AS | 563 | 7 | AM10307-SS-NL | 13 | 19 |
| AD07706 | AM10723-AS | 564 | 7 | AM10307-SS-NL | 13 | 19 |
| AD07707 | AM10724-AS | 565 | 7 | AM10307-SS-NL | 13 | 19 |
| AD07708 | AM10723-AS | 564 | 7 | AM10725-SS-NL | 644 | 19 |
| AD07715 | AM10317-AS | 547 | 803 | AM10737-SS-NL | 645 | 841 |
| AD07725 | AM10752-AS | 566 | 9 | AM10751-SS-NL | 646 | 20 |
| AD07726 | AM10754-AS | 4 | 8 | AM10753-SS-NL | 15 | 21 |
| AD07727 | AM10756-AS | 568 | 818 | AM10755-SS-NL | 648 | 861 |
| AD07728 | AM10758-AS | 569 | 819 | AM10757-SS-NL | 649 | 862 |
| AD07729 | AM10760-AS | 570 | 820 | AM10759-SS-NL | 650 | 863 |
| AD07730 | AM10762-AS | 571 | 821 | AM10761-SS-NL | 651 | 864 |
| AD07736 | AM10774-AS | 572 | 822 | AM10773-SS-NL | 652 | 865 |
| AD07737 | AM10776-AS | 573 | 823 | AM10775-SS-NL | 653 | 866 |
| AD07738 | AM10778-AS | 574 | 824 | AM10777-SS-NL | 654 | 867 |
| AD07739 | AM10780-AS | 575 | 825 | AM10779-SS-NL | 655 | 868 |
| AD07740 | AM10782-AS | 576 | 826 | AM10781-SS-NL | 656 | 869 |
| AD07741 | AM10784-AS | 577 | 827 | AM10783-SS-NL | 657 | 870 |
| AD07742 | AM10786-AS | 578 | 828 | AM10785-SS-NL | 658 | 871 |
| AD07743 | AM10788-AS | 579 | 829 | AM10787-SS-NL | 659 | 872 |
| AD07972 | AM11103-AS | 580 | 7 | AM10307-SS-NL | 13 | 19 |
| AD07973 | AM11104-AS | 581 | 7 | AM10307-SS-NL | 13 | 19 |
| AD07974 | AM11104-AS | 581 | 7 | AM11105-SS-NL | 660 | 19 |
| AD07975 | AM11104-AS | 581 | 7 | AM11106-SS-NL | 13 | 19 |
| AD07976 | AM11104-AS | 581 | 7 | AM11107-SS-NL | 662 | 19 |
| AD08030 | AM10309-AS | 3 | 7 | AM10721-SS-NL | 643 | 858 |
| AD08031 | AM11188-AS | 582 | 7 | AM10725-SS-NL | 644 | 19 |
| AD08032 | AM10723-AS | 564 | 7 | AM11189-SS-NL | 663 | 858 |
| AD08033 | AM11188-AS | 582 | 7 | AM11189-SS-NL | 663 | 858 |
| AD08034 | AM11190-AS | 583 | 7 | AM10725-SS-NL | 644 | 19 |

TABLE 7A-continued

AGE RNAi Agent Duplexes with Corresponding Sense and Antisense Strand ID Numbers and Sequence ID numbers for the modified and unmodified nucleotide sequences. (Shown without Linking Agents or Conjugates)

| Duplex | AS ID | AS modified SEQID NO: | AS unmodified SEQ ID NO: | SS ID | SS modified SEQ ID NO: | SS unmodified SEQ ID NO: |
|---|---|---|---|---|---|---|
| AD08035 | AM11191-AS | 584 | 7 | AM10725-SS-NL | 644 | 19 |
| AD08036 | AM11192-AS | 585 | 7 | AM10725-SS-NL | 644 | 19 |
| AD08037 | AM11194-AS | 586 | 815 | AM11193-SS-NL | 664 | 855 |
| AD08038 | AM11196-AS | 587 | 830 | AM11195-SS-NL | 665 | 873 |
| AD08039 | AM10723-AS | 564 | 7 | AM11197-SS-NL | 666 | 874 |
| AD08258 | AM10309-AS | 3 | 7 | AM11512-SS-NL | 667 | 19 |
| AD08259 | AM10309-AS | 3 | 7 | AM11513-SS-NL | 13 | 19 |
| AD08260 | AM10309-AS | 3 | 7 | AM11514-SS-NL | 13 | 19 |
| AD08261 | AM10309-AS | 3 | 7 | AM11515-SS-NL | 670 | 19 |
| AD08262 | AM10309-AS | 3 | 7 | AM11516-SS-NL | 13 | 19 |
| AD08263 | AM10309-AS | 3 | 7 | AM11517-SS-NL | 672 | 19 |
| AD08432 | AM11757-AS | 588 | 7 | AM10725-SS-NL | 644 | 19 |
| AD08433 | AM11758-AS | 589 | 7 | AM10725-SS-NL | 644 | 19 |
| AD08434 | AM11759-AS | 590 | 815 | AM11193-SS-NL | 664 | 855 |
| AD08435 | AM11760-AS | 591 | 815 | AM11193-SS-NL | 664 | 855 |
| AD08436 | AM11761-AS | 592 | 815 | AM11193-SS-NL | 664 | 855 |
| AD08437 | AM11762-AS | 593 | 7 | AM10725-SS-NL | 644 | 19 |
| AD08438 | AM11763-AS | 594 | 815 | AM11193-SS-NL | 664 | 855 |
| AD08439 | AM11764-AS | 595 | 815 | AM11193-SS-NL | 664 | 855 |
| AD08510 | AM11889-AS | 596 | 831 | AM11888-SS-NL | 673 | 875 |
| AD08511 | AM11889-AS | 596 | 831 | AM11890-SS-NL | 674 | 876 |
| AD08512 | AM11892-AS | 597 | 832 | AM11891-SS-NL | 675 | 877 |
| AD08513 | AM11894-AS | 598 | 833 | AM11893-SS-NL | 676 | 878 |
| AD08514 | AM11895-AS | 599 | 9 | AM10751-SS-NL | 646 | 20 |
| AD08515 | AM11897-AS | 5 | 9 | AM11896-SS-NL | 677 | 20 |
| AD08516 | AM11898-AS | 6 | 9 | AM11896-SS-NL | 677 | 20 |
| AD08517 | AM11898-AS | 6 | 9 | AM11899-SS-NL | 678 | 879 |
| AD08518 | AM11897-AS | 5 | 9 | AM11900-SS-NL | 14 | 20 |
| AD08519 | AM11898-AS | 6 | 9 | AM11900-SS-NL | 14 | 20 |
| AD08520 | AM11897-AS | 5 | 9 | AM11901-SS-NL | 680 | 20 |
| AD08521 | AM11898-AS | 6 | 9 | AM11901-SS-NL | 680 | 20 |
| AD08711 | AM12234-AS | 602 | 8 | AM10753-SS-NL | 15 | 21 |
| AD08712 | AM12236-AS | 603 | 8 | AM12235-SS-NL | 681 | 21 |
| AD08713 | AM12237-AS | 604 | 8 | AM12235-SS-NL | 681 | 21 |
| AD08714 | AM12236-AS | 603 | 8 | AM12238-SS-NL | 682 | 880 |
| AD08715 | AM12236-AS | 603 | 8 | AM12239-SS-NL | 683 | 881 |
| AD08716 | AM12240-AS | 605 | 8 | AM12238-SS-NL | 682 | 880 |
| AD08717 | AM12241-AS | 606 | 8 | AM12238-SS-NL | 682 | 880 |
| AD08718 | AM12236-AS | 603 | 8 | AM12242-SS-NL | 684 | 882 |
| AD08719 | AM12236-AS | 603 | 8 | AM12243-SS-NL | 685 | 883 |
| AD08720 | AM12245-AS | 607 | 834 | AM12244-SS-NL | 686 | 884 |
| AD08898 | AM10309-AS | 3 | 7 | AM10644-SS-NL | 13 | 19 |
| AD08944 | AM12593-AS | 608 | 835 | AM12592-SS-NL | 687 | 885 |
| AD08945 | AM12594-AS | 609 | 9 | AM11900-SS-NL | 14 | 20 |
| AD08946 | AM12596-AS | 610 | 836 | AM12595-SS-NL | 688 | 886 |
| AD08947 | AM11897-AS | 5 | 9 | AM12597-SS-NL | 689 | 20 |
| AD09051 | AM10754-AS | 4 | 8 | AM12754-SS-NL | 690 | 880 |
| AD09052 | AM12234-AS | 602 | 8 | AM12754-SS-NL | 690 | 880 |
| AD09053 | AM12236-AS | 603 | 8 | AM10753-SS-NL | 15 | 21 |
| AD09054 | AM10754-AS | 4 | 8 | AM12235-SS-NL | 681 | 21 |
| AD09055 | AM12755-AS | 611 | 8 | AM12235-SS-NL | 681 | 21 |
| AD09056 | AM12756-AS | 612 | 8 | AM12235-SS-NL | 681 | 21 |
| AD09057 | AM12757-AS | 613 | 8 | AM12235-SS-NL | 681 | 21 |
| AD09150 | AM11897-AS | 5 | 9 | AM12910-SS-NL | 14 | 20 |
| AD09151 | AM11898-AS | 6 | 9 | AM12910-SS-NL | 14 | 20 |
| AD09152 | AM10754-AS | 4 | 8 | AM12911-SS-NL | 15 | 21 |
| AD09797 | AM10309-AS | 3 | 7 | AM13987-SS-NL | 13 | 19 |
| AD09868 | AM10308-AS | 2 | 7 | AM13987-SS-NL | 13 | 19 |
| AD09870 | AM14090-AS | 614 | 7 | AM10725-SS-NL | 644 | 19 |
| AD09871 | AM14091-AS | 615 | 7 | AM10725-SS-NL | 644 | 19 |
| AD09872 | AM14091-AS | 615 | 7 | AM14092-SS-NL | 694 | 19 |
| AD09873 | AM14093-AS | 616 | 9 | AM11900-SS-NL | 14 | 20 |
| AD09874 | AM14094-AS | 617 | 9 | AM11900-SS-NL | 14 | 20 |
| AD09875 | AM14095-AS | 618 | 9 | AM11900-SS-NL | 14 | 20 |
| AD09876 | AM14095-AS | 618 | 9 | AM12597-SS-NL | 689 | 20 |
| AD09877 | AM14095-AS | 618 | 9 | AM11896-SS-NL | 677 | 20 |
| AD10543 | AM15021-AS | 619 | 830 | AM11195-SS-NL | 665 | 873 |
| AD11078 | AM15767-AS | 620 | 837 | AM15766-SS-NL | 695 | 887 |
| AD11080 | AM15770-AS | 621 | 801 | AM10310-SS-NL | 623 | 839 |
| AD11353 | AM10309-AS | 3 | 7 | AM16133-SS-NL | 13 | 19 |

TABLE 7B

RAGE RNAi Agent Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD07474 | AM10308-AS | 2 | 7 | AM10307-SS | 16 | 19 |
| AD07475 | AM10309-AS | 3 | 7 | AM10307-SS | 16 | 19 |
| AD07476 | AM10311-AS | 543 | 801 | AM10310-SS | 698 | 839 |
| AD07477 | AM10312-AS | 544 | 801 | AM10310-SS | 698 | 839 |
| AD07478 | AM10314-AS | 545 | 802 | AM10313-SS | 699 | 840 |
| AD07479 | AM10315-AS | 546 | 802 | AM10313-SS | 699 | 840 |
| AD07480 | AM10317-AS | 547 | 803 | AM10316-SS | 700 | 841 |
| AD07481 | AM10318-AS | 548 | 803 | AM10316-SS | 700 | 841 |
| AD07559 | AM10467-AS | 549 | 804 | AM10466-SS | 701 | 842 |
| AD07560 | AM10469-AS | 550 | 805 | AM10468-SS | 702 | 843 |
| AD07561 | AM10471-AS | 551 | 806 | AM10470-SS | 703 | 844 |
| AD07562 | AM10473-AS | 552 | 807 | AM10472-SS | 704 | 845 |
| AD07563 | AM10475-AS | 553 | 808 | AM10474-SS | 705 | 846 |
| AD07564 | AM10477-AS | 554 | 809 | AM10476-SS | 706 | 847 |
| AD07565 | AM10479-AS | 555 | 810 | AM10478-SS | 707 | 848 |
| AD07566 | AM10481-AS | 556 | 811 | AM10480-SS | 708 | 849 |
| AD07567 | AM10483-AS | 557 | 812 | AM10482-SS | 709 | 850 |
| AD07621 | AM10571-AS | 558 | 813 | AM10570-SS | 710 | 851 |
| AD07622 | AM10573-AS | 559 | 813 | AM10572-SS | 711 | 852 |
| AD07623 | AM10575-AS | 560 | 814 | AM10574-SS | 712 | 853 |
| AD07624 | AM10575-AS | 560 | 814 | AM10576-SS | 713 | 854 |
| AD07661 | AM10308-AS | 2 | 7 | AM10644-SS | 16 | 19 |
| AD07700 | AM10717-AS | 561 | 815 | AM10716-SS | 715 | 855 |
| AD07701 | AM10308-AS | 2 | 7 | AM10718-SS | 716 | 856 |
| AD07702 | AM10308-AS | 2 | 7 | AM10719-SS | 717 | 857 |
| AD07703 | AM10720-AS | 562 | 7 | AM10307-SS | 16 | 19 |
| AD07704 | AM10308-AS | 2 | 7 | AM10721-SS | 718 | 858 |
| AD07705 | AM10722-AS | 563 | 7 | AM10307-SS | 16 | 19 |
| AD07706 | AM10723-AS | 564 | 7 | AM10307-SS | 16 | 19 |
| AD07707 | AM10724-AS | 565 | 7 | AM10307-SS | 16 | 19 |
| AD07708 | AM10723-AS | 564 | 7 | AM10725-SS | 719 | 19 |
| AD07715 | AM10317-AS | 547 | 803 | AM10737-SS | 720 | 841 |
| AD07725 | AM10752-AS | 566 | 9 | AM10751-SS | 721 | 20 |
| AD07726 | AM10754-AS | 4 | 8 | AM10753-SS | 18 | 21 |
| AD07727 | AM10756-AS | 568 | 818 | AM10755-SS | 723 | 861 |
| AD07728 | AM10758-AS | 569 | 819 | AM10757-SS | 724 | 862 |
| AD07729 | AM10760-AS | 570 | 820 | AM10759-SS | 725 | 863 |
| AD07730 | AM10762-AS | 571 | 821 | AM10761-SS | 726 | 864 |
| AD07736 | AM10774-AS | 572 | 822 | AM10773-SS | 727 | 865 |
| AD07737 | AM10776-AS | 573 | 823 | AM10775-SS | 728 | 866 |
| AD07738 | AM10778-AS | 574 | 824 | AM10777-SS | 729 | 867 |
| AD07739 | AM10780-AS | 575 | 825 | AM10779-SS | 730 | 868 |
| AD07740 | AM10782-AS | 576 | 826 | AM10781-SS | 731 | 869 |
| AD07741 | AM10784-AS | 577 | 827 | AM10783-SS | 732 | 870 |
| AD07742 | AM10786-AS | 578 | 828 | AM10785-SS | 733 | 871 |
| AD07743 | AM10788-AS | 579 | 829 | AM10787-SS | 734 | 872 |
| AD07972 | AM11103-AS | 580 | 7 | AM10307-SS | 16 | 19 |
| AD07973 | AM11104-AS | 581 | 7 | AM10307-SS | 16 | 19 |
| AD07974 | AM11104-AS | 581 | 7 | AM11105-SS | 735 | 19 |
| AD07975 | AM11104-AS | 581 | 7 | AM11106-SS | 736 | 19 |
| AD07976 | AM11104-AS | 581 | 7 | AM11107-SS | 737 | 19 |
| AD08030 | AM10309-AS | 3 | 7 | AM10721-SS | 718 | 858 |
| AD08031 | AM11188-AS | 582 | 7 | AM10725-SS | 719 | 19 |
| AD08032 | AM10723-AS | 564 | 7 | AM11189-SS | 738 | 858 |
| AD08033 | AM11188-AS | 582 | 7 | AM11189-SS | 738 | 858 |
| AD08034 | AM11190-AS | 583 | 7 | AM10725-SS | 719 | 19 |
| AD08035 | AM11191-AS | 584 | 7 | AM10725-SS | 719 | 19 |
| AD08036 | AM11192-AS | 585 | 7 | AM10725-SS | 719 | 19 |
| AD08037 | AM11194-AS | 586 | 815 | AM11193-SS | 739 | 855 |
| AD08038 | AM11196-AS | 587 | 830 | AM11195-SS | 740 | 873 |
| AD08039 | AM10723-AS | 564 | 7 | AM11197-SS | 741 | 874 |
| AD08258 | AM10309-AS | 3 | 7 | AM11512-SS | 742 | 19 |
| AD08259 | AM10309-AS | 3 | 7 | AM11513-SS | 16 | 19 |
| AD08260 | AM10309-AS | 3 | 7 | AM11514-SS | 16 | 19 |
| AD08261 | AM10309-AS | 3 | 7 | AM11515-SS | 745 | 19 |
| AD08262 | AM10309-AS | 3 | 7 | AM11516-SS | 16 | 19 |
| AD08263 | AM10309-AS | 3 | 7 | AM11517-SS | 747 | 19 |
| AD08432 | AM11757-AS | 588 | 7 | AM10725-SS | 719 | 19 |
| AD08433 | AM11758-AS | 589 | 7 | AM10725-SS | 719 | 19 |
| AD08434 | AM11759-AS | 590 | 815 | AM11193-SS | 739 | 855 |
| AD08435 | AM11760-AS | 591 | 815 | AM11193-SS | 739 | 855 |

TABLE 7B-continued

RAGE RNAi Agent Duplexes with Corresponding Sense and Antisense Strand ID Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO: | SS unmodified SEQ ID NO: |
|---|---|---|---|---|---|---|
| AD08436 | AM11761-AS | 592 | 815 | AM11193-SS | 739 | 855 |
| AD08437 | AM11762-AS | 593 | 7 | AM10725-SS | 719 | 19 |
| AD08438 | AM11763-AS | 594 | 815 | AM11193-SS | 739 | 855 |
| AD08439 | AM11764-AS | 595 | 815 | AM11193-SS | 739 | 855 |
| AD08510 | AM11889-AS | 596 | 831 | AM11888-SS | 748 | 875 |
| AD08511 | AM11889-AS | 596 | 831 | AM11890-SS | 749 | 876 |
| AD08512 | AM11892-AS | 597 | 832 | AM11891-SS | 750 | 877 |
| AD08513 | AM11894-AS | 598 | 833 | AM11893-SS | 751 | 878 |
| AD08514 | AM11895-AS | 599 | 9 | AM10751-SS | 721 | 20 |
| AD08515 | AM11897-AS | 5 | 9 | AM11896-SS | 752 | 20 |
| AD08516 | AM11898-AS | 6 | 9 | AM11896-SS | 752 | 20 |
| AD08517 | AM11898-AS | 6 | 9 | AM11899-SS | 753 | 879 |
| AD08518 | AM11897-AS | 5 | 9 | AM11900-SS | 17 | 20 |
| AD08519 | AM11898-AS | 6 | 9 | AM11900-SS | 17 | 20 |
| AD08520 | AM11897-AS | 5 | 9 | AM11901-SS | 755 | 20 |
| AD08521 | AM11898-AS | 6 | 9 | AM11901-SS | 755 | 20 |
| AD08711 | AM12234-AS | 602 | 8 | AM10753-SS | 18 | 21 |
| AD08712 | AM12236-AS | 603 | 8 | AM12235-SS | 756 | 21 |
| AD08713 | AM12237-AS | 604 | 8 | AM12235-SS | 756 | 21 |
| AD08714 | AM12236-AS | 603 | 8 | AM12238-SS | 757 | 880 |
| AD08715 | AM12236-AS | 603 | 8 | AM12239-SS | 758 | 881 |
| AD08716 | AM12240-AS | 605 | 8 | AM12238-SS | 757 | 880 |
| AD08717 | AM12241-AS | 606 | 8 | AM12238-SS | 757 | 880 |
| AD08718 | AM12236-AS | 603 | 8 | AM12242-SS | 759 | 882 |
| AD08719 | AM12236-AS | 603 | 8 | AM12243-SS | 760 | 883 |
| AD08720 | AM12245-AS | 607 | 834 | AM12244-SS | 761 | 884 |
| AD08898 | AM10309-AS | 3 | 7 | AM10644-SS | 16 | 19 |
| AD08944 | AM12593-AS | 608 | 835 | AM12592-SS | 762 | 885 |
| AD08945 | AM12594-AS | 609 | 9 | AM11900-SS | 17 | 20 |
| AD08946 | AM12596-AS | 610 | 836 | AM12595-SS | 763 | 886 |
| AD08947 | AM11897-AS | 5 | 9 | AM12597-SS | 764 | 20 |
| AD09051 | AM10754-AS | 4 | 8 | AM12754-SS | 765 | 880 |
| AD09052 | AM12234-AS | 602 | 8 | AM12754-SS | 765 | 880 |
| AD09053 | AM12236-AS | 603 | 8 | AM10753-SS | 18 | 21 |
| AD09054 | AM10754-AS | 4 | 8 | AM12235-SS | 756 | 21 |
| AD09055 | AM12755-AS | 611 | 8 | AM12235-SS | 756 | 21 |
| AD09056 | AM12756-AS | 612 | 8 | AM12235-SS | 756 | 21 |
| AD09057 | AM12757-AS | 613 | 8 | AM12235-SS | 756 | 21 |
| AD09150 | AM11897-AS | 5 | 9 | AM12910-SS | 17 | 20 |
| AD09151 | AM11898-AS | 6 | 9 | AM12910-SS | 17 | 20 |
| AD09152 | AM10754-AS | 4 | 8 | AM12911-SS | 18 | 21 |
| AD09797 | AM10309-AS | 3 | 7 | AM13987-SS | 16 | 19 |
| AD09868 | AM10308-AS | 2 | 7 | AM13987-SS | 16 | 19 |
| AD09870 | AM14090-AS | 614 | 7 | AM10725-SS | 719 | 19 |
| AD09871 | AM14091-AS | 615 | 7 | AM10725-SS | 719 | 19 |
| AD09872 | AM14091-AS | 615 | 7 | AM14092-SS | 769 | 19 |
| AD09873 | AM14093-AS | 616 | 9 | AM11900-SS | 17 | 20 |
| AD09874 | AM14094-AS | 617 | 9 | AM11900-SS | 17 | 20 |
| AD09875 | AM14095-AS | 618 | 9 | AM11900-SS | 17 | 20 |
| AD09876 | AM14095-AS | 618 | 9 | AM12597-SS | 764 | 20 |
| AD09877 | AM14095-AS | 618 | 9 | AM11896-SS | 752 | 20 |
| AD10543 | AM15021-AS | 619 | 830 | AM11195-SS | 740 | 873 |
| AD11078 | AM15767-AS | 620 | 837 | AM15766-SS | 770 | 887 |
| AD11080 | AM15770-AS | 621 | 801 | AM10310-SS | 698 | 839 |
| AD11353 | AM10309-AS | 3 | 7 | AM16133-SS | 771 | 19 |

TABLE 8

RAGE RNAi Agent Duplexes with Corresponding Sense and Antisense Strand ID Numbers and Sequence ID numbers for the modified and unmodified nucleotide sequences. (Shown with Targeting Ligand Conjugates)

| Duplex | AS ID | AS modified SEQ ID NO: | AS unmodified SEQ ID NO: | SSID | SS modified SEQ ID NO: | SS unmodified SEQ ID NO: |
|---|---|---|---|---|---|---|
| AC000286 | AM10308-AS | 2 | 7 | CS000363 | 10 | 19 |
| AC000287 | AM10309-AS | 3 | 7 | CS000363 | 10 | 19 |
| AC000288 | AM11103-AS | 580 | 7 | CS000363 | 10 | 19 |
| AC000289 | AM11104-AS | 581 | 7 | CS000363 | 10 | 19 |
| AC000290 | AM11104-AS | 581 | 7 | CS000368 | 773 | 19 |
| AC000291 | AM11104-AS | 581 | 7 | CS000369 | 774 | 19 |
| AC000292 | AM10309-AS | 3 | 7 | CS000363 | 10 | 19 |
| AC000293 | AM11103-AS | 580 | 7 | CS000363 | 10 | 19 |
| AC000294 | AM11104-AS | 581 | 7 | CS000363 | 10 | 19 |
| AC000312 | AM11104-AS | 581 | 7 | CS000386 | 775 | 19 |
| AC000414 | AM11188-AS | 582 | 7 | CS000497 | 776 | 858 |
| AC000415 | AM11190-AS | 583 | 7 | CS000499 | 777 | 19 |
| AC000416 | AM11191-AS | 584 | 7 | CS000499 | 777 | 19 |
| AC000417 | AM11192-AS | 585 | 7 | CS000499 | 777 | 19 |
| AC000418 | AM11194-AS | 586 | 815 | CS000503 | 778 | 855 |
| AC000419 | AM11196-AS | 587 | 830 | CS000505 | 779 | 873 |
| AC000420 | AM10723-AS | 564 | 7 | CS000507 | 780 | 874 |
| AC000438 | AM10308-AS | 2 | 7 | CS000531 | 781 | 858 |
| AC000439 | AM10723-AS | 564 | 7 | CS000499 | 777 | 19 |
| AC000440 | AM10309-AS | 3 | 7 | CS000531 | 781 | 858 |
| AC000441 | AM11188-AS | 582 | 7 | CS000499 | 777 | 19 |
| AC000442 | AM10723-AS | 564 | 7 | CS000497 | 776 | 858 |
| AC000549 | AM10309-AS | 3 | 7 | CS000672 | 782 | 19 |
| AC000550 | AM10309-AS | 3 | 7 | CS000673 | 783 | 19 |
| AC000551 | AM10309-AS | 3 | 7 | CS000674 | 784 | 19 |
| AC000552 | AM10309-AS | 3 | 7 | CS000675 | 785 | 19 |
| AC000567 | AM10309-AS | 3 | 7 | CS000690 | 786 | 19 |
| AC000568 | AM10309-AS | 3 | 7 | CS000691 | 787 | 19 |
| AC000790 | AM10717-AS | 561 | 815 | CS000986 | 788 | 855 |
| AC000791 | AM10308-AS | 2 | 7 | CS000988 | 789 | 856 |
| AC000792 | AM10308-AS | 2 | 7 | CS000989 | 790 | 857 |
| AC000793 | AM10720-AS | 562 | 7 | CS000363 | 10 | 19 |
| AC000794 | AM10722-AS | 563 | 7 | CS000363 | 10 | 19 |
| AC000795 | AM10723-AS | 564 | 7 | CS000363 | 10 | 19 |
| AC000796 | AM10724-AS | 565 | 7 | CS000363 | 10 | 19 |
| AC000818 | AM10311-AS | 543 | 801 | CS001021 | 791 | 839 |
| AC000819 | AM10312-AS | 544 | 801 | CS001021 | 791 | 839 |
| AC000820 | AM10314-AS | 545 | 802 | CS001024 | 792 | 840 |
| AC000821 | AM10315-AS | 546 | 802 | CS001024 | 792 | 840 |
| AC000822 | AM10317-AS | 547 | 803 | CS001027 | 793 | 841 |
| AC000823 | AM10318-AS | 548 | 803 | CS001027 | 793 | 841 |
| AC001134 | AM11762-AS | 593 | 7 | CS000499 | 777 | 19 |
| AC001266 | AM11897-AS | 5 | 9 | CS001579 | 11 | 20 |
| AC001267 | AM11898-AS | 6 | 9 | CS001579 | 11 | 20 |
| AC001268 | AM10754-AS | 4 | 8 | CS001582 | 12 | 21 |
| AC001274 | AM11757-AS | 588 | 7 | CS000499 | 777 | 19 |
| AC001653 | AM14090-AS | 614 | 7 | CS000499 | 777 | 19 |
| AC001654 | AM14091-AS | 615 | 7 | CS000499 | 777 | 19 |
| AC001655 | AM14091-AS | 615 | 7 | CS002138 | 796 | 19 |
| AC001877 | AM11897-AS | 5 | 9 | CS002399 | 797 | 20 |
| AC002047 | AM15021-AS | 619 | 830 | CS000505 | 779 | 873 |
| AC002345 | AM15767-AS | 620 | 837 | CS002976 | 798 | 887 |
| AC002347 | AM15770-AS | 621 | 801 | CS001021 | 791 | 839 |
| AC002399 | AM10309-AS | 3 | 7 | CS003048 | 799 | 19 |

TABLE 9A

Conjugate Duplex ID Numbers Referencing Position Targeted On AGER (RAGE) Gene

| Duplex | AS ID | SS ID | Targeted AGER Gene Position (Of SEQ ID NO: 1) |
|---|---|---|---|
| AC000286 | AM10308-AS | CS000363 | 177 |
| AC000287 | AM10309-AS | CS000363 | 177 |
| AC000288 | AM11103-AS | CS000363 | 177 |
| AC000289 | AM11104-AS | CS000363 | 177 |

TABLE 9A-continued

Conjugate Duplex ID Numbers Referencing Position Targeted On AGER (RAGE) Gene

| Duplex | AS ID | SS ID | Targeted AGER Gene Position (Of SEQ ID NO: 1) |
|---|---|---|---|
| AC000290 | AM11104-AS | CS000368 | 177 |
| AC000291 | AM11104-AS | CS000369 | 177 |
| AC000292 | AM10309-AS | CS000363 | 177 |
| AC000293 | AM11103-AS | CS000363 | 177 |

TABLE 9A-continued

Conjugate Duplex ID Numbers Referencing Position Targeted On AGER (RAGE) Gene

| Duplex | AS ID | SS ID | Targeted AGER Gene Position (Of SEQ ID NO: 1) |
|---|---|---|---|
| AC000294 | AM11104-AS | CS000363 | 177 |
| AC000312 | AM11104-AS | CS000386 | 177 |
| AC000414 | AM11188-AS | CS000497 | 177 |
| AC000415 | AM11190-AS | CS000499 | 177 |
| AC000416 | AM11191-AS | CS000499 | 177 |
| AC000417 | AM11192-AS | CS000499 | 177 |
| AC000418 | AM11194-AS | CS000503 | 177 |
| AC000419 | AM11196-AS | CS000505 | 177 |
| AC000420 | AM10723-AS | CS000507 | 177 |
| AC000438 | AM10308-AS | CS000531 | 177 |
| AC000439 | AM10723-AS | CS000499 | 177 |
| AC000440 | AM10309-AS | CS000531 | 177 |
| AC000441 | AM11188-AS | CS000499 | 177 |
| AC000442 | AM10723-AS | CS000497 | 177 |
| AC000549 | AM10309-AS | CS000672 | 177 |
| AC000550 | AM10309-AS | CS000673 | 177 |
| AC000551 | AM10309-AS | CS000674 | 177 |
| AC000552 | AM10309-AS | CS000675 | 177 |
| AC000567 | AM10309-AS | CS000690 | 177 |
| AC000568 | AM10309-AS | CS000691 | 177 |
| AC000790 | AM10717-AS | CS000986 | 177 |
| AC000791 | AM10308-AS | CS000988 | 177 |
| AC000792 | AM10308-AS | CS000989 | 177 |
| AC000793 | AM10720-AS | CS000363 | 177 |
| AC000794 | AM10722-AS | CS000363 | 177 |
| AC000795 | AM10723-AS | CS000363 | 177 |
| AC000796 | AM10724-AS | CS000363 | 177 |
| AC000818 | AM10311-AS | CS001021 | 178 |
| AC000819 | AM10312-AS | CS001021 | 178 |
| AC000820 | AM10314-AS | CS001024 | 384 |
| AC000821 | AM10315-AS | CS001024 | 384 |
| AC000822 | AM10317-AS | CS001027 | 391 |
| AC000823 | AM10318-AS | CS001027 | 391 |
| AC001134 | AM11762-AS | CS000499 | 177 |
| AC001266 | AM11897-AS | CS001579 | 90 |
| AC001267 | AM11898-AS | CS001579 | 90 |
| AC001268 | AM10754-AS | CS001582 | 330 |
| AC001274 | AM11757-AS | CS000499 | 177 |
| AC001653 | AM14090-AS | CS000499 | 177 |
| AC001654 | AM14091-AS | CS000499 | 177 |
| AC001655 | AM14091-AS | CS002138 | 177 |
| AC001877 | AM11897-AS | CS002399 | 90 |
| AC002047 | AM15021-AS | CS000505 | 177 |
| AC002345 | AM15767-AS | CS002976 | 392 |
| AC002347 | AM15770-AS | CS001021 | 178 |
| AC002399 | AM10309-AS | CS003048 | 177 |

TABLE 9B

Conjugate ID Numbers and Corresponding AD Duplex Numbers, Referencing Position Targeted On RAGE (AGER) Gene

| AC Duplex Number | Corresponding AD Duplex Number | Targeted AGER Gene Position (Of SEQ ID NO: 1) |
|---|---|---|
| AC000286 | AD07474 | 177 |
| AC000287 | AD07475 | 177 |
| AC000288 | AD07972 | 177 |
| AC000289 | AD07973 | 177 |
| AC000290 | AD07974 | 177 |
| AC000291 | AD07975 | 177 |
| AC000292 | AD07475 | 177 |
| AC000293 | AD07972 | 177 |
| AC000294 | AD07973 | 177 |
| AC000312 | AD07976 | 177 |
| AC000414 | AD08033 | 177 |
| AC000415 | AD08034 | 177 |
| AC000416 | AD08035 | 177 |
| AC000417 | AD08036 | 177 |
| AC000418 | AD08037 | 177 |
| AC000419 | AD08038 | 177 |
| AC000420 | AD08039 | 177 |
| AC000438 | AD07704 | 177 |
| AC000439 | AD07708 | 177 |
| AC000440 | AD08030 | 177 |
| AC000441 | AD08031 | 177 |
| AC000442 | AD08032 | 177 |
| AC000549 | AD08260 | 177 |
| AC000550 | AD08261 | 177 |
| AC000551 | AD08262 | 177 |
| AC000552 | AD08263 | 177 |
| AC000567 | AD08260 | 177 |
| AC000568 | AD08261 | 177 |
| AC000790 | AD07700 | 177 |
| AC000791 | AD07701 | 177 |
| AC000792 | AD07702 | 177 |
| AC000793 | AD07703 | 177 |
| AC000794 | AD07705 | 177 |
| AC000795 | AD07706 | 177 |
| AC000796 | AD07707 | 177 |
| AC000818 | AD07476 | 178 |
| AC000819 | AD07477 | 178 |
| AC000820 | AD07478 | 384 |
| AC000821 | AD07479 | 384 |
| AC000822 | AD07480 | 391 |
| AC000823 | AD07481 | 391 |
| AC001134 | AD08437 | 177 |
| AC001266 | AD09150 | 90 |
| AC001267 | AD09151 | 90 |
| AC001268 | AD09152 | 330 |
| AC001274 | AD08432 | 177 |
| AC001653 | AD09870 | 177 |
| AC001654 | AD09871 | 177 |
| AC001655 | AD09872 | 177 |
| AC001877 | AD10075 | 90 |
| AC002047 | AD10543 | 177 |
| AC002345 | AD11078 | 392 |
| AC002347 | AD11080 | 178 |
| AC002399 | AD11353 | 177 |

TABLE 10

Conjugate ID Numbers With Chemically Modified Antisense and Sense Strands (including Linkers and Conjugates)

| AC ID Number | Sense Strand (Fully Modified with Conjugated Targeting Ligand) (5'→3') | SEQ ID NO: | Antisense Strand (5'→3') | SEQ ID NO: |
|---|---|---|---|---|
| AC000286 | Tri-SM6.1-avβ6-(TA14)csggaauggAfAfAfcugaacacaas(invAb) | 10 | usUfsgsUfgUfuCfaGfuUfuCfcAfuUfcCfsg | 2 |
| AC000287 | Tri-SM6.1-avβ6-(TA14)csggaauggAfAfAfcugaacacaas(invAb) | 10 | cPrpusUfsgsUfgUfuCfaGfuUfuCfcAfuUfcCfsg | 3 |
| AC000288 | Tri-SM6.1-avβ6-(TA14)csggaauggAfAfAfcugaacacaas(invAb) | 10 | cPrpusUfgUfgUfuCfaGfuUfuCfcAfuUfcCfsg | 580 |
| AC000289 | Tri-SM6.1-avβ6-(TA14)csggaauggAfAfAfcugaacacaas(invAb) | 10 | cPrpuUfgUfgUfuCfaGfuUfuCfcAfuUfcCfsg | 581 |
| AC000290 | Tri-SM6.1-avβ6-(TA14)cggaauggAfAfAfcugaacacaas(invAb) | 773 | cPrpuUfgUfgUfuCfaGfuUfuCfcAfuUfcCfsg | 581 |
| AC000291 | Tri-SM6.1-avβ6-(TA14)csggaauggAfAfAfcugaacacaa(invAb) | 774 | cPrpuUfgUfgUfuCfaGfuUfuCfcAfuUfcCfsg | 581 |
| AC000292 | Tri-SM6.1-avβ6-(TA14)csggaauggAfAfAfcugaacacaas(invAb) | 10 | cPrpusUfsgsUfgUfuCfaGfuUfuCfcAfuUfcCfsg | 3 |
| AC000293 | Tri-SM6.1-avβ6-(TA14)csggaauggAfAfAfcugaacacaas(invAb) | 10 | cPrpusUfgUfgUfuCfaGfuUfuCfcAfuUfcCfsg | 580 |
| AC000294 | Tri-SM6.1-avβ6-(TA14)csggaauggAfAfAfcugaacacaas(invAb) | 10 | cPrpuUfgUfgUfuCfaGfuUfuCfcAfuUfcCfsg | 581 |
| AC000312 | Tri-SM6.1-avβ6-(TA14)cggaauggAfAfAfcugaacacaa(invAb) | 775 | cPrpuUfgUfgUfuCfaGfuUfuCfcAfuUfcCfsg | 581 |
| AC000414 | Tri-SM6.1-avβ6-(TA14)csggaauGfgAfaAfcugaauacaas(invAb) | 776 | cPrpusUfsgsuguucaguUfuCfcAfuuccsg | 582 |
| AC000415 | Tri-SM6.1-avβ6-(TA14)csggaauGfgAfaAfcugaacacaas(invAb) | 777 | usUfsgsuguuC$_{UNA}$aguUfuCfcAfuuccsg | 583 |
| AC000416 | Tri-SM6.1-avβ6-(TA14)csggaauGfgAfaAfcugaacacaas(invAb) | 777 | usUfsgsuguU$_{UNA}$caguUfuCfcAfuuccsg | 584 |
| AC000417 | Tri-SM6.1-avβ6-(TA14)csggaauGfgAfaAfcugaacacaas(invAb) | 777 | usUfsgsugU$_{UNA}$UcaguUfuCfcAfuuccsg | 585 |
| AC000418 | Tri-SM6.1-avβ6-(TA14)gsggaauGfgAfaAfcugaacacaas(invAb) | 778 | usUfsgsuguucaguUfuCfcAfuuccsc | 586 |
| AC000419 | Tri-SM6.1-avβ6-(TA14)usggaauGfgAfaAfcugaacacaas(invAb) | 779 | usUfsgsuguucaguUfuCfcAfuuccsa | 587 |
| AC000420 | Tri-SM6.1-avβ6-(TA14)csggaauGfgAfa_2NAfcugaacacaas(invAb) | 780 | usUfsgsuguucaguUfuCfcAfuuccsg | 564 |
| AC000438 | Tri-SM6.1-avβ6-(TA14)csggaauggAfAfAfcugaauacaas(invAb) | 781 | usUfsgsUfgUfuCfaGfuUfuCfcAfuUfcCfsg | 2 |
| AC000439 | Tri-SM6.1-avβ6-(TA14)csggaauGfgAfaAfcugaacacaas(invAb) | 777 | usUfsgsuguucaguUfuCfcAfuuccsg | 564 |
| AC000440 | Tri-SM6.1-avβ6-(TA14)csggaauggAfAfAfcugaauacaas(invAb) | 781 | cPrpusUfsgsUfgUfuCfaGfuUfuCfcAfuUfcCfsg | 3 |
| AC000441 | Tri-SM6.1-avβ6-(TA14)csggaauGfgAfaAfcugaacacaas(invAb) | 777 | cPrpusUfsgsuguucaguUfuCfcAfuuccsg | 582 |
| AC000442 | Tri-SM6.1-avβ6-(TA14)csggaauGfgAfaAfcugaauacaas(invAb) | 776 | usUfsgsuguucaguUfuCfcAfuuccsg | 564 |
| AC000549 | avβ6-SM6.1-L6-C6-csggaauggAfAfAfcugaacacaas(invAb) | 782 | cPrpusUfsgsUfgUfuCfaGfuUfuCfcAfuUfcCfsg | 3 |

TABLE 10-continued

| Conjugate ID Numbers With Chemically Modified Antisense and Sense Strands (including Linkers and Conjugates) | | | | |
|---|---|---|---|---|
| AC ID Number | Sense Strand (Fully Modified with Conjugated Targeting Ligand) (5'→3') | SEQ ID NO: | Antisense Strand (5'→3') | SEQ ID NO: |
| AC000550 | avβ6-SM6.1-L6-C6s-(invAb)scggaauggAfAfAfcugaacacaas(invAb) | 783 | cPrpusUfsgsUfgUfuCfaGfuUfuCfcAfuUfcCfsg | 3 |
| AC000551 | avβ6-SM6.1-Alk-cyHex-csggaauggAfAfAfcugaacacaas(invAb) | 784 | cPrpusUfsgsUfgUfuCfaGfuUfuCfcAfuUfcCfsg | 3 |
| AC000552 | avβ6-SM6.1-Alk-cyHexs-(invAb)scggaauggAfAfAfcugaacacaas(invAb) | 785 | cPrpusUfsgsUfgUfuCfaGfuUfuCfcAfuUfcCfsg | 3 |
| AC000567 | av6-pep1-C6-csggaauggAfAfAfcugaacacaas(invAb) | 786 | cPrpusUfsgsUfgUfuCfaGfuUfuCfcAfuUfcCfsg | 3 |
| AC000568 | avβ6-pep1-C6s-(invAb)scggaauggAfAfAfcugaacacaas(invAb) | 787 | cPrpusUfsgsUfgUfuCfaGfuUfuCfcAfuUfcCfsg | 3 |
| AC000790 | Tri-SM6.1-avβ6-(TA14)gsggaauggAfAfAfcugaacacaas(invAb) | 788 | usUfsgsUfgUfuCfaGfuUfuCfcAfuUfcCfsc | 561 |
| AC000791 | Tri-SM6.1-avβ6-(TA14)csggaauggAfAfAfcuiaacacaas(invAb) | 789 | usUfsgsUfgUfuCfaGfuUfuCfcAfuUfcCfsg | 2 |
| AC000792 | Tri-SM6.1-avβ6-(TA14)csggaauggAfa_2NAfcuiaacacaas(invAb) | 790 | usUfsgsUfgUfuCfaGfuUfuCfcAfuUfcCfsg | 2 |
| AC000793 | Tri-SM6.1-avβ6-(TA14)csggaauggAfAfAfcugaacacaas(invAb) | 10 | usUfsgsUfgUfU$_{UNA}$CfaGfuUfuCfcAfuUfcCfsg | 562 |
| AC000794 | Tri-SM6.1-avβ6-(TA14)csggaauggAfAfAfcugaacacaas(invAb) | 10 | usUfsgsUfgUfucaguUfuCfcAfuUfcCfsg | 563 |
| AC000795 | Tri-SM6.1-avβ6-(TA14)csggaauggAfAfAfcugaacacaas(invAb) | 10 | usUfsgsuguucaguUfuCfcAfuuccsg | 564 |
| AC000796 | Tri-SM6.1-avβ6-(TA14)csggaauggAfAfAfcugaacacaas(invAb) | 10 | usUfsgsuguucaGfuUfuCfcAfuuccsg | 565 |
| AC000818 | Tri-SM6.1-avβ6-(TA14)gsgaauggaAfAfCfugaacacaias(invAb) | 791 | usCfsusGfuGfuUfcAfgUfuUfcCfaUfuCfsc | 543 |
| AC000819 | Tri-SM6.1-avβ6-(TA14)gsgaauggaAfAfCfugaacacaias(invAb) | 791 | cPrpusCfsusGfuGfuUfcAfgUfuUfcCfaUfuCfsc | 544 |
| AC000820 | Tri-SM6.1-avβ6-(TA14)asccagauuCfCfUfgggaaiccaas(invAb) | 792 | usUfsgsGfcUfuCfcCfaGfgAfaUfcUfgGfsu | 545 |
| AC000821 | Tri-SM6.1-avβ6-(TA14)asccagauuCfCfUfgggaaiccaas(invAb) | 792 | cPrpusUfsgsGfcUfuCfcCfaGfgAfaUfcUfgGfsu | 546 |
| AC000822 | Tri-SM6.1-avβ6-(TA14)usccugggaAfGfCfcagaaauugus(invAb) | 793 | asCfsasAfuUfuCfuGfgCfuUfcCfcAfgGfsa | 547 |
| AC000823 | Tri-SM6.1-av6-(TA14)usccugggaAfGfCfcagaaauugus(invAb) | 793 | cPrpasCfsasAfuUfuCfuGfgCfuUfcCfcAfgGfsa | 548 |
| AC001134 | Tri-SM6.1-avβ6-(TA14)csggaauGfgAfaAfcugaacacaas(invAb) | 777 | cPrpusUfsgsuguU$_{UNA}$caguUfuCfcAfuuccsg | 593 |

TABLE 10-continued

| Conjugate ID Numbers With Chemically Modified Antisense and Sense Strands (including Linkers and Conjugates) | | | | |
|---|---|---|---|---|
| AC ID Number | Sense Strand (Fully Modified with Conjugated Targeting Ligand) (5'→3') | SEQ ID NO: | Antisense Strand (5'→3') | SEQ ID NO: |
| AC001266 | Tri-SM6.1-avβ6-(TA14)gsaguagGfuGfcUfcaaaacaucas(invAb) | 11 | usGfsasuguuuugaGfcAfcCfuacusc | 5 |
| AC001267 | Tri-SM6.1-avβ6-(TA14)gsaguagGfuGfcUfcaaaacaucas(invAb) | 11 | cPrpusGfsasuguuuugaGfcAfcCfuacusc | 6 |
| AC001268 | Tri-SM6.1-avβ6-(TA14)asggcaaugAfAfCfaggaauigaas(invAb) | 12 | usUfscsCfaUfuCfcUfgUfuCfaUfuGfcCfsu | 4 |
| AC001274 | Tri-SM6.1-avβ6-(TA14)csggaauGfgAfaAfcugaacacaas(invAb) | 777 | cPrpuUfguguucaguUfuCfcAfuuccsg | 588 |
| AC001653 | Tri-SM6.1-avβ6-(TA14)csggaauGfgAfaAfcugaacacaas(invAb) | 777 | usUfsgsUfguucaguUfuCfcAfuuccsg | 614 |
| AC001654 | Tri-SM6.1-avβ6-(TA14)csggaauGfgAfaAfcugaacacaas(invAb) | 777 | usUfsgsuguUfcaguUfuCfcAfuuccsg | 615 |
| AC001655 | Tri-SM6.1-avβ6-(TA14)csggaauggAfaAfcUfgaacacaas(invAb) | 796 | usUfsgsuguUfcaguUfuCfcAfuuccsg | 615 |
| AC001877 | Tri-SM6.1-avβ6-(TA14)gsaguagGfuGfcUfcaaaacauca(invAb) | 797 | usGfsasuguuuugaGfcAfcCfuacusc | 5 |
| AC002047 | Tri-SM6.1-avβ6-(TA14)usggaauGfgAfaAfcugaacacaas(invAb) | 779 | cPrpusUfsgsuguucaguUfuCfcAfuuccsa | 619 |
| AC002345 | Tri-SM6.1-avβ6-(TA14)cscugggaaGfCfCfagaaauuguas(invAb) | 798 | cPrpusAfscsAfaUfuucugGfcUfuCfcCfagsg | 620 |
| AC002347 | Tri-SM6.1-avβ6-(TA14)gsgaauggaAfAfCfugaacacaias(invAb) | 791 | cPrpusCfsusGfuGfuucagUfuUfcCfaUfucsc | 621 |
| AC002399 | Tri-SM6.1-avβ6-(TA14)scsggaauggAfAfAfcugaacacaas(invAb) | 799 | cPrpusUfsgsUfgUfuCfaGfuUfuCfcAfuUfcCfsg | 3 |

In some embodiments, a RAGE RNAi agent is prepared or provided as a salt, mixed salt, or a free-acid. In some embodiments, a RAGE RNAi agent is prepared or provided as a pharmaceutically acceptable salt. In some embodiments, a RAGE RNAi agent is prepared or provided as a pharmaceutically acceptable sodium or potassium salt The RNAi agents described herein, upon delivery to a cell expressing an AGER gene, inhibit or knockdown expression of one or more AGER genes in vivo and/or in vitro.

Targeting Groups, Linking Groups, Pharmacokinetic/Pharmacodynamic (PK/PD) Modulators, and Delivery Vehicles In some embodiments, a RAGE RNAi agent contains or is conjugated to one or more non-nucleotide groups including, but not limited to, a targeting group, a linking group, a pharmacokinetic/pharmacodynamic (PK/PD) modulator, a delivery polymer, or a delivery vehicle. The non-nucleotide group can enhance targeting, delivery, or attachment of the RNAi agent. The non-nucleotide group can be covalently linked to the 3' and/or 5' end of either the sense strand and/or the antisense strand. In some embodiments, a RAGE RNAi agent contains a non-nucleotide group linked to the 3' and/or 5' end of the sense strand. In some embodiments, a non-nucleotide group is linked to the 5' end of a RAGE RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting moieties enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers.

A targeting group, with or without a linker, can be attached to the 5' or 3' end of any of the sense and/or antisense strands disclosed in Tables 2, 3, 4, 5, 6, and 10. A linker, with or without a targeting group, can be attached to the 5' or 3' end of any of the sense and/or antisense strands disclosed in Tables 2, 3, 4, 5, 6, and 10.

The RAGE RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

For example, in some embodiments, the RAGE RNAi agents disclosed herein are synthesized having an NH2-C6 group at the 5'-terminus of the sense strand of the RNAi agent. The terminal amino group subsequently can be reacted to form a conjugate with, for example, a group that includes an $\alpha v\beta 6$ integrin targeting ligand. In some embodiments, the RAGE RNAi agents disclosed herein are synthesized having one or more alkyne groups at the 5'-terminus of the sense strand of the RNAi agent. The terminal alkyne group(s) can subsequently be reacted to form a conjugate with, for example, a group that includes an $\alpha v\beta 6$ integrin targeting ligand.

In some embodiments, a targeting group comprises an integrin targeting ligand. In some embodiments, an integrin targeting ligand is an $\alpha v\beta 6$ integrin targeting ligand. The use of an $\alpha v\beta 6$ integrin targeting ligand facilitates cell-specific targeting to cells having $\alpha v\beta 6$ on its respective surface, and binding of the integrin targeting ligand can facilitate entry of the therapeutic agent, such as an RNAi agent, to which it is linked, into cells such as epithelial cells, including pulmonary epithelial cells and renal epithelial cells. Integrin targeting ligands can be monomeric or monovalent (e.g., having a single integrin targeting moiety) or multimeric or multivalent (e.g., having multiple integrin targeting moieties). The targeting group can be attached to the 3' and/or 5' end of the RNAi oligonucleotide using methods known in the art. The preparation of targeting groups, such as $\alpha v\beta 6$ integrin targeting ligands, is described, for example, in International Patent Application Publication No. WO 2018/085415 and in International Patent Application Publication No. WO 2019/089765, the contents of each of which are incorporated herein in its entirety.

In some embodiments, targeting groups are linked to the RAGE RNAi agents without the use of an additional linker. In some embodiments, the targeting group is designed having a linker readily present to facilitate the linkage to a RAGE RNAi agent. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

In some embodiments, a linking group is conjugated to the RNAi agent. The linking group facilitates covalent linkage of the agent to a targeting group, pharmacokinetic modulator, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include but are not limited to: C6-SS-C6, 6-SS-6, reactive groups such a primary amines (e.g., NH2-C6) and alkynes, alkyl groups, abasic residues/nucleotides, amino acids, tri-alkyne functionalized groups, ribitol, and/or PEG groups. Examples of certain linking groups are provided in Table 11.

A linker or linking group is a connection between two atoms that links one chemical group (such as an RNAi agent) or segment of interest to another chemical group (such as a targeting group, pharmacokinetic modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description. In some embodiments, a RAGE RNAi agent is conjugated to a polyethylene glycol (PEG) moiety, or to a hydrophobic group having 12 or more carbon atoms, such as a cholesterol or palmitoyl group.

In some embodiments, a RAGE RNAi agent is linked to one or more pharmacokinetic/pharmacodynamic (PK/PD) modulators. PK/PD modulators can increase circulation time of the conjugated drug and/or increase the activity of the RNAi agent through improved cell receptor binding, improved cellular uptake, and/or other means. Various PK/PD modulators suitable for use with RNAi agents are known in the art. In some embodiments, the PK/PD modulatory can be cholesterol or cholesteryl derivatives, or in some circumstances a PK/PD modulator can be comprised of alkyl groups, alkenyl groups, alkynyl groups, aryl groups, aralkyl groups, aralkenyl groups, or aralkynyl groups, each of which may be linear, branched, cyclic, and/or substituted or unsubstituted. In some embodiments, the location of attachment for these moieties is at the 5' or 3' end of the sense strand, at the 2' position of the ribose ring of any given nucleotide of the sense strand, and/or attached to the phosphate or phosphorothioate backbone at any position of the sense strand.

Any of the RAGE RNAi agent nucleotide sequences listed in Tables 2, 3, 4, 5, 6, and 10, whether modified or unmodified, can contain 3' and/or 5' targeting group(s), linking group(s), and/or PK/PD modulator(s). Any of the RAGE RNAi agent sequences listed in Tables 3, 4, 5, 6, and 10, or are otherwise described herein, which contain a 3' or 5' targeting group, linking group, and/or PK/PD modulator can alternatively contain no 3' or 5' targeting group, linking group, or PK/PD modulator, or can contain a different 3' or 5' targeting group, linking group, or pharmacokinetic modulator including, but not limited to, those depicted in Table 11. Any of the RAGE RNAi agent duplexes listed in Tables 7A, 7B, 8, 9A, 9B, and 10, whether modified or unmodified, can further comprise a targeting group or linking group, including, but not limited to, those depicted in Table 11, and the targeting group or linking group can be attached to the 3' or 5' terminus of either the sense strand or the antisense strand of the RAGE RNAi agent duplex.

Examples of certain modified nucleotides, capping moieties, and linking groups are

TABLE 11

Structures Representing Various Modified Nucleotides, Capping Moieties, Targeting Ligands and Targeting and Linking Groups (wherein ⌇ indicates the point of connection)

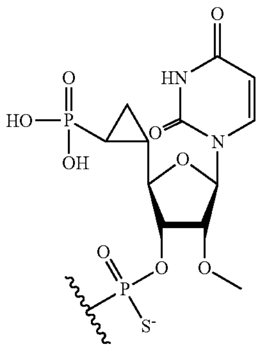

cPrpus

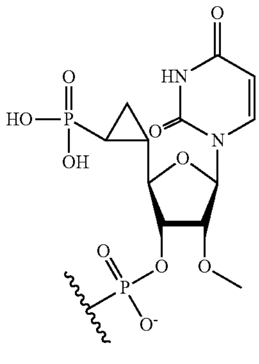

cPrpu

TABLE 11-continued
Structures Representing Various Modified Nucleotides, Capping Moieties, Targeting Ligands and Targeting and Linking Groups (wherein ⌇ indicates the point of connection)
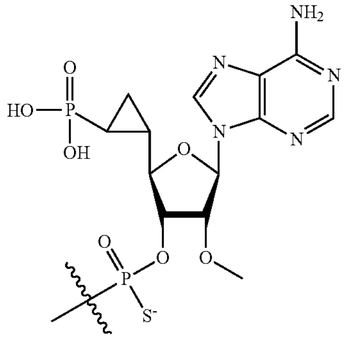
cPrpas
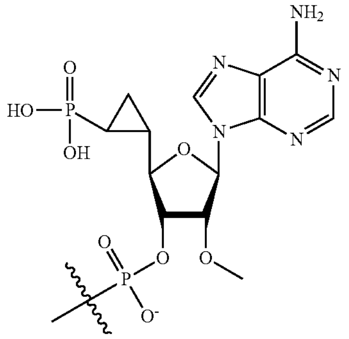
cPrpa
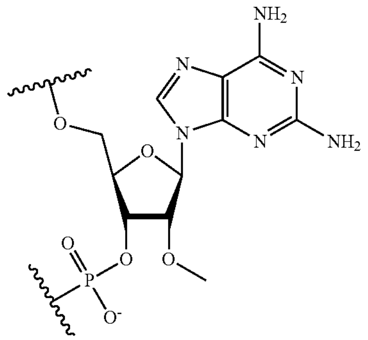
a_2N
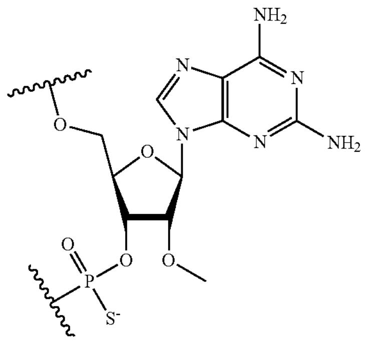
a_2Ns TABLE 11-continued Structures Representing Various Modified Nucleotides, Capping Moieties, Targeting Ligands and Targeting and Linking Groups (wherein ⌇ indicates the point of connection)

When positioned internally:

linkage towards 5′ end

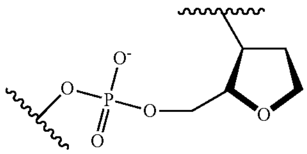

linkage towards 3′ end (invAb)

When positioned internally:

linkage towards 5′ end

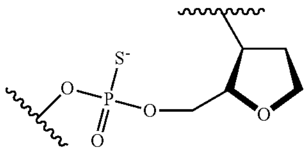

linkage towards 3′ end (invAb)s

When positioned at the 3' terminal end:

linkage towards 5′ end

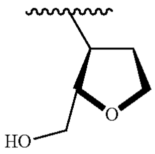

(invAb)

When positioned at the 3' terminal end:

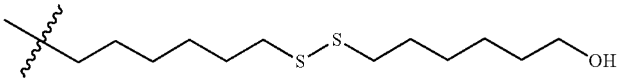

linkage towards 5′ end (C6-SS-C6)

When positioned internally:

linkage towards 5′ end linkage towards 3′ end

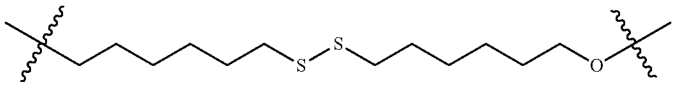

(C6-SS-C6)

When positioned at the 3' terminal end:

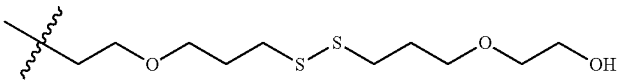

linkage towards 5′ end (6-SS-6)

TABLE 11-continued
Structures Representing Various Modified Nucleotides, Capping Moieties, Targeting Ligands and Targeting and Linking Groups (wherein ⌇ indicates the point of connection)
When positioned internally:
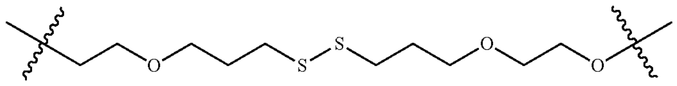
linkage towards 5′ end
linkage towards 3′ end
(6-SS-6)
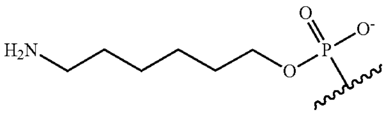
(NH2-C6)
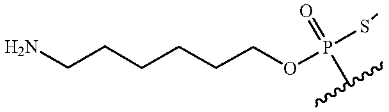
(NH2-C6)s
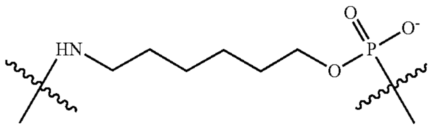
-C6-
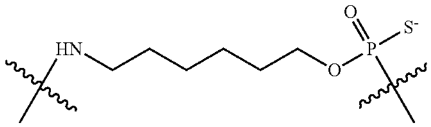
-C6s-
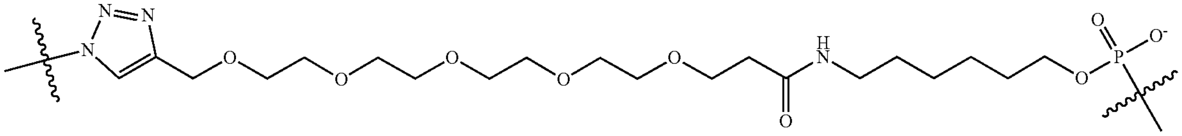
-L6-C6-
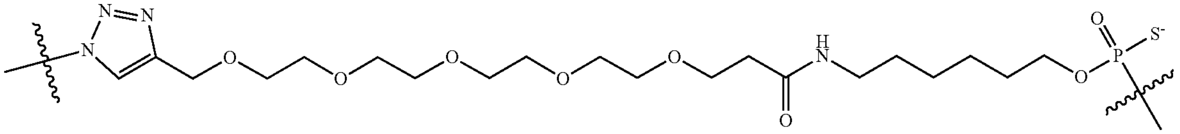
-L6-C6s-
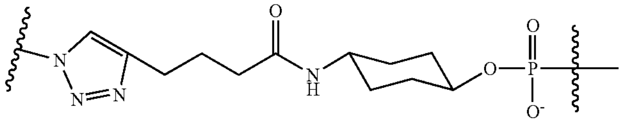
-Alk-cyHex- TABLE 11-continued
| Structures Representing Various Modified Nucleotides, Capping Moieties, Targeting Ligands and Targeting and Linking Groups (wherein ⌇ indicates the point of connection) |
| --- |
| 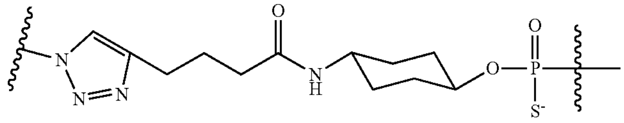 |
| -Alk-cyHexs- |
| 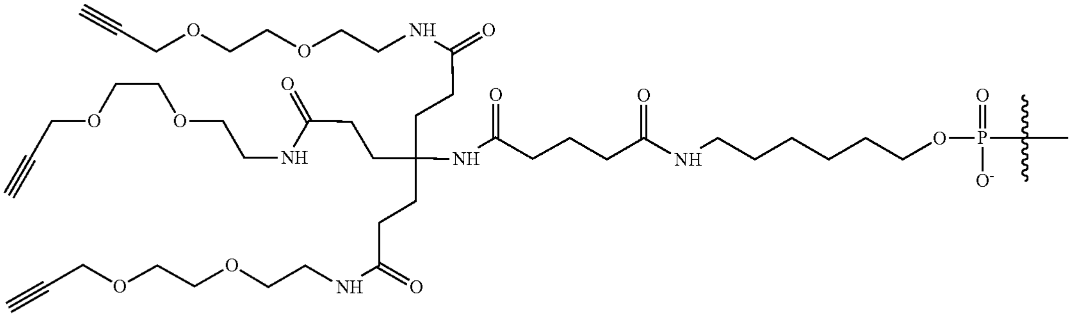 |
| (TriAlk14) |
| 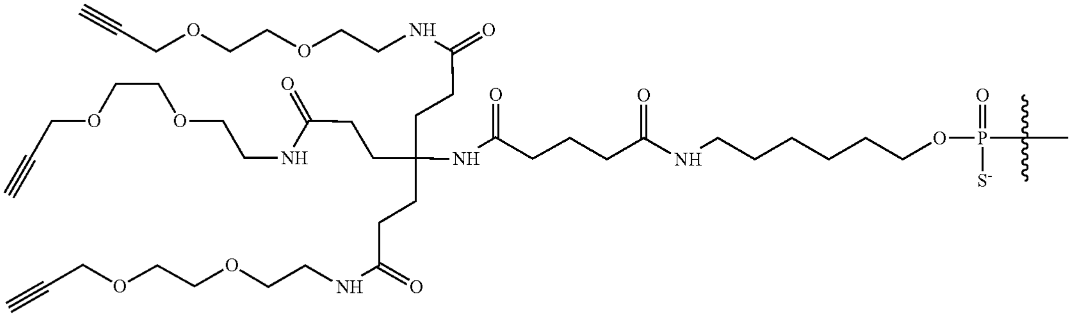 |
| (TriAlk14)s |
| 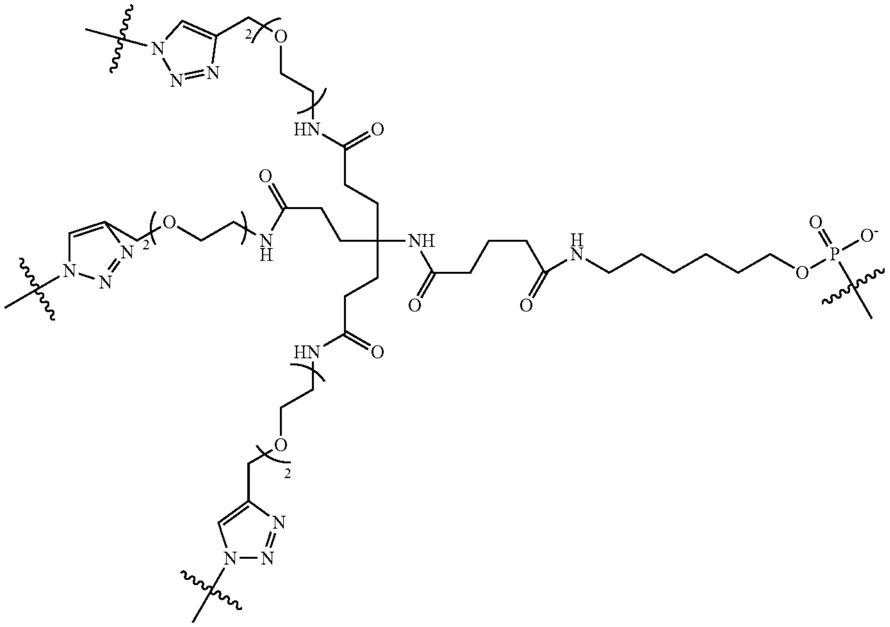 |
| (TA14) |

TABLE 11-continued
Structures Representing Various Modified Nucleotides, Capping Moieties, Targeting Ligands and Targeting and Linking Groups (wherein ⌇ indicates the point of connection)
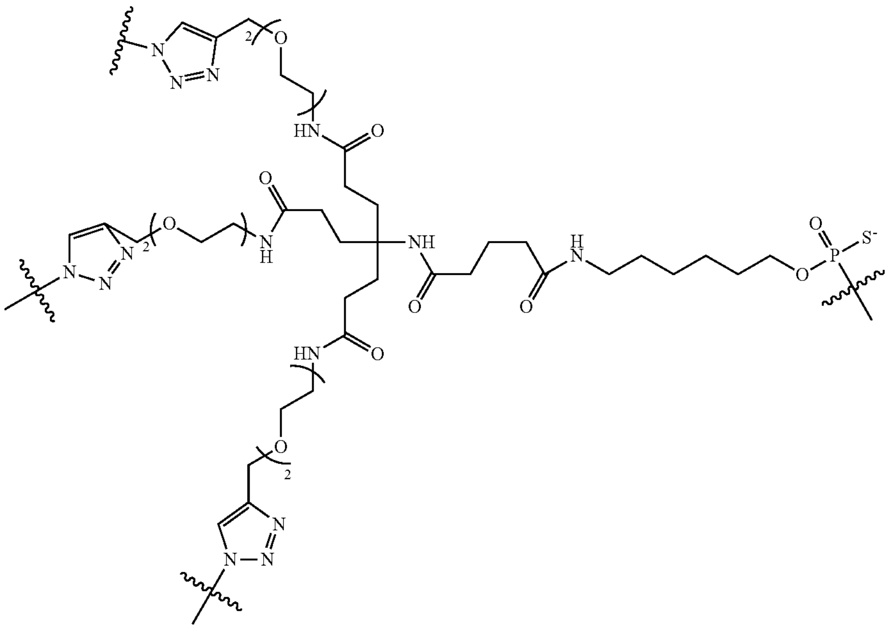
(TA14)s
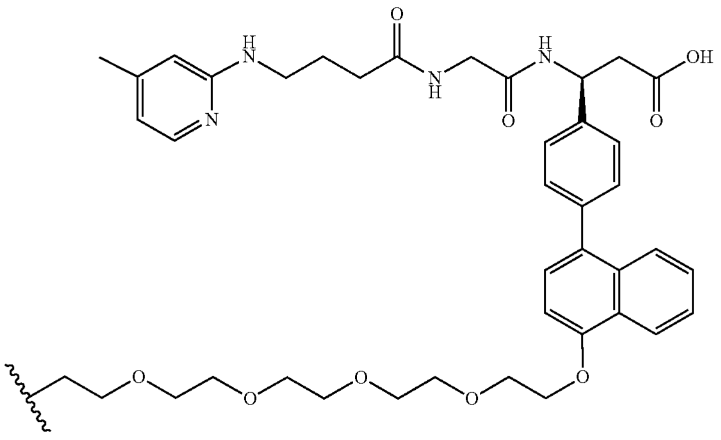
SM6.1-αvβ6
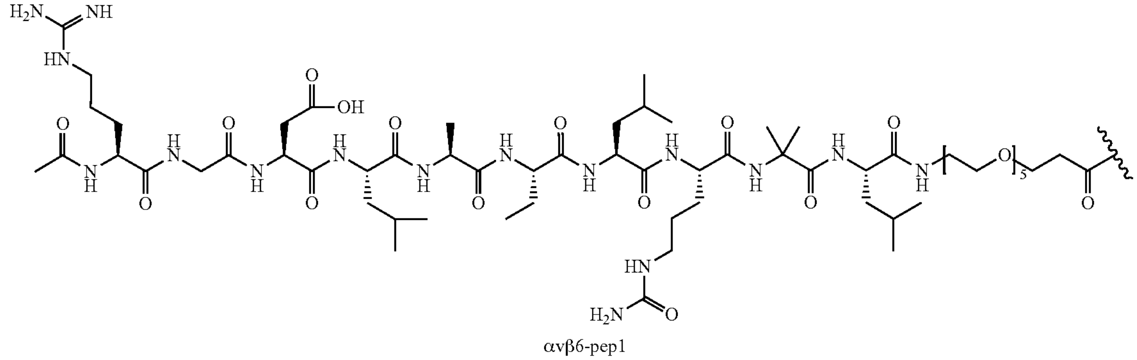
αvβ6-pep1

TABLE 11-continued
| Structures Representing Various Modified Nucleotides, Capping Moieties, Targeting Ligands and Targeting and Linking Groups (wherein ⌇ indicates the point of connection) |
| --- |
| 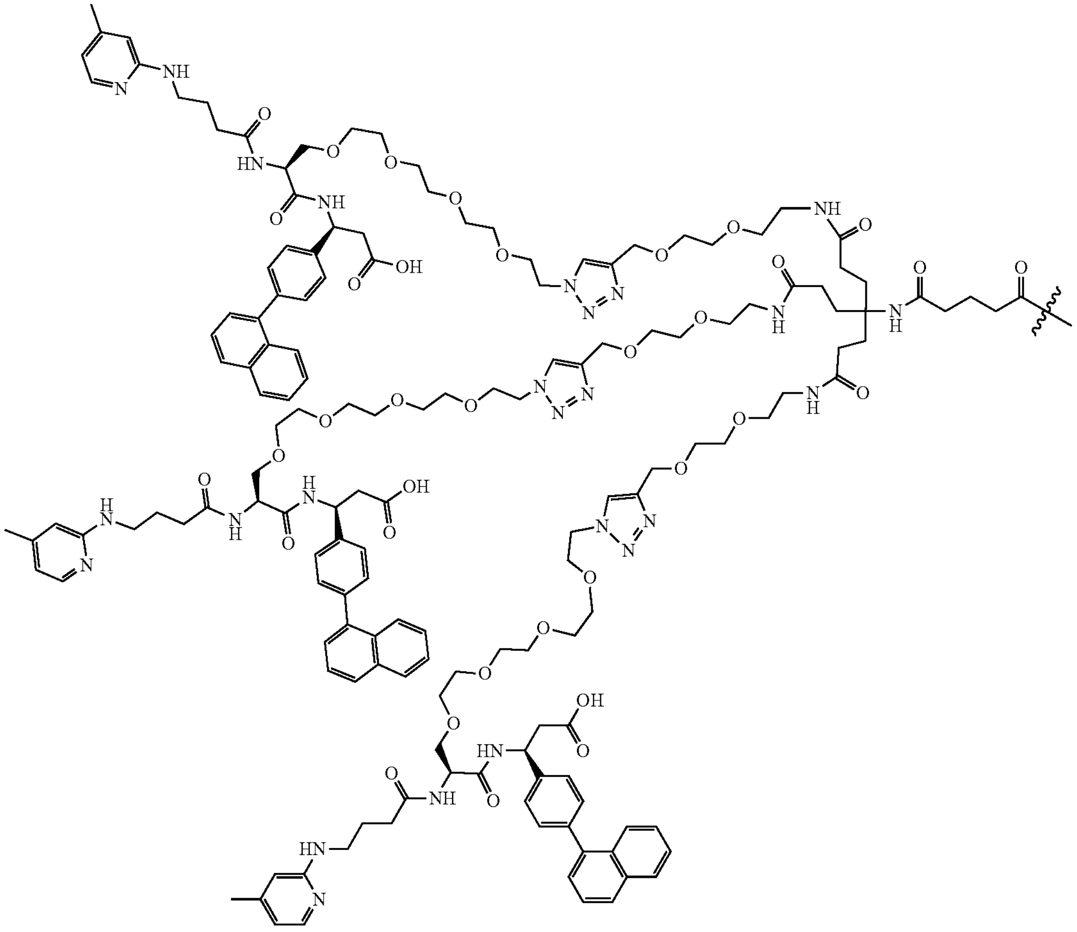 [SMILES: *C(=O)CCCC(=O)NC(CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1)(CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1)CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1] |

TABLE 11-continued
Structures Representing Various Modified Nucleotides, Capping Moieties, Targeting Ligands and Targeting and Linking Groups (wherein ⌇ indicates the point of connection)
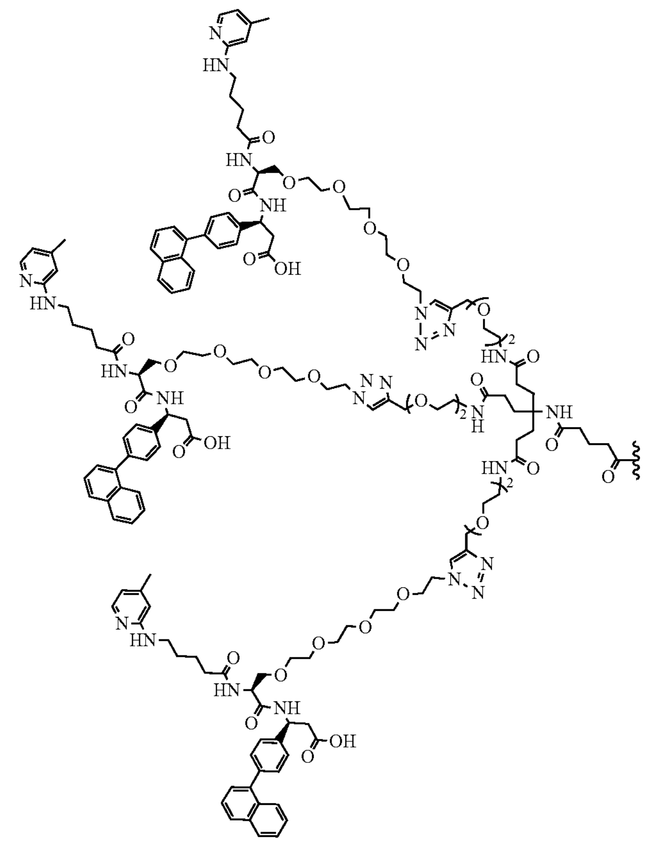

TABLE 11-continued
| Structures Representing Various Modified Nucleotides, Capping Moieties, Targeting Ligands and Targeting and Linking Groups (wherein ⌇ indicates the point of connection) |
| --- |
| 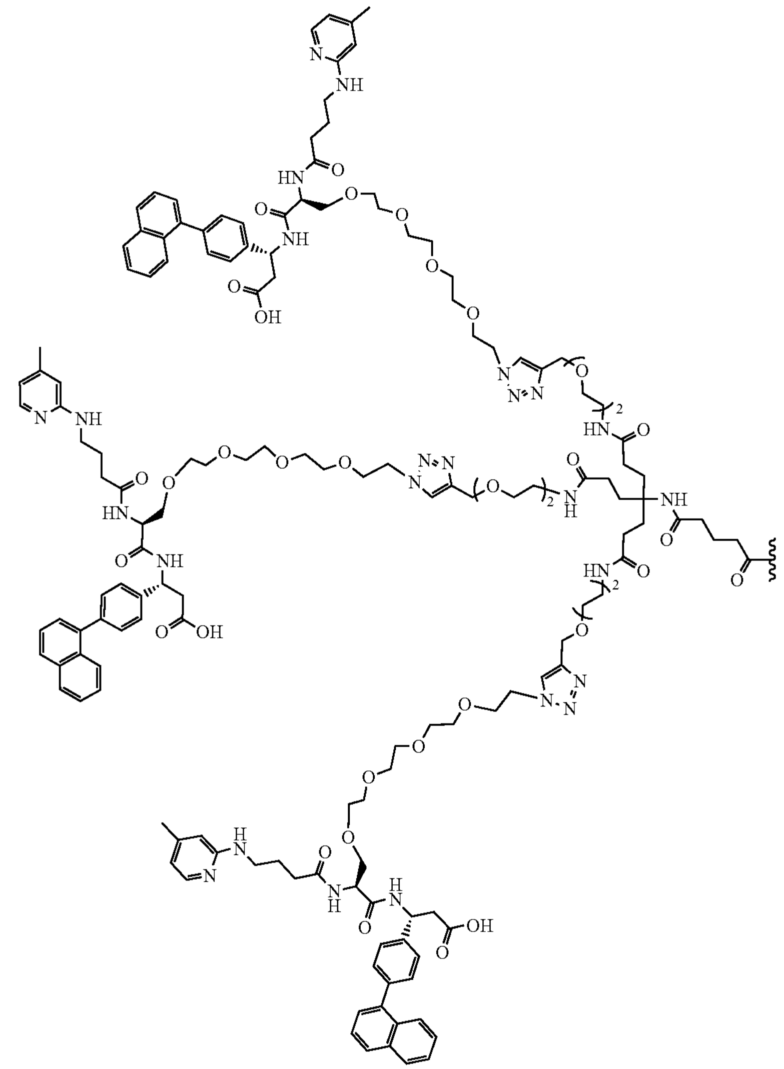 |

TABLE 11-continued
| Structures Representing Various Modified Nucleotides, Capping Moieties, Targeting Ligands and Targeting and Linking Groups (wherein ⌇ indicates the point of connection) |
| --- |
| 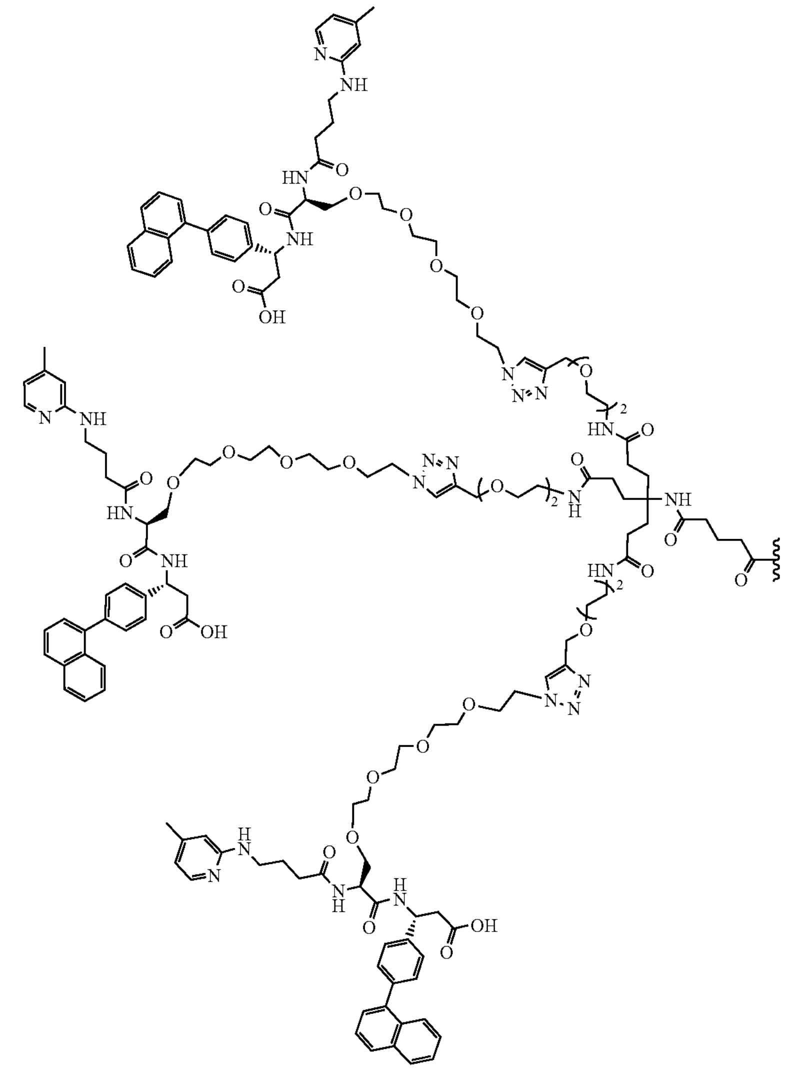 |

TABLE 11-continued
| Structures Representing Various Modified Nucleotides, Capping Moieties, Targeting Ligands and Targeting and Linking Groups (wherein ⌇ indicates the point of connection) |
|---|
| 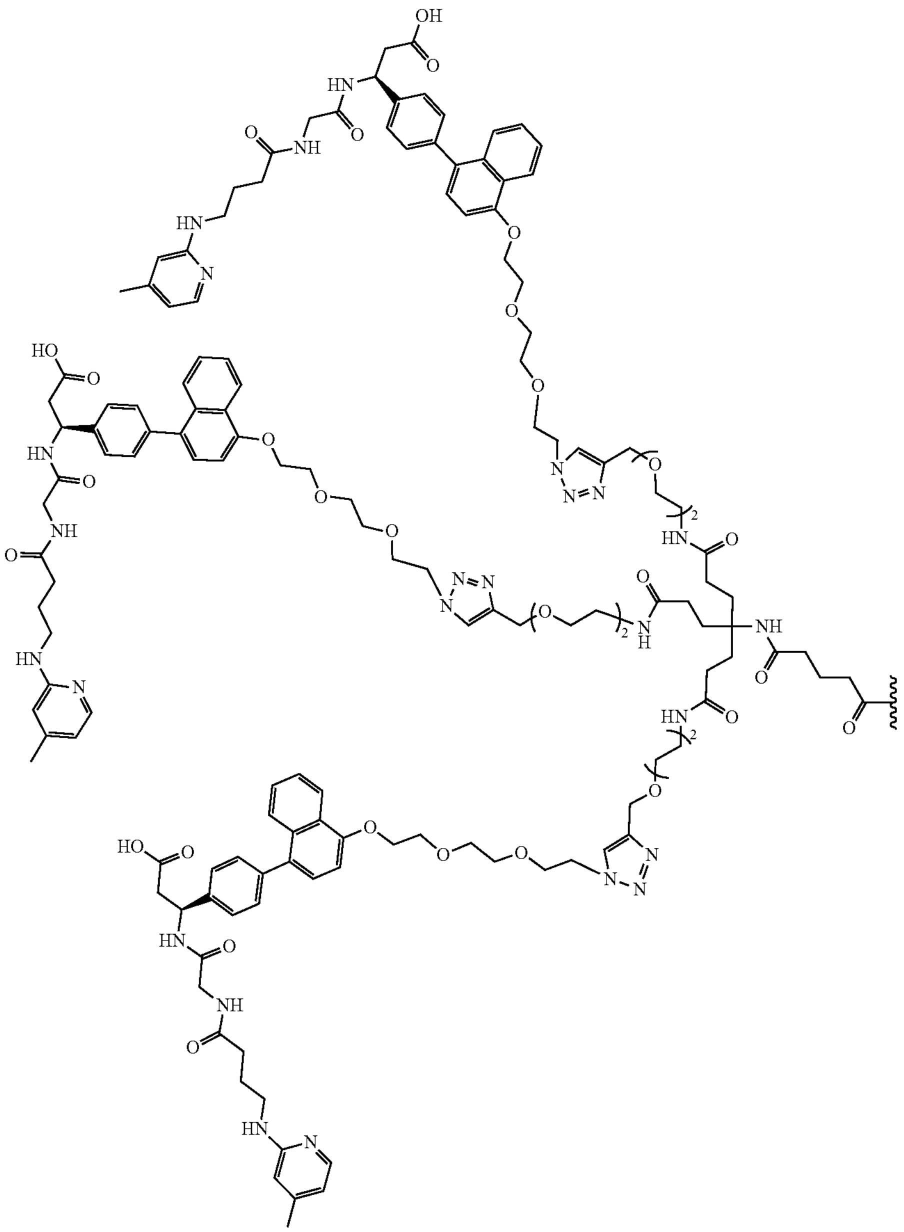 |

TABLE 11-continued
Structures Representing Various Modified Nucleotides, Capping Moieties, Targeting Ligands and Targeting and Linking Groups (wherein ⌇ indicates the point of connection)
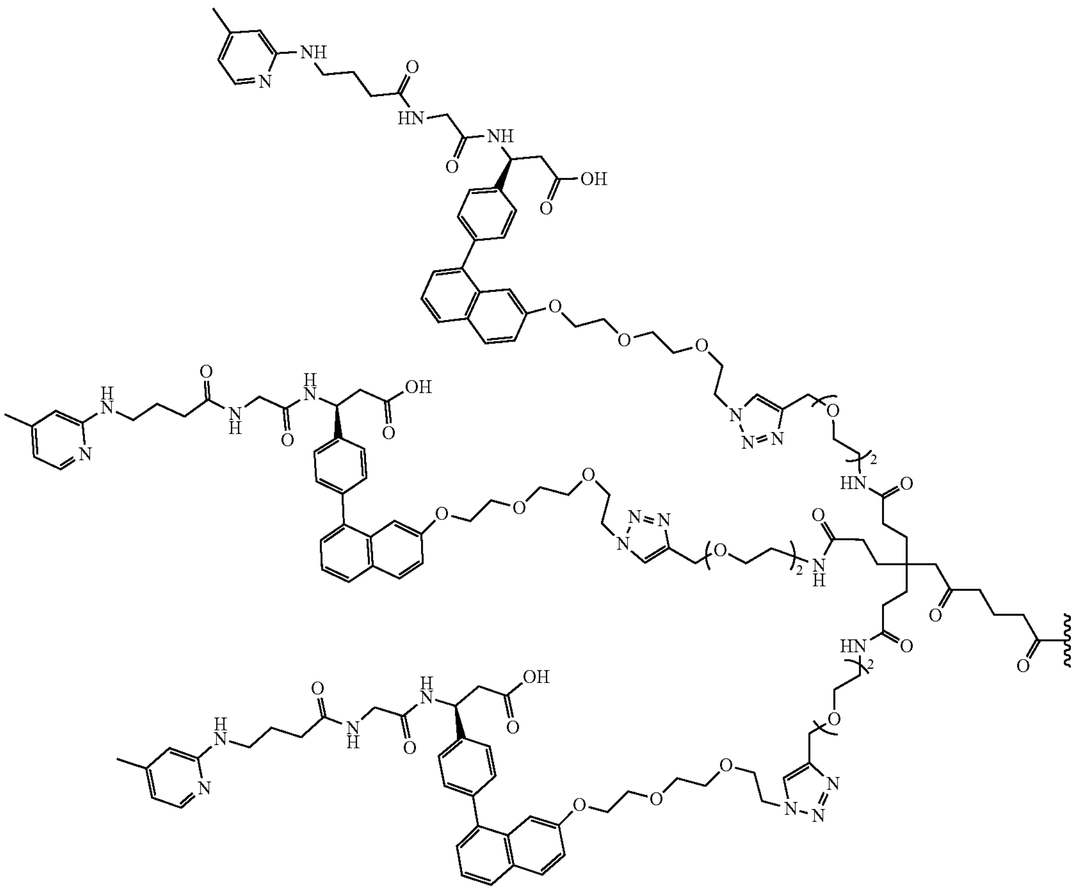

TABLE 11-continued
| Structures Representing Various Modified Nucleotides, Capping Moieties, Targeting Ligands and Targeting and Linking Groups (wherein ⌇ indicates the point of connection) |
| --- |
| 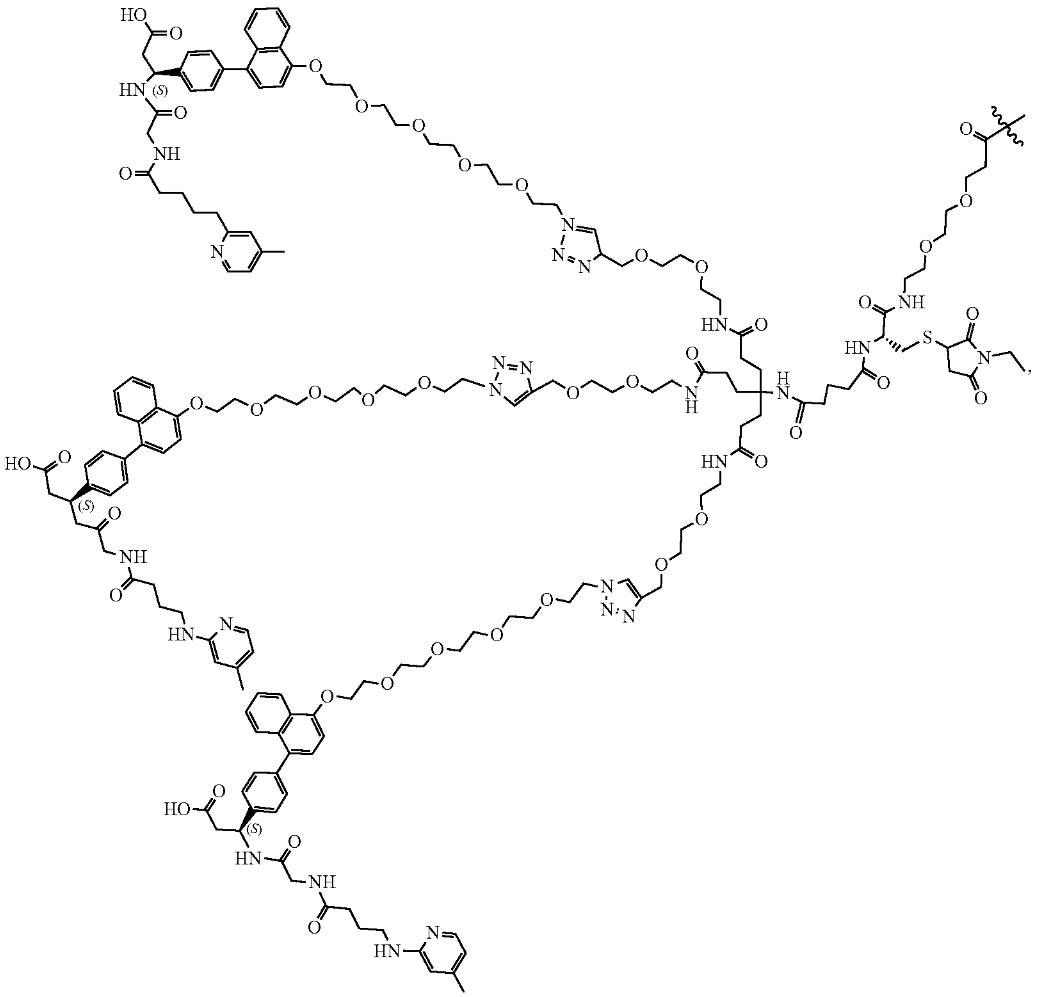 |

TABLE 11-continued
Structures Representing Various Modified Nucleotides, Capping Moieties, Targeting Ligands and Targeting and Linking Groups (wherein ⌇ indicates the point of connection)
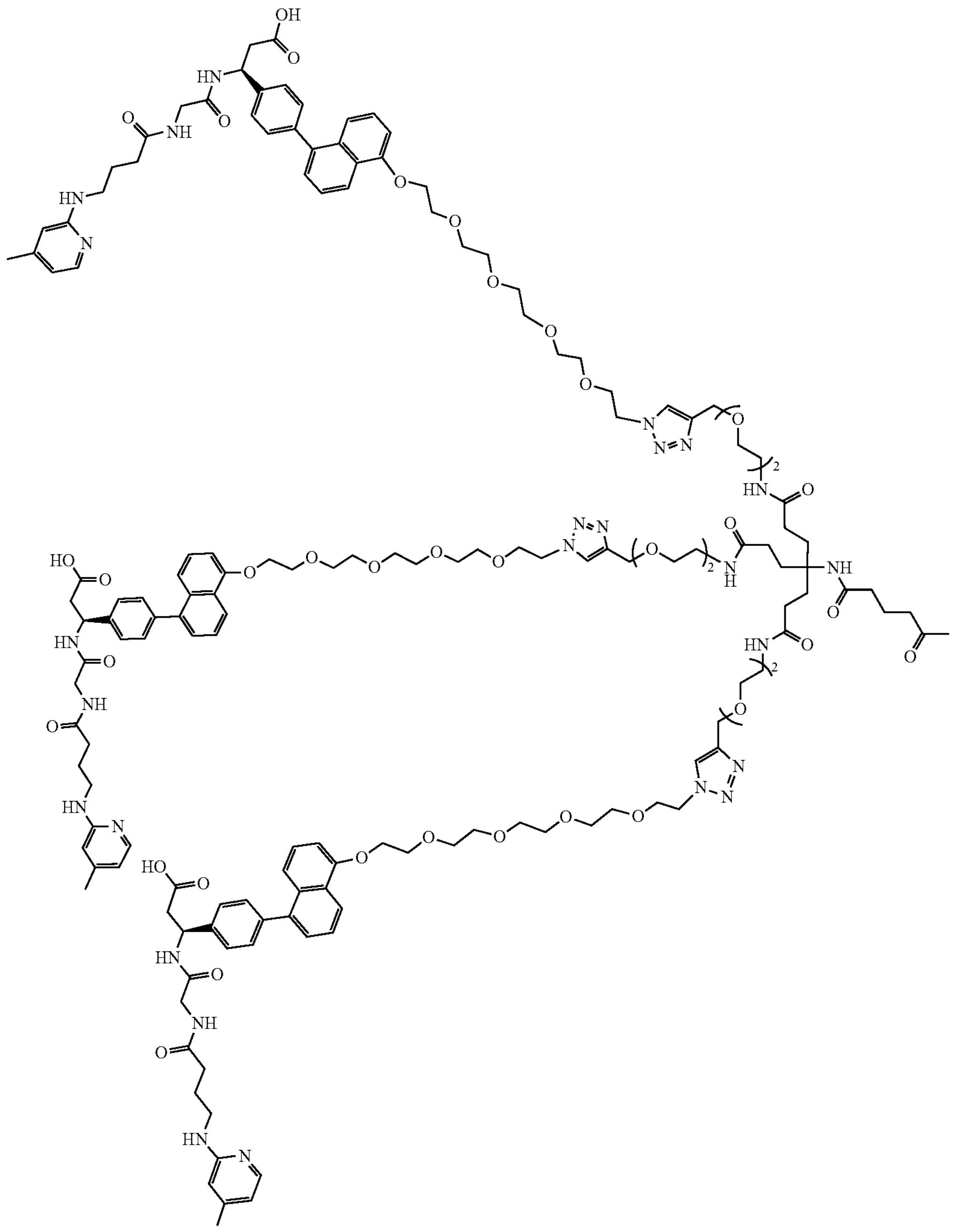

TABLE 11-continued
| Structures Representing Various Modified Nucleotides, Capping Moieties, Targeting Ligands and Targeting and Linking Groups (wherein ⌇ indicates the point of connection) |
|---|
| 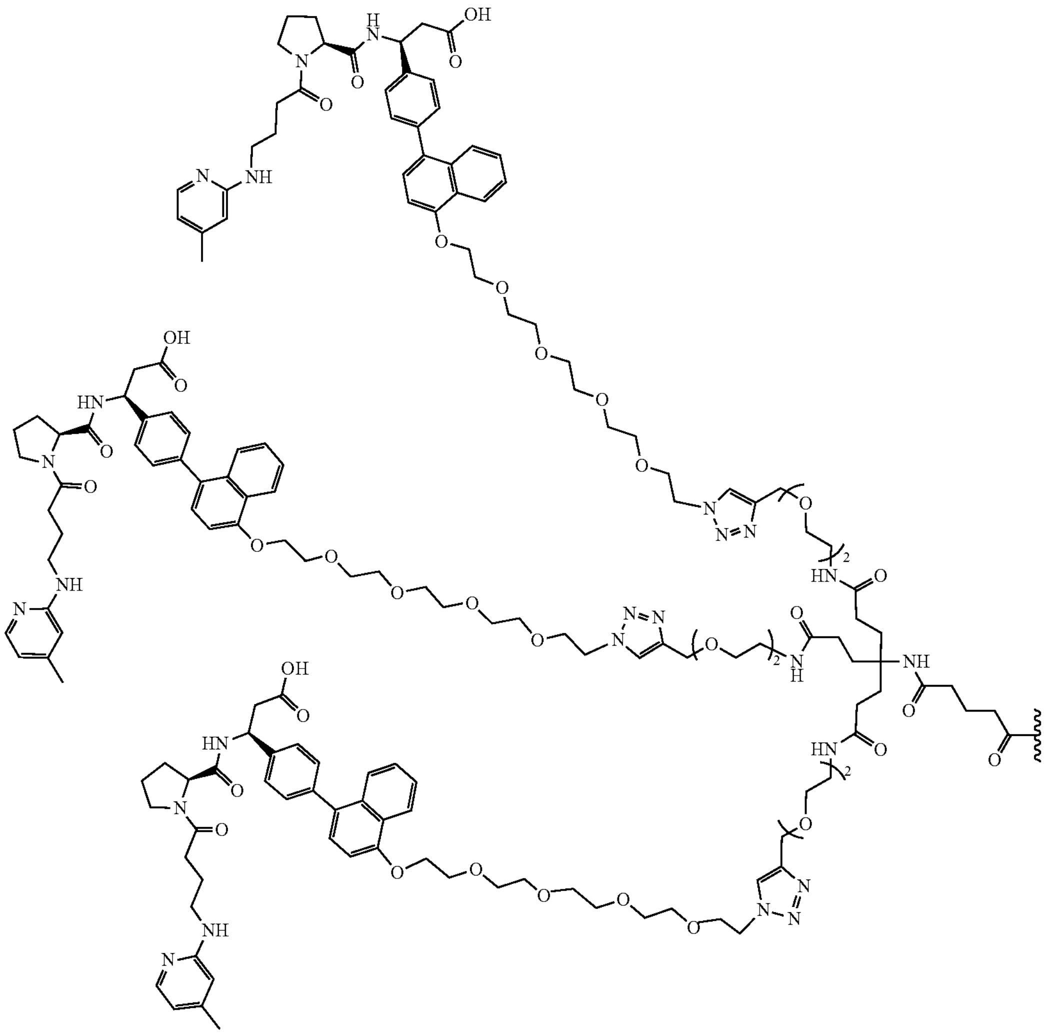 |

TABLE 11-continued

| Structures Representing Various Modified Nucleotides, Capping Moieties, Targeting Ligands and Targeting and Linking Groups (wherein ⌇ indicates the point of connection) |
| --- |
| 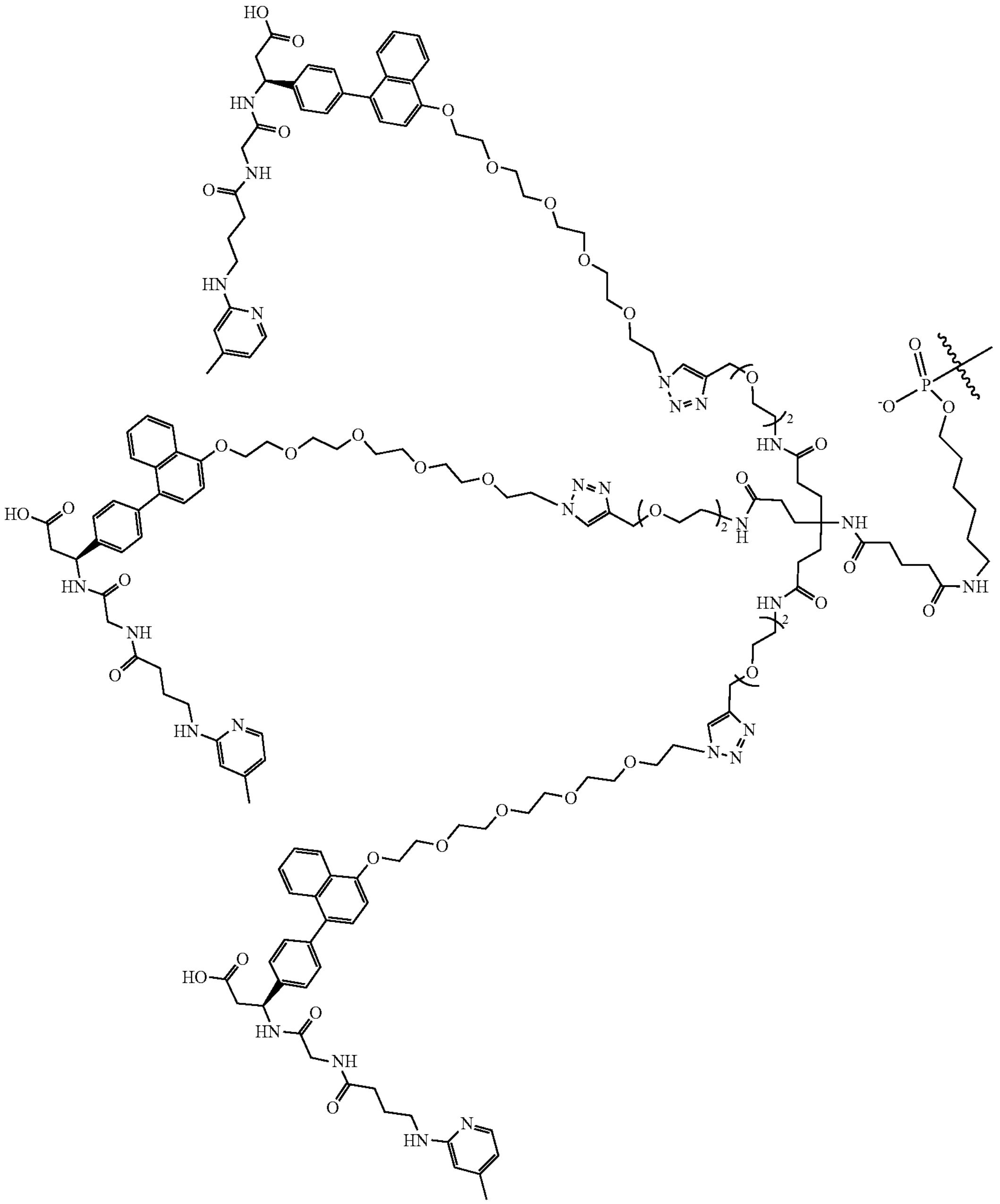 |

Alternatively, other linking groups known in the art may be used. In many instances, linking groups can be commercially acquired or alternatively, are incorporated into commercially available nucleotide phosphoramidites. (See, e.g., International Patent Application Publication No. WO 2019/161213, which is incorporated herein by reference in its entirety).

In some embodiments, a RAGE RNAi agent is delivered without being conjugated to a targeting ligand or pharmacokinetic/pharmacodynamic (PK/PD) modulator (referred to as being "naked" or a "naked RNAi agent").

In some embodiments, a RAGE RNAi agent is conjugated to a targeting group, a linking group, a PK modulator, and/or another non-nucleotide group to facilitate delivery of the RAGE RNAi agent to the cell or tissue of choice, for example, to an epithelial cell in vivo. In some embodiments, a RAGE RNAi agent is conjugated to a targeting group wherein the targeting group includes an integrin targeting ligand. In some embodiments, the integrin targeting ligand is an αvβ6 integrin targeting ligand. In some embodiments, a targeting group includes one or more αvβ6 integrin targeting ligands.

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art for nucleic acid delivery. The RNAi agents can also be chemically conjugated to targeting groups, lipids (including, but not limited to cholesteryl and cholesteryl derivatives), encapsulating in nanoparticles, liposomes, micelles, conjugating to polymers or DPCs (see, for example WO 2000/053722, WO 2008/022309, WO 2011/104169, and WO 2012/083185, WO 2013/032829, WO 2013/158141, each of which is incorporated herein by reference), by iontophoresis, or by incorporation into other delivery vehicles or systems available in the art such as hydrogels, cyclodextrins, biodegradable nanocapsules, bioadhesive microspheres, or proteinaceous vectors. In some embodiments the RNAi agents can be conjugated to antibodies having affinity for pulmonary epithelial cells. In some embodiments, the RNAi agents can be linked to targeting ligands that have affinity for pulmonary epithelial cells or receptors present on pulmonary epithelial cells.

Pharmaceutical Compositions and Formulations

The RAGE RNAi agents disclosed herein can be prepared as pharmaceutical compositions or formulations (also referred to herein as "medicaments"). In some embodiments, pharmaceutical compositions include at least one RAGE RNAi agent. These pharmaceutical compositions are particularly useful in the inhibition of the expression of AGER mRNA in a target cell, a group of cells, a tissue, or an organism. The pharmaceutical compositions can be used to treat a subject having a disease, disorder, or condition that would benefit from reduction in the level of the target mRNA, or inhibition in expression of the target gene. The pharmaceutical compositions can be used to treat a subject at risk of developing a disease or disorder that would benefit from reduction of the level of the target mRNA or an inhibition in expression the target gene. In one embodiment, the method includes administering a RAGE RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include a RAGE RNAi agent, thereby forming a pharmaceutical formulation or medicament suitable for in vivo delivery to a subject, including a human.

The pharmaceutical compositions that include a RAGE RNAi agent and methods disclosed herein decrease the level of the target mRNA in a cell, group of cells, group of cells, tissue, organ, or subject, including by administering to the subject a therapeutically effective amount of a herein described RAGE RNAi agent, thereby inhibiting the expression of AGER mRNA in the subject. In some embodiments, the subject has been previously identified or diagnosed as having a disease or disorder that can be mediated at least in part by a reduction in RAGE expression. In some embodiments, the subject has been previously diagnosed with having one or more pulmonary diseases such as asthma (including severe asthma), acute respiratory distress syndrome, idiopathic pulmonary fibrosis, chronic obstructive pulmonary disease (COPD), cystic fibrosis, pneumonia, lung cancer, or bronchopulmonary dysplasia. In some embodiments the pulmonary diseases is severe asthma.

In some embodiments the subject has been previously diagnosed with having cardiovascular disease (atherosclerosis, myocardial infarction, heart failure, peripheral vascular disease), cancer diabetes, chronic kidney disease, neurodegenerative disease, rheumatoid arthritis, non-alcoholic steatohepatitis, injury caused by certain viral infections including SARS-CoV-2, certain ocular inflammatory conditions, or skeletal muscle wasting.

In some embodiments, the subject has been previously diagnosed with having one or more ocular diseases related to ocular inflammation.

Embodiments of the present disclosure include pharmaceutical compositions for delivering a RAGE RNAi agent to a pulmonary epithelial cell in vivo. Such pharmaceutical compositions can include, for example, a RAGE RNAi agent conjugated to a targeting group that comprises an integrin targeting ligand. In some embodiments, the integrin targeting ligand is comprised of an $\alpha v\beta 6$ integrin ligand.

In some embodiments, the described pharmaceutical compositions including a RAGE RNAi agent are used for treating or managing clinical presentations in a subject that would benefit from the inhibition of expression of RAGE. In some embodiments, a therapeutically or prophylactically effective amount of one or more of pharmaceutical compositions is administered to a subject in need of such treatment. In some embodiments, administration of any of the disclosed RAGE RNAi agents can be used to decrease the number, severity, and/or frequency of symptoms of a disease in a subject.

In some embodiments, the described RAGE RNAi agents are optionally combined with one or more additional (i.e., second, third, etc.) therapeutics. A second therapeutic can be another RAGE RNAi agent (e.g., a RAGE RNAi agent that targets a different sequence within an AGER (RAGE) gene). In some embodiments, a second therapeutic can be an RNAi agent that targets the AGER gene. An additional therapeutic can also be a small molecule drug, antibody, antibody fragment, and/or aptamer. The RAGE RNAi agents, with or without the one or more additional therapeutics, can be combined with one or more excipients to form pharmaceutical compositions.

The described pharmaceutical compositions that include a RAGE RNAi agent can be used to treat at least one symptom in a subject having a disease or disorder that would benefit from reduction or inhibition in expression of AGER mRNA. In some embodiments, the subject is administered a therapeutically effective amount of one or more pharmaceutical compositions that include a RAGE RNAi agent thereby treating the symptom. In other embodiments, the subject is administered a prophylactically effective amount of one or more RAGE RNAi agents, thereby preventing or inhibiting the at least one symptom.

In some embodiments, one or more of the described RAGE RNAi agents are administered to a mammal in a pharmaceutically acceptable carrier or diluent. In some embodiments, the mammal is a human.

The route of administration is the path by which a RAGE RNAi agent is brought into contact with the body. In general, methods of administering drugs, oligonucleotides, and nucleic acids, for treatment of a mammal are well known in the art and can be applied to administration of the compositions described herein. The RAGE RNAi agents disclosed herein can be administered via any suitable route in a preparation appropriately tailored to the particular route. Thus, in some embodiments, the herein described pharmaceutical compositions are administered via inhalation, intranasal administration, intratracheal administration, or oropharyngeal aspiration administration. In some embodiments, the pharmaceutical compositions can be administered by injection, for example, intravenously, intramuscularly, intracutaneously, subcutaneously, intraarticularly, intraocularly, or intraperitoneally, or topically.

The pharmaceutical compositions including a RAGE RNAi agent described herein can be delivered to a cell, group of cells, tissue, or subject using oligonucleotide delivery technologies known in the art. In general, any suitable method recognized in the all for delivering a nucleic acid molecule (in vitro or in vivo) can be adapted for use with the compositions described herein. For example, delivery can be by local administration, (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In some embodiments, the compositions are administered via inhalation, intranasal administration, oropharyngeal aspiration administration, or intratracheal administration. For example, in some embodiments, it is desired that the RAGE RNAi agents described herein inhibit the expression of an AGER gene in the pulmonary epithelium, for which administration via inhalation (e.g., by an inhaler device, such as a metered-dose inhaler, or a nebulizer such as a jet or vibrating mesh nebulizer, or a soft mist inhaler) is particularly suitable and advantageous In some embodiments, the pharmaceutical compositions described herein comprise one or more pharmaceutically acceptable excipients. The pharmaceutical compositions described herein are formulated for administration to a subject.

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., RAGE RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® ELTM (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

Formulations suitable for inhalation administration can be prepared by incorporating the active compound in the desired amount in an appropriate solvent, followed by sterile filtration. In general, formulations for inhalation administration are sterile solutions at physiological pH and have low viscosity (<5 cP). Salts may be added to the formulation to balance tonicity. In some cases, surfactants or co-solvents can be added to increase active compound solubility and improve aerosol characteristics. In some cases, excipients can be added to control viscosity in order to ensure size and distribution of nebulized droplets.

In some embodiments, pharmaceutical formulations that include the RAGE RNAi agents disclosed herein suitable for inhalation administration can be prepared in water for injection (sterile water), or an aqueous sodium phosphate buffer (for example, the RAGE RNAi agent formulated in 0.5 mM sodium phosphate monobasic, 0.5 mM sodium phosphate dibasic, in water).

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The RAGE RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another RAGE RNAi agent (e.g., a RAGE RNAi agent that targets a different sequence within the RAGE target). In other embodiments, the second therapeutic can be a small molecule drug, an antibody, an antibody fragment, and/or an aptamer.

In some embodiments, described herein are compositions that include a combination or cocktail of at least two RAGE RNAi agents having different sequences. In some embodiments, the two or more RAGE RNAi agents are each separately and independently linked to targeting groups. In some embodiments, the two or more RAGE RNAi agents are each linked to targeting groups that include or consist of integrin targeting ligands. In some embodiments, the two or more RAGE RNAi agents are each linked to targeting groups that include or consist of αvβ6 integrin targeting ligands.

Described herein are compositions for delivery of RAGE RNAi agents to pulmonary epithelial cells. Furthermore, compositions for delivery of RAGE RNAi agents to cells, including renal epithelial cells and/or epithelial cells in the GI or reproductive tract and/or and ocular surface epithelial cells in the eye, in vivo, are generally described herein.

Generally, an effective amount of a RAGE RNAi agent disclosed herein will be in the range of from about 0.0001 to about 20 mg/kg of body weight/deposited dose, e.g., from about 0.001 to about 5 mg/kg of body weight/deposited dose. In some embodiments, an effective amount of a RAGE RNAi agent will be in the range of from about 0.01 mg/kg to about 3.0 mg/kg of body weight per deposited dose. In some embodiments, an effective amount of a RAGE RNAi agent will be in the range of from about 0.03 mg/kg to about 2.0 mg/kg of body weight per deposited dose. In some embodiments, an effective amount of a RAGE RNAi agent will be in the range of from about 0.01 to about 1.0 mg/kg of deposited dose per body weight. In some embodiments, an effective amount of a RAGE RNAi agent will be in the range of from about 0.50 to about 1.0 mg/kg of deposited dose per body weight. The amount administered will also likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum. In some embodiments, a dose is administered daily. In some embodiments, a dose is administered weekly. In further embodiments, a dose is administered bi-weekly, tri-weekly, once monthly, or once quarterly (i.e., once every three months).

For treatment of disease or for formation of a medicament or composition for treatment of a disease, the pharmaceutical compositions described herein including a RAGE RNAi agent can be combined with an excipient or with a second therapeutic agent or treatment including, but not limited to: a second or other RNAi agent, a small molecule drug, an antibody, an antibody fragment, peptide, and/or an aptamer.

The described RAGE RNAi agents, when added to pharmaceutically acceptable excipients or adjuvants, can be packaged into kits, containers, packs, or dispensers. The pharmaceutical compositions described herein can be packaged in dry powder or aerosol inhalers, other metered-dose inhalers, nebulizers, pre-filled syringes, or vials.

Methods of Treatment and Inhibition of RAGE Expression

The RAGE RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from a reduction and/or inhibition in expression of AGER mRNA and/or a reduction in RAGE receptor levels.

In some embodiments, the RNAi agents disclosed herein can be used to treat a subject (e.g., a human) having a disease or disorder for which the subject would benefit from reduction in RAGE receptors, including but not limited to, pulmonary diseases such as asthma (including severe asthma), acute respiratory distress syndrome, idiopathic pulmonary fibrosis, lung cancer, bronchopulmonary dysplasia, chronic obstructive pulmonary disease (COPD), or cystic fibrosis. In some embodiments the pulmonary diseases is severe asthma. In some embodiments the subject has been previously diagnosed with having cardiovascular disease (atherosclerosis, myocardial infarction, heart failure, peripheral vascular disease), cancer, diabetes, chronic kidney disease, neurodegenerative disease, rheumatoid arthritis, non-alcoholic steatohepatitis, injury caused by certain viral infections including SARS-CoV-2, certain ocular inflammatory conditions, or skeletal muscle wasting. Treatment of a subject can include therapeutic and/or prophylactic treatment. The subject is administered a therapeutically effective amount of any one or more RAGE RNAi agents described herein. The subject can be a human, patient, or human patient. The subject may be an adult, adolescent, child, or infant. Administration of a pharmaceutical composition described herein can be to a human being or animal.

Increased membrane RAGE activity is known to promote inflammation in tissues. In some embodiments, the described RAGE RNAi agents are used to treat at least one symptom mediated at least in part by a reduction in RAGE levels, in a subject. The subject is administered a therapeutically effective amount of any one or more of the described RAGE RNAi agents. In some embodiments, the subject is administered a prophylactically effective amount of any one or more of the described RNAi agents, thereby treating the subject by preventing or inhibiting the at least one symptom.

In certain embodiments, the present disclosure provides methods for treatment of diseases, disorders, conditions, or pathological states mediated at least in part by AGER gene expression, in a patient in need thereof, wherein the methods include administering to the patient any of the RAGE RNAi agents described herein.

In some embodiments, the RAGE RNAi agents are used to treat or manage a clinical presentation or pathological state in a subject, wherein the clinical presentation or pathological state is mediated at least in part by a reduction in RAGE expression. The subject is administered a therapeutically effective amount of one or more of the RAGE RNAi agents or RAGE RNAi agent-containing compositions described herein. In some embodiments, the method comprises administering a composition comprising a RAGE RNAi agent described herein to a subject to be treated.

In a further aspect, the disclosure features methods of treatment (including prophylactic or preventative treatment) of diseases or symptoms that may be addressed by a reduction in RAGE receptor levels, the methods comprising administering to a subject in need thereof a RAGE RNAi agent that includes an antisense strand comprising the sequence of any of the sequences in Table 2, Table 3, or Table 10. Also described herein are compositions for use in such methods.

The described RAGE RNAi agents and/or compositions that include RAGE RNAi agents can be used in methods for therapeutic treatment of disease or conditions caused by enhanced or elevated RAGE receptor activity levels. Such methods include administration of a RAGE RNAi agent as described herein to a subject, e.g., a human or animal subject.

In another aspect, the disclosure provides methods for the treatment (including prophylactic treatment) of a pathological state (such as a condition or disease) mediated at least in part by RAGE expression, wherein the methods include administering to a subject a therapeutically effective amount of an RNAi agent that includes an antisense strand comprising the sequence of any of the sequences in Table 2, Table 3, or Table 10.

In some embodiments, methods for inhibiting expression of an AGER gene are disclosed herein, wherein the methods include administering to a cell an RNAi agent that includes an antisense strand comprising the sequence of any of the sequences in Table 2, Table 3, or Table 10.

In some embodiments, methods for the treatment (including prophylactic treatment) of a pathological state mediated at least in part by RAGE expression are disclosed herein, wherein the methods include administering to a subject a therapeutically effective amount of an RNAi agent that includes a sense strand comprising the sequence of any of the sequences in Table 2, Table 4, Table 5, Table 6, or Table 10.

In some embodiments, methods for inhibiting expression of an AGER gene are disclosed herein, wherein the methods comprise administering to a cell an RNAi agent that includes a sense strand comprising the sequence of any of the sequences in Table 2, Table 4, Table 5, Table 6, or Table 10.

In some embodiments, methods for the treatment (including prophylactic treatment) of a pathological state mediated at least in part by RAGE expression are disclosed herein, wherein the methods include administering to a subject a therapeutically effective amount of an RNAi agent that includes a sense strand comprising the sequence of any of the sequences in Table 4, Table 5, Table 6, or Table 10, and an antisense strand comprising the sequence of any of the sequences in Table 3 or Table 10.

In some embodiments, methods for inhibiting expression of an AGER (RAGE) gene are disclosed herein, wherein the methods include administering to a cell an RNAi agent that includes a sense strand comprising the sequence of any of the sequences in Table 4, Table 5, Table 6, or Table 10, and an antisense strand comprising the sequence of any of the sequences in Table 3 or Table 10.

In some embodiments, methods of inhibiting expression of an AGER gene are disclosed herein, wherein the methods include administering to a subject a RAGE RNAi agent that includes a sense strand consisting of the nucleobase sequence of any of the sequences in Table 4, Table 5, Table 6, or Table 10, and the antisense strand consisting of the nucleobase sequence of any of the sequences in Table 3 or Table 10. In other embodiments, disclosed herein are methods of inhibiting expression of an AGER gene, wherein the methods include administering to a subject a RAGE RNAi agent that includes a sense strand consisting of the modified sequence of any of the modified sequences in Table 4, Table 5, Table 6, or Table 10, and the antisense strand consisting of the modified sequence of any of the modified sequences in Table 3 or Table 10.

In some embodiments, methods for inhibiting expression of an AGER gene in a cell are disclosed herein, wherein the methods include administering one or more RAGE RNAi agents comprising a duplex structure of one of the duplexes set forth in Tables 7A, 7B, 8, 9A, 9B, and 10.

In some embodiments, the gene expression level and/or mRNA level of an AGER gene in certain epithelial cells of subject to whom a described RAGE RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the RAGE RNAi agent or to a subject not receiving the RAGE RNAi agent. In some embodiments, the RAGE receptor or RAGE protein levels in certain epithelial cells of a subject to whom a described RAGE RNAi agent is administered is reduced by at least about 5%, 10%, 15%, 20%, 25%, 30%, 35%, 40%, 45%, 50%, 55% 60%, 65%, 70%, 75%, 80%, 85%, 90%, 95%, 96%, 97%, 98%, 99%, or greater than 99%, relative to the subject prior to being administered the RAGE RNAi agent or to a subject not receiving the RAGE RNAi agent. The gene expression level, protein level, and/or mRNA level in the subject may be reduced in a cell, group of cells, and/or tissue of the subject. In some embodiments, the AGER mRNA levels in certain epithelial cells subject to whom a described RAGE RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the RAGE RNAi agent or to a subject not receiving the RAGE RNAi agent.

A reduction in gene expression, mRNA, and protein levels can be assessed by any methods known in the art. Reduction or decrease in RAGE receptor activity level and/or RAGE protein levels are collectively referred to herein as a decrease in, reduction of, or inhibition of RAGE expression. The Examples set forth herein illustrate known methods for assessing inhibition of RAGE expression and AGER gene expression.

Cells, Tissues, Organs, and Non-Human Organisms

Cells, tissues, organs, and non-human organisms that include at least one of the RAGE RNAi agents described herein are contemplated. The cell, tissue, organ, or non-human organism is made by delivering the RNAi agent to the cell, tissue, organ, or non-human organism.

Additional Illustrative Embodiments

Provided here are certain additional illustrative embodiments of the disclosed technology. These embodiments are illustrative only and do not limit the scope of the present disclosure or of the claims attached hereto.

Embodiment 1. An RNAi agent for inhibiting expression of a receptor for advanced glycation end-products gene, comprising:

- an antisense strand comprising at least 15 contiguous nucleotides differing by 0, 1, 2, or 3, nucleotides from any one of the antisense strand sequences disclosed in Table 2 or Table 3; and
- a sense strand comprising a nucleotide sequence that is at least partially complementary to the antisense strand.

Embodiment 2. An RNAi agent for inhibiting expression of a receptor for advanced glycation end-products gene, comprising:

- a sense strand comprising at least 15 contiguous nucleotides differing by 0, 1, 2, or 3 nucleotides from a stretch of the same length of nucleotides of SEQ ID NO: 1; and an antisense strand comprising a nucleotide sequences that is at least partially complementary to the sense strand.

Embodiment 3. An inhibitor of an AGER (RAGE) gene comprising an antisense strand comprising a nucleotide sequence having at least 15 contiguous nucleotides differing by 0, 1, 2, or 3 nucleotides that are complementary to any of the target nucleotide sequences in Table 1.

Embodiment 4. An RNAi agent comprising (i) an antisense strand comprising a nucleotide sequence having at least 15 contiguous nucleotides differing by 0, 1, 2, or 3 nucleotides from any of the nucleotide sequences in Table 2, Table 3 or Table 10, and (ii) a sense strand at least partially complementary to the antisense strand.

Embodiment 5. An RNAi agent comprising (i) an antisense strand comprising, consisting of, or consisting essentially of a nucleotide sequence from any of the antisense strand nucleotide sequences in Table 2, Table 3 or Table 10, and (ii) a sense strand comprising, consisting of, or consisting essentially of a nucleotide sequence from any of the sense strand nucleotide sequences in Table 2, Table 4, Table 5, Table 6, or Table 10.

Embodiment 6. An RNAi agent comprising an antisense strand and sense strand annealed to form a duplex, wherein the duplex has the structure of any of the duplexes set forth in Table 7A, Table 7B, Table 8, Table 9, or Table 10.

Embodiment 7. an RNAi agent capable of inhibiting expression of a Receptor for Advanced Glycation End-products gene comprising:

- (i) an antisense strand that is between 18 and 49 nucleotides in length that is at least partially complementary to a Receptor for Advanced Glycation End-products gene (SEQ ID NO:1);
- (ii) a sense strand that is at least partially complementary to the antisense strand; and
- (iii) a targeting ligand linked to the sense strand.

Embodiment 8. An RNAi agent for inhibiting expression of a Receptor for Advanced Glycation End-products gene, comprising:

- an antisense strand comprising at least 17 contiguous nucleotides differing by 0 or 1 nucleotides from any one of the sequences provided in Table 2 or Table 3; and
- a sense strand comprising a nucleotide sequence that is at least partially complementary to the antisense strand.

Embodiment 9. The RNAi agent of any one of embodiments 1-8, wherein the antisense strand comprises nucleotides 2-18 of any one of the sequences provided in Table 2 or Table 3.

Embodiment 10. The RNAi agent of any one of embodiments 1-9, wherein the sense strand comprises a nucleotide sequence of at least 17 contiguous nucleotides differing by 0 or 1 nucleotides from any one of the sequences provided in Table 2 or Table 4, and wherein the sense strand has a region of at least 85% complementarity over the 17 contiguous nucleotides to the antisense strand.

Embodiment 11. The RNAi agent of any one of embodiments 1-10, wherein at least one nucleotide of the RNAi agent is a modified nucleotide or includes a modified internucleoside linkage.

Embodiment 12. The RNAi agent of any one of embodiments 1-11, wherein all or substantially all of the nucleotides are modified nucleotides.

Embodiment 13. The RNAi agent of any one of embodiments 11-12, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate-containing nucleotide, cyclopropyl phosphonate-containing nucleotide, and 3'-O-methyl nucleotide.

Embodiment 14. The RNAi agent of embodiment 12, wherein all or substantially all of the nucleotides are modified with 2'-O-methyl nucleotides, 2'-fluoro nucleotides, or combinations thereof.

Embodiment 15. The RNAi agent of any one of embodiments 1-14, wherein the antisense strand comprises the nucleotide sequence of any one of the modified sequences provided in Table 3.

Embodiment 16. The RNAi agent of any one of embodiments 1-15, wherein the sense strand comprises the nucleotide sequence of any one of the modified sequences provided in Table 4.

Embodiment 17. The RNAi agent of embodiment 1, wherein the antisense strand comprises the nucleotide sequence of any one of the modified sequences provided in Table 3 and the sense strand comprises the nucleotide sequence of any one of the modified sequences provided in Table 4.

Embodiment 18. The RNAi agent of any one of embodiments 1-17, wherein the sense strand is between 18 and 30 nucleotides in length, and the antisense strand is between 18 and 30 nucleotides in length.

Embodiment 19. The RNAi agent of embodiment 18, wherein the sense strand and the antisense strand are each between 18 and 27 nucleotides in length.

Embodiment 20. The RNAi agent of embodiment 19, wherein the sense strand and the antisense strand are each between 18 and 24 nucleotides in length.

Embodiment 21. The RNAi agent of embodiment 20, wherein the sense strand and the antisense strand are each 21 nucleotides in length.

Embodiment 22. The RNAi agent of embodiment 21, wherein the RNAi agent has two blunt ends.

Embodiment 23. The RNAi agent of any one of embodiments 1-22, wherein the sense strand comprises one or two terminal caps.

Embodiment 24. The RNAi agent of any one of embodiments 1-23, wherein the sense strand comprises one or two inverted abasic residues.

Embodiment 25. The RNAi agent of embodiment 8, wherein the RNAi agent is comprised of a sense strand and an antisense strand that form a duplex having the structure of any one of the duplexes in Table 7A, Table 7B, Table 8, Table 9A, Table 9B, or Table 10.

Embodiment 26. The RNAi agent of embodiment 25, wherein all or substantially all of the nucleotides are modified nucleotides.

Embodiment 27. The RNAi agent of embodiment 1, comprising an antisense strand that consists of, consists essentially of, or comprises a nucleotide sequence that differs by 0 or 1 nucleotides from one of the following nucleotide sequences (5'→3'):

UUGUGUUCAGUUUCCAUUC; (SEQ ID NO: 55)

UGAUGUUUUGAGCACCUAC; (SEQ ID NO: 65)

UUCCAUUCCUGUUCAUUGC; (SEQ ID NO: 73)

UUGUGUUCAGUUUCCAUUCCG; (SEQ ID NO: 7)

UGAUGUUUUGAGCACCUACUC; (SEQ ID NO: 9)

or

UUCCAUUCCUGUUCAUUGCCU. (SEQ ID NO: 8)

Embodiment 28. The RNAi agent of embodiment 27, wherein the sense strand consists of, consists essentially of, or comprises a nucleotide sequence that differs by 0 or 1 nucleotides from one of the following nucleotide sequences (5'→3'):

GAAUGGAAACUGAACACAA; (SEQ ID NO: 298)

GUAGGUGCUCAAAACAUCA; (SEQ ID NO: 308)

GCAAUGAACAGGAAUIGAA; (SEQ ID NO: 316)

CGGAAUGGAAACUGAACACAA; (SEQ ID NO: 19)

GAGUAGGUGCUCAAAACAUCA; (SEQ ID NO: 20)

or

AGGCAAUGAACAGGAAUIGAA. (SEQ ID NO: 21)

Embodiment 29. The RNAi agent of embodiment 27 or 28, wherein all or substantially all of the nucleotides are modified nucleotides.

Embodiment 30. The RNAi agent of embodiment 1, comprising an antisense strand that comprises, consists of, or consists essentially of a modified nucleotide sequence that differs by 0 or 1 nucleotides from one of the following nucleotide sequences (5'→3'):

usUfsgsUfgUfuCfaGfuUfuCfcAfuUfcCfsg; (SEQ ID NO: 2)

cPrpusUfsgsUfgUfuCfaGfuUfuCfcAfuUfcCfsg; (SEQ ID NO: 3)

usGfsasuguuuugaGfcAfcCfuacusc; (SEQ ID NO: 5)

cPrpusGfsasuguuuugaGfcAfcCfuacusc; (SEQ ID NO: 6)

usUfscsCfaUfuCfcUfgUfuCfaUfuGfcCfsu; (SEQ ID NO: 4)

wherein a, c, g, and u represent 2'-O-methyl adenosine, 2'-O-methyl cytidine, 2'-O-methyl guanosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; cPrpu represents a 5'-cyclopropyl phosphonate-2'-O-methyl uridine; s represents a phosphorothioate linkage; and wherein all or substantially all of the nucleotides on the sense strand are modified nucleotides.

Embodiment 31. The RNAi agent of embodiment 1, wherein the sense strand comprises, consists of, or consists essentially of a modified nucleotide sequence that differs by 0 or 1 nucleotides from one of the following nucleotide sequences (5'→3'):

gsaguagGfuGfcUfcaaaacauca; (SEQ ID NO: 14)

asggcaaugAfAfCfaggaauigaa; (SEQ ID NO: 15)

csggaauggAfAfAfcugaacacaa; (SEQ ID NO: 13)

wherein a, c, g, i, and u represent 2'-O-methyl adenosine, 2'-O-methyl cytidine, 2'-O-methyl guanosine, 2'-O-methyl inosine, and 2'-O-methyl uridine, respectively; Af, Cf, Gf, and Uf represent 2'-fluoro adenosine, 2'-fluoro cytidine, 2'-fluoro guanosine, and 2'-fluoro uridine, respectively; and s represents a phosphorothioate linkage; and wherein all or substantially all of the nucleotides on the antisense strand are modified nucleotides.

Embodiment 32. The RNAi agent of any one of embodiments 27-31, wherein the sense strand further includes inverted abasic residues at the 3' terminal end of the nucleotide sequence, at the 5' end of the nucleotide sequence, or at both.

Embodiment 33. The RNAi agent of any one of embodiments 1-32, wherein the RNAi agent is linked to a targeting ligand.

Embodiment 34. The RNAi agent of embodiment 33, wherein the targeting ligand has affinity for a cell receptor expressed on an epithelial cell.

Embodiment 35. The RNAi agent of embodiment 34, wherein the targeting ligand comprises an integrin targeting ligand.

Embodiment 36. The RNAi agent of embodiment 35, wherein the integrin targeting ligand is an αvβ6 integrin targeting ligand.

Embodiment 37. The RNAi agent of embodiment 36, wherein the targeting ligand comprises the structure:

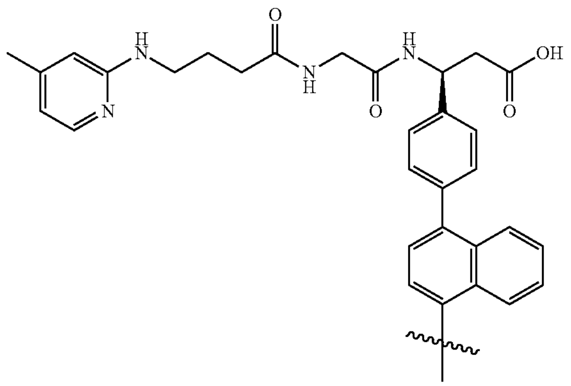 [SMILES: *c1ccc(-c2ccc([C@H](CC(=O)O)NC(=O)CNC(=O)CCCNc3cc(C)ccn3)cc2)c2ccccc12]

or a pharmaceutically acceptable salt thereof, or

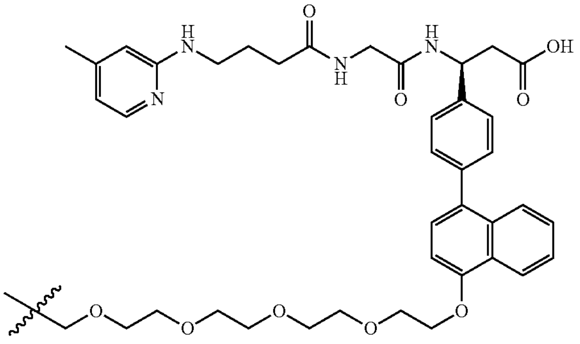 [SMILES: *COCCOCCOCCOCCOc1ccc(-c2ccc([C@H](CC(=O)O)NC(=O)CNC(=O)CCCNc3cc(C)ccn3)cc2)c2ccccc12]

or a pharmaceutically acceptable salt thereof, wherein  indicates the point of connection to the RNAi agent.

Embodiment 38. The RNAi agent of any one of embodiments 33-36, wherein the targeting ligand has a structure selected from the group consisting of:

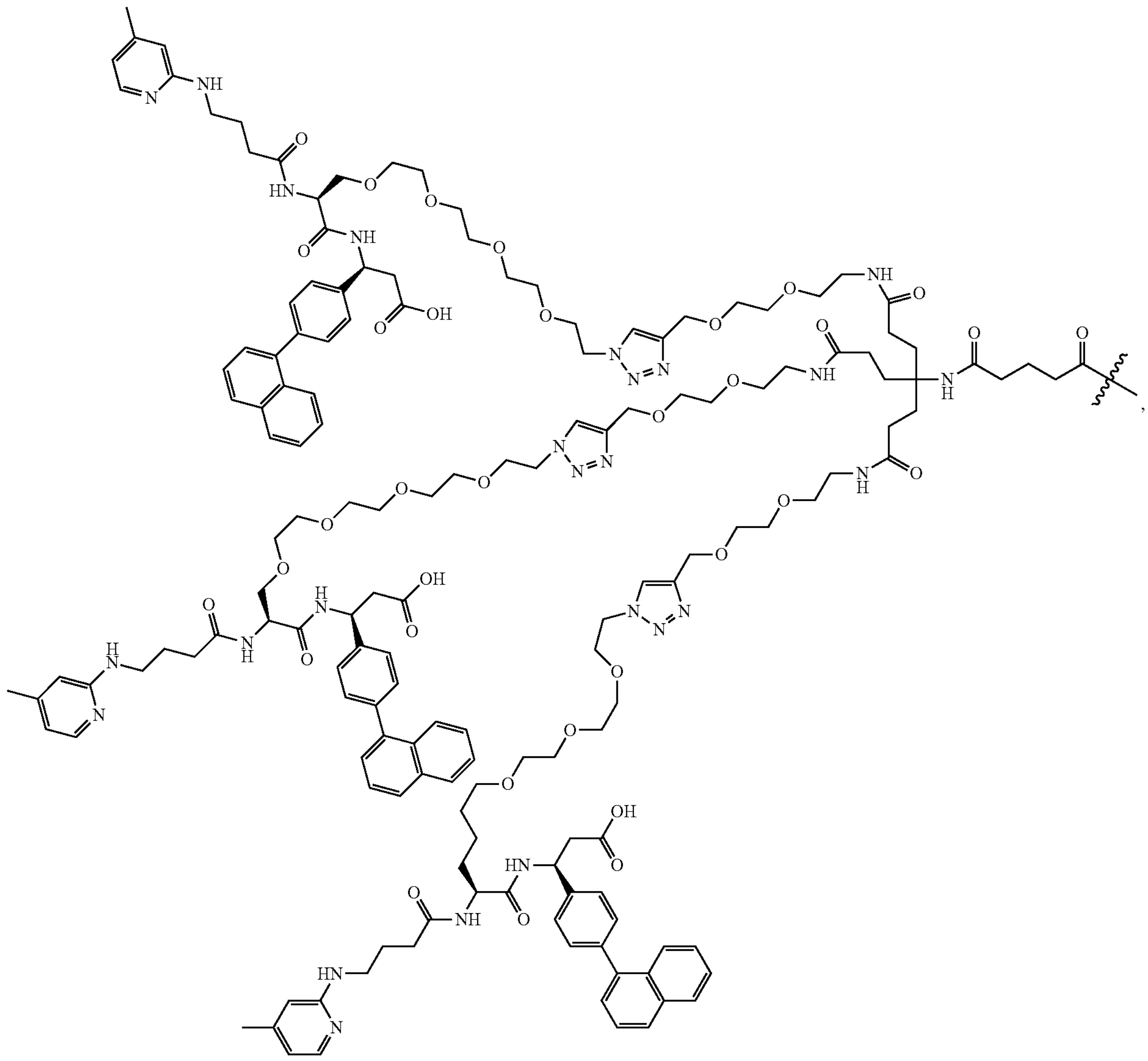 [SMILES: *C(=O)CCCC(=O)NC(CCC(=O)NCCOCCOCc1cn(CCOCCOCCOCCCC[C@H](NC(=O)CCCNc2cc(C)ccn2)C(=O)N[C@@H](CC(=O)O)c2ccc(-c3cccc4ccccc34)cc2)nn1)(CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1)CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1]

,

-continued
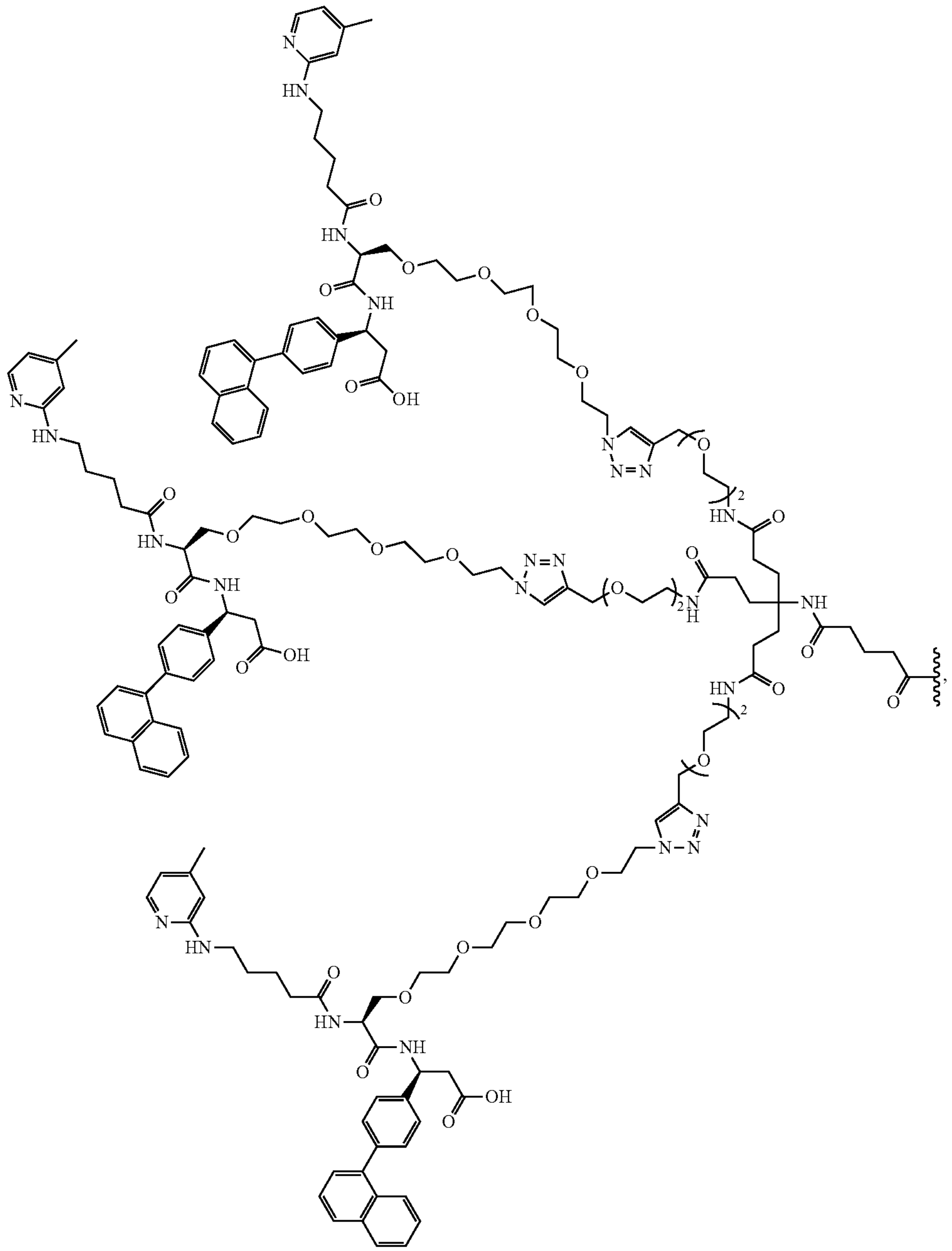
,

-continued
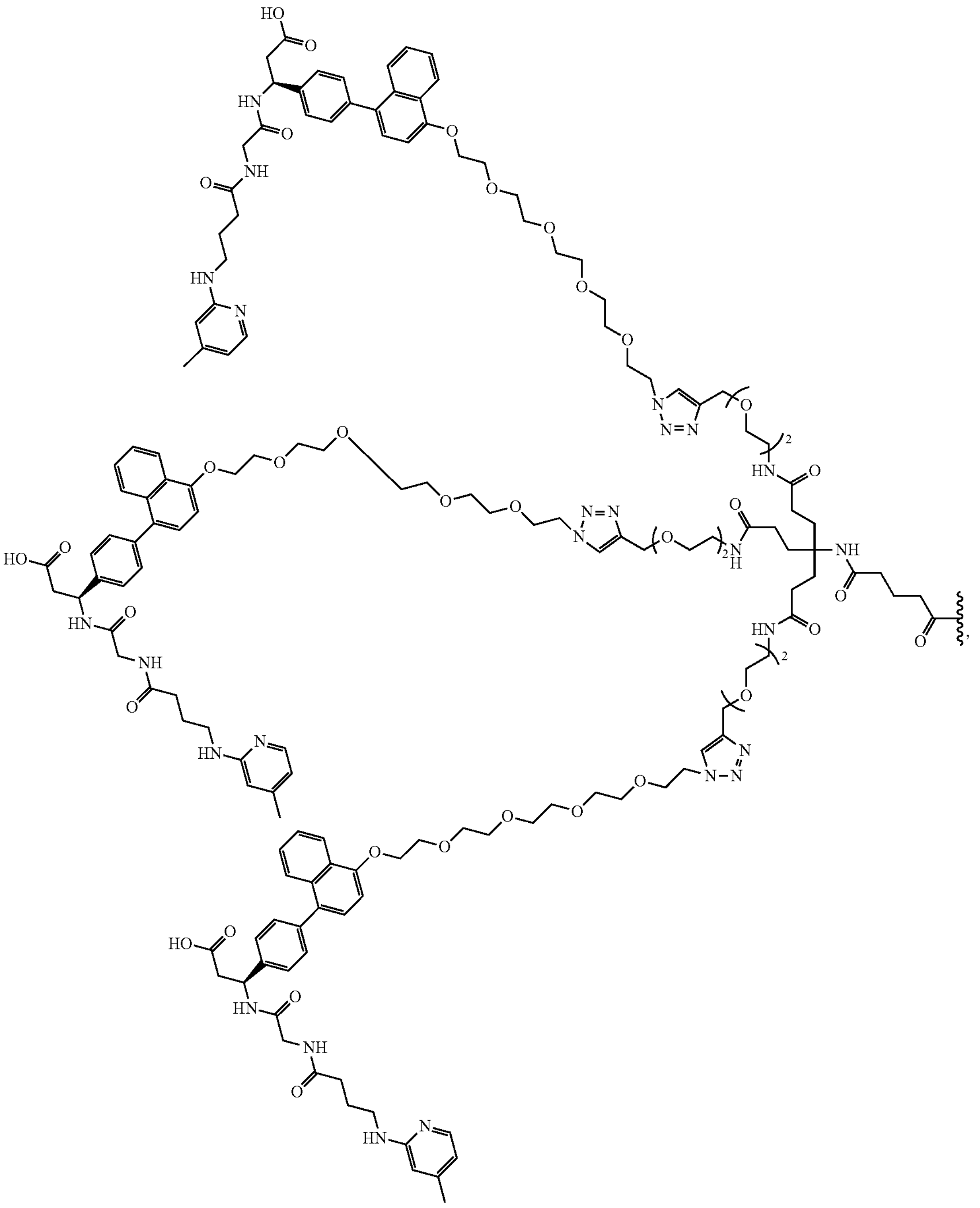

-continued
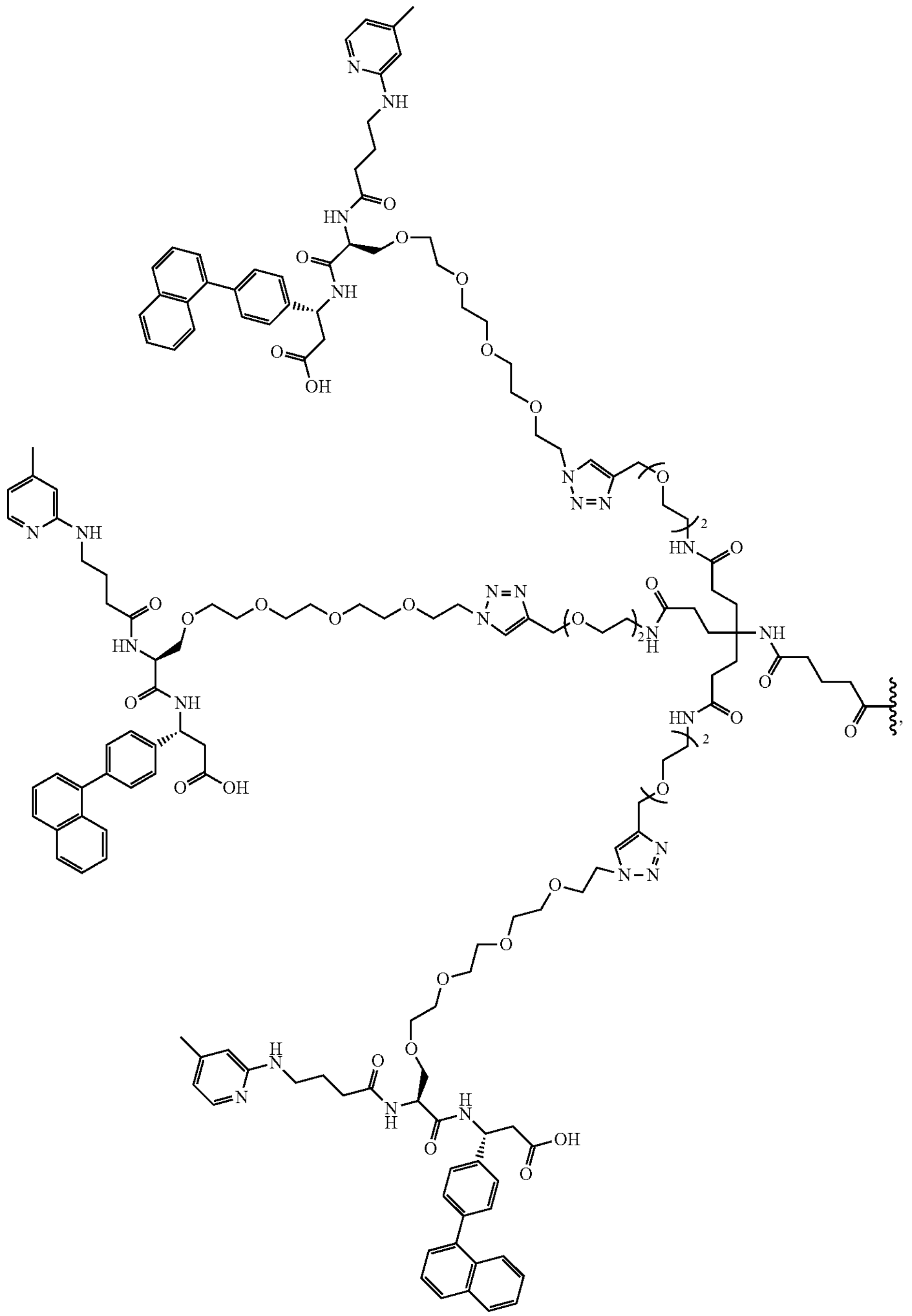

-continued
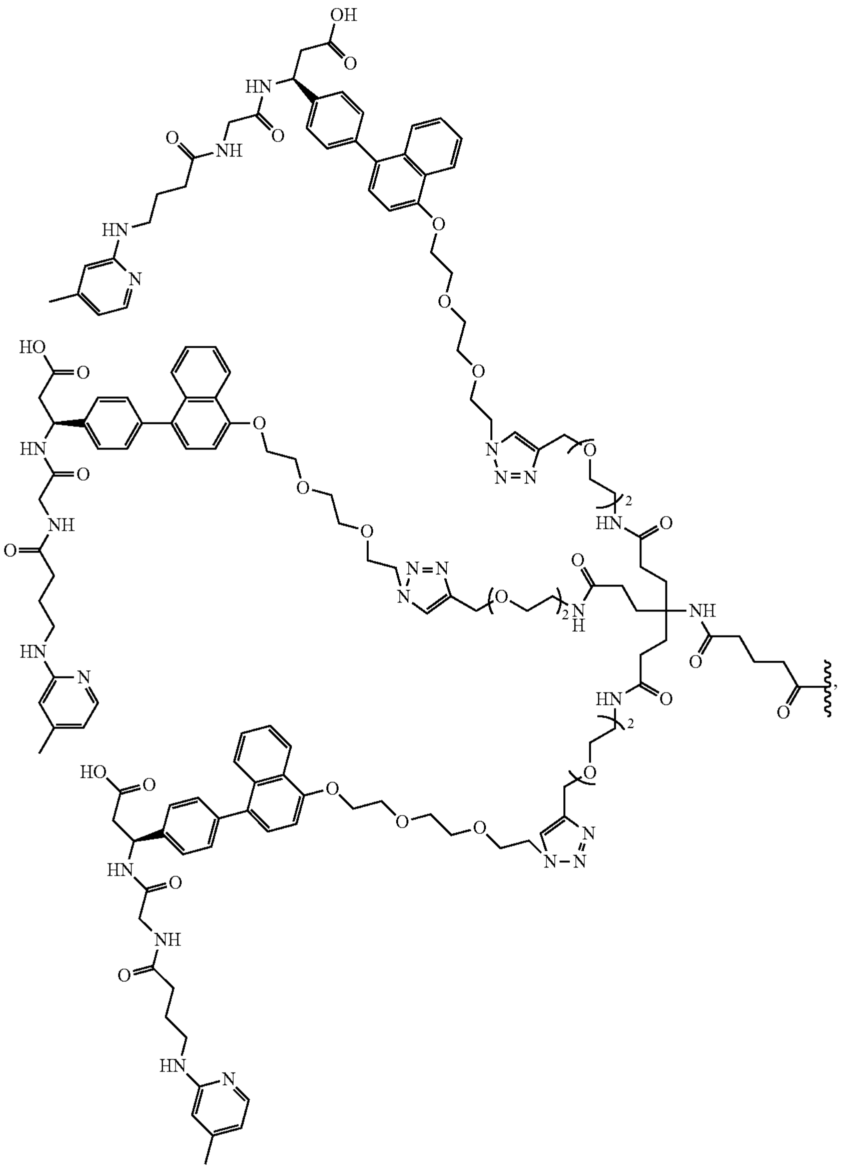

-continued
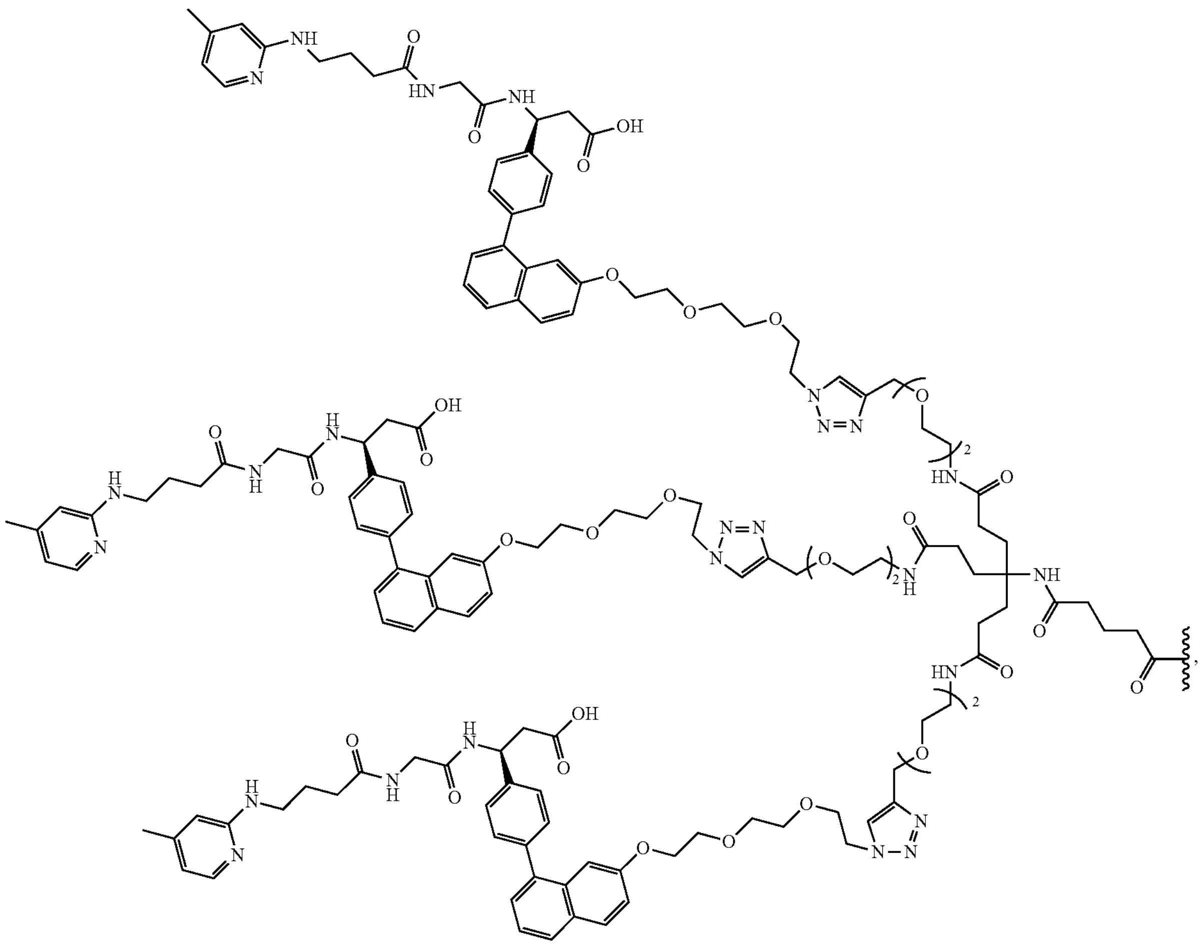

-continued
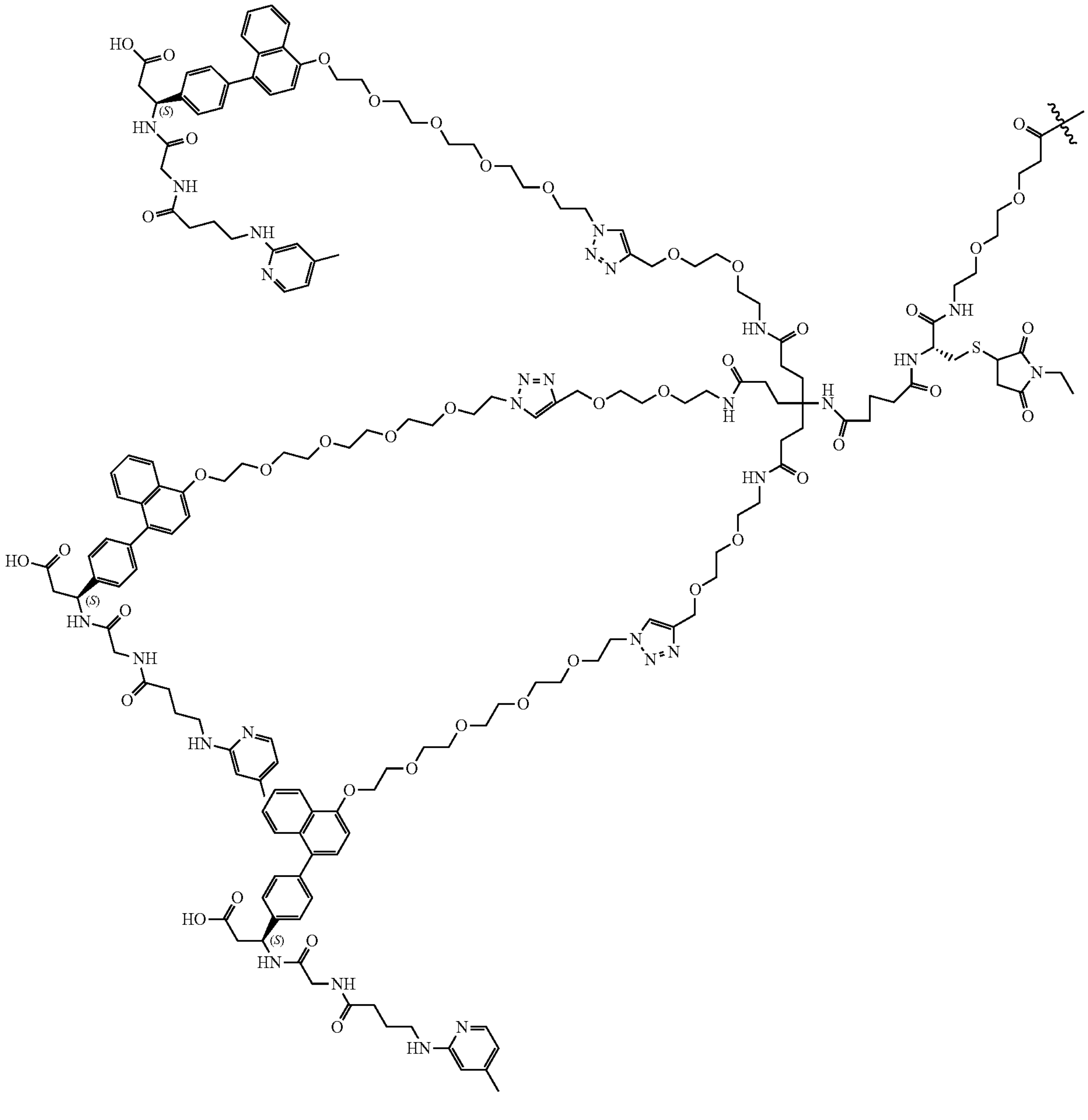
,

-continued
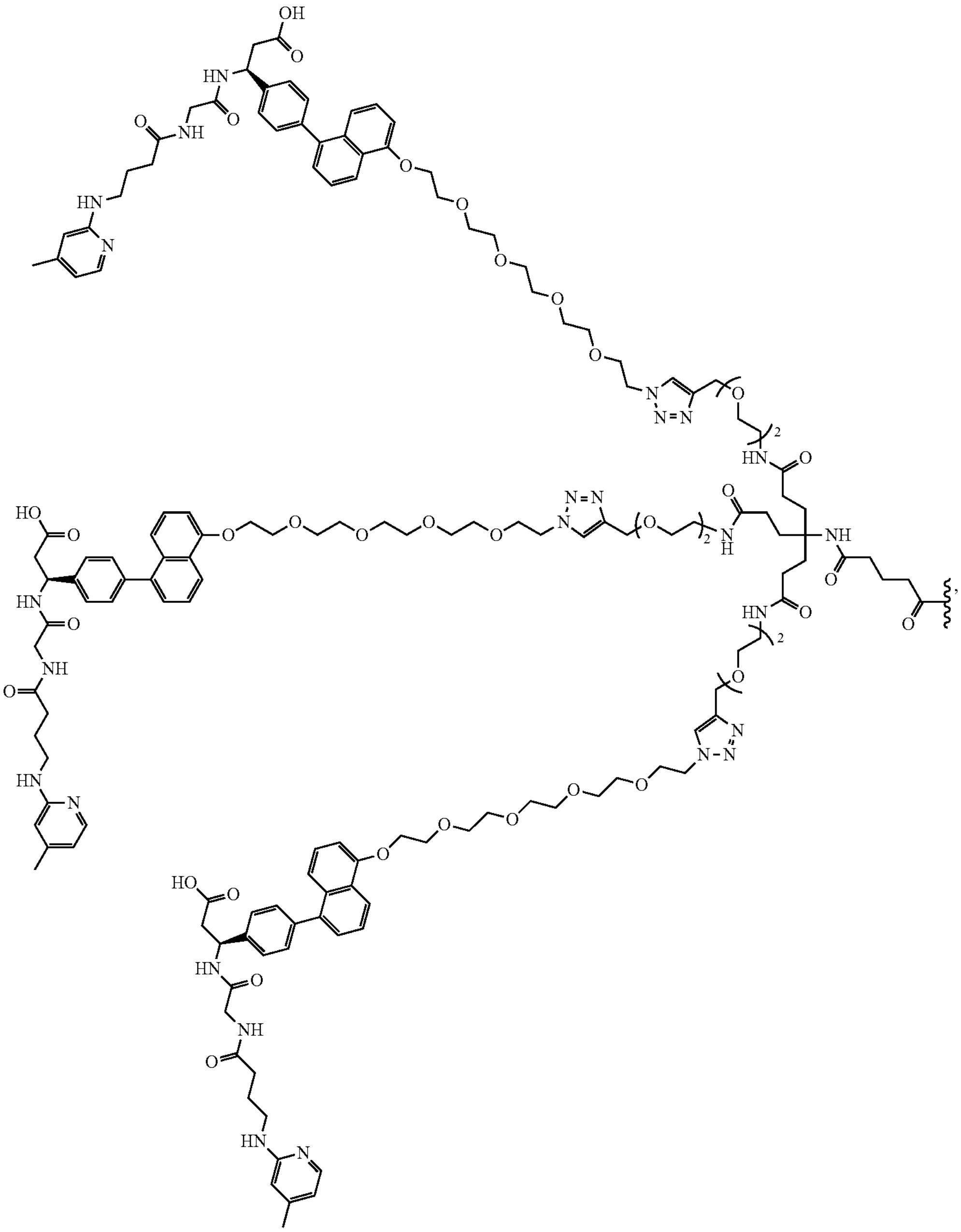
, and

-continued
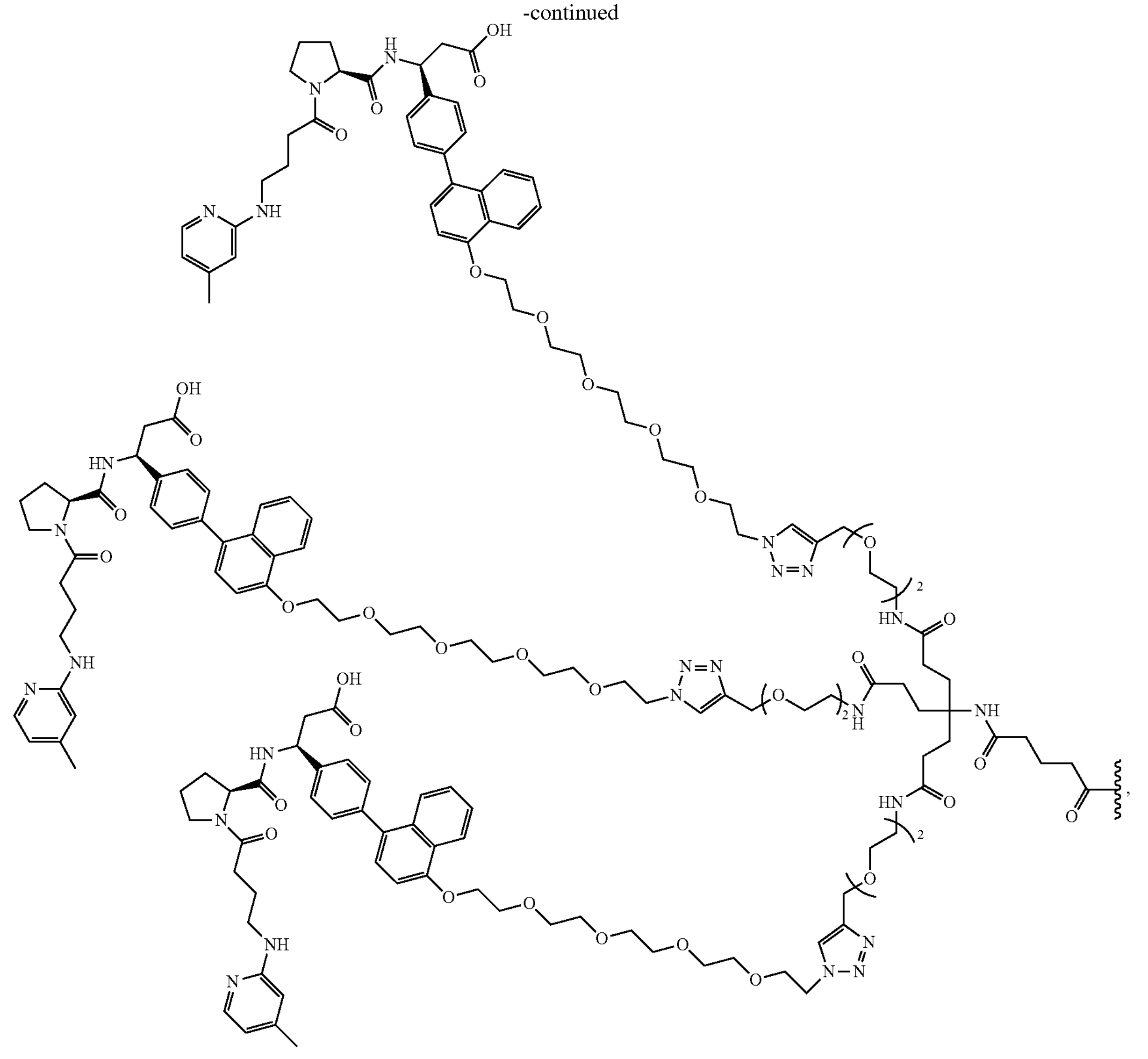
wherein ⌇ indicates the point of connection to the RNAi agent.
Embodiment 39. The RNAi agent of embodiment 38, wherein RNAi agent is conjugated to a targeting ligand having the following structure:

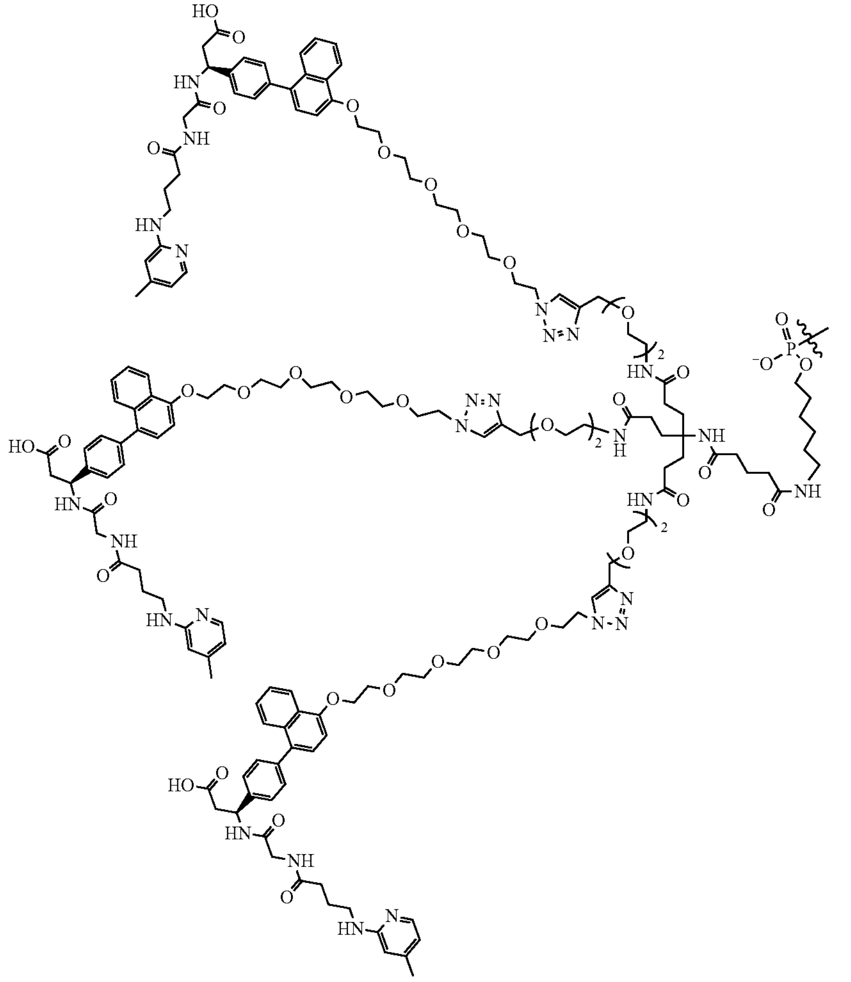
Embodiment 40. The RNAi agent of any one of embodiments 33-36, wherein the targeting ligand has the following structure:
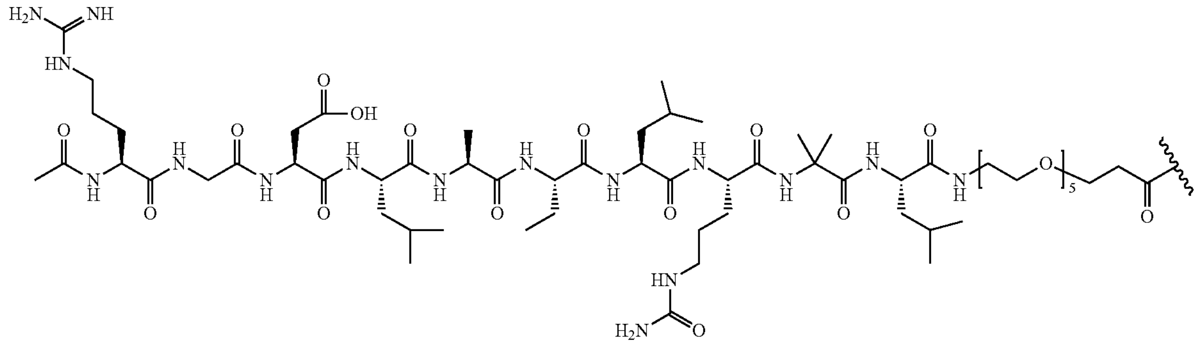

Embodiment 41. The RNAi agent of any one of embodiments 33-36, wherein the targeting ligand is conjugated to the sense strand.

Embodiment 42. The RNAi agent of embodiment 41, wherein the targeting ligand is conjugated to the 5' terminal end of the sense strand.

Embodiment 43. The RNAi agent of any of the preceding embodiments, wherein the RNAi agent is conjugated to a targeting ligand and has the duplex structure of AC000292, AC001266, AC001267, or AC001268.

Embodiment 44. A composition comprising the RNAi agent of any one of embodiments 1-43, wherein the composition further comprises a pharmaceutically acceptable excipient.

Embodiment 45. The composition of embodiment 44, further comprising a second RNAi agent capable of inhibiting the expression of Receptor for Advanced Glycation End-products gene expression.

Embodiment 46. The composition of any one of embodiments 44-45, further comprising one or more additional therapeutics.

Embodiment 47. The composition of any one of embodiments 44-46, wherein the composition is formulated for administration by inhalation.

Embodiment 48. The composition of embodiment 47, wherein the composition is delivered by a metered-dose inhaler, jet nebulizer, vibrating mesh nebulizer, or soft mist inhaler.

Embodiment 49. The composition of any of embodiments 44-48, wherein the RNAi agent is a sodium salt.

Embodiment 50. The composition of any of embodiments 44-49, wherein the pharmaceutically acceptable excipient is water for injection.

Embodiment 51. The composition of any of embodiments 44-49, wherein the pharmaceutically acceptable excipient is a buffered saline solution.

Embodiment 52. A method for inhibiting expression of a Receptor for Advanced Glycation End-products gene in a cell, the method comprising introducing into a cell an effective amount of an RNAi agent of any one of embodiments 1-43 or the composition of any one of embodiments 44-51.

Embodiment 53. The method of embodiment 52, wherein the cell is within a subject.

Embodiment 54. The method of embodiment 53, wherein the subject is a human subject.

Embodiment 55. The method of any one of embodiments 52-54, wherein following the administration of the RNAi agent the Receptor for Advanced Glycation End-products gene expression is inhibited by at least about 30%.

Embodiment 56. A method of treating one or more symptoms or diseases associated with enhanced or elevated membrane RAGE activity levels, the method comprising administering to a human subject in need thereof a therapeutically effective amount of the composition of any one of embodiments 44-51.

Embodiment 57. The method of embodiment 56, wherein the disease is a respiratory disease.

Embodiment 58. The method of embodiment 57, wherein the respiratory disease is cystic fibrosis, pneumonia, chronic bronchitis, non-cystic fibrosis bronchiectasis, chronic obstructive pulmonary disease (COPD), asthma, respiratory tract infections, primary ciliary dyskinesia, or lung carcinoma cystic fibrosis.

Embodiment 59. The method of embodiment 58, wherein the disease is chronic obstructive pulmonary disease (COPD).

Embodiment 60. The method of embodiment 56, wherein the disease is an ocular disease.

Embodiment 61. The method of embodiment 60, wherein the ocular disease is dry eye syndrome.

Embodiment 62. The method of any one of embodiments 52-61, wherein the RNAi agent is administered at a deposited dose of about 0.01 mg/kg to about 5.0 mg/kg of body weight of the subject.

Embodiment 63. The method of any one of embodiments 52-61, wherein the RNAi agent is administered at a deposited dose of about 0.03 mg/kg to about 2.0 mg/kg of body weight of the subject.

Embodiment 64. The method of any of embodiments 52-61, wherein the RNAi agent is administered in two or more doses.

Embodiment 65. Use of the RNAi agent of any one of embodiments 1-43, for the treatment of a disease, disorder, or symptom that is mediated at least in part by membrane RAGE activity and/or AGER gene expression.

Embodiment 66. Use of the composition according to any one of embodiments 44-51, for the treatment of a disease, disorder, or symptom that is mediated at least in part by Receptor for Advanced Glycation End-products receptor activity and/or Receptor for Advanced Glycation End-products gene expression.

Embodiment 67. Use of the composition according to any one of embodiments 44-51, for the manufacture of a medicament for treatment of a disease, disorder, or symptom that is mediated at least in part by Receptor for Advanced Glycation End-products receptor activity and/or Receptor for Advanced Glycation End-products gene expression.

Embodiment 68. The use of any one of embodiments 65-67, wherein the disease is pulmonary inflammation.

Embodiment 69. A method of making an RNAi agent of any one of embodiments 1-43, comprising annealing a sense strand and an antisense strand to form a double-stranded ribonucleic acid molecule.

Embodiment 70. The method of embodiment 69, wherein the sense strand comprises a targeting ligand.

Embodiment 71. The method of embodiment 70, comprising conjugating a targeting ligand to the sense strand.

The above provided embodiments and items are now illustrated with the following, non-limiting examples.

EXAMPLES

Example 1. Synthesis of RAGE RNAi Agents

RAGE RNAi agent duplexes disclosed herein were synthesized in accordance with the following:

A. Synthesis. The sense and antisense strands of the RAGE RNAi agents were synthesized according to phosphoramidite technology on solid phase used in oligonucleotide synthesis. Depending on the scale, a MerMade96E® (Bioautomation), a MerMadel2® (Bioautomation), or an OP Pilot 100 (GE Healthcare) was used. Syntheses were performed on a solid support made of controlled pore glass (CPG, 500 Å or 600A, obtained from Prime Synthesis, Aston, PA, USA). The monomer positioned at the 3' end of the respective strand was attached to the solid support as a starting point for synthesis. All RNA and 2'-modified RNA phosphoramidites were purchased from Thermo Fisher Scientific (Milwaukee, WI, USA). Specifically, the 2'-O-methyl phosphoramidites that were used included the following: (5'-O-dimethoxytrityl-$N^6$-(benzoyl)-2'-O-methyl-adenosine-3'-O-(2-cyanoethyl-N,N-diisopropylamino) phosphoramidite, 5'-O-dimethoxy-trityl-$N^4$-(acetyl)-2'-O-methyl-cytidine-3'-O-(2-cyanoethyl-N,N-diisopropyl-amino) phosphoramidite, (5'-O-dimethoxytrityl-$N^2$-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA). The following UNA phosphoramidites were used: 5'-(4,4'-Dimethoxytrityl)-N6-(benzoyl)-2',3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diisopropyl)]-phosphoramidite. TFA aminolink phosphoramidites were also commercially purchased (ThermoFisher). Linker L6 was purchased as propargyl-PEG5-NHS from BroadPharm (catalog #BP-20907) and coupled to the $NH_2$-$C_6$ group from an aminolink phosphoramidite to form -L6-C6-, using standard coupling conditions. The linker Alk-cyHex was similarly commercially purchased from Lumiprobe (alkyne phosphoramidite, 5'-terminal) as a propargyl-containing compound phosphoramidite compound to form the linker -Alk-cyHex-. In each case, phosphorothioate linkages were introduced as specified using the conditions set forth herein. The cyclopropyl phosphonate phosphoramidites were synthesized in accordance with International Patent Application Publication No. WO 2017/214112.

Tri-alkyne-containing phosphoramidites were dissolved in anhydrous dichloromethane or anhydrous acetonitrile (50 mM), while all other amidites were dissolved in anhydrous acetonitrile (50 mM) and molecular sieves (3A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

Alternatively, tri-alkyne moieties were introduced post-synthetically (see section E, below). For this route, the sense strand was functionalized with a 5' and/or 3' terminal nucleotide containing a primary amine. TFA aminolink phosphoramidite was dissolved in anhydrous acetonitrile (50 mM) and molecular sieves (3A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 10 minutes (RNA), 90 seconds (2' O-Me), and 60 seconds (2' F). In order to introduce phosphorothioate linkages, a 100 mM solution of 3-phenyl 1,2,4-dithiazoline-5-one (POS, obtained from PolyOrg, Inc., Leominster, MA, USA) in anhydrous acetonitrile was employed.

B. Cleavage and deprotection of support bound oligomraer. After finalization of the solid phase synthesis. the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification. Crude oligomers were purified by anionic exchange HPLC using a TSKgel SuperQ-5PW 13 μm column and Shimadzu LC-8 system. Buffer A was 20 mM Tris, 5 mM EDTA, $p^H$ 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water. Alternatively, pooled fractions were desalted and exchanged into an appropriate buffer or solvent system via tangential flow filtration.

D. Annealing. Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor (0.050 mg/(mL·cm)) and the dilution factor to determine the duplex concentration.

E. Conjugation of Tri-alkyne linker. In some embodiments a tri-alkyne linker is conjugated to the sense strand of the RNAi agent on resin as a phosphoramidite (see Example 1G for the synthesis of an example tri-alkyne linker phosphoramidite and Example TA for the conjugation of the phosphoramidite.). In other embodiments, a tri-alkyne linker may be conjugated to the sense strand following cleavage from the resin, described as follows: either prior to or after annealing, in some embodiments, the 5' or 3' amine functionalized sense strand is conjugated to a tri-alkyne linker. An example tri-alkyne linker structure that can be used in forming the constructs disclosed herein is as follows:

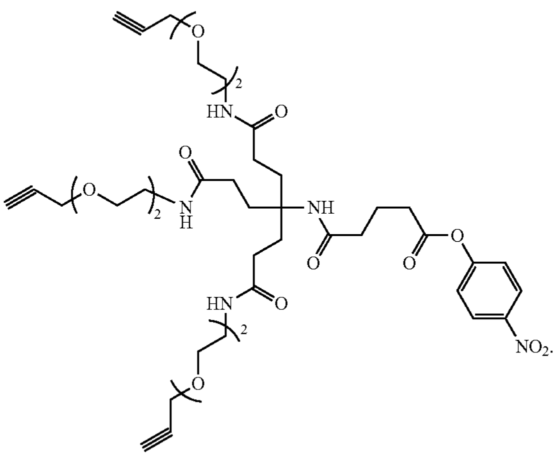

To conjugate the tri-alkyne linker to the annealed duplex, amine-functionalized duplex was dissolved in 90% DMSO/10% $H_2O$, at ~50-70 mg/mL. 40 equivalents triethylamine was added, followed by 3 equivalents tri-alkyne-PNP. Once complete, the conjugate was precipitated twice in a solvent system of 1× phosphate buffered saline/acetonitrile (1:14 ratio), and dried.

F. Synthesis of Targeting Ligand SM6.1

((S)-3-(4-(4-((14-azido-3,6,9,12-tetraoxatetradecyl)oxy)naphthalen-1-yl)phenyl)-3-(2-(4-((4-methylpvridin-2-vl)amino)butanamido)acetamido)propanoic acid)

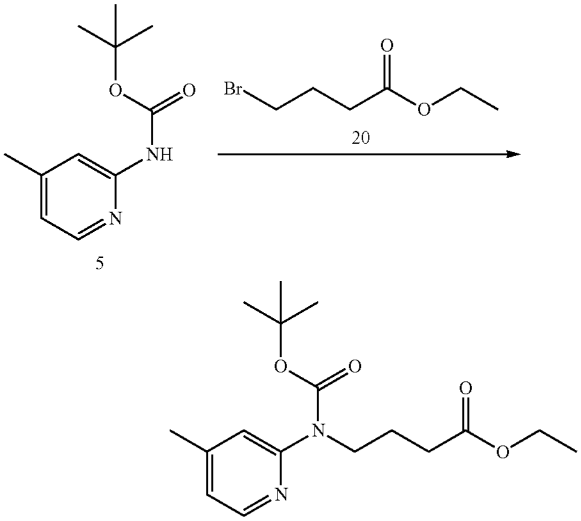

5

20

21

Compound 5 (tert-Butyl(4-methylpyridin-2-yl)carbamate) (0.501 g, 2.406 mmol, 1 equiv.) was dissolved in DMF (17 mL). To the mixture was added NaH (0.116 mg, 3.01 mmol, 1.25 eq, 60% dispersion in oil) The mixture stirred for 10 min before adding Compound 20 (Ethyl 4-Bromobutyrate (0.745 g, 3.82 mmol, 0.547 mL)) (Sigma 167118). After 3 hours the reaction was quenched with ethanol (18 mL) and concentrated. The concentrate was dissolved in DCM (50 mL) and washed with saturated aq. NaCl solution (1×50 mL), dried over $Na_2SO_4$, filtered and concentrated. The product was purified on silica column, gradient 0-5% Methanol in DCM.

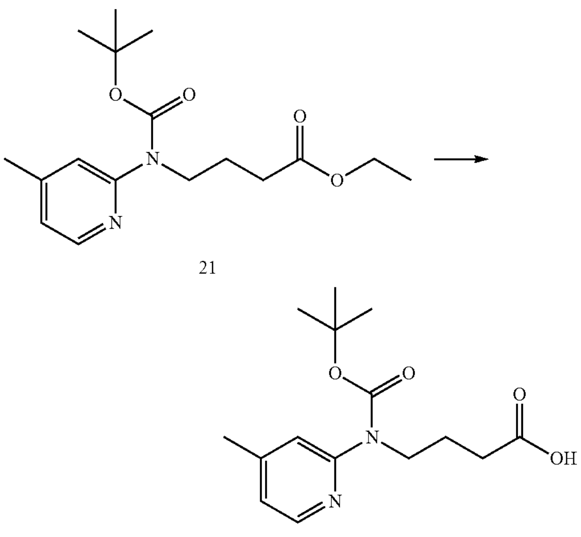

21

22

Compound 21 was dissolved (0.80 g, 2.378 mmol) in 100 mL of Acetone: 0.1 M NaOH [1:1]. The reaction was monitored by TLC (5% ethyl acetate in hexane). The organics were concentrated away, and the residue was acidified to pH 3-4 with 0.3 M Citric Acid (40 mL). The product was extracted with DCM (3×75 mL). The organics were pooled, dried over $Na_2SO_4$, filtered and concentrated. The product was used without further purification.

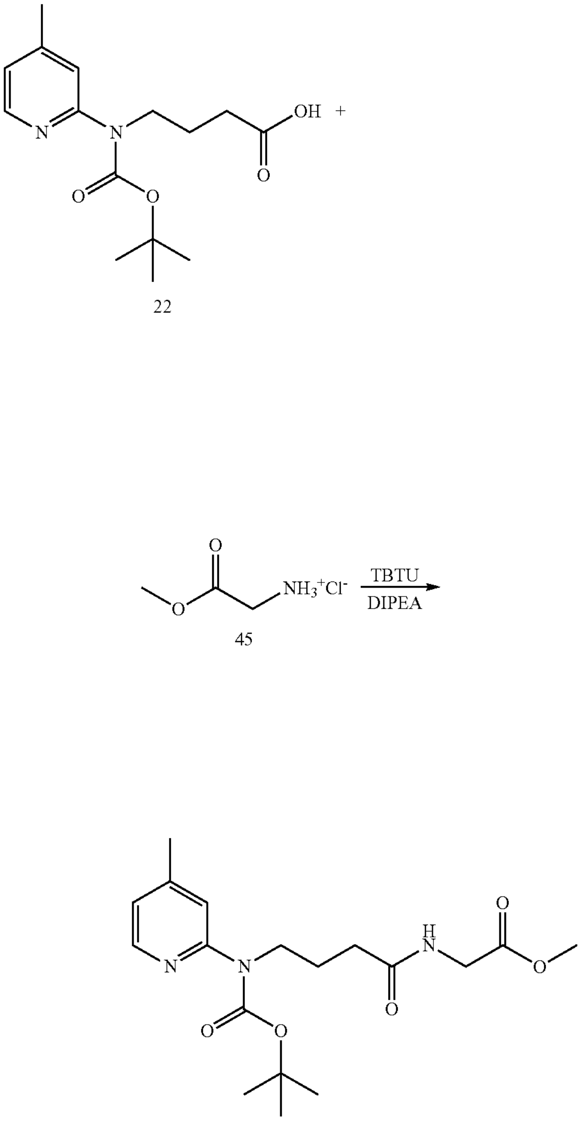

22

45

60

To a solution of Compound 22 (1.1 g, 3.95 mmol, 1 equiv.), Compound 45 (595 mg, 4.74 mmol, 1.2 equiv.), and TBTU (1.52 g, 4.74 mmol, 1.2 equiv.) in anhydrous DMF (10 mL) was added diisopropylethylamine (2.06 mL, 11.85 mmol, 3 equiv.) at 0° C. The reaction mixture was warmed to room temperature and stirred 3 hours. The reaction was quenched by saturated $NaHCO_3$ solution (10 mL). The aqueous phase was extracted with ethyl acetate (3×10 mL) and the organic phase was combined, dried over anhydrous $Na_2SO_4$, and concentrated. The product was separated by CombiFlash® using silica gel as the stationary phase. LC-MS: calculated [M+H]+ 366.20, found 367.

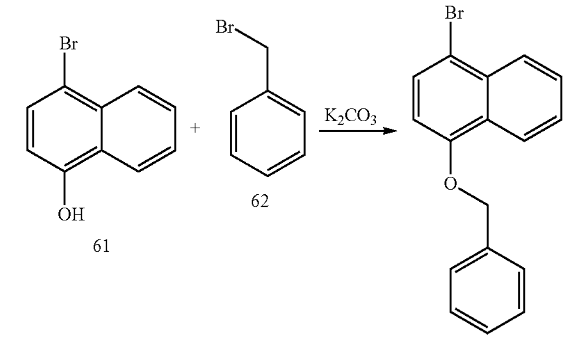

61 62 63

To a solution of compound 61 (2 g, 8.96 mmol, 1 equiv.), and compound 62 (2.13 mL, 17.93 mmol, 2 equiv.) in anhydrous DMF (10 mL) was added $K_2CO_3$ (2.48 g, 17.93 mmol, 2 equiv.) at 0° C. The reaction mixture was warmed to room temperature and stirred overnight. The reaction was quenched by water (10 mL). The aqueous phase was extracted with ethyl acetate (3×10 mL) and the organic phase was combined, dried over anhydrous $Na_2SO_4$, and concentrated. The product was separated by CombiFlash® using silica gel as the stationary phase.

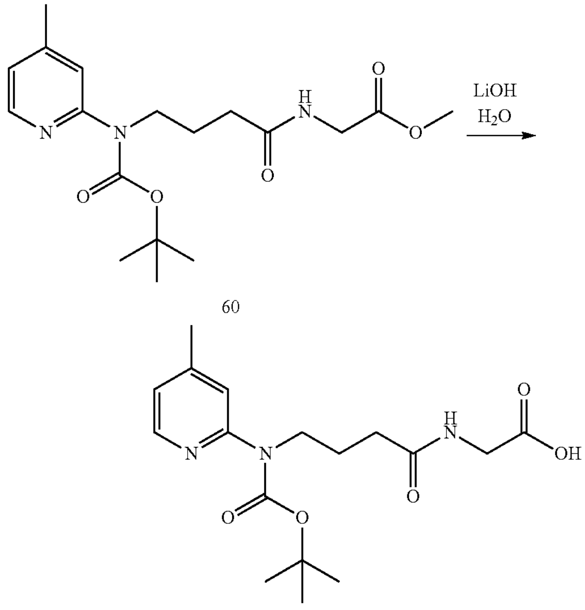

60

64

To a solution of compound 60 (1.77 g, 4.84 mmol, 1 equiv.) in THF (5 mL) and $H_2O$ (5 mL) was added lithium hydroxide monohydrate (0.61 g, 14.53 mmol, 3 equiv.) portion-wise at 0° C. The reaction mixture was warmed to room temperature. After stirring at room temperature for 3 hours, the reaction mixture was acidified by HCl (6 N) to pH 3.0. The aqueous phase was extracted with ethyl acetate (3×20 mL) and the organic layer was combined, dried over $Na_2SO_4$, and concentrated. LC-MS: calculated [M+H]+ 352.18, found 352.

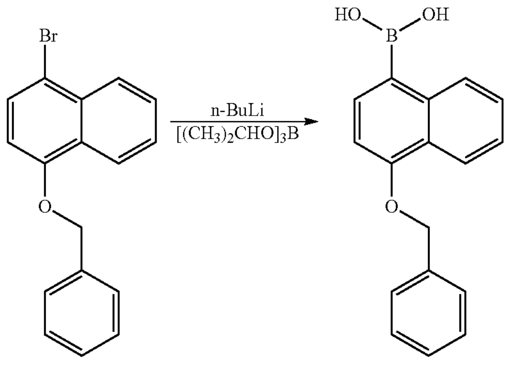

63 65

To a solution of compound 63 (1.88 g, 6.0 mmol, 1.0 equiv.) in anhydrous THF (20 mL) was added n-BuLi in hexane (3.6 mL, 9.0 mmol, 1.5 equiv.) drop-wise at −78° C. The reaction was kept at −78° C. for another 1 hour. Triisopropylborate (2.08 mL, 9.0 mmol, 1.5 equiv.) was then added into the mixture at −78° C. The reaction was then warmed up to room temperature and stirred for another 1 hour. The reaction was quenched by saturated $NH_4Cl$ solution (20 mL) and the pH was adjusted to 3. The aqueous phase was extracted with EtOAc (3×20 mL) and the organic phase was combined, dried over $Na_2SO_4$, and concentrated.

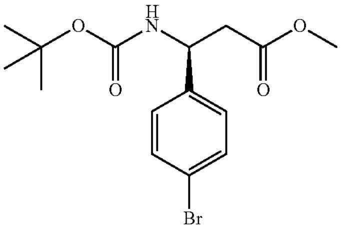
+

12

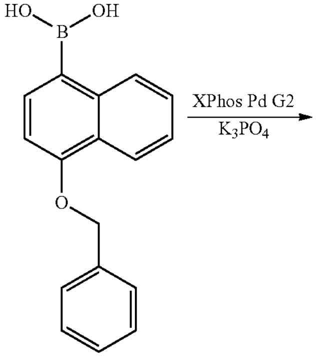

65

-continued

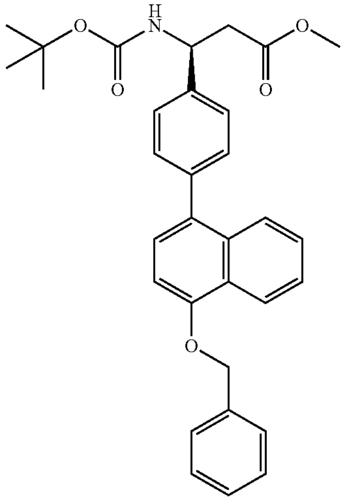

66

Compound 12 (300 mg, 0.837 mmol, 1.0 equiv.), Compound 65 (349 mg, 1.256 mmol, 1.5 equiv.), XPhos Pd G2 (13 mg, 0.0167 mmol, 0.02 equiv.), and $K_3P04$ (355 mg, 1.675 mmol, 2.0 equiv.) were mixed in a round-bottom flask. The flask was sealed with a screw-cap septum, and then evacuated and backfilled with nitrogen (this process was repeated a total of 3 times). Then, THF (8 mL) and water (2 mL) were added via syringe. The mixture was bubbled with nitrogen for 20 min and the reaction was kept at room temperature for overnight. The reaction was quenched with water (10 mL), and the aqueous phase was extracted with ethyl acetate (3×10 mL). The organic phase was dried over $Na_2SO_4$, concentrated, and purified via CombiFlash® using silica gel as the stationary phase and was eluted with 15% EtOAc in hexane. LC-MS: calculated [M+H]+ 512.24, found 512.56.

-continued

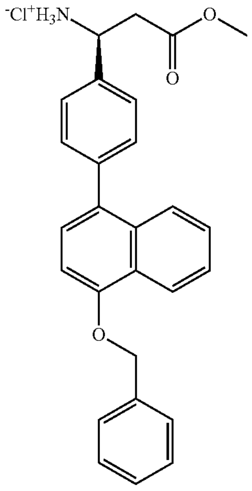

67

Compound 66 (858 mg, 1.677 mmol, 1.0 equiv.) was cooled by ice bath. HCl in dioxane (8.4 mL, 33.54 mmol, 20 equiv.) was added into the flask. The reaction was warmed to room temperature and stirred for another 1 hr. The solvent was removed by rotary evaporator and the product was directly used without further purification. LC-MS: calculated [M+H]+ 412.18, found 412.46.

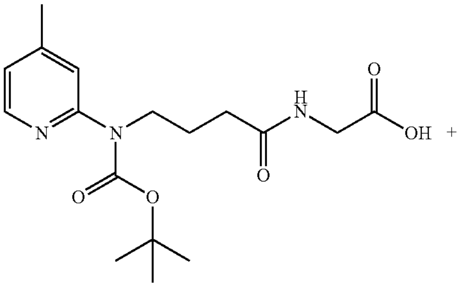

64

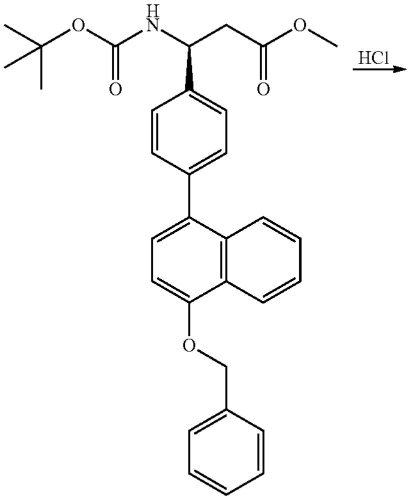

66

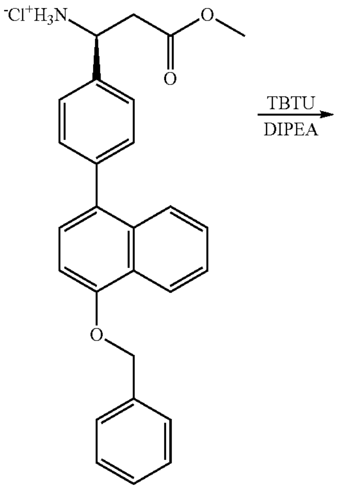

67

-continued

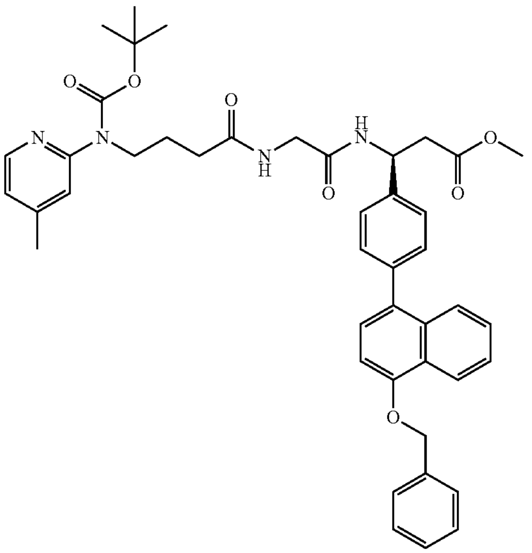

68

To a solution of compound 64 (500 mg, 1.423 mmol, 1 equiv.), compound 67 (669 mg, 1.494 mmol, 1.05 equiv.), and TBTU (548 mg, 0.492 mmol, 1.2 equiv.) in anhydrous DMF (15 mL) was added diisopropylethylamine (0.744 mL, 4.268 mmol, 3 equiv.) at 0° C. The reaction mixture was warmed to room temperature and stirred for another 1 hr. The reaction was quenched by saturated $NaHCO_3$ aqueous solution (10 mL) and the product was extracted with ethyl acetate (3×20 mL). The organic phase was combined, dried over $Na_2SO_4$, and concentrated. The product was purified by CombiFlashR using silica gel as the stationary phase and was eluted with 3-4% methanol in DCM. The yield was 96.23%. LC-MS: calculated [M+H]+ 745.35, found 746.08.

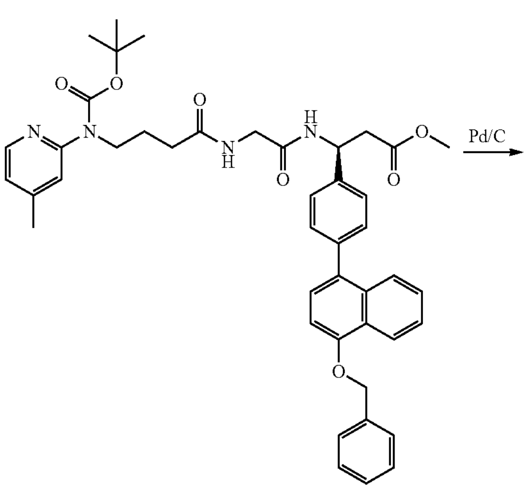

68

-continued

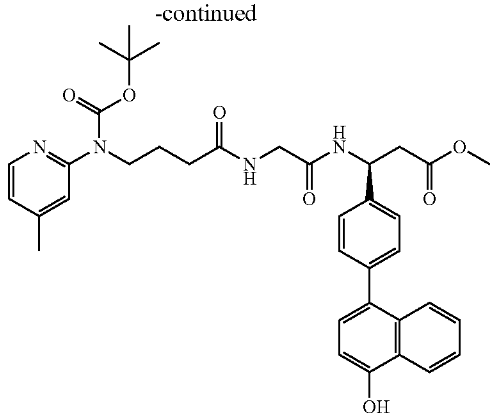

69

To a solution of compound 68 (1.02 g, 1.369 mmol, 1 equiv.) in ethyl acetate (10 mL) was added 10% Pd/C (0.15 g, 50% $H_2O$) at room temperature. The reaction mixture was warmed to room temperature and the reaction was monitored by LC-MS. The reaction was kept at room temperature overnight. The solids were filtered through Celite® and the solvent was removed by rotary evaporator. The product was directly used without further purification. LC-MS: [M+H]+ 655.31, found 655.87.

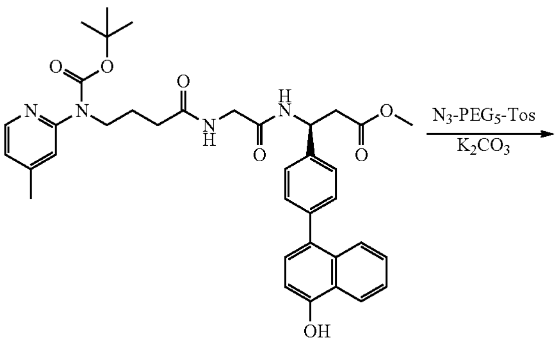

69

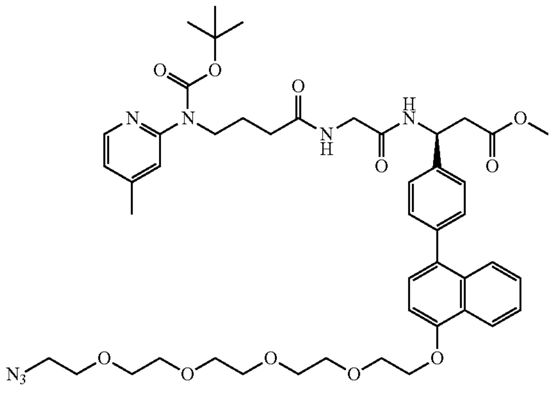

72

To a solution of compound 69 (100 mg, 0.152 mmol, 1 equiv.) and azido-PEG5-OTs (128 mg, 0.305 mmol, 2 equiv.) in anhydrous DMF (2 mL) was added $K_2CO_3$ (42 mg, 0.305 mmol, 2 equiv.) at 0° C. The reaction mixture was stirred for 6 hours at 80° C. The reaction was quenched by saturated $NaHCO_3$ solution and the aqueous layer was extracted with ethyl acetate (3×10 mL). The organic phase was combined, dried over $Na_2SO_4$, and concentrated. LC-MS: calculated [M+H]+ 900.40, found 901.46.

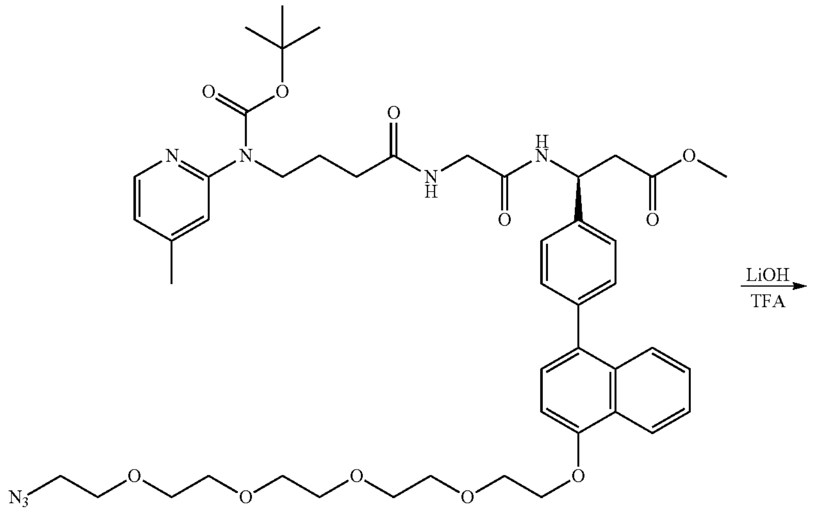

72

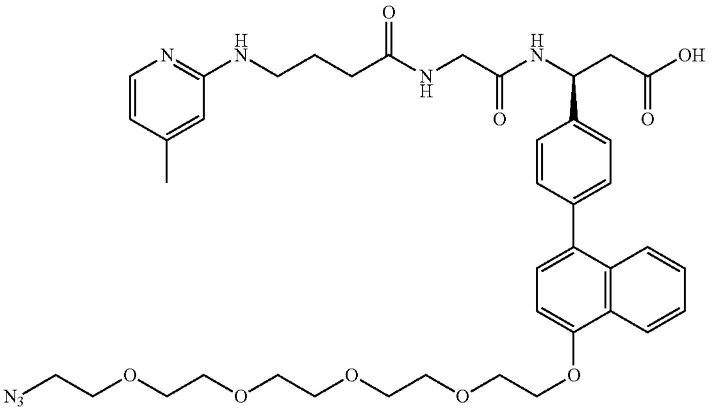

•TFA

Structure 6.1b

To a solution of compound 72 (59 mg, 0.0656 mmol, 1.0 equiv.) in THF (2 mL) and water (2 mL) was added lithium hydroxide (5 mg, 0.197 mmol, 3.0 equiv.) at room temperature. The mixture was stirred at room temperature for another 1 hr. The pH was adjusted to 3.0 by HCl (6N) and the aqueous phase was extracted with EtOAc (3×10 mL). The organic phase was combined, dried over $Na_2SO_4$, and concentrated. TFA (0.5 mL) and DCM (0.5 mL) was added into the residue and the mixture was stirred at room temperature for another 3 hr. The solvent was removed by rotary evaporator. LC-MS: calculated [M+H]+ 786.37, found 786.95.

G. Synthesis of TriAlk 14

TriAlk14 and (TriAlk14)s as shown in Table 11, above, may be synthesized using the synthetic route shown below. Compound 14 may be added to the sense strand as a phosphoramidite using standard oligonucleotide synthesis techniques, or compound 22 may be conjugated to the sense strand comprising an amine in an amide coupling reaction.

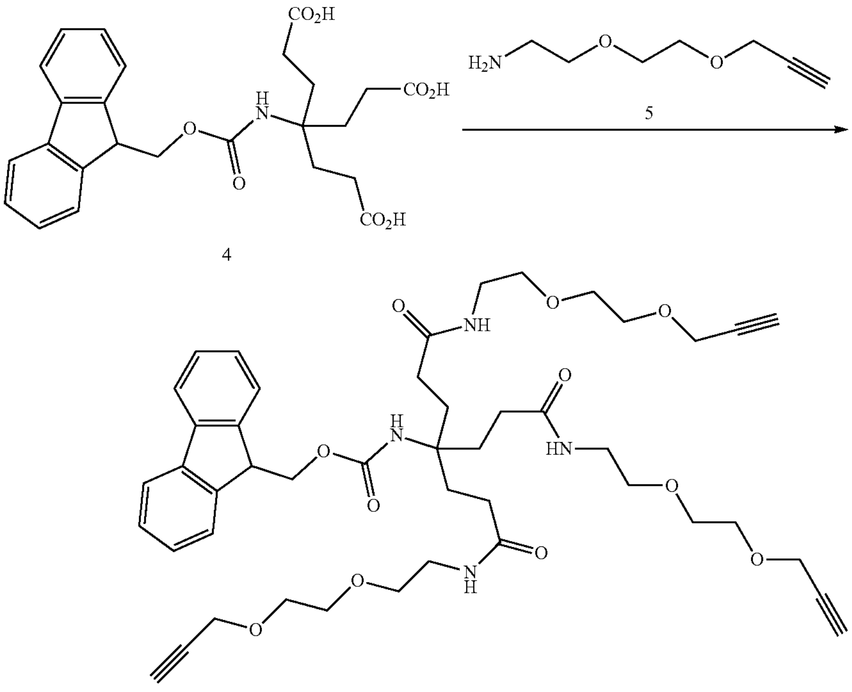

4

6

To a 3-L jacketed reactor was added 500 mL DCM and 4 (75.0 g, 0.16 mol). The internal temperature of the reaction was cooled to 0° C. and TBTU (170.0 g, 0.53 mol) was added. The suspension was then treated with the amine 5 (75.5 g, 0.53 mol) dropwise keeping the internal temperature less than 5° C. The reaction was then treated with DIPEA (72.3 g, 0.56 mol) slowly, keeping the internal temperature less than 5° C. After the addition was complete, the reaction was warmed up to 23° C. over 1 hour, and allowed to stir for 3 hours. A 10% kicker charge of all three reagents were added and allowed to stir an additional 3 hours. The reaction was deemed complete when <1% of 4 remained. The reaction mixture was washed with saturated ammonium chloride solution (2×500 mL) and once with saturated sodium bicarbonate solution (500 mL). The organic layer was then dried over sodium sulfate and concentrated to an oil. The mass of the crude oil was 188 g which contained 72% 6 by QNMR. The crude oil was carried to the next step. Calculated mass for $C_{46}H_{60}N_4O_{11}$=845.0 m/z. Found [M+H]=846.0.

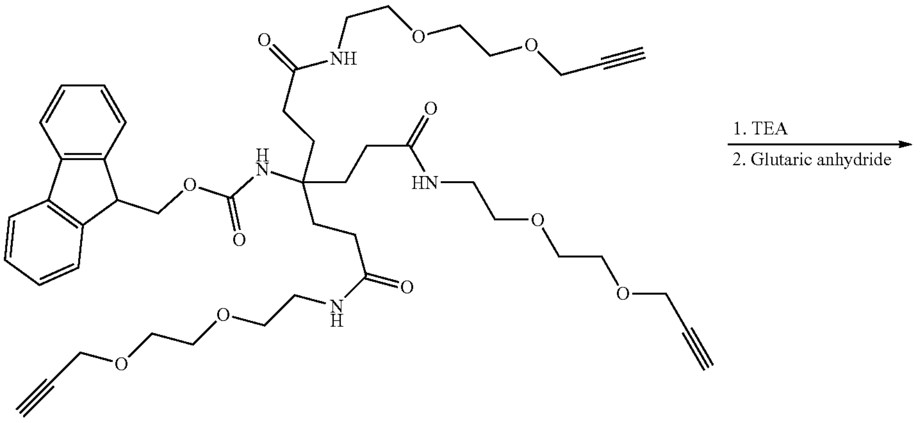

6

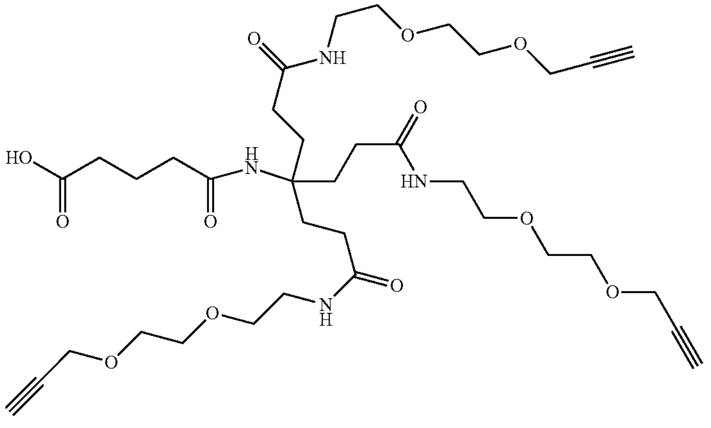

8

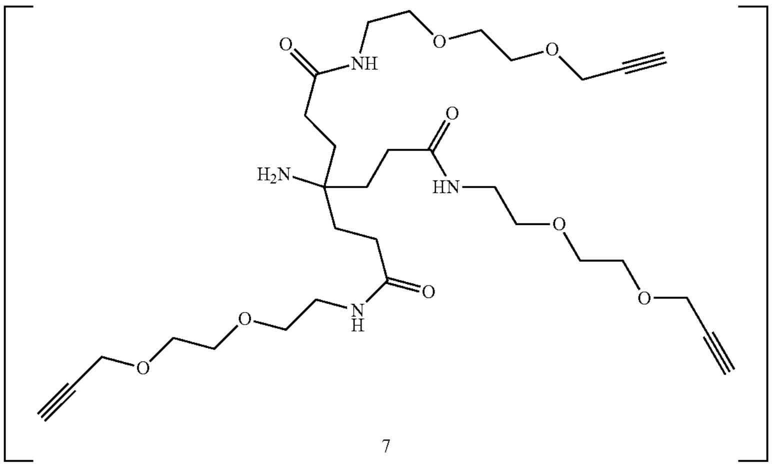

7

Figure 2:
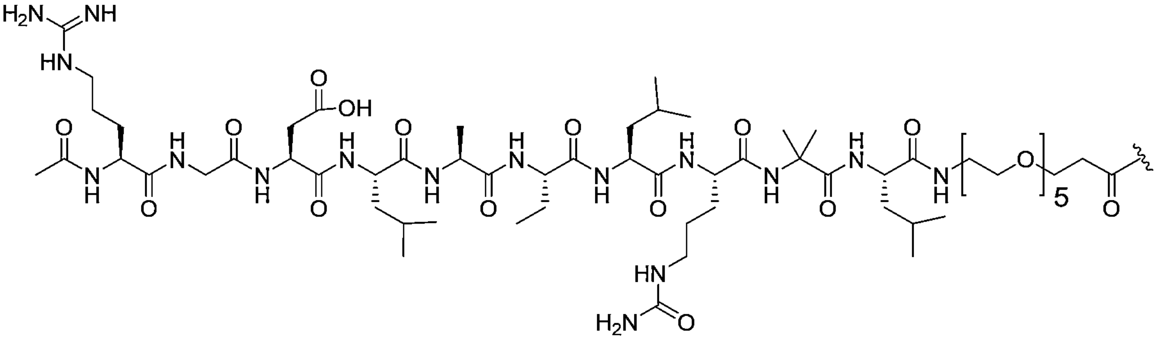
FIG. 2. Chemical structure representation of the peptide αvβ6 epithelial cell targeting ligand referred to herein as αvβ36-pep1.
Figure 3A:
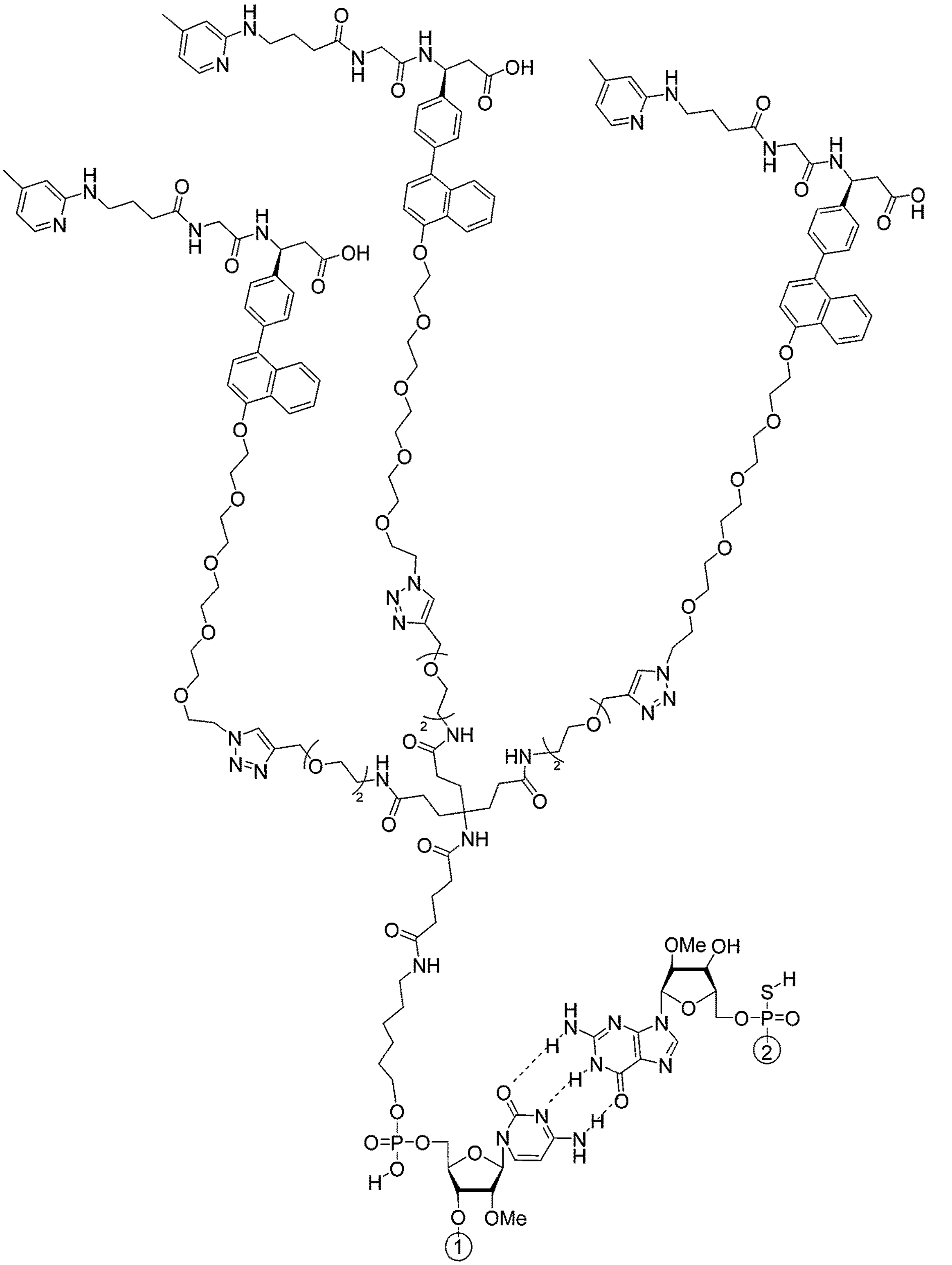
FIG. 3A to 3E. Chemical structure representation of RAGE RNAi agent conjugate AC000292 (AM10309-AS (SEQ ID NO: 3), CS000363 (SEQ ID NO: 10)) shown as a free acid.
Figure 3B:
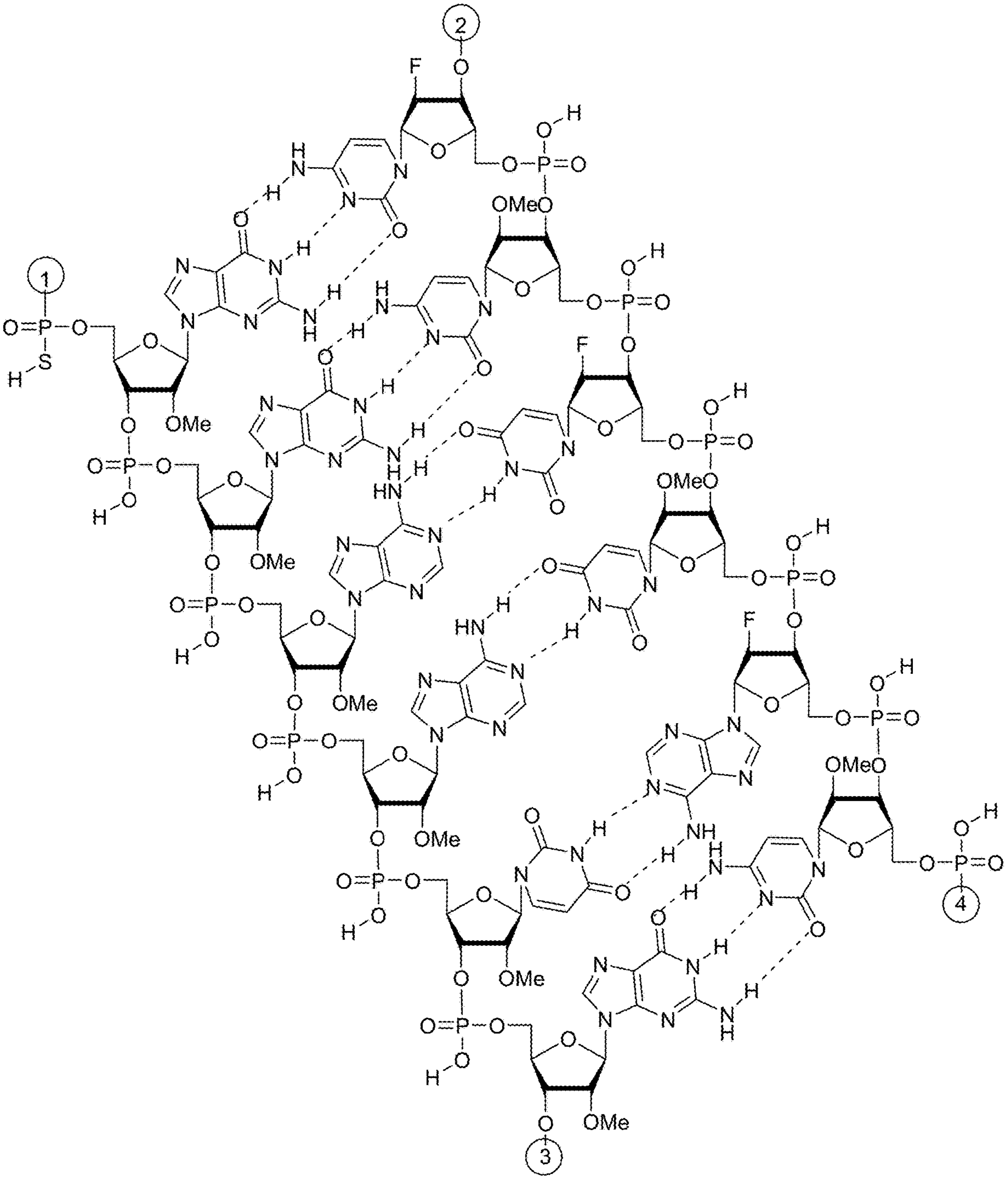
Figure 3C:
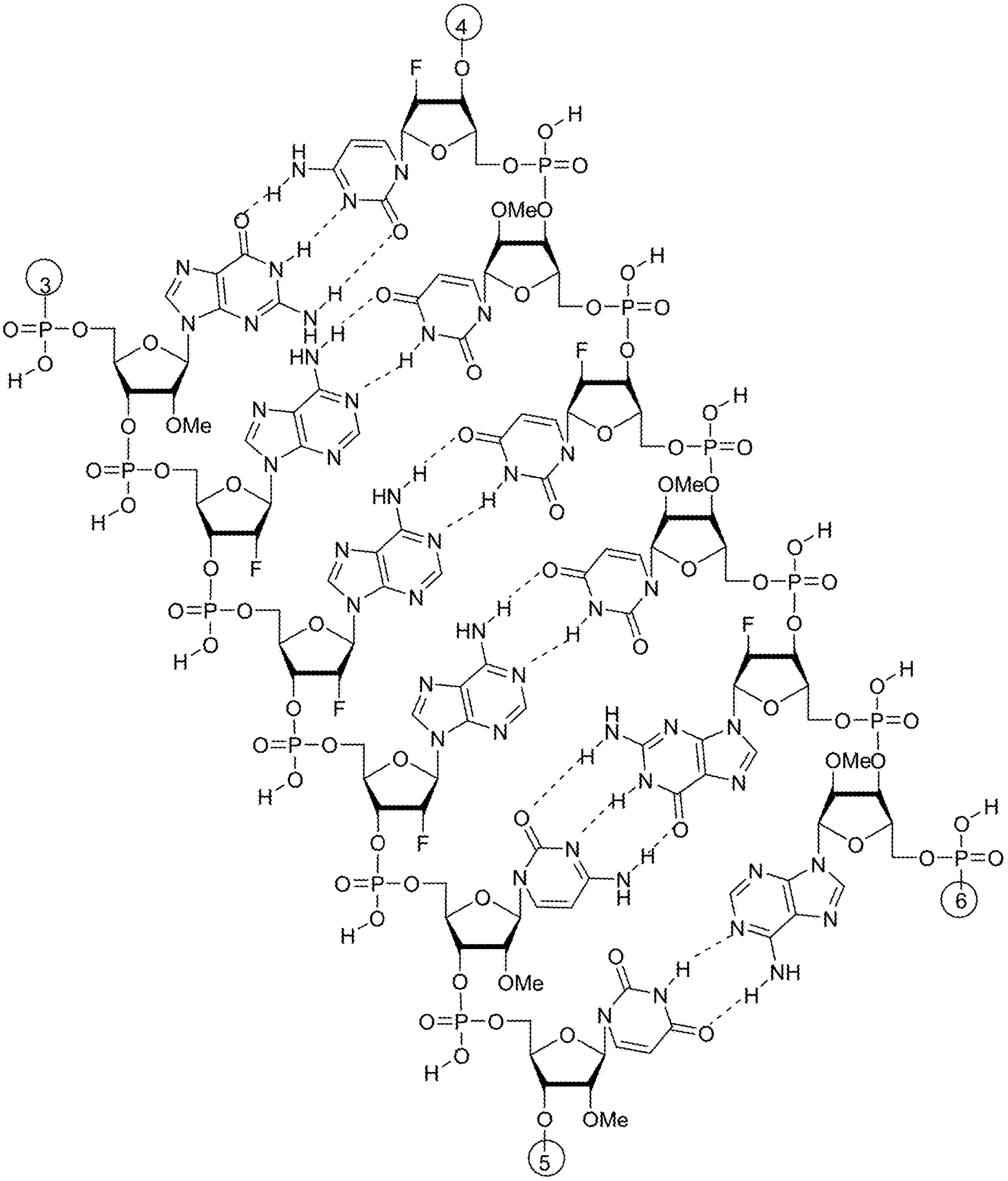
Figure 3D:
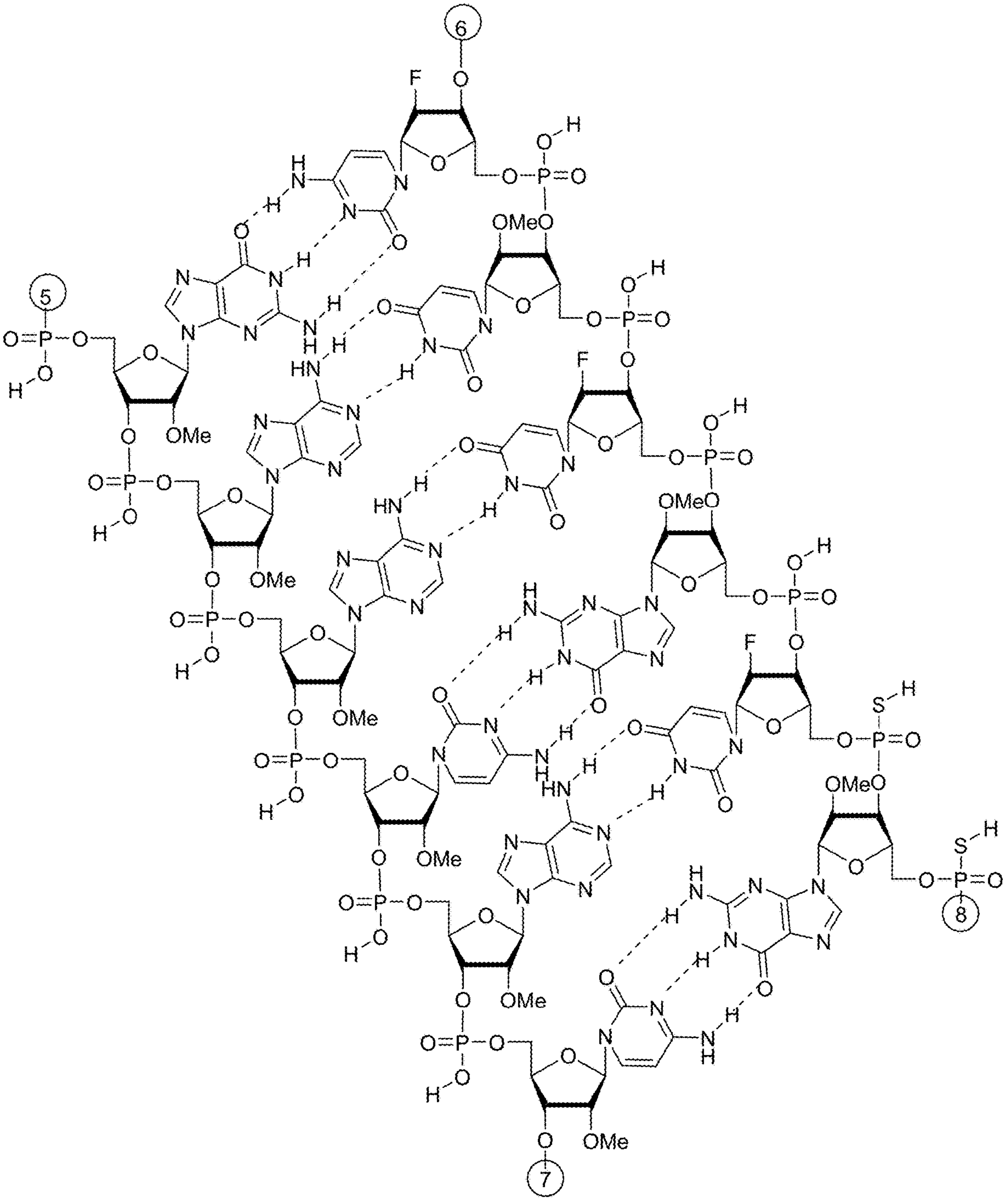
Figure 3E:
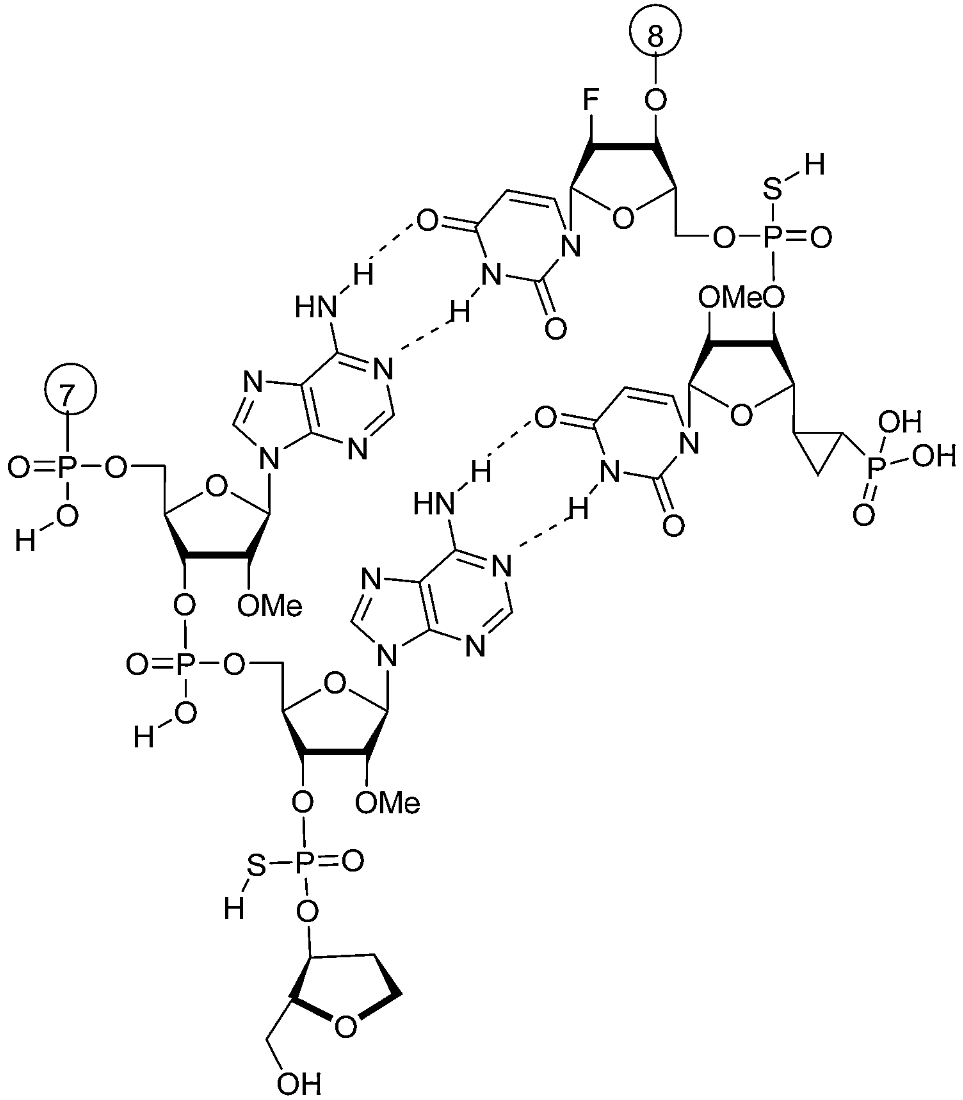
Figure 4A:
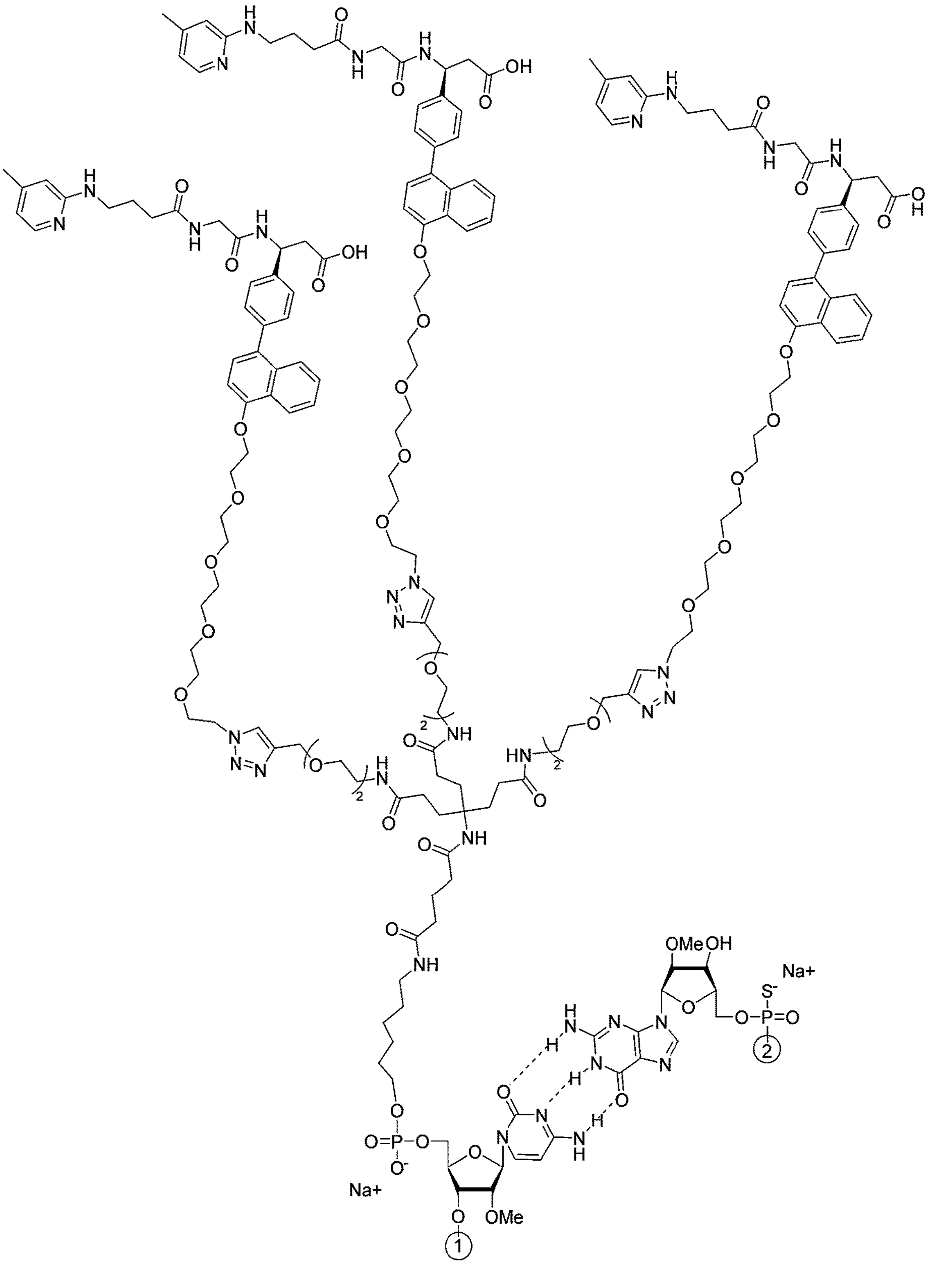
FIG. 4A to 4E. Chemical structure representation of RAGE RNAi agent conjugate AC000292 (AM10309-AS (SEQ ID NO: 3), CS000363 (SEQ ID NO: 10)) shown as a sodium salt.
Figure 4B:
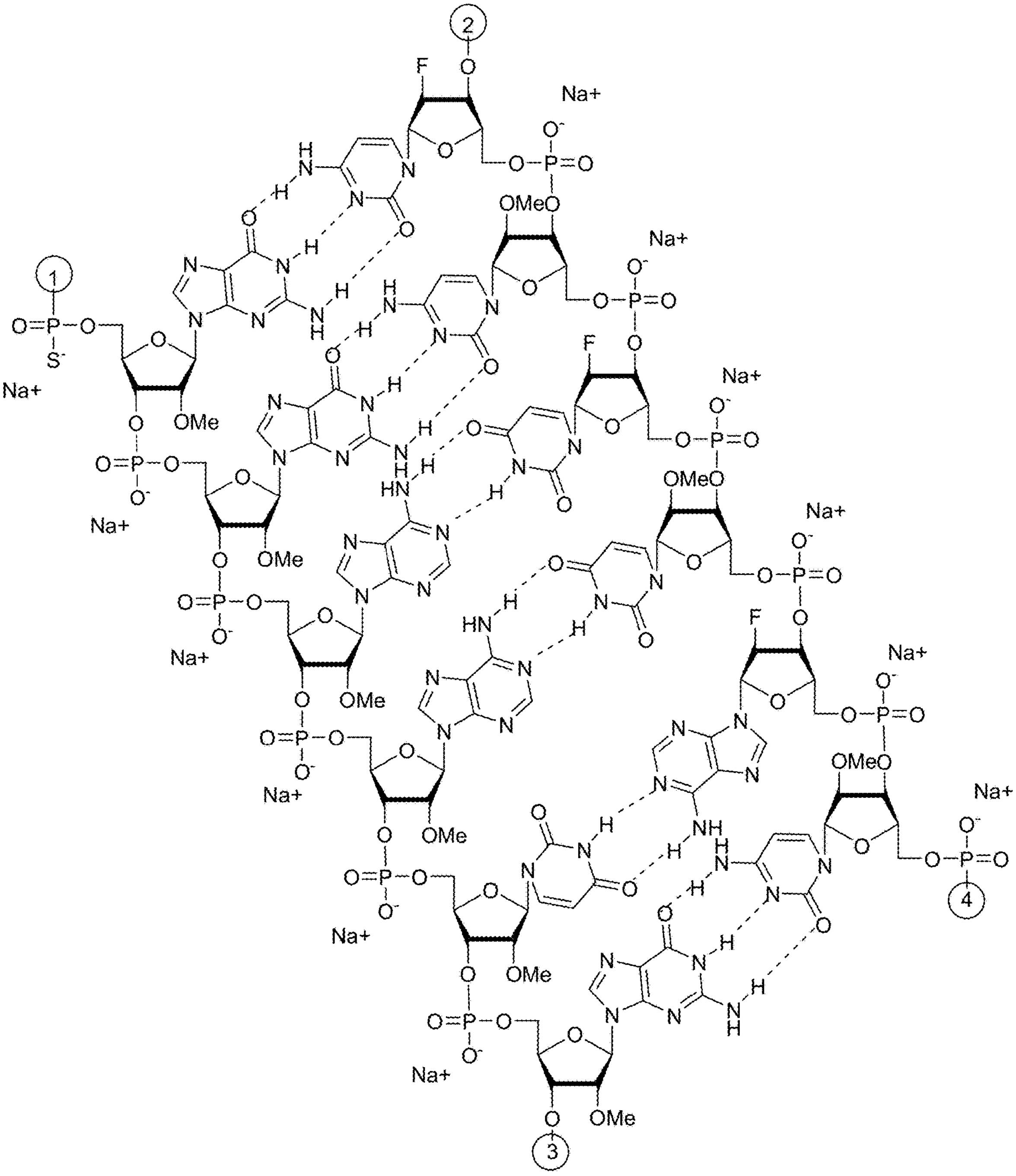
Figure 4C:
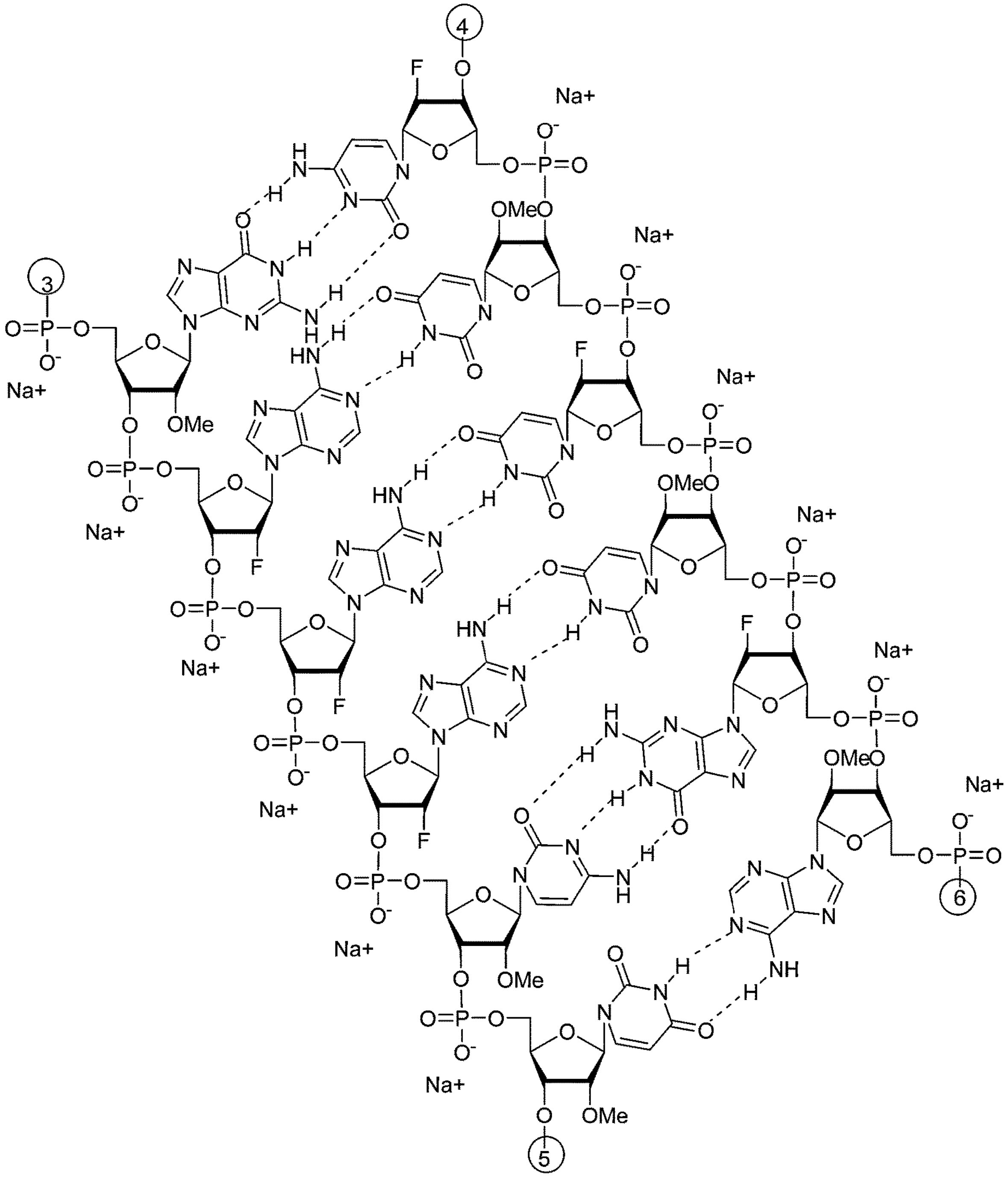
Figure 4D:
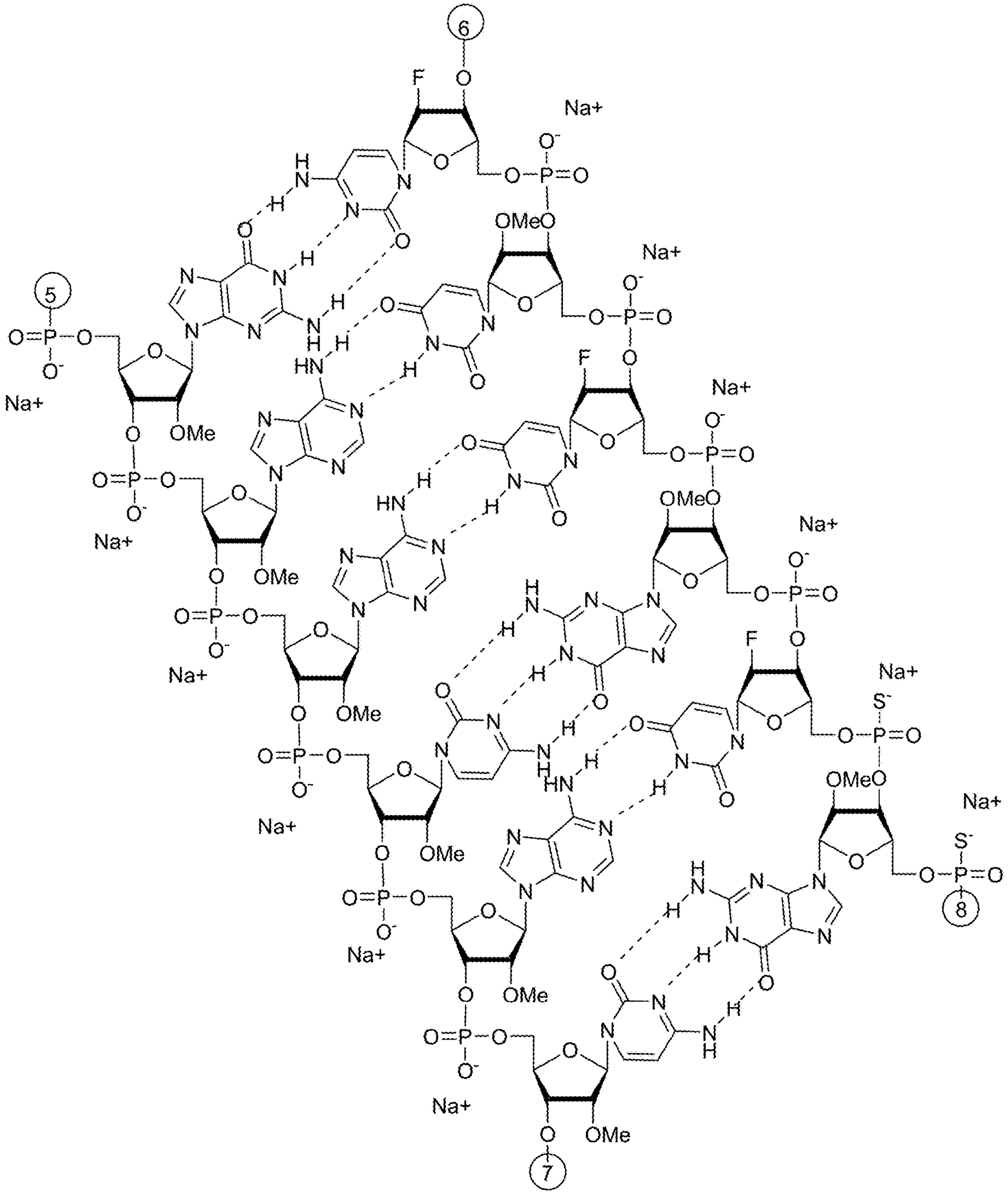
Figure 4E:
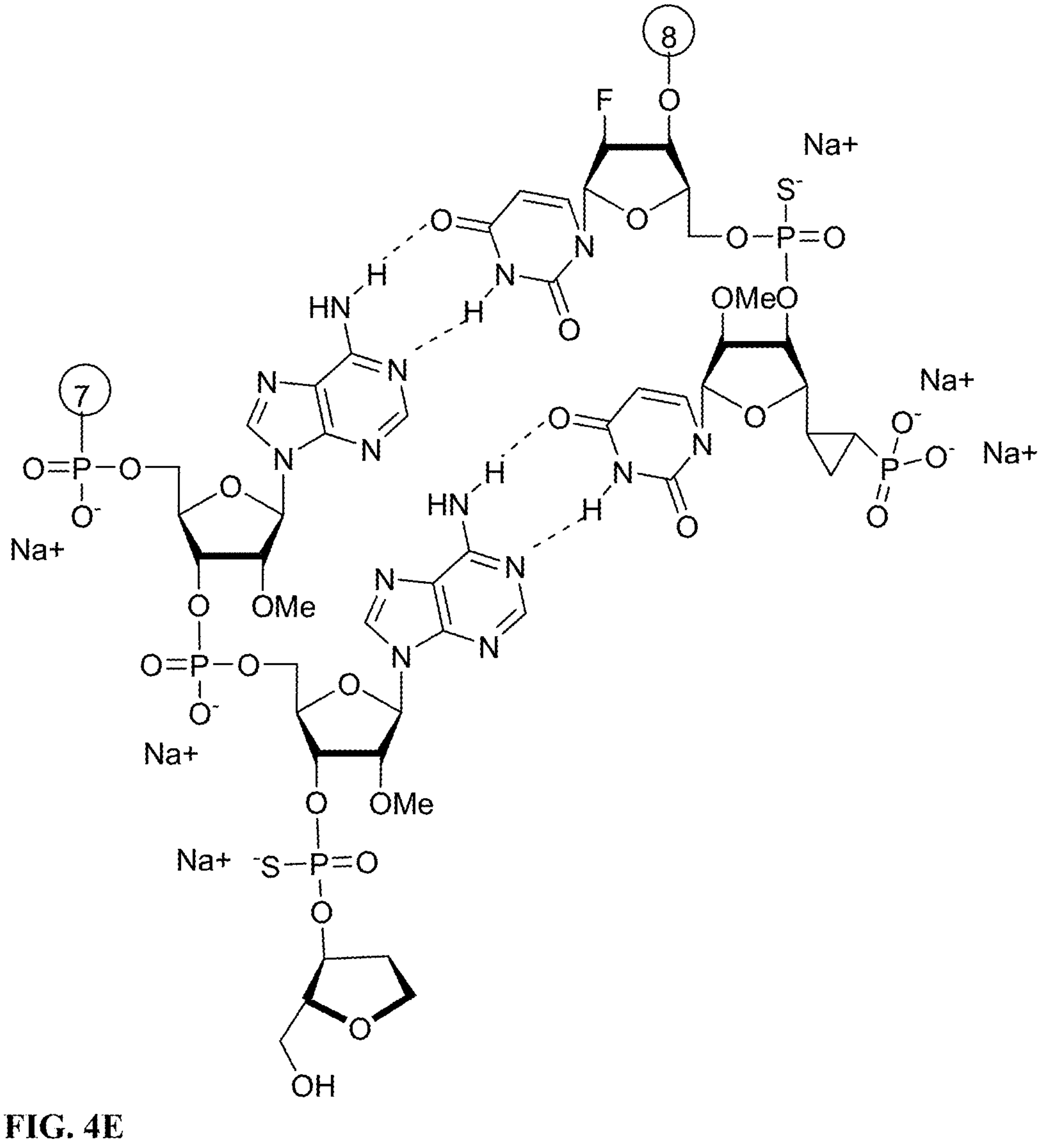
Figure 5A:
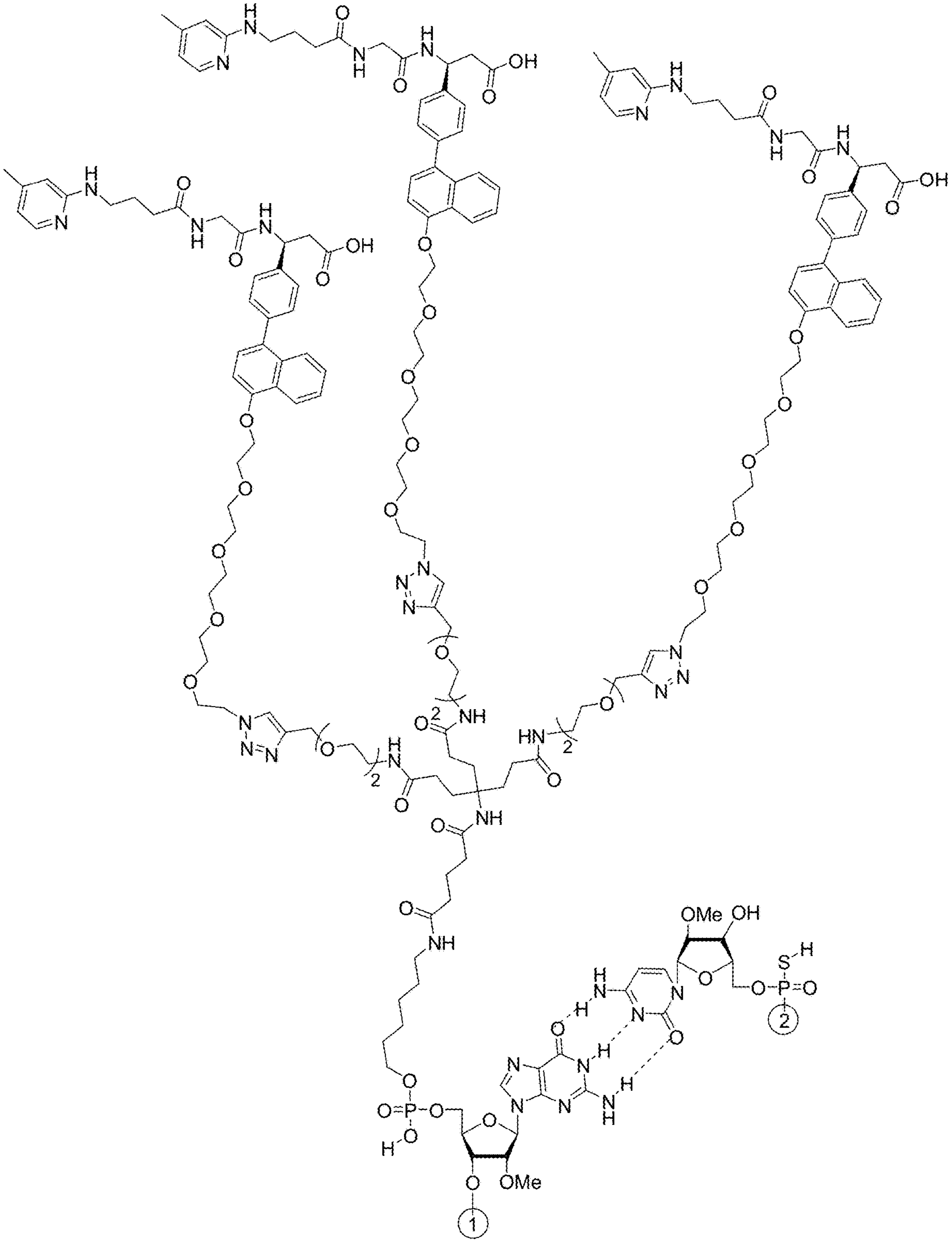
FIG. 5A to 5E. Chemical structure representation of RAGE RNAi agent conjugate AC001266 (AM11897-AS (SEQ ID NO: 5), CS001579 (SEQ ID NO: 11)) shown as a free acid.
Figure 5B:
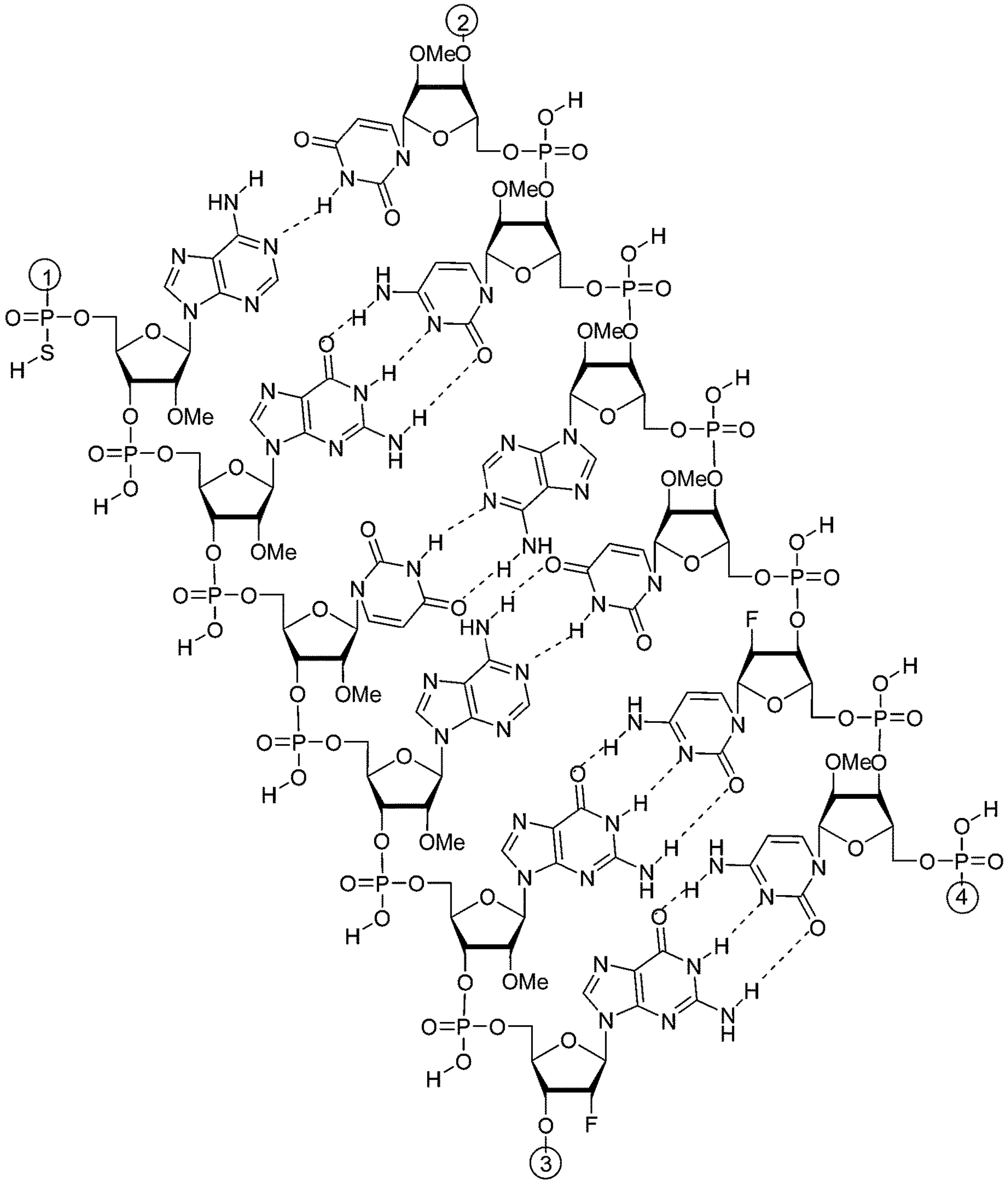
Figure 5C:
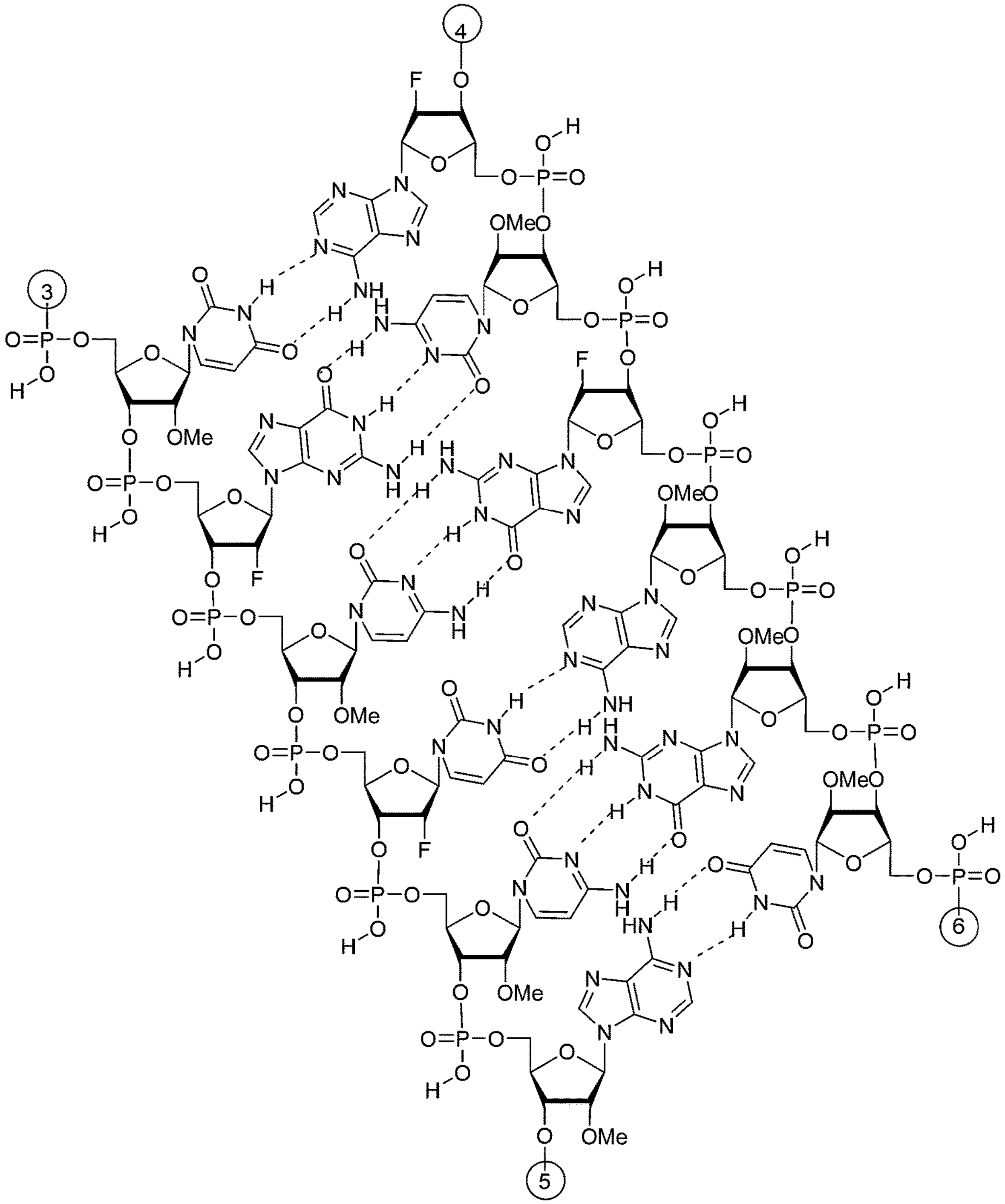
Figure 5D:
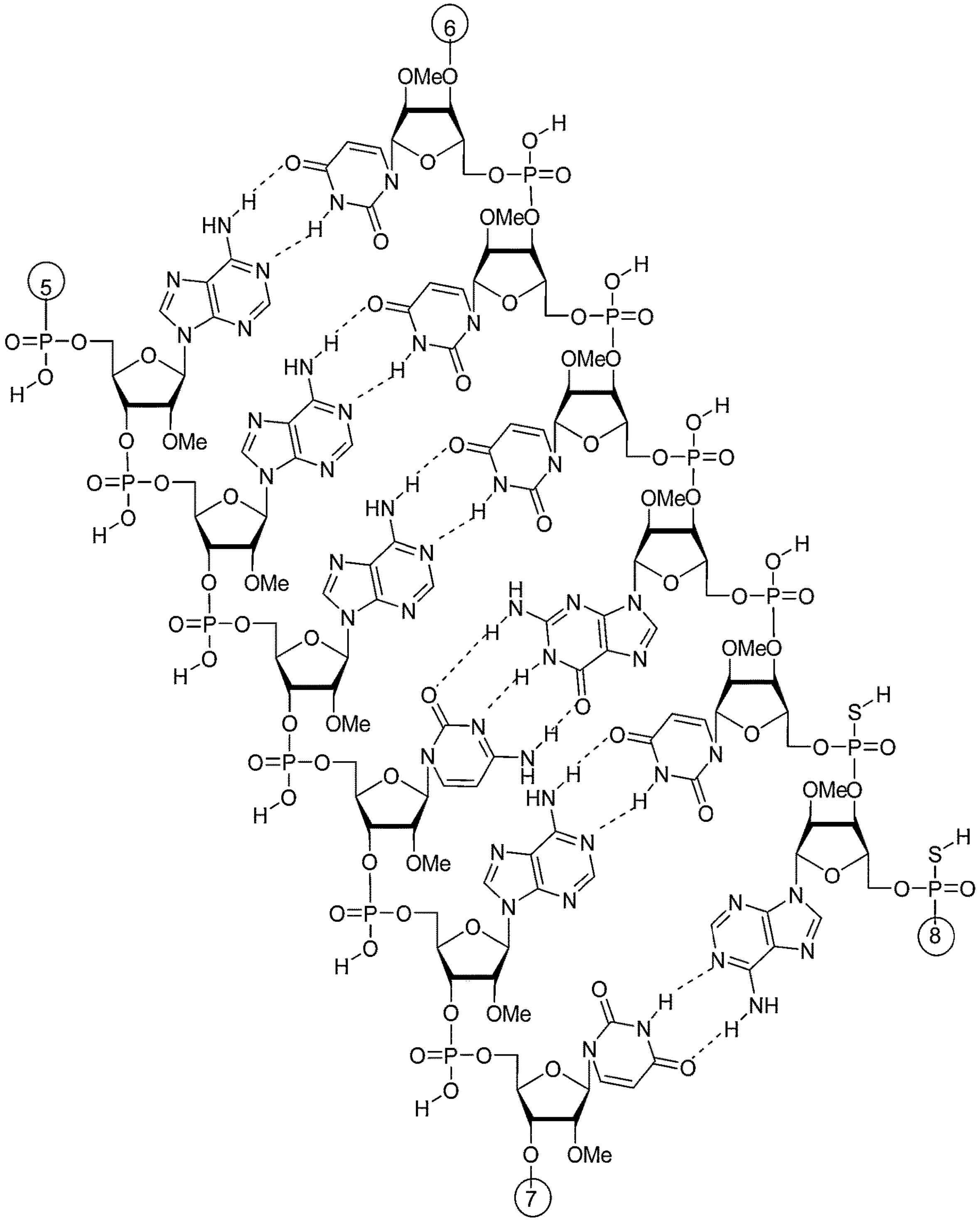
Figure 5E:
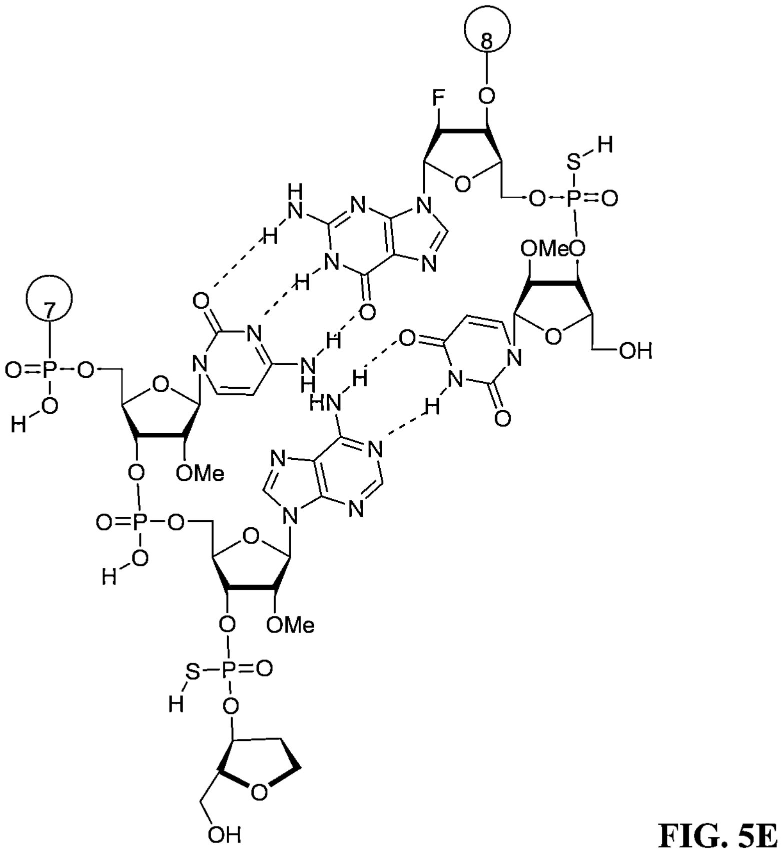
Figure 6A:
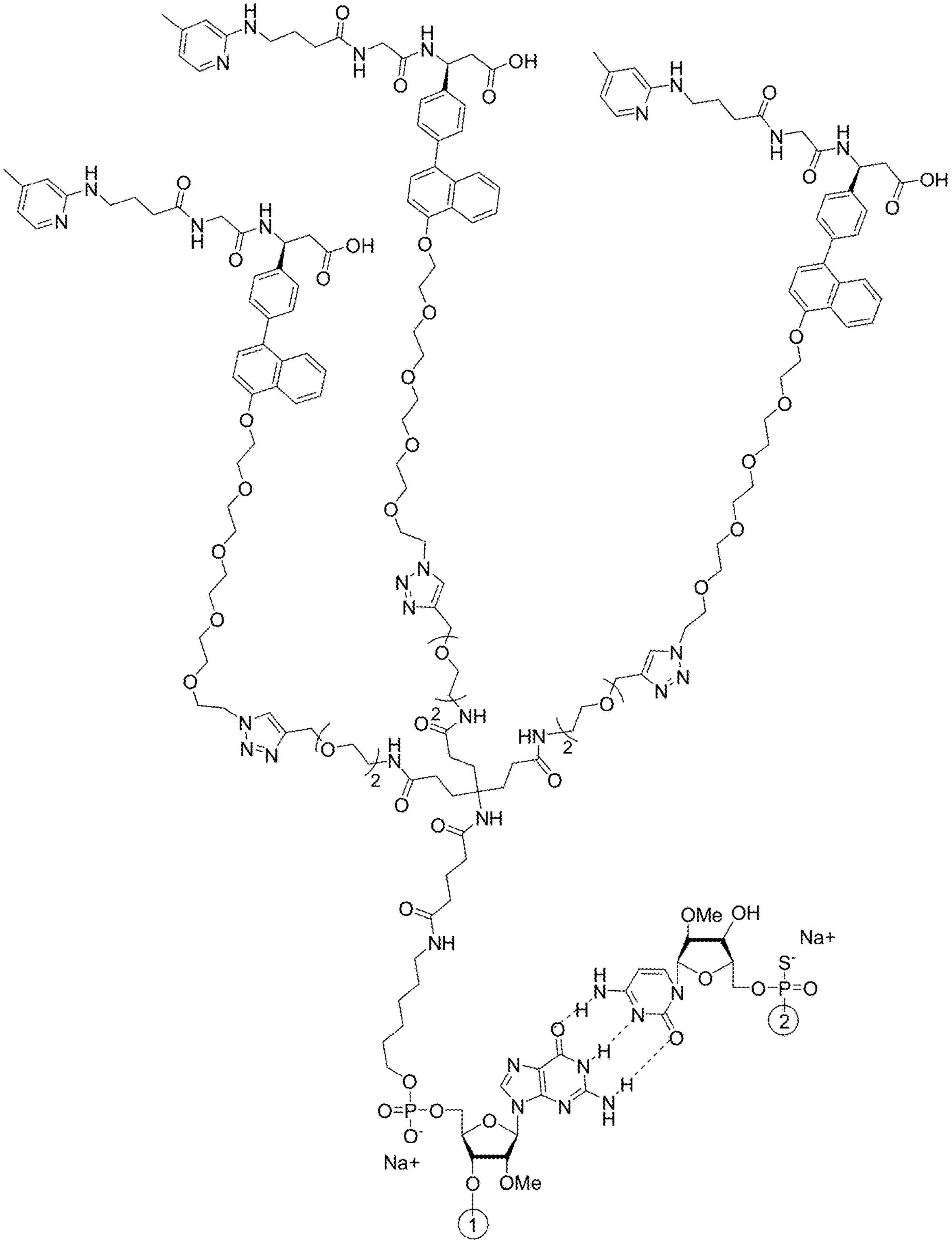
FIG. 6A to 6E. Chemical structure representation of RAGE RNAi agent conjugate AC001266 (AM11897-AS (SEQ ID NO: 5), CS001579 (SEQ ID NO: 11)) shown as a sodium salt.
Figure 6B:
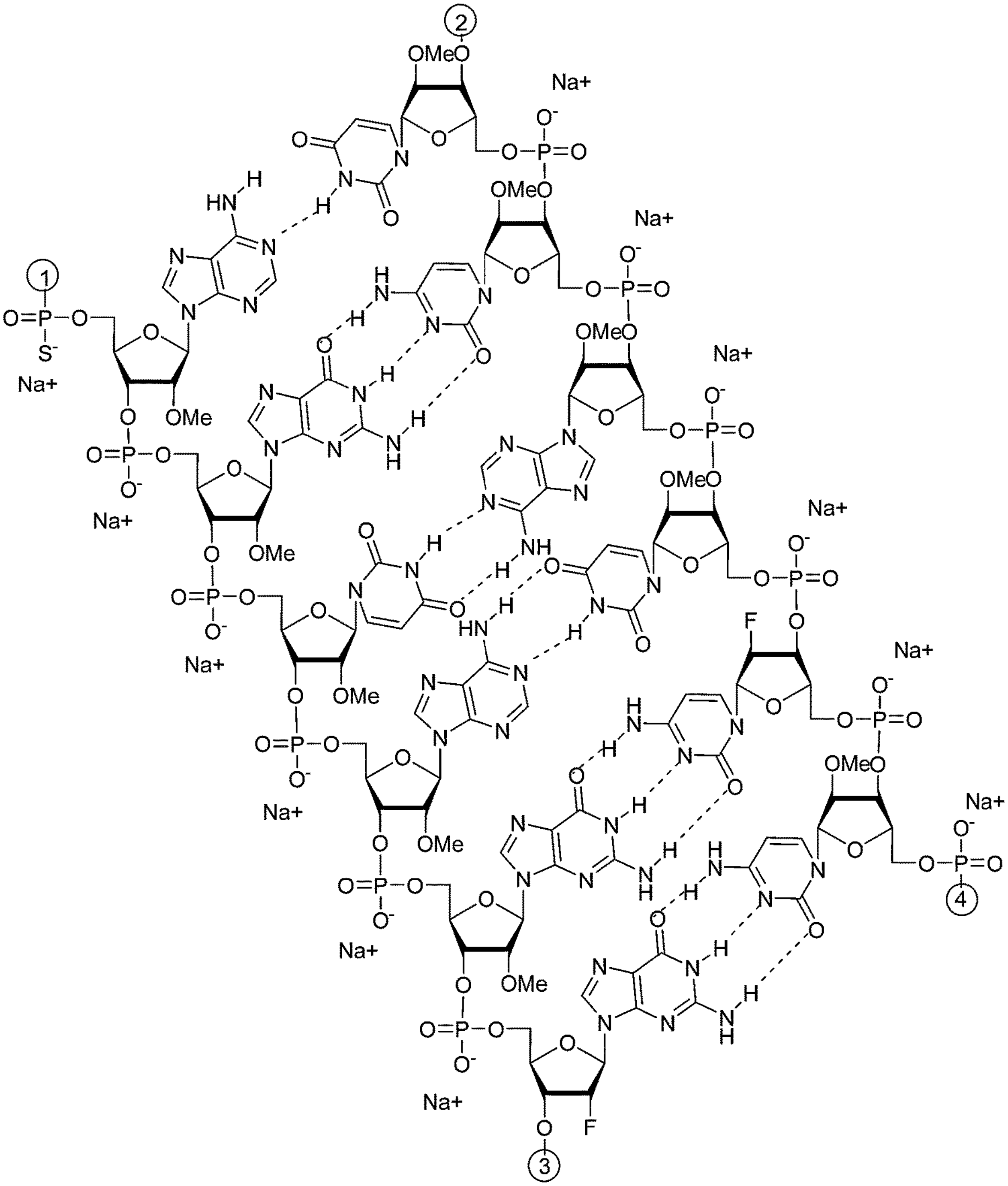
Figure 6C:
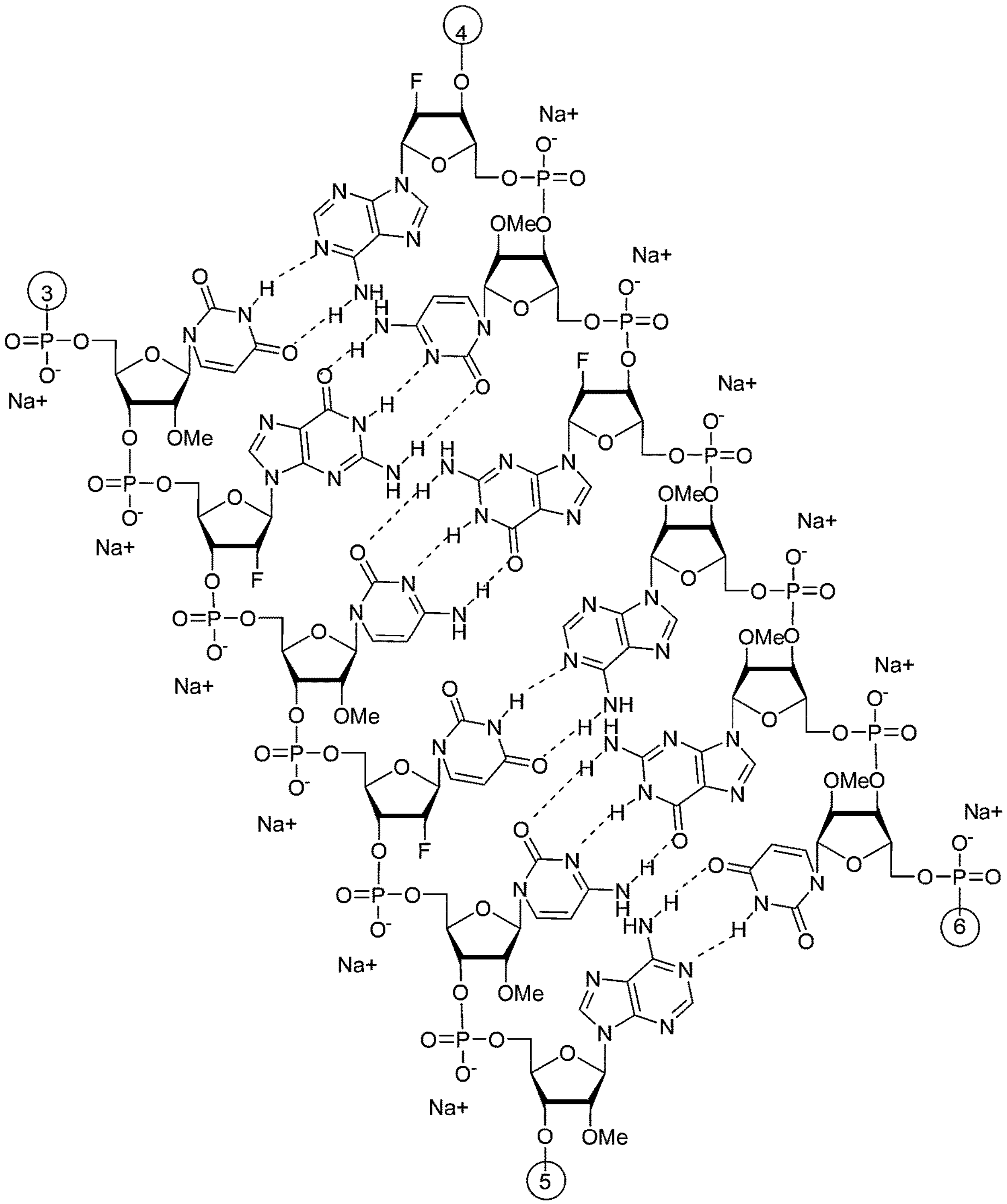
Figure 6D:
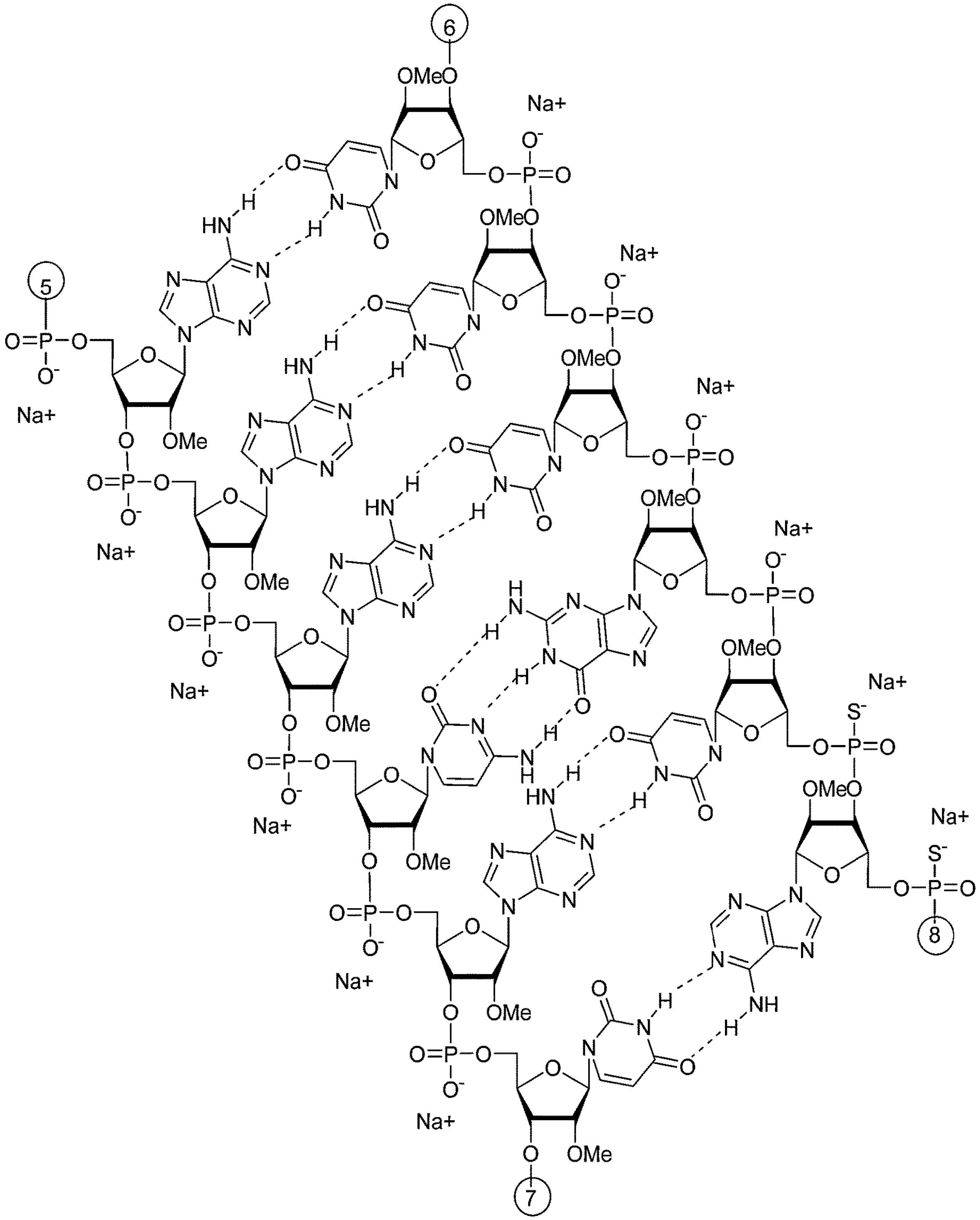
Figure 6E:
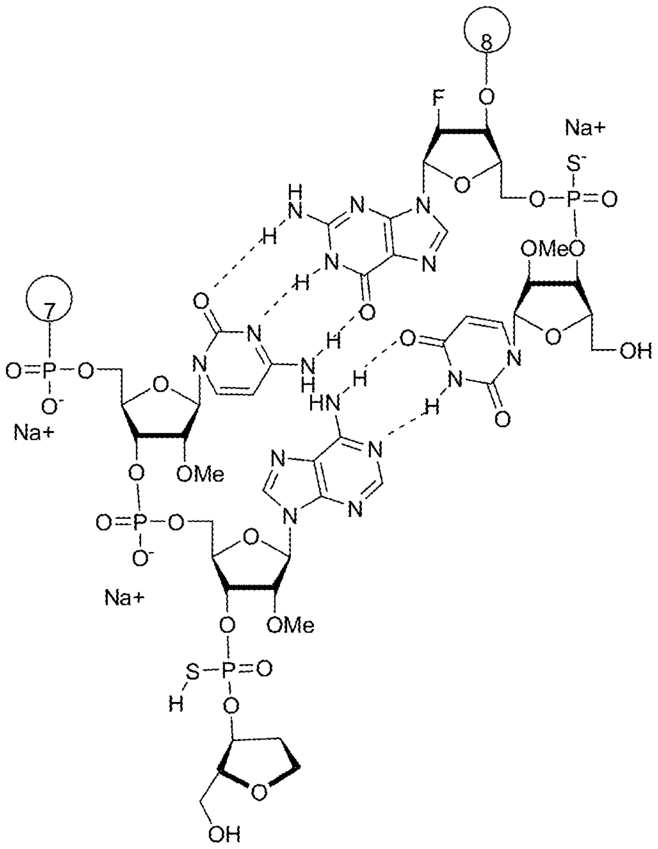
Figure 7A:
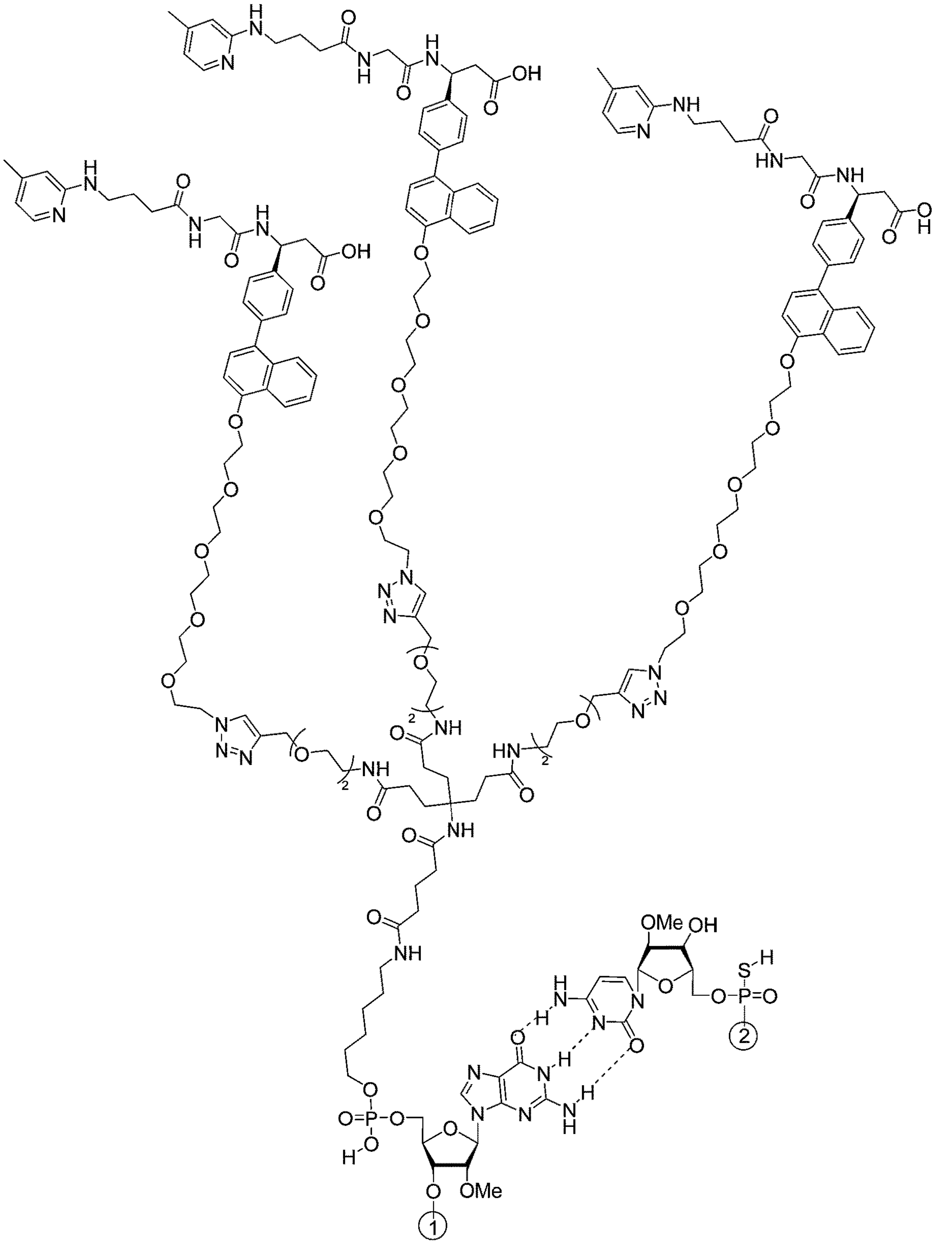
FIG. 7A to 7E. Chemical structure representation of RAGE RNAi agent conjugate AC001267 (AM11898-AS (SEQ ID NO: 6), CS001579 (SEQ ID NO: 11)) shown as a free acid.
Figure 7B:
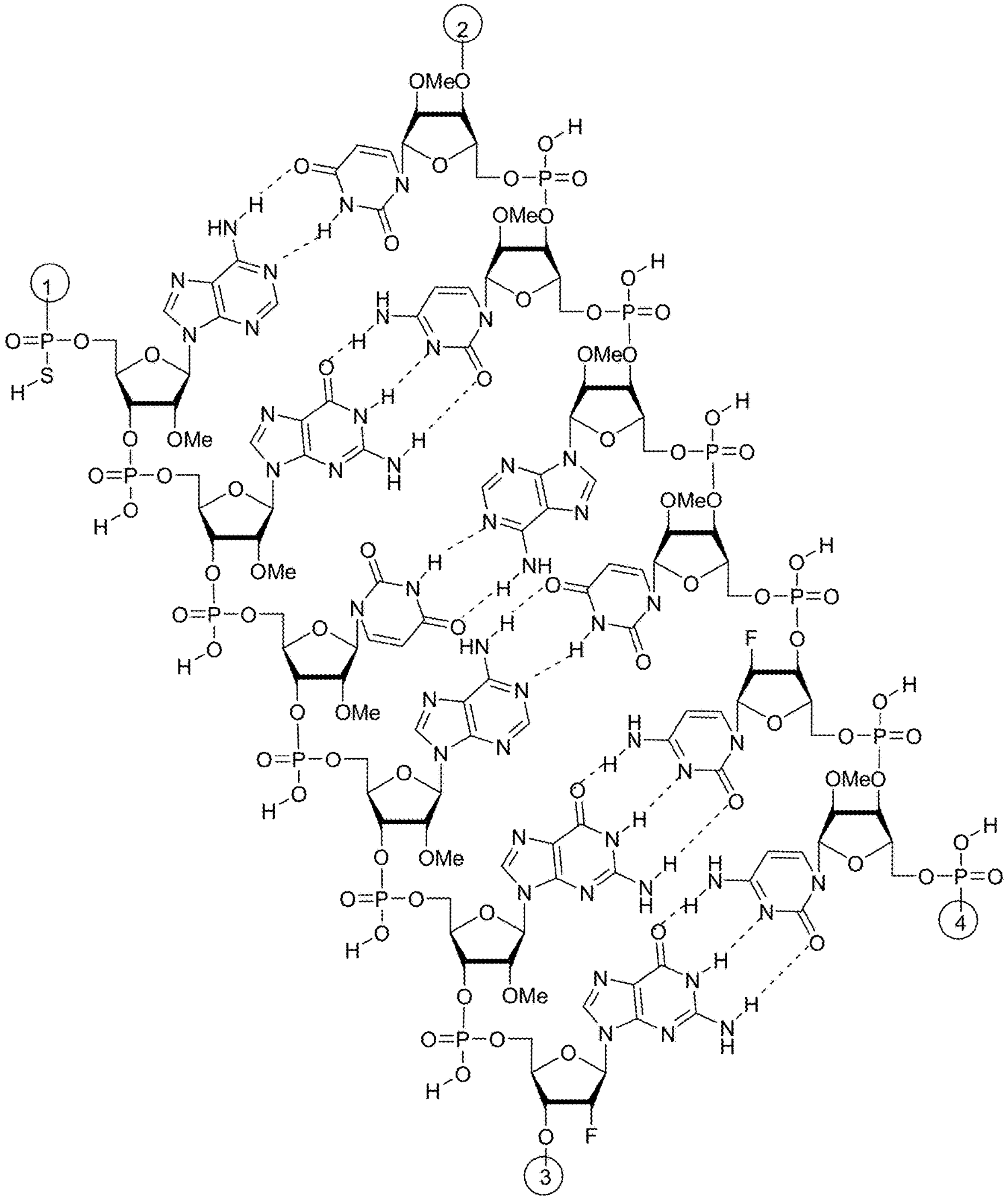
Figure 7C:
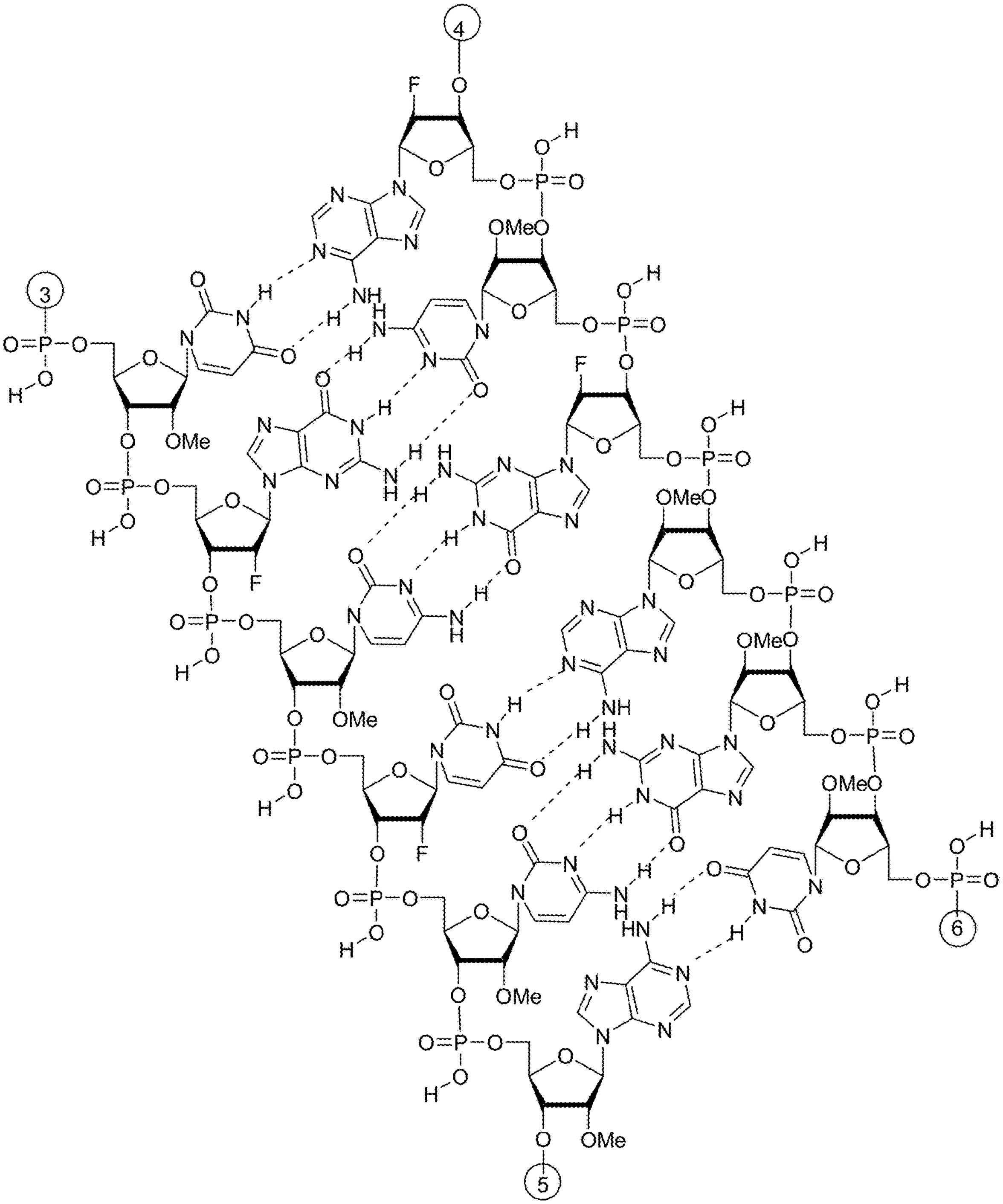
Figure 7D:
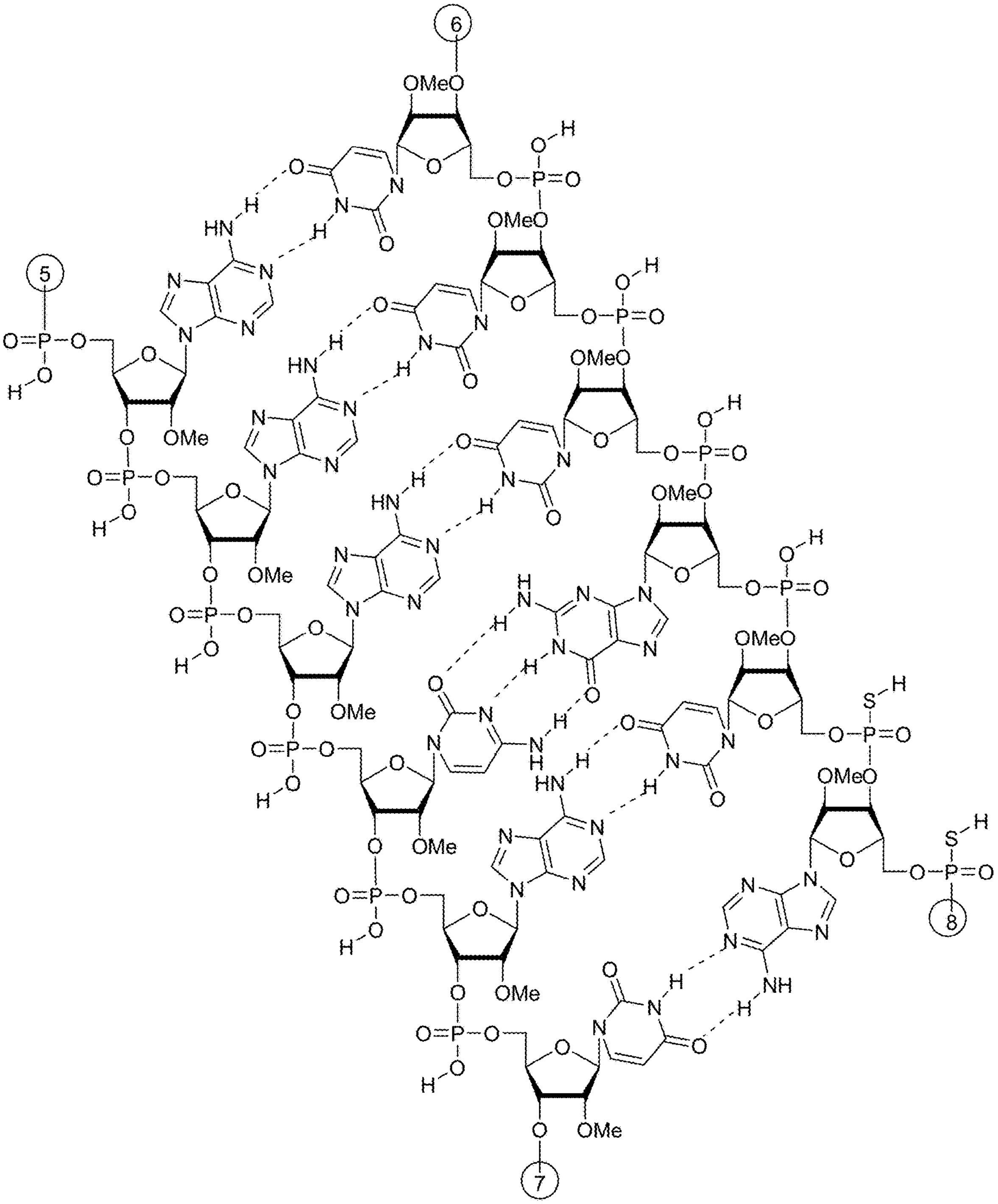
Figure 7E:
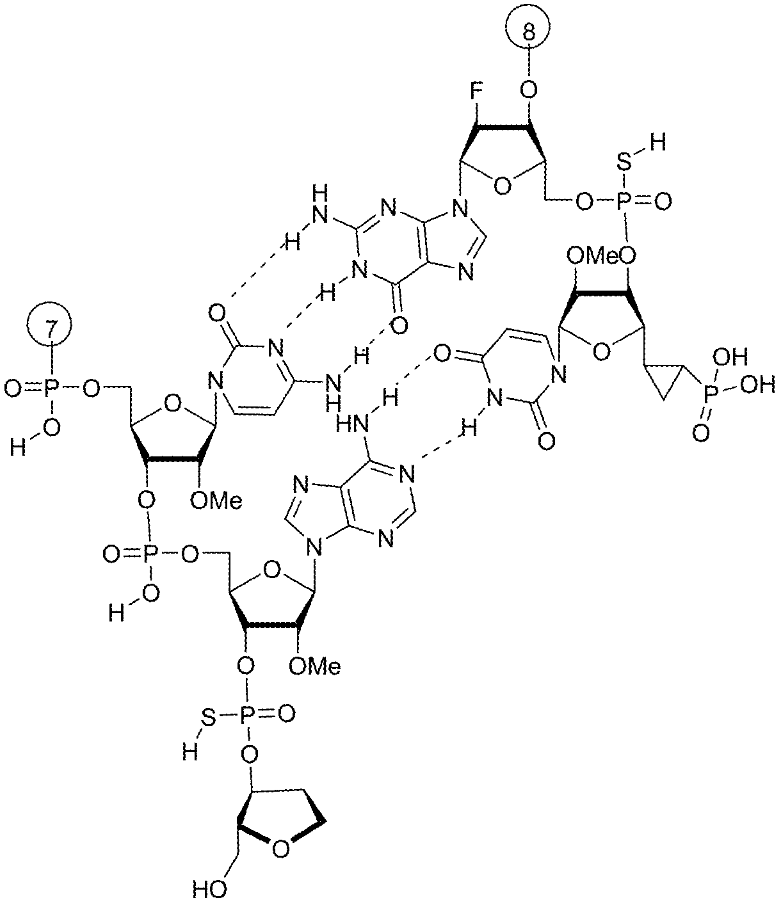
Figure 8A:
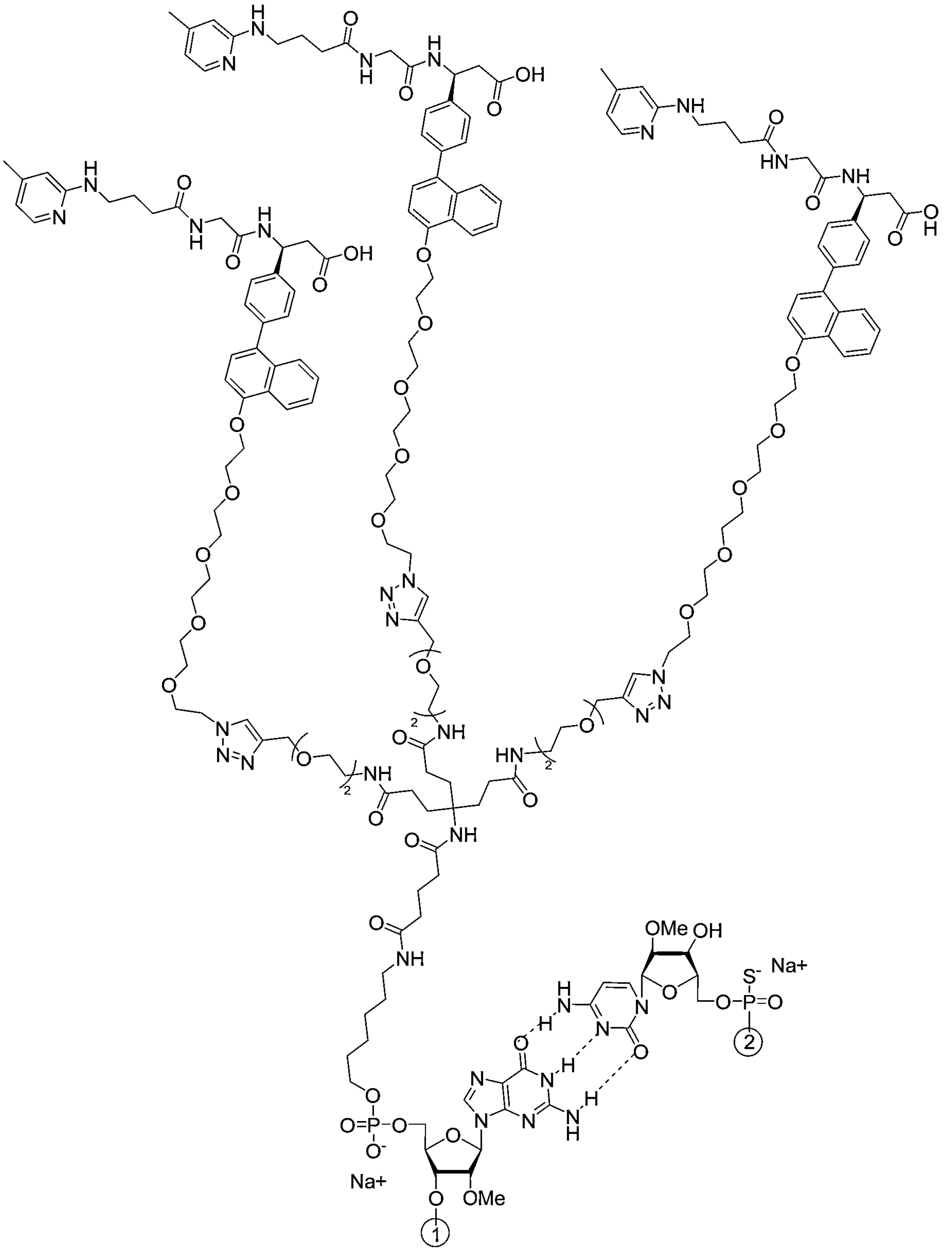
FIG. 8A to 8E. Chemical structure representation of RAGE RNAi agent conjugate AC001267 (AM11898-AS (SEQ ID NO: 6), CS001579 (SEQ ID NO: 11)) shown as a sodium salt.
Figure 8B:
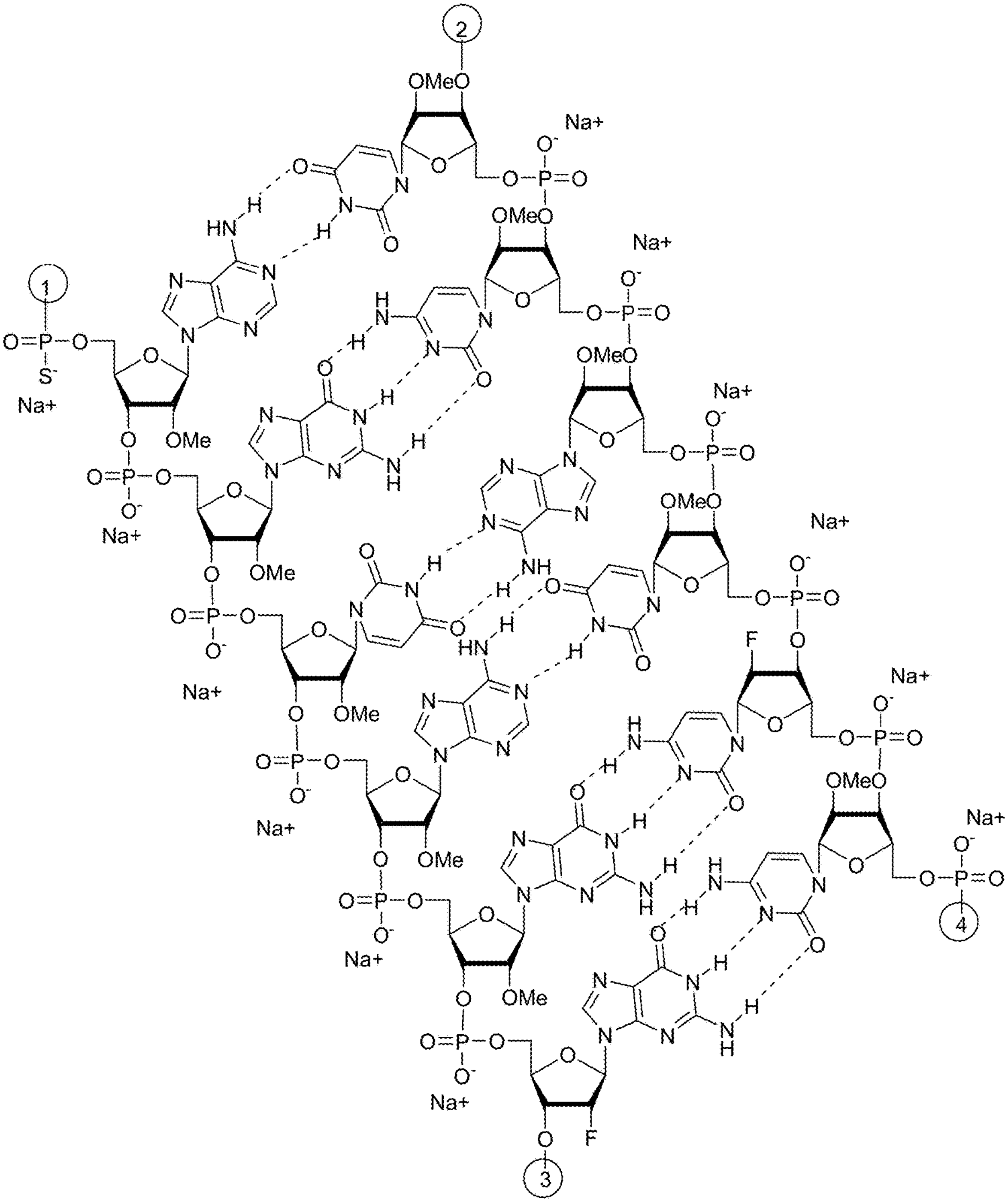
Figure 8C:
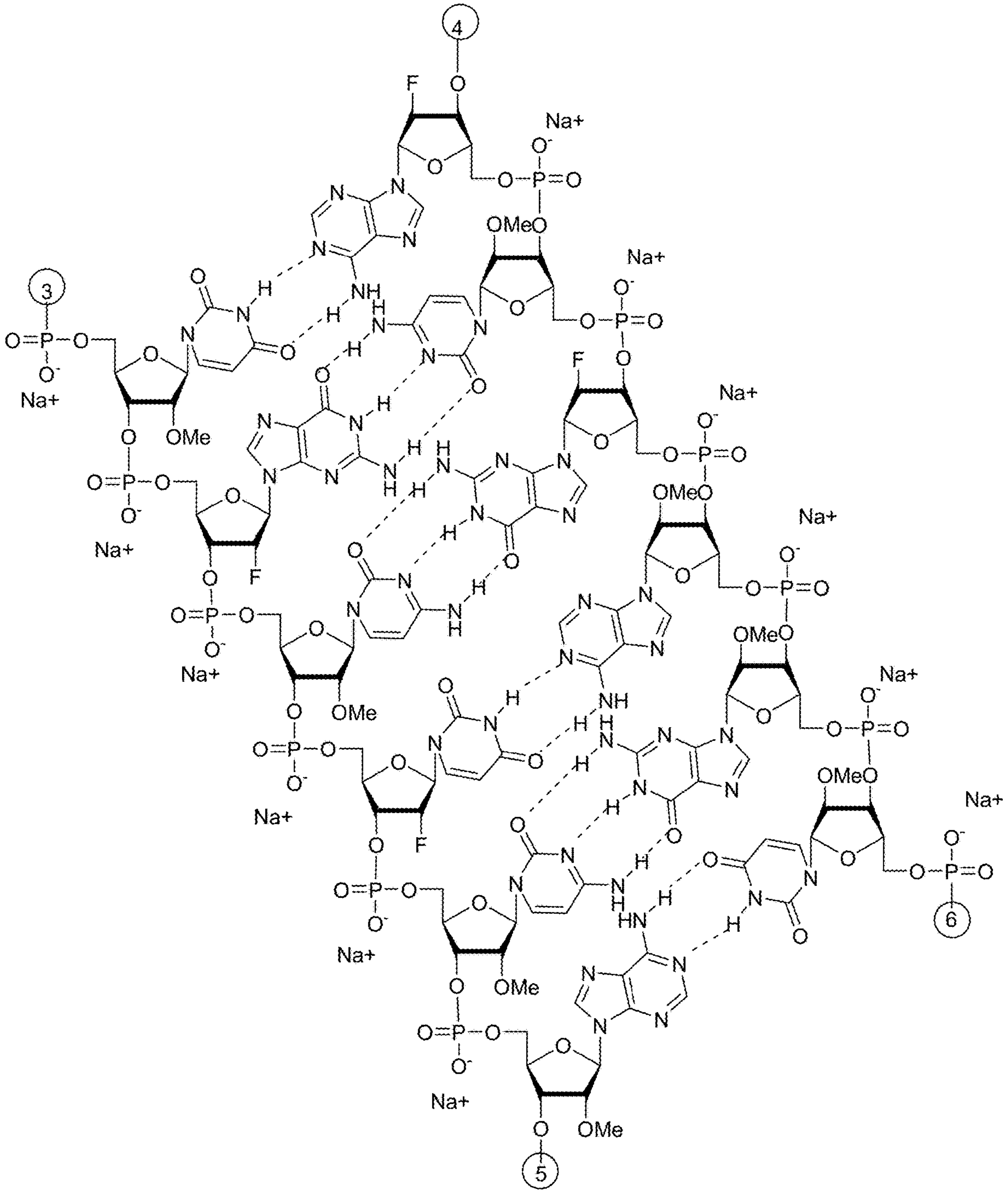
Figure 8D:
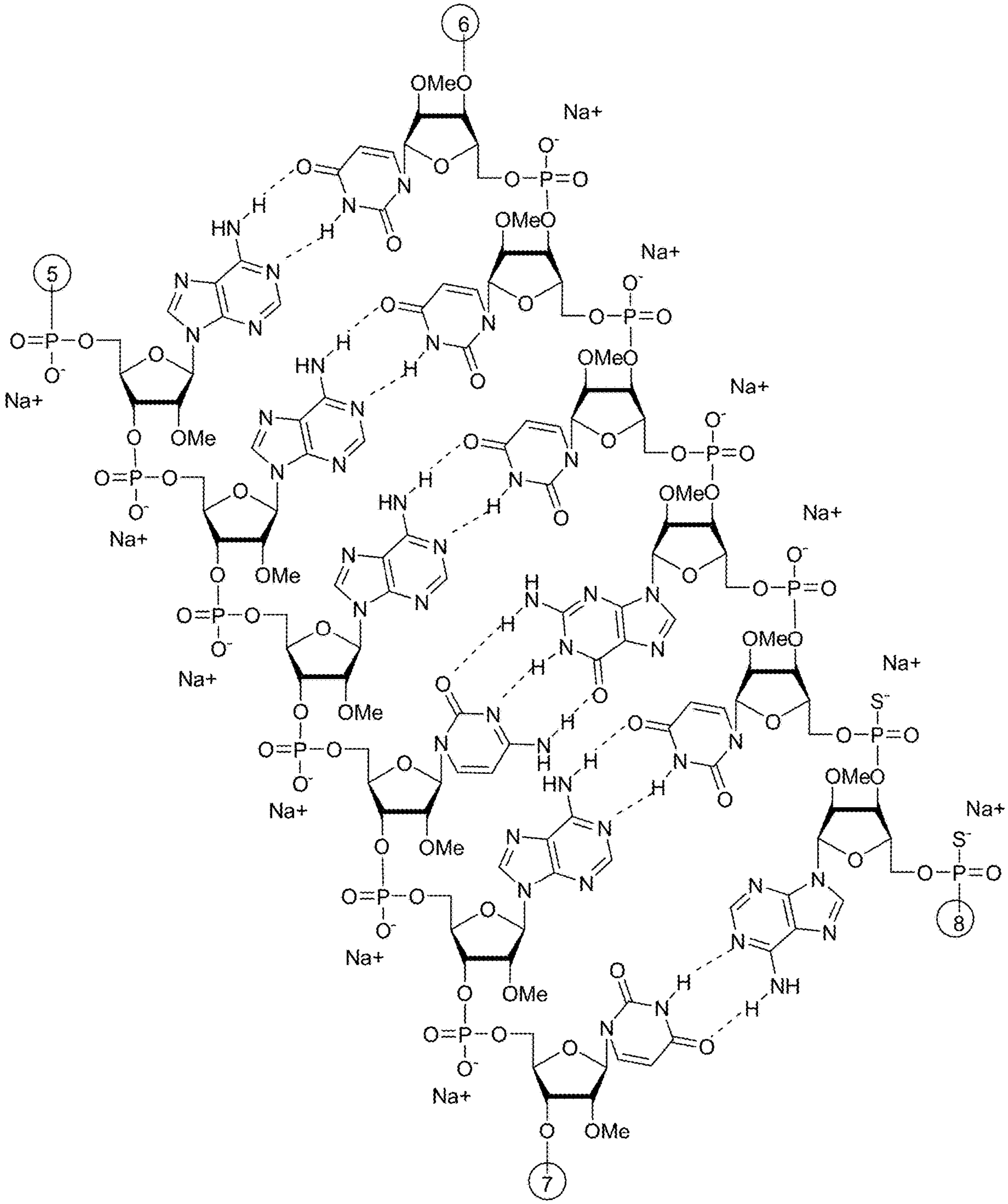
Figure 8E:
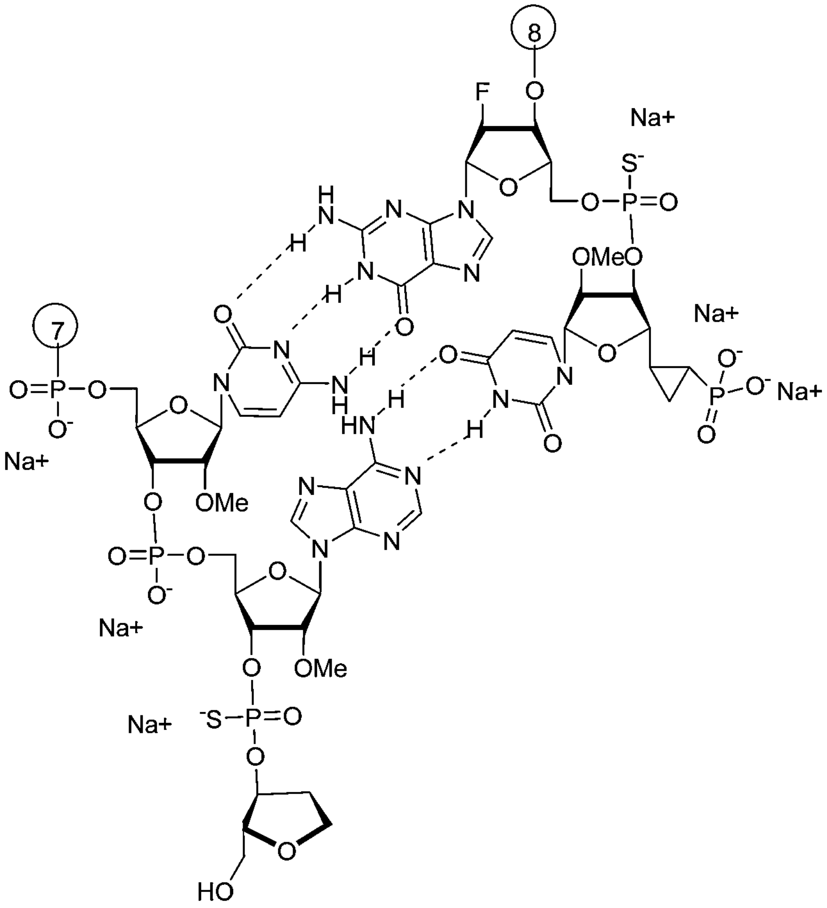
Figure 9A:
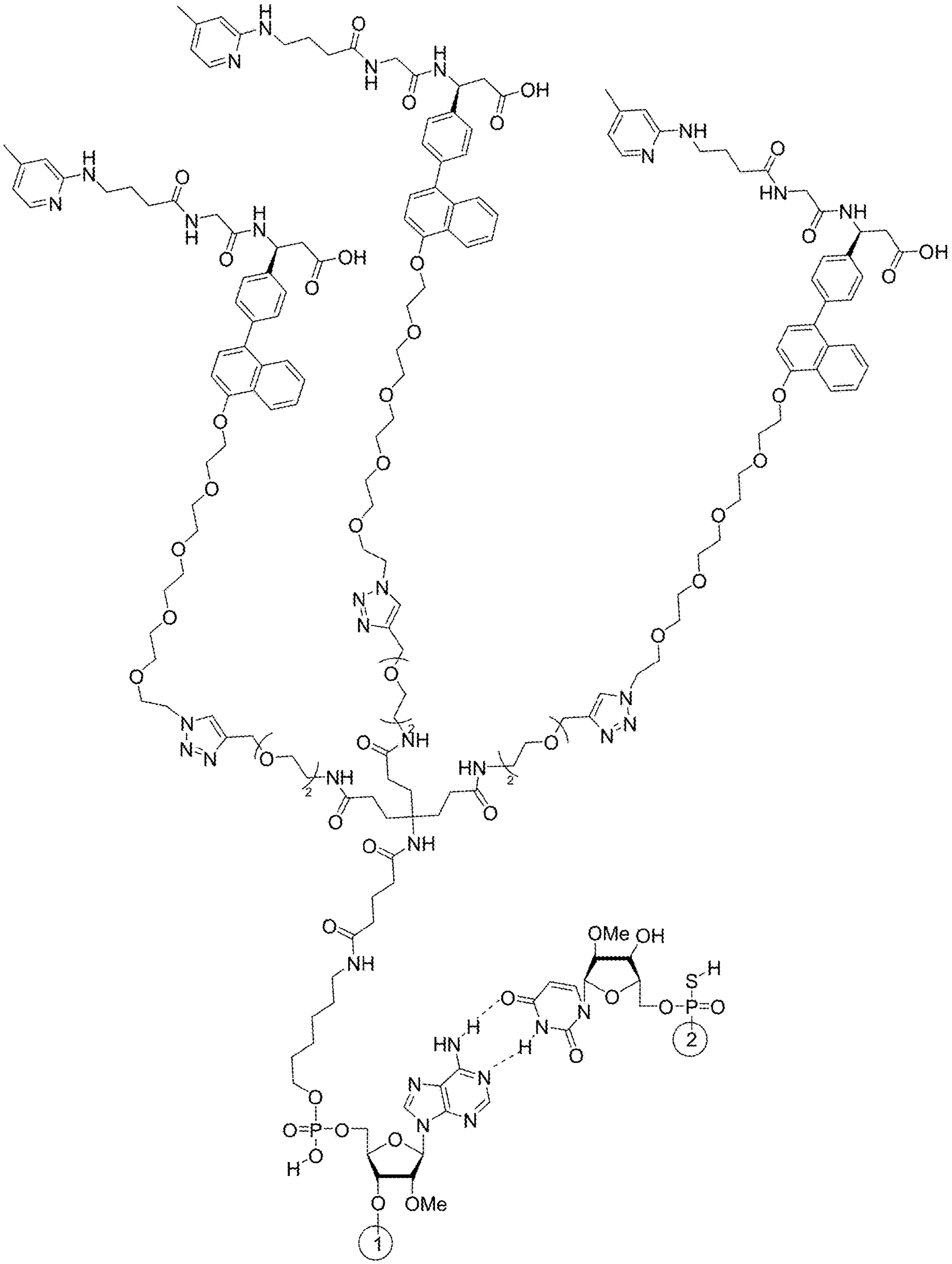
FIG. 9A to 9E. Chemical structure representation of RAGE RNAi agent conjugate AC001268 (AM10754-AS (SEQ ID NO: 4), CS001582 (SEQ ID NO: 12)) shown as a free acid.
Figure 9B:
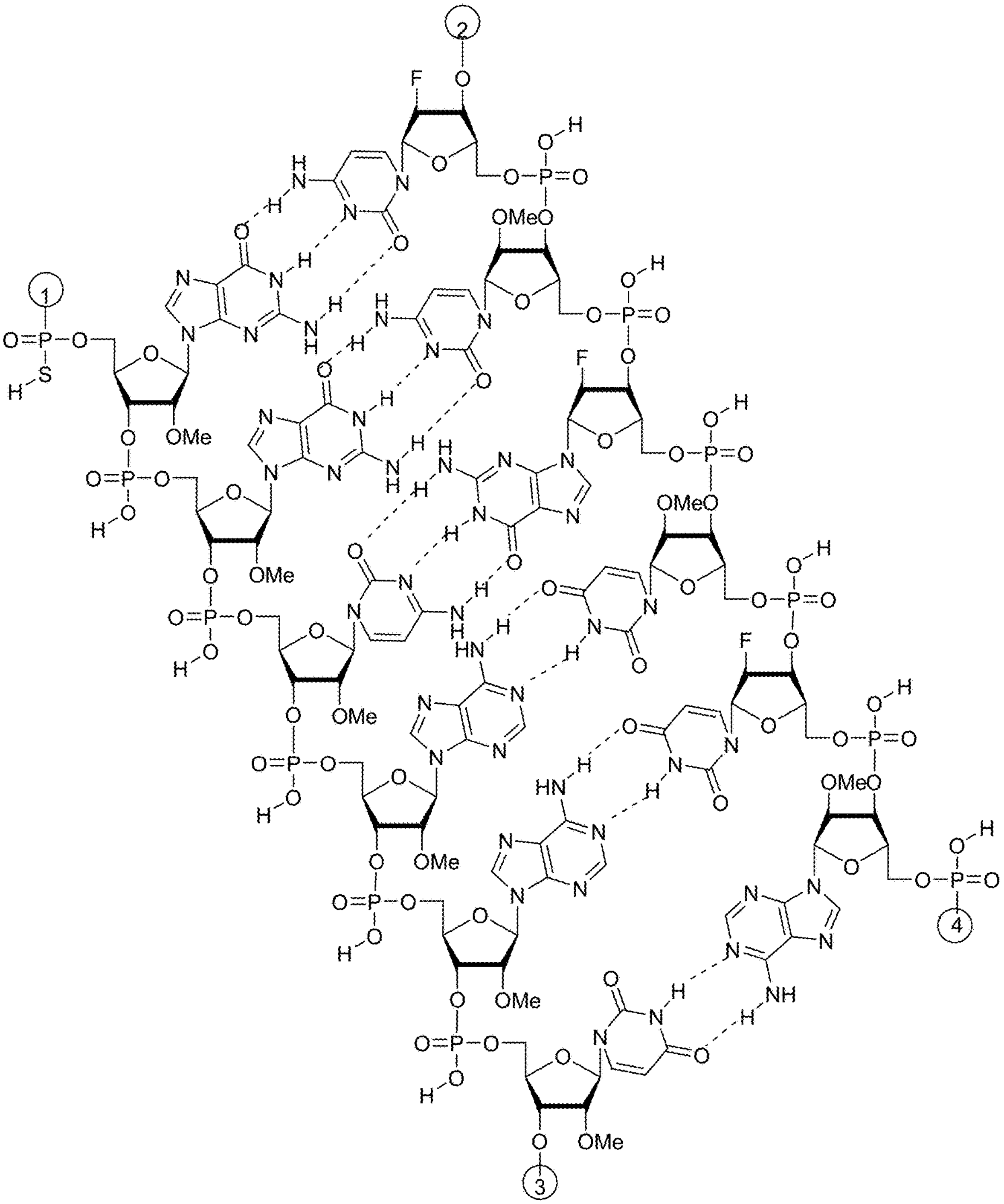
Figure 9C:
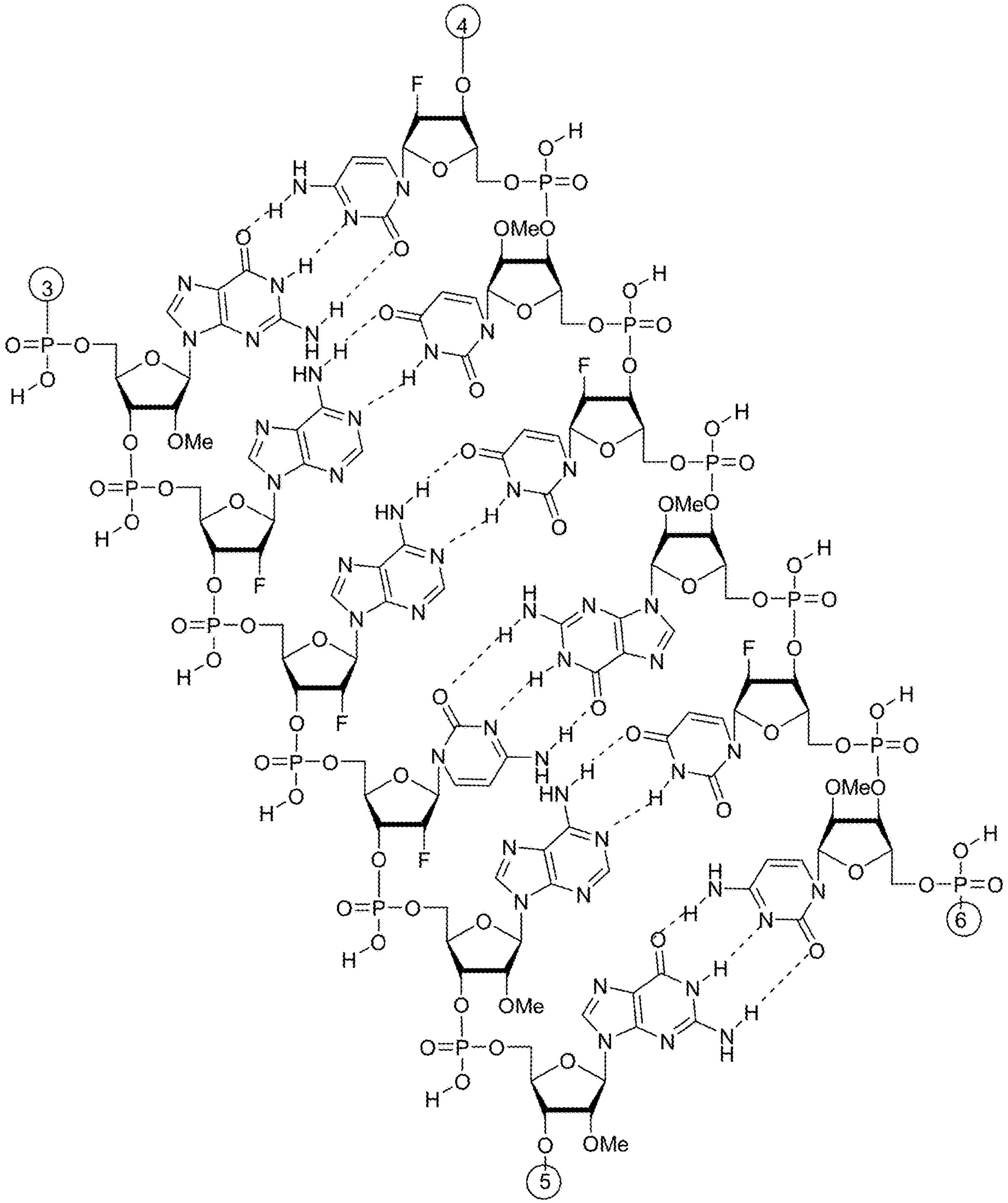
Figure 9D:
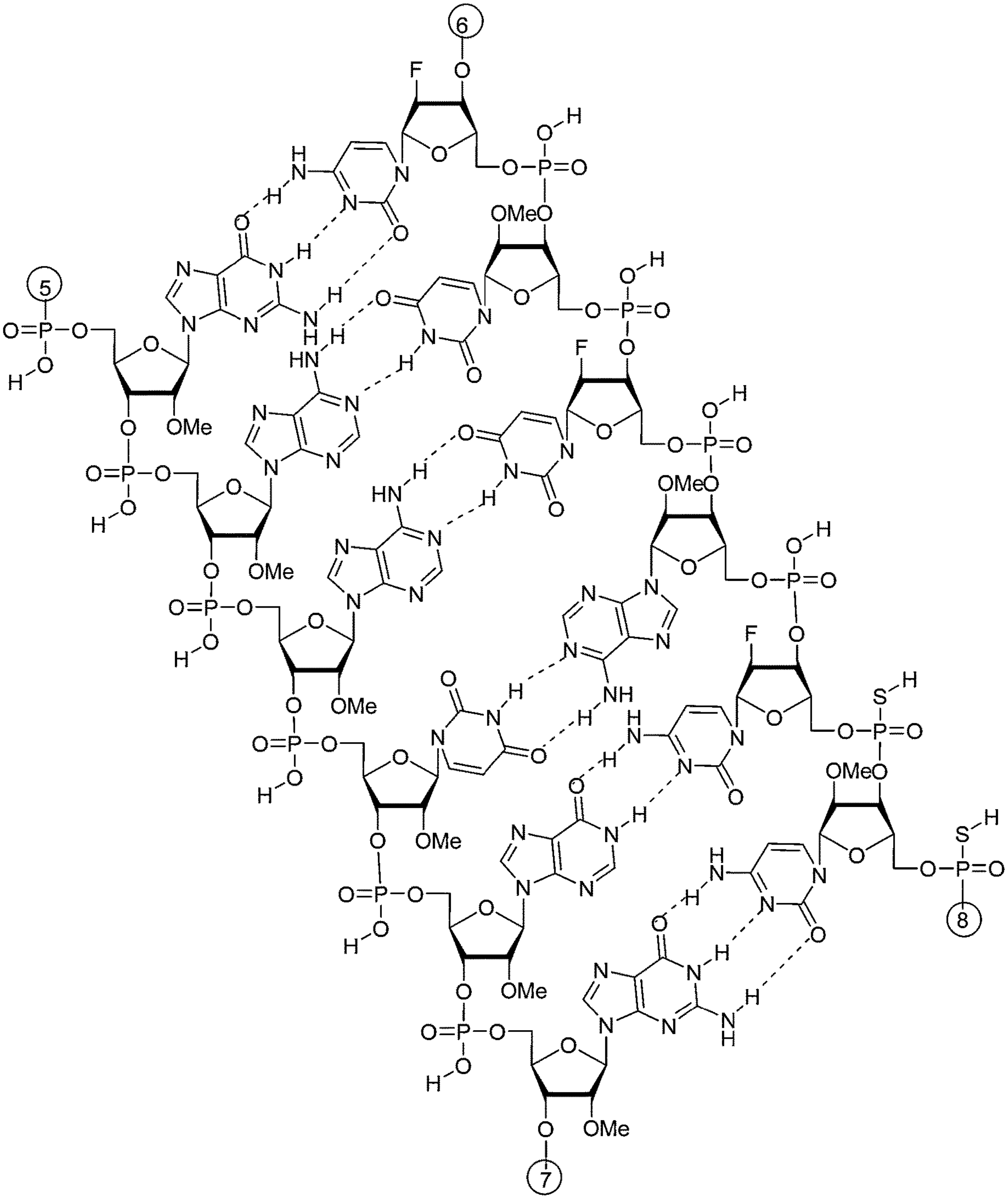
Figure 9E:
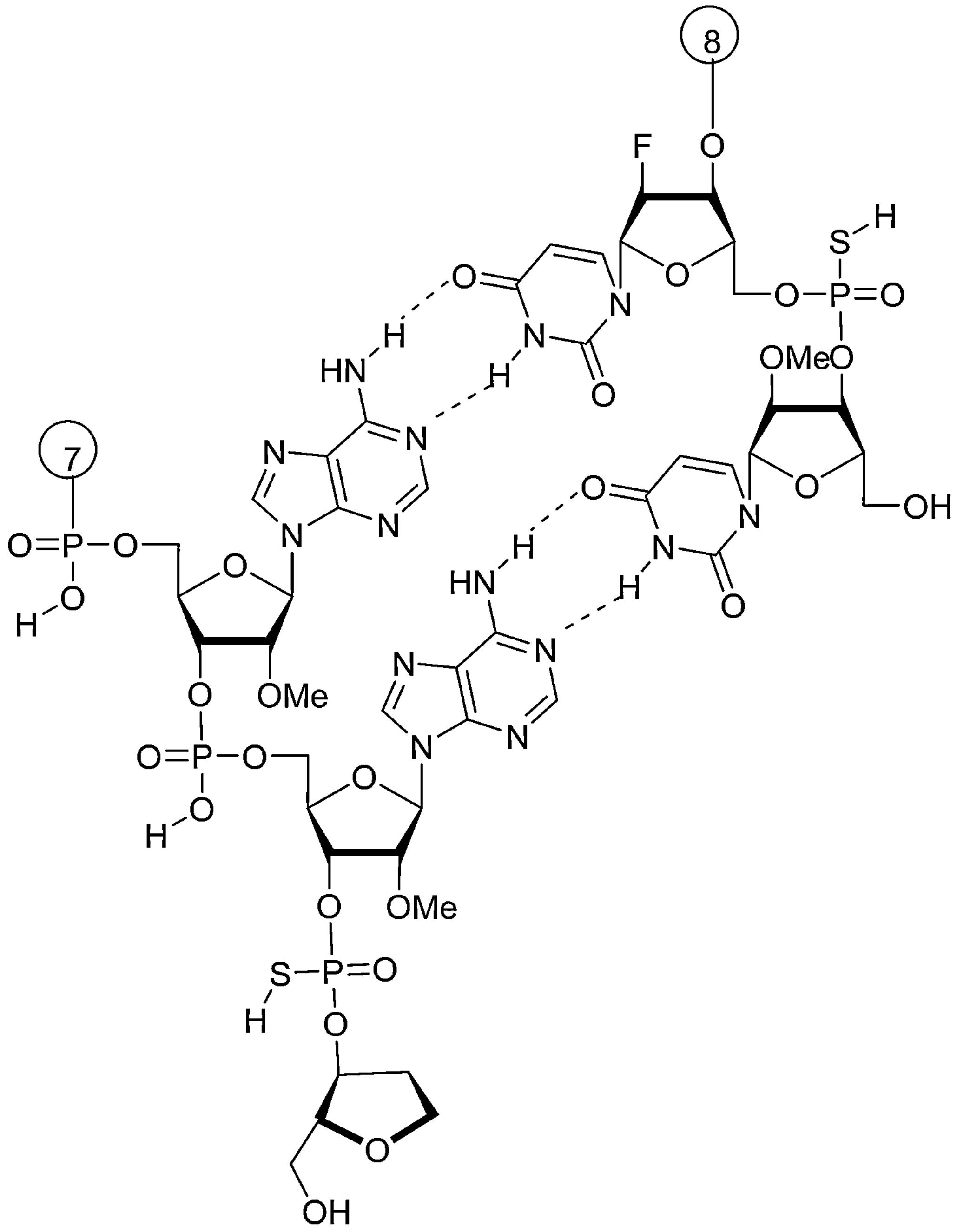
Figure 10A:
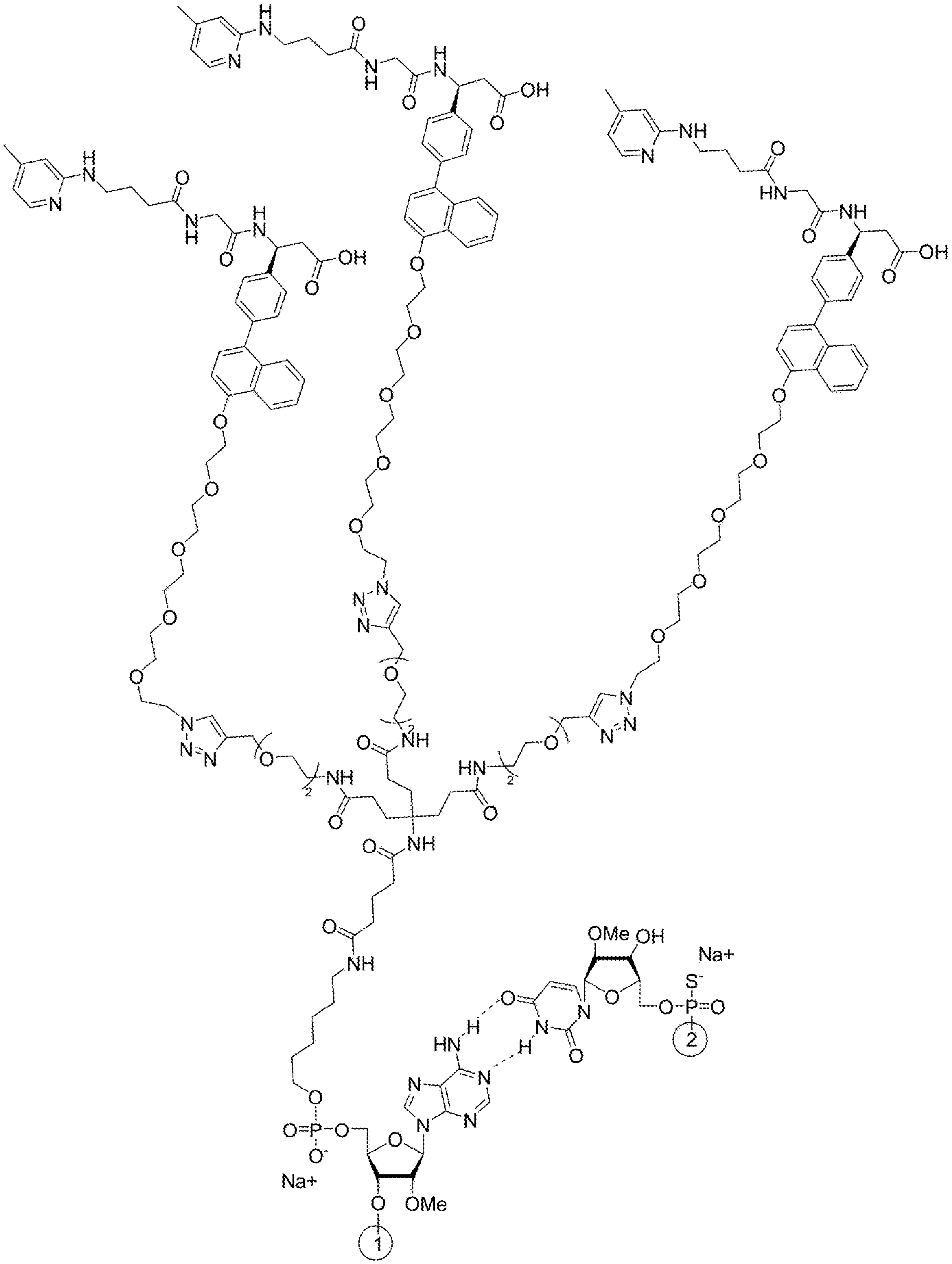
FIG. 10A to 10E. Chemical structure representation of RAGE RNAi agent conjugate AC001268 (AM10754-AS (SEQ ID NO: 4), CS001582 (SEQ ID NO: 12)) shown as a sodium salt.
Figure 10B:
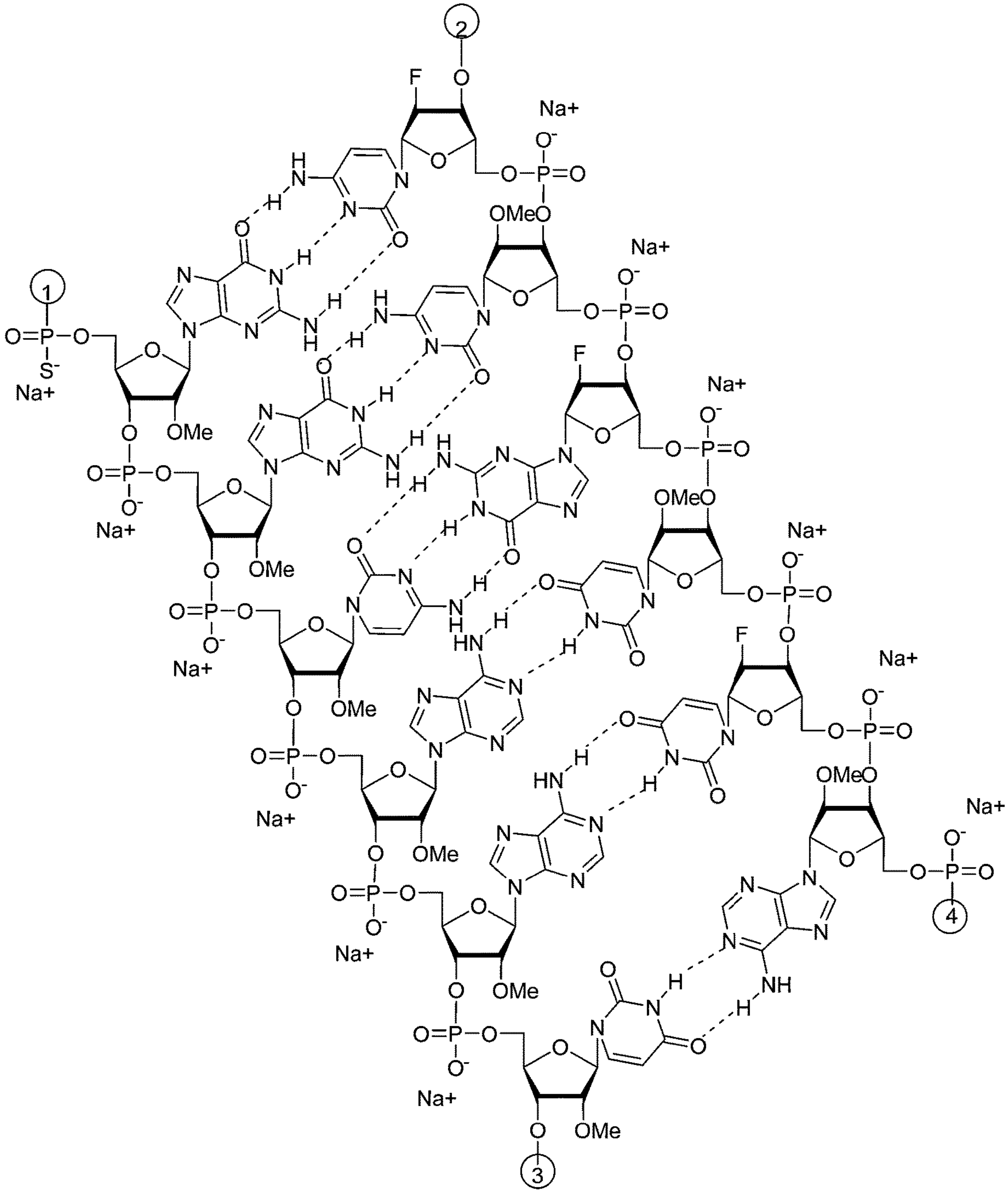
Figure 10C:
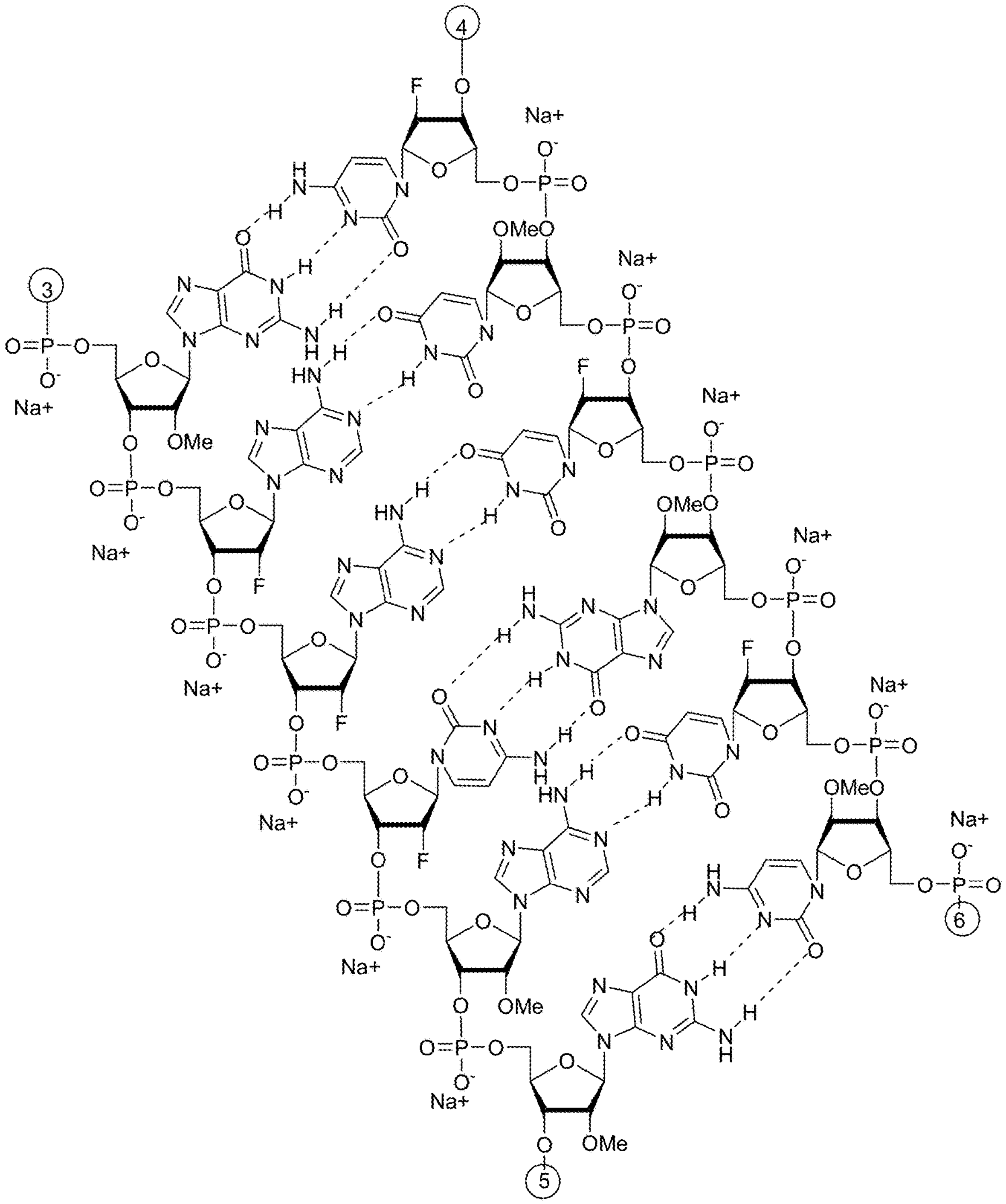
Figure 10D:
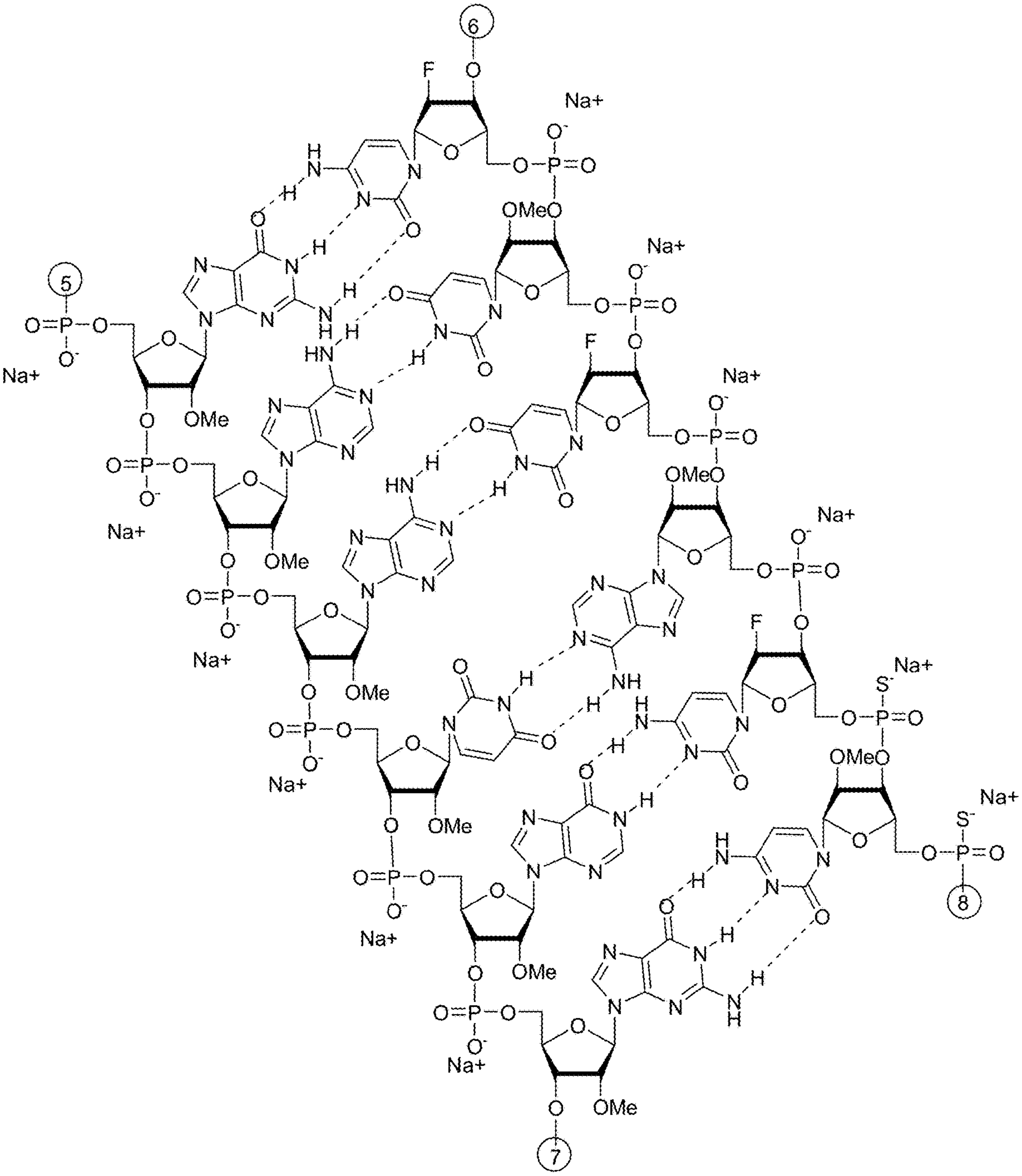
Figure 10E:
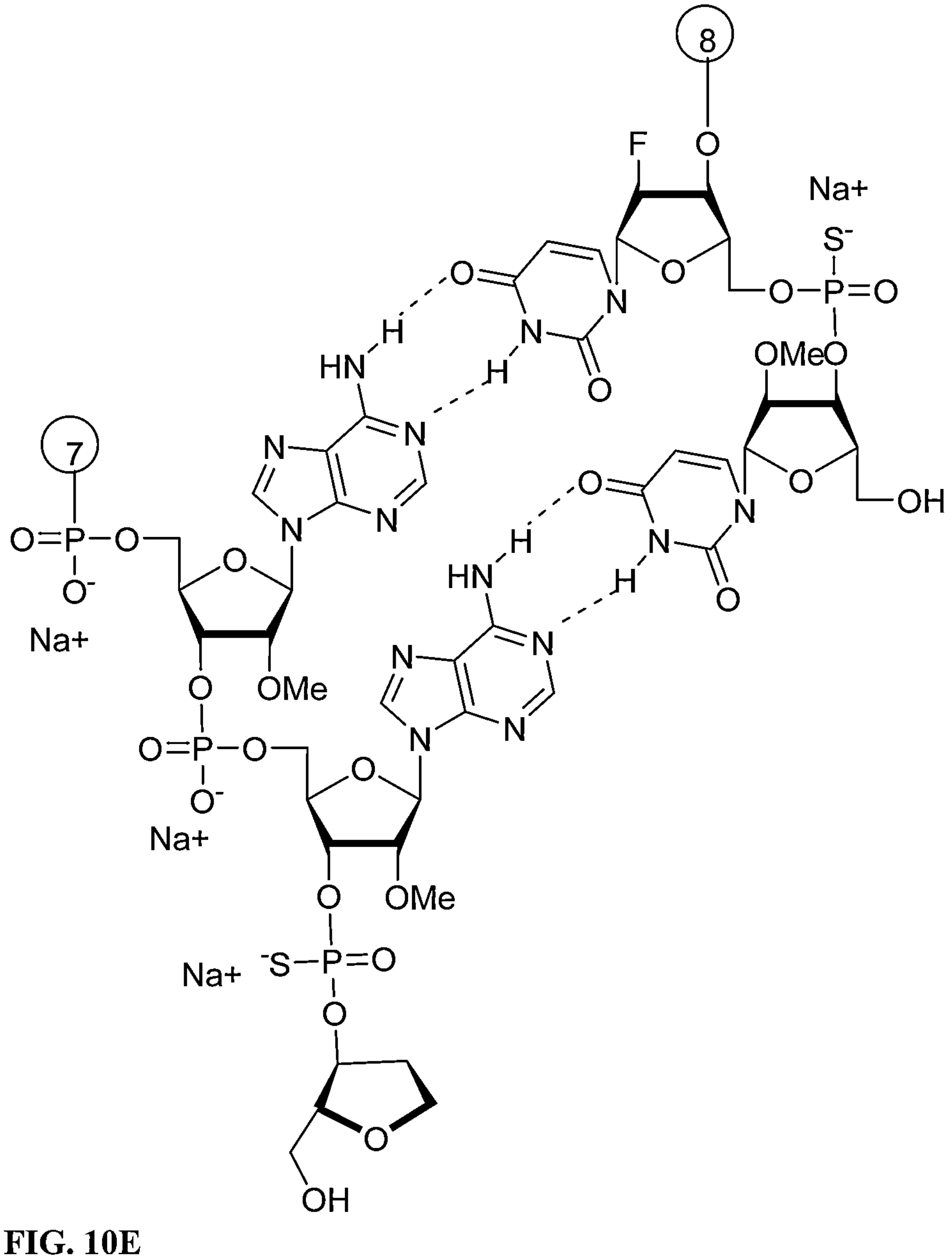
Figure 11A:
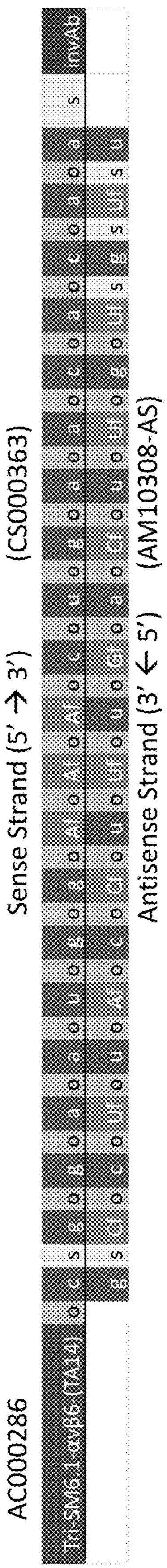
FIG. 11A. Schematic diagram of the modified sense and antisense strands of the RAGE RNAi agent conjugate having the structure of AC000286 (AM10308-AS (SEQ ID NO: 2), CS000363 (SEQ ID NO: 10)) (see, e.g., Tables 8 and 10), having a tridentate αvβ6 epithelial cell targeting ligand linked at the 5' end of the sense strand. The following abbreviations are used in FIGS. 11A to 11J: a, c, g, i, and u are 2'-O-methyl modified nucleotides; Af, Cf, Gf, and Uf are 2'-fluoro modified nucleotides; o is a phosphodiester linkage; s is a phosphorothioate linkage; invAb is an inverted abasic residue (see, e.g., Table 11); cPrpu is a 5'-cyclopropyl phosphonate-2'-O-methyluridine modified nucleotide (see, e.g., Table 11); Tri-SM6.1-αvβ6-(TA14) is the tridentate αvβ6 epithelial cell targeting ligand having the structure shown in FIG. 1; and (TriAlk14) is the linking group as shown in Table 11, which is suitable for subsequent coupling to targeting ligands (See also, Example 1 herein).
Figure 11B:
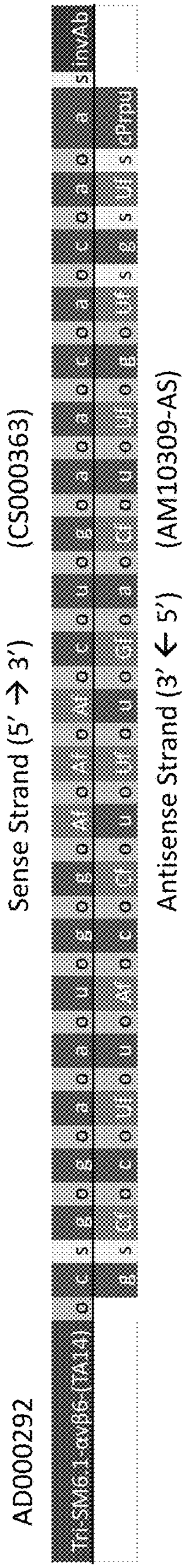
FIG. 11B. Schematic diagram of the modified sense and antisense strands of the RAGE RNAi agent conjugate having the structure of AC000292 (AM10309-AS (SEQ ID NO: 3), CS000363 (SEQ ID NO: 10)) (see, e.g., Tables 8 and 10), having a tridentate αvβ6 epithelial cell targeting ligand linked at the 5' end of the sense strand.
Figure 11C:
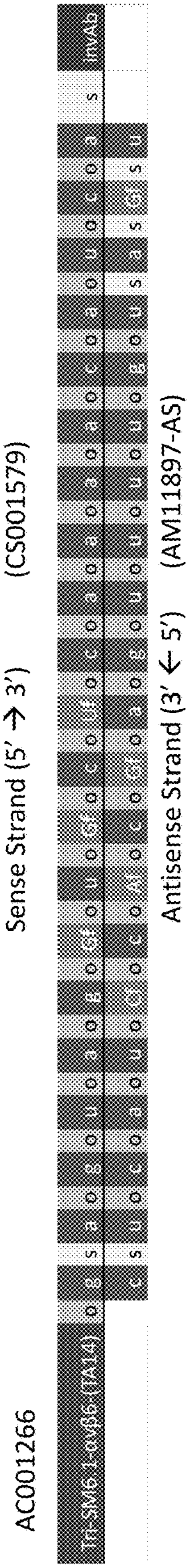
FIG. 11C. Schematic diagram of the modified sense and antisense strands of the RAGE RNAi agent conjugate having the structure of AC001266 (AM11897-AS (SEQ ID NO: 5), CS001579 (SEQ ID NO: 11)) (see, e.g., Tables 8 and 10), having a tridentate αvβ6 epithelial cell targeting ligand linked at the 5' end of the sense strand.
Figure 11D:
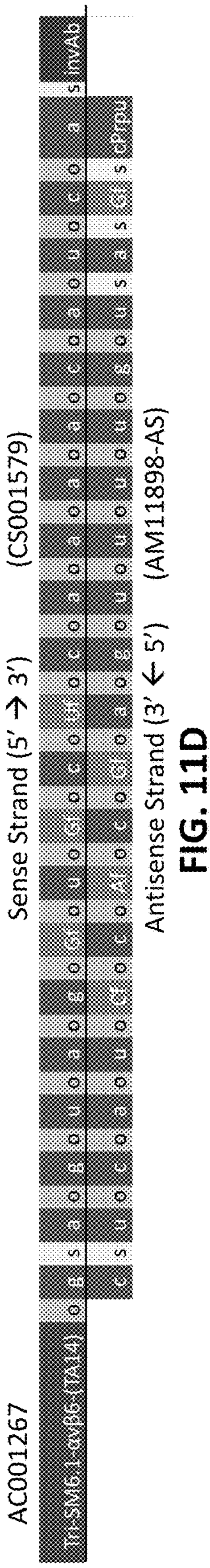
FIG. 11D. Schematic diagram of the modified sense and antisense strands of the RAGE RNAi agent conjugate having the structure of AC001267 (AM11898-AS (SEQ ID NO: 6), CS001579 (SEQ ID NO: 11)) (see, e.g., Tables 8 and 10), having a tridentate αvβ6 epithelial cell targeting ligand linked at the 5' end of the sense strand.
Figure 11E:
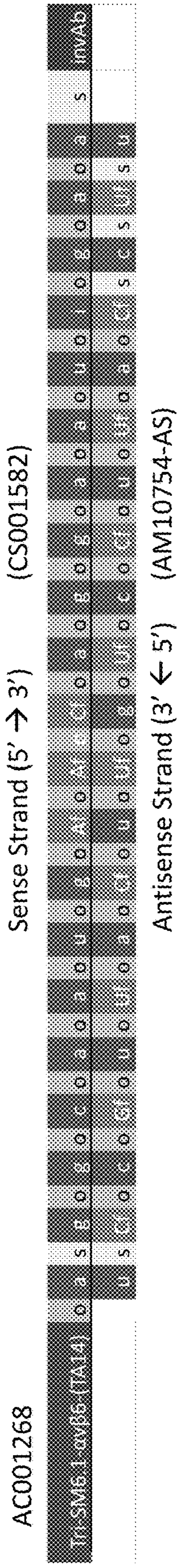
FIG. 11E. Schematic diagram of the modified sense and antisense strands of the RAGE RNAi agent conjugate having the structure of AC001268 (AM10754-AS (SEQ ID NO: 4), CS001582 (SEQ ID NO: 12)) (see, e.g., Tables 8 and 10), having a tridentate αvβ6 epithelial cell targeting ligand linked at the 5' end of the sense strand.
Figure 11F:
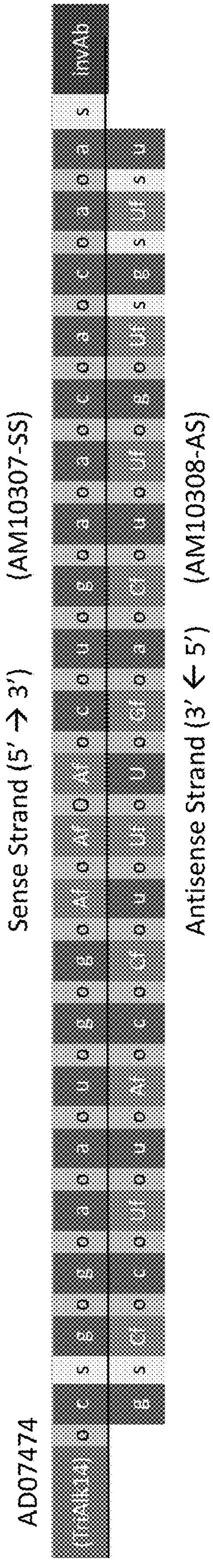
FIG. 11F. Schematic diagram of the modified sense and antisense strands of the RAGE RNAi agent duplex having the structure of AD07474 (AM10308-AS (SEQ ID NO: 2), AM10307-SS (SEQ ID NO: 16)) (see, e.g., Table 7B), having a (TriAlk14) linker at the 5' end of the sense strand.
Figure 11G:
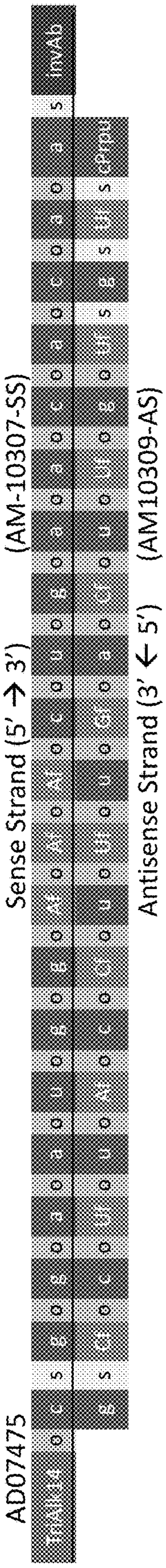
FIG. 11G. Schematic diagram of the modified sense and antisense strands of the RAGE RNAi agent duplex having the structure of AD07475 (AM10309-AS (SEQ ID NO: 3), AM10307-SS (SEQ ID NO: 16)) (see, e.g., Table 7B), having a (TriAlk14) linker at the 5' end of the sense strand.
Figure 11H:
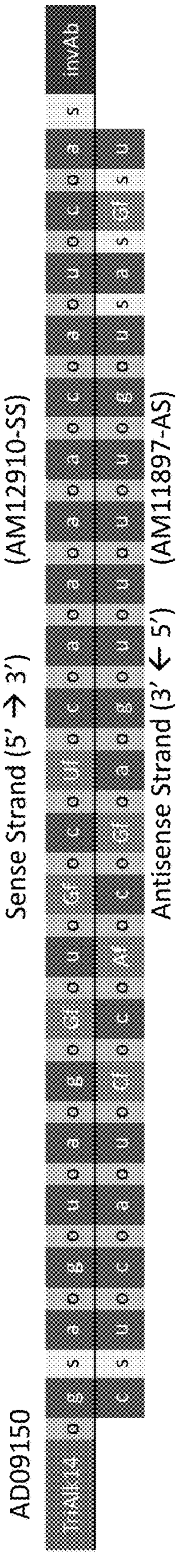
FIG. 11H. Schematic diagram of the modified sense and antisense strands of the RAGE RNAi agent duplex having the structure of AD09150 (AM11897-AS (SEQ ID NO: 5), AM12910-SS (SEQ ID NO: 17)) (see, e.g., Table 7B), having a (TriAlk14) linker at the 5' end of the sense strand.
Figure 11I:
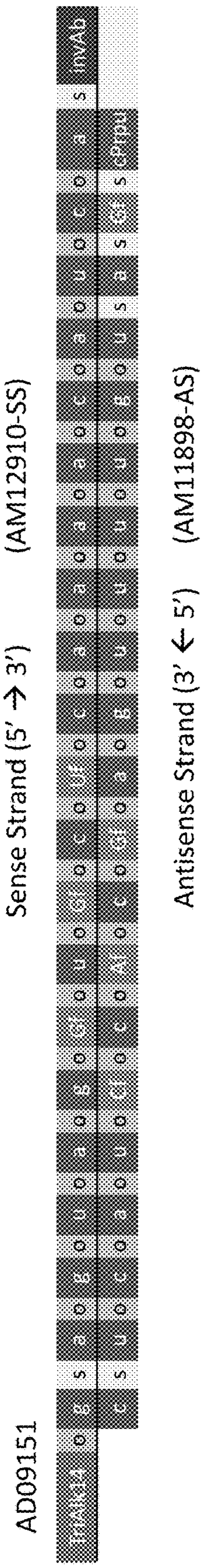
FIG. 11I. Schematic diagram of the modified sense and antisense strands of the RAGE RNAi agent duplex having the structure of AD09151 (AM11898-AS (SEQ ID NO: 6), AM12910-SS (SEQ ID NO: 17)) (see, e.g., Table 7B), having a (TriAlk14) linker at the 5' end of the sense strand.
Figure 11J:
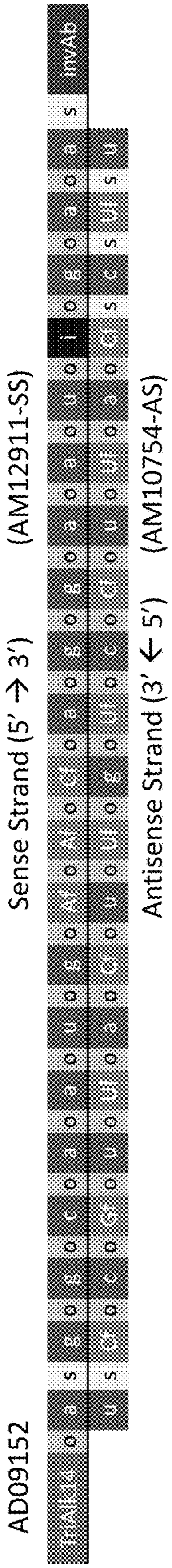
FIG. 11J. Schematic diagram of the modified sense and antisense strands of the RAGE RNAi agent duplex having the structure of AD09152 (AM10754-AS (SEQ ID NO: 4), AM12911-SS (SEQ ID NO: 18)) (see, e.g., Table 7B), having a (TriAlk14) linker at the 5' end of the sense strand.

The 121.2 g of crude oil containing 72 wt % compound 6 (86.0 g, 0.10 mol) was dissolved in DMF (344 mL) and treated with TEA (86 mL, 20 v/v %), keeping the internal temperature below 23° C. The formation of dibenzofulvene (DBF) relative to the consumption of Fmoc-amine 6 was monitored via HPLC method 1 (FIG. 2) and the reaction was complete within 10 hours. To the solution was added glutaric anhydride (12.8 g, 0.11 mol) and the intermediate amine 7 was converted to compound 8 within 2 hours. Upon completion, the DMF and TEA were removed at 30° C. under reduced pressure resulting in 100 g of a crude oil. Due to the high solubility of compound 7 in water, an aqueous workup could not be used, and chromatography is the only way to remove DBF, TMU, and glutaric anhydride. The crude oil (75 g) was purified on a Teledyne ISCO Combi-Flash® purification system in three portions. The crude oil (25 g) was loaded onto a 330 g silica column and eluted from 0-20% methanol/DCM over 30 minutes resulting in 42 g of compound 8 (54% yield over 3 steps). Calculated mass for $C_{36}$H55N4012=736.4 m/z. Found [M+H]=737.0.

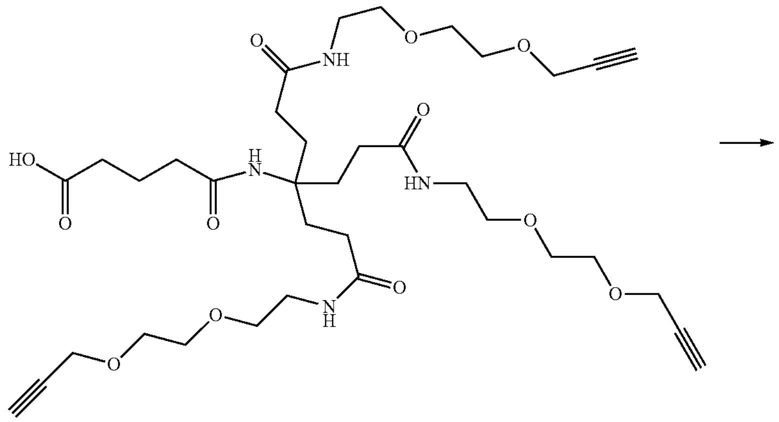

8

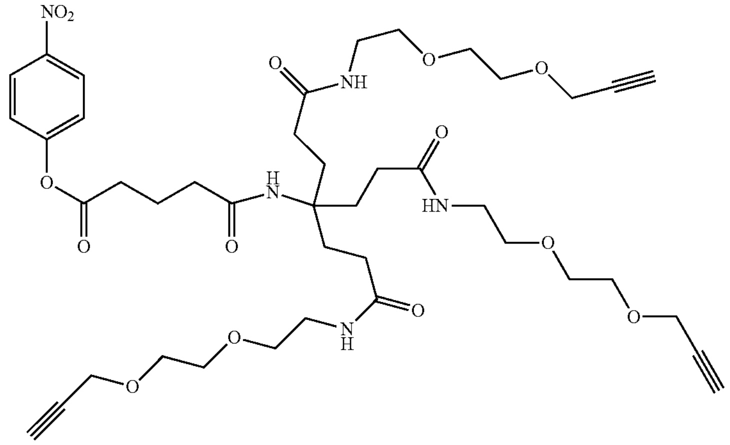

9
Compound 22

Compound 8 (42.0 g, 0.057 mol) was co-stripped with 10 volumes of acetonitrile prior to use to remove any residual methanol from chromatography solvents. The oil was redissolved in DMF (210 mL) and cooled to 0° C. The solution was treated with 4-nitrophenol (8.7 g, 0.063 moL) followed by EDC-hydrochloride (12.0 g, 0.063 mol) and found to reach completion within 10 hours. The solution was cooled to 0° C. and 10 volumes ethyl acetate was added followed by 10 volumes saturated ammonium chloride solution, keeping the internal temperature below 15° C. The layers were allowed to separate and the ethyl acetate layer was washed with brine. The combined aqueous layers were extracted twice with 5 volumes ethyl acetate. The combined organic layers were dried over sodium sulfate and concentrated to an oil. The crude oil (55 g) was purified on a Teledyne ISCO Combi-Flash® purification system in three portions. The crude oil (25 g) was loaded onto a 330 g silica column and eluted from 0-10% methanol/DCM over 30 minutes resulting in 22 g of pure 9 (Compound 22) (50% yield). Calculated mass for $C_{42}H_{59}N_5O_{14}$=857.4 m/z. Found [M+H]=858.0.

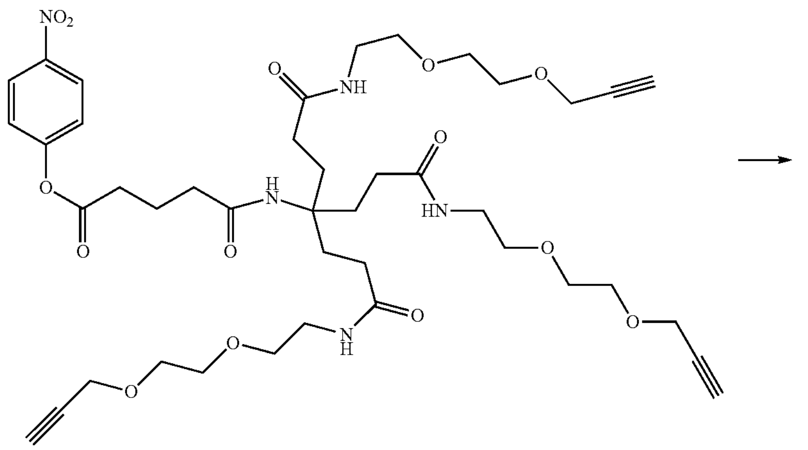

9

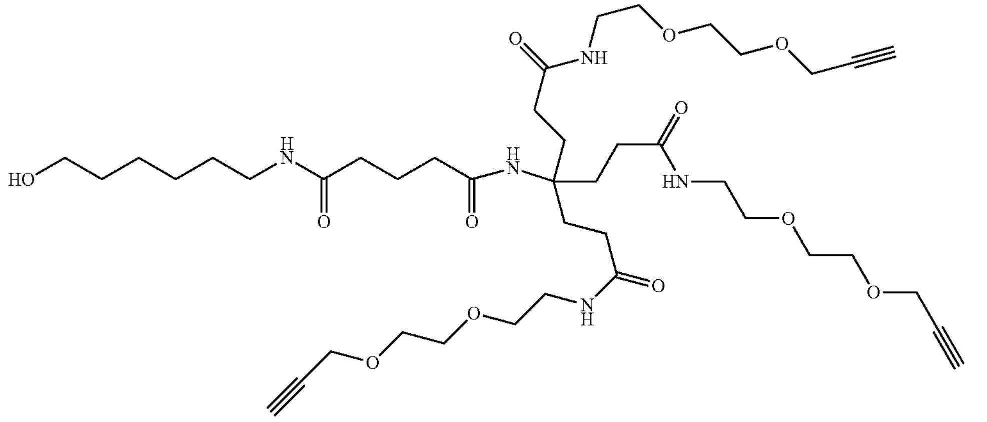

10

A solution of ester 9 (49.0 g, 57.1 mmol) and 6-amino-1-hexanol (7.36 g, 6.28 mmol) in dichloromethane (3 volumes) was treated with triethylamine (11.56 g, 111.4 mmol) dropwise. The reaction was monitored by observing the disappearance of compound 9 on HPLC Method 1 and was found to be complete in 10 minutes. The crude reaction mixture was diluted with 5 volumes dichloromethane and washed with saturated ammonium chloride (5 volumes) and brine (5 volumes). The organic layer was dried over sodium sulfate and concentrated to an oil. The crude oil was purified on a Teledyne ISCO Combi-Flash® purification system using a 330 g silica column. The 4-nitrophenol was eluted with 100% ethyl acetate and 10 was flushed from the column using 20% methanol/DCM resulting in a colorless oil (39 g, 81% yield). Calculated mass for $C_{42}H_{69}N_5O_{12}$=836.0 m/z. Found [M+H]=837.0.

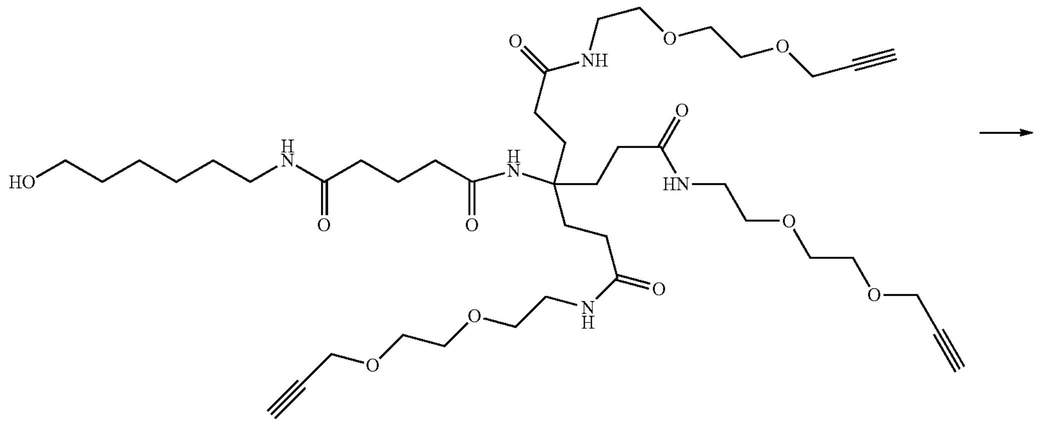

10

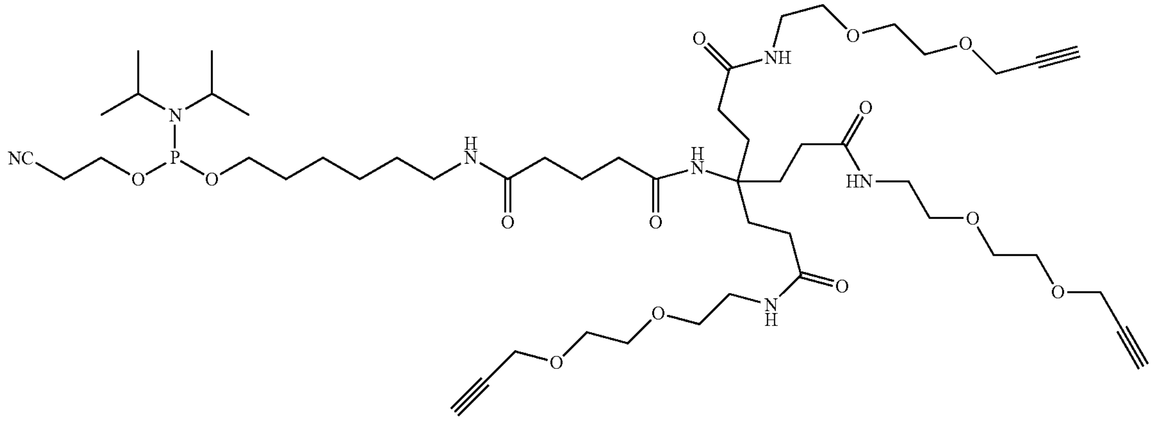

Compound 14

Alcohol 10 was co-stripped twice with 10 volumes of acetonitrile to remove any residual methanol from chromatography solvents and once more with dry dichloromethane (KF <60 ppm) to remove trace water. The alcohol 10 (2.30 g, 2.8 mmol) was dissolved in 5 volumes dry dichloromethane (KF<50 ppm) and treated with diisopropylammonium tetrazolide (188 mg, 1.1 mmol). The solution was cooled to 0° C. and treated with 2-cyanoethyl N,N,N',N'-tetraisopropylphosphoramidite (1.00 g, 3.3 mmol) dropwise. The solution was removed from ice-bath and stirred at 20° C. The reaction was found to be complete within 3-6 hours. The reaction mixture was cooled to 0° C. and treated with 10 volumes of a 1:1 solution of saturated ammonium bicarbonate/brine and then warmed to ambient over 1 minute and allowed to stir an additional 3 minutes at 20° C. The biphasic mixture was transferred to a separatory funnel and 10 volumes of dichloromethane was added. The organic layer was separated and washed with 10 volumes of saturated sodium bicarbonate solution to hydrolyze unreacted bis-phosphorous reagent. The organic layer was dried over sodium sulfate and concentrated to an oil resulting in 3.08 g of 94 wt % Compound 14. Calculated mass for $C_{51}H_{86}N_7O_{13}P$=1035.6 m/z. Found [M+H]=1036.

H. Conjugation of Targeting Ligands. Either prior to or after annealing, the 5' or 3' tridentate alkyne functionalized sense strand is conjugated to targeting ligands. The following example describes the conjugation of targeting ligands to the annealed duplex: Stock solutions of 0.5M Tris(3-hydroxypropyltriazolylmethyl)amine (THPTA), 0.5M of Cu(II) sulfate pentahydrate ($Cu(II)SO_{45}H_2O$) and 2M solution of sodium ascorbate were prepared in deionized water. A 75 mg/mL solution in DMSO of targeting ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. Targeting ligand was added to the reaction (6 equivalents/duplex, 2 equivalents/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 μL of 0.5M $Cu(II)SO_4.5H_2O$, vortexed, and incubated at room temp for 5 min. After 5 min, THPTA/Cu solution (7.2 μL, 6 equivalents 5:1 THPTA:Cu) was added to the reaction vial, and vortexed. Immediately afterwards, 2M ascorbate (5 μL, 50 equivalents per duplex, 16.7 per alkyne) was added to the reaction vial and vortexed. Once the reaction was complete (typically complete in 0.5-1h), the reaction was immediately purified by non-denaturing anion exchange chromatography.

Example 2. In Vivo Intratracheal Administration of RAGE RNAi Agents in Rats

On study day 1, male Sprague Dawley rats were administered 200 microliters via a microsprayer device (Penn Century, Philadelphia, PA) suitable for intratracheal (IT) administration of isotonic saline or 1.0 mg/kg of one of the following RAGE RNAi agents:

TABLE 12

| RAGE RNAi Agent and Dosing for Example 2 | |
|---|---|
| Group ID | AC Duplex Number |
| Group 1 (isotonic saline) | N/A |
| Group 2 (1.0 mg/kg Tri-SM6.1-αvβ6-AD06949) | AC000614 |
| Group 3 (1.0 mg/kg Tri-SM6.1-αvβ6-AD07256) | AC000186 |
| Group 4 (1.0 mg/kg Tri-SM6.1-αvβ6-AD07474) | AC000286 |
| Group 5 (1.0 mg/kg Tri-SM6.1-αvβ6-AD07475) | AC000292 |
| Group 6 (1.0 mg/kg Tri-SM6.1-αvβ6-AD07476) | AC000818 |
| Group 7 (1.0 mg/kg Tri-SM6.1-αvβ6-AD07477) | AC000819 |

As noted in Table 12, each of the RAGE RNAi agents were conjugated to a tridentate small molecule αvβ6 epithelial cell targeting ligand (Tri-SM6.1, see FIG. 1) at the 5' terminal end of the sense strand, formulated in isotonic saline.

The chemically modified sequences for RAGE RNAi agents AD07474, AD07475, AD07476, and AD07477 are shown in Table 7B (showing duplex), Table 3 (showing respective antisense strand), and Table 5 (showing respective sense strand with linker but without tridentate small molecule αvβ6 epithelial cell targeting ligand (Tri-SM6.1).

AD06949 and AD07256 are rat and mouse-specific sequences that do not have homology with the human AGER gene, and were chemically modified as follows:

```
Tri-SM6.1-avβ6-AD06949
Modified Sense Strand (5'→3'):
                                                (SEQ ID NO: 888)
Tri-SM6.1-avβ6-(TA14)cscacaugaUfCfCfaugcuiaguas(invAb)

Modified Antisense Strand (5'→3'):
                                                (SEQ ID NO: 889)
usAfscsUfcAfgCfaUfgGfaUfcAfuGfuGfsg

Tri-SM6.1-avβ6-AD07256
Modified Sense Strand (5'→3'):
                                                (SEQ ID NO: 890)
Tri-SM6.1-avβ6-(TA14)cscacaugaUfCfCfaugcuiaguas(invAb)

Modified Antisense Strand (5'→3'):
                                                (SEQ ID NO: 891)
cPrpusAfscsUfcAfgCfaUfgGfaUfcAfuGfuGfsg
```

Five (5) rats were dosed per group. Rats were sacrificed on study day 8, and total RNA was isolated from both lungs following collection and homogenization. Rat AGER mRNA expression was quantitated by probe-based quantitative PCR, normalized to rat GAPDH expression, and expressed as fraction of vehicle control group (geometric mean, +/−95% confidence interval).

TABLE 13

| Average Relative Rat RAGE mRNA Expression at Sacrifice (Day 8) in Example 2 | | | |
|---|---|---|---|
| Group ID | Average Relative rAGER mRNA Expression (n = 5) | Low (error) | High (error) |
| Group 1 (isotonic saline) | 1.000 | 0.060 | 0.065 |
| Group 2 (1.0 mg/kg Tri-SM6.1-αvβ6-AD06949) | 0.306 | 0.019 | 0.017 |
| Group 3 (1.0 mg/kg Tri-SM6.1-αvβ6-AD07256) | 0.142 | 0.019 | 0.010 |
| Group 4 (1.0 mg/kg Tri-SM6.1-αvβ6-AD07474) | 0.195 | 0.031 | 0.067 |
| Group 5 (1.0 mg/kg Tri-SM6.1-αvβ6-AD07475) | 0.125 | 0.037 | 0.038 |
| Group 6 (1.0 mg/kg Tri-SM6.1-αvβ6-AD07476) | 0.294 | 0.039 | 0.057 |
| Group 7 (1.0 mg/kg Tri-SM6.1-αvβ6-AD07477) | 0.230 | 0.037 | 0.038 |

As shown in the data in Table 13 above, each of the RAGE RNAi agents showed significant AGER gene inhibition, with the RAGE RNAi agents targeted to inhibit expression at position 177 (Group 4 (80.5 inhibition) and Group 5 (87.5 inhibition)) provided slightly better inhibition compared to the RAGE RNAi agents targeting position 178 of the AGER gene (Group 6 (70.60m inhibition) and Group 7 (77 inhibition)).

Example 3. In Vivo Intratracheal Administration of RAGERNAi Agents in Mice

On study day 1, male c57bl/6 Mice were administered 50 microliters via a microsprayer device (Penn Century, Philadelphia, PA) suitable for intratracheal (IT) administration of isotonic saline of isotonic saline or 3.0 mg/kg of one of the following RAGE RNAi agents:

TABLE 14

| RAGE RNAi Agent and Dosing for Example 3 | |
|---|---|
| Group ID | AC Duplex Number |
| Group 1 (isotonic saline) | N/A |
| Group 2 (1.0 mg/kg Tri-SM6.1-αvβ6-AD06949) | AC000614 |
| Group 3 (1.0 mg/kg Tri-SM6.1-αvβ6-AD07256) | AC000186 |
| Group 4 (1.0 mg/kg Tri-SM6.1-αvβ6-AD07478) | AC000820 |
| Group 5 (1.0 mg/kg Tri-SM6.1-αvβ6-AD07479) | AC000821 |
| Group 6 (1.0 mg/kg Tri-SM6.1-αvβ6-AD07480) | AC000822 |
| Group 7 (1.0 mg/kg Tri-SM6.1-αvβ6-AD07481) | AC000822 |

As noted in Table 14, each of the RAGE RNAi agents were conjugated to a tridentate small molecule αvβ36 epithelial cell targeting ligand (Tri-SM6.1, see FIG. 1) at the 5' terminal end of the sense strand, formulated in isotonic saline.

The chemically modified sequences for RAGE RNAi agents AD07478, AD07479, AD07480, and AD07481 are shown in Table 7B (showing duplex), Table 3 (showing respective antisense strand), and Table 5 (showing respective sense strand with linker but without tridentate small molecule αvβ6 epithelial cell targeting ligand (Tri-SM6.1)).

The chemically modified sequences for RAGE RNAi agents AD06949 and AD07256 are shown in Example 2, above.

Five (5) mice were dosed per group. Mice were sacrificed on study day 8, and total RNA was isolated from both lungs following collection and homogenization. Murine AGER mRNA expression was quantitated by probe-based quantitative PCR, normalized to rat GAPDH expression, and expressed as fraction of vehicle control group (geometric mean, +/−95 confidence interval).

TABLE 15

Average Relative Murine RAGE mRNA Expression at Sacrifice (Day 8) in Example 3.

| Group ID | Average Relative mAGER mRNA Expression (n = 5) | Low (error) | High (error) |
|---|---|---|---|
| Group 1 (isotonic saline) | 1.000 | 0.225 | 0.290 |
| Group 2 (1.0 mg/kg Tri-SM6.1-αvβ6-AD06949) | 0.403 | 0.116 | 0.164 |
| Group 3 (1.0 mg/kg Tri-SM6.1-αvβ6-AD07256) | 0.358 | 0.153 | 0.268 |
| Group 4 (1.0 mg/kg Tri-SM6.1-αvβ6-AD07478) | 1.016 | 0.205 | 0.257 |
| Group 5 (1.0 mg/kg Tri-SM6.1-αvβ6-AD07479) | 1.063 | 0.132 | 0.150 |
| Group 6 (1.0 mg/kg Tri-SM6.1-αvβ6-AD07480) | 0.718 | 0.115 | 0.137 |
| Group 7 (1.0 mg/kg Tri-SM6.1-αvβ6-AD07481) | 0.681 | 0.077 | 0.086 |

As shown in the data in Table 15 above, the RAGE RNAi agents of Groups 4 and 5 (targeting position 384) showed no inhibition and were completely inactive in vivo. The RAGE RNAi agents of Groups 6 and 7 (targeting position 391) showed relatively limited inhibition in vivo and appear insufficiently active to be considered as viable therapeutic candidates for treatment of humans.

Example 4. In Vivo Intratracheal Administration of RAGE RNAi Agents in Rats

On study day 1, male Sprague Dawley rats were administered 200 microliters via a microsprayer device (Penn Century, Philadelphia, PA) suitable for intratracheal (IT) administration of isotonic saline or 0.5 mg/kg of one of the following RAGE RNAi agents:

TABLE 16

RAGE RNAi Agent and Dosing for Example 4

| Group ID | AC Duplex Number |
|---|---|
| Group 1 (isotonic saline) | N/A |
| Group 2 (0.5 mg/kg Tri-SM6.1-αvβ6-AD07474) | AC000286 |
| Group 3 (0.5 mg/kg Tri-SM6.1-αvβ6-AD07475) | AC000292 |
| Group 4 (0.5 mg/kg Tri-SM6.1-αvβ6-AD07700) | AC000790 |
| Group 5 (0.5 mg/kg Tri-SM6.1-αvβ6-AD07701) | AC000791 |
| Group 6 (0.5 mg/kg Tri-SM6.1-αvβ6-AD07702) | AC000792 |
| Group 7 (0.5 mg/kg Tri-SM6.1-αvβ6-AD07703) | AC000793 |
| Group 8 (0.5 mg/kg Tri-SM6.1-αvβ6-AD07704) | AC000438 |
| Group 9 (0.5 mg/kg Tri-SM6.1-αvβ6-AD07705) | AC000794 |
| Group 10 (0.5 mg/kg Tri-SM6.1-αvβ6-AD07706) | AC000795 |
| Group 11 (0.5 mg/kg Tri-SM6.1-αvβ6-AD07707) | AC000796 |
| Group 12 (0.5 mg/kg Tri-SM6.1-αvβ6-AD07708) | AC000439 |

As noted in Table 16, each of the RAGE RNAi agents were conjugated to a tridentate small molecule αvβ6 epithelial cell targeting ligand (Tri-SM6.1, see FIG. 1) at the 5' terminal end of the sense strand, formulated in isotonic saline.

The chemically modified sequences for RAGE RNAi agents AD07474, AD07475, AD07700, AD07701, AD07702, AD07703, AD07704, AD07705, AD07706, AD07707, and AD07708 are shown in Table 7B (showing duplex), Table 3 (showing respective antisense strand), and Table 5 (showing respective sense strand with linker but without tridentate small molecule αvβ6 epithelial cell targeting ligand (Tri-SM6.1).

Five (5) rats were dosed per group. Rats were sacrificed on study day 8, and total RNA was isolated from both lungs following collection and homogenization. Rat AGER mRNA expression was quantitated by probe-based quantitative PCR, normalized to rat GAPDH expression, and expressed as fraction of vehicle control group (geometric mean, +/−95% confidence interval).

TABLE 17

Average Relative Rat RAGE mRNA Expression at Sacrifice (Day 3) in Example 4

| Group ID | Average Relative rAGER mRNA Expression (n = 5) | Low (error) | High (error) |
|---|---|---|---|
| Group 1 (isotonic saline) | 1.000 | 0.075 | 0.081 |
| Group 2 (0.5 mg/kg Tri-SM6.1-αvβ6-AD07474) | 0.355 | 0.147 | 0.250 |
| Group 3 (0.5 mg/kg Tri-SM6.1-αvβ6-AD07475) | 0.193 | 0.110 | 0.254 |
| Group 4 (0.5 mg/kg Tri-SM6.1-αvβ6-AD07700) | 0.233 | 0.060 | 0.080 |
| Group 5 (0.5 mg/kg Tri-SM6.1-αvβ6-AD07701) | 0.344 | 0.135 | 0.221 |
| Group 6 (0.5 mg/kg Tri-SM6.1-αvβ6-AD07702) | 0.194 | 0.036 | 0.044 |
| Group 7 (0.5 mg/kg Tri-SM6.1-αvβ6-AD07703) | 0.265 | 0.024 | 0.026 |
| Group 8 (0.5 mg/kg Tri-SM6.1-αvβ6-AD07704) | 0.174 | 0.030 | 0.036 |
| Group 9 (0.5 mg/kg Tri-SM6.1-αvβ6-AD07705) | 0.188 | 0.052 | 0.071 |
| Group 10 (0.5 mg/kg Tri-SM6.1-αvβ6-AD07706) | 0.215 | 0.077 | 0.119 |
| Group 11 (0.5 mg/kg Tri-SM6.1-αvβ6-AD07707) | 0.182 | 0.059 | 0.087 |

As shown in the data in Table 17 above, each of the RAGE RNAi agents showed significant AGER gene inhibition at a dose of only 0.5 mg/kg. Each of the RAGE RNAi agents tested including different chemical modifications but all included underlying nucleotide sequences targeting position 177 of the AGER gene.

Example 5. In Vivo Inhaled Aerosolized Administration of RAGE RNAi Agents in Rats On study day 1, male Sprague Dawley rats were administered a single pulmonary deposited dose (PDD) of 0.5 mg/kgof the RAGE RNAi agent Tri-SM6.1-αvβ6-AD07475. Using a jet nebulizer (Misty Max 10), aerosol was delivered to a rodent single-tier flow-past nose-only inhalation exposure chamber (CH Technologies). One of the ports was equipped with a filter housing so that RNAi agent aerosol concentration could be assessed. Using an assumed respiratory minute volume allometrically scaled to rodent body weight, along with aerosol concentration determined from filter collection and RNAi agent quantification, exposure times were adjusted to target the reported PDD of 0.5 mg/kg. As noted, the RAGE RNAi agent was conjugated to a tridentate small molecule αvβ6 epithelial cell targeting ligand (Tri-SM6.1, see FIG. 1) at the 5' terminal end of the sense strand, formulated in isotonic saline. The chemically modified sequences for RAGE RNAi agent AD07475 are shown in Table 7B (showing duplex), Table 3 (showing respective antisense strand), and Table 5 (showing respective sense strand with linker but without tridentate small molecule αvβ6 epithelial cell targeting ligand (Tri-SM6.1).

Five (5) rats were dosed per group. Rats were sacrificed on various study days after administration in accordance with the following schedule:

TABLE 18

RAGE RNAi Agent and Dosing for Example 5

| Group ID | Date Of Sacrifice After Administartion |
|---|---|
| Group 1 (isotonic saline) | Day 8 |
| Group 2 (Tri-SM6.1-αvβ6-AD07475) | Day 2 |
| Group 3 (Tri-SM6.1-αvβ6-AD07475) | Day 3 |
| Group 4 (Tri-SM6.1-αvβ6-AD07475) | Day 4 |
| Group 5 (Tri-SM6.1-αvβ6-AD07475) | Day 5 |
| Group 6 (Tri-SM6.1-αvβ6-AD07475) | Day 8 |
| Group 7 (Tri-SM6.1-αvβ6-AD07475) | Day 15 |
| Group 8 (Tri-SM6.1-αvβ6-AD07475) | Day 22 |
| Group 9 (Tri-SM6.1-αvβ6-AD07475) | Day 29 |
| Group 10 (Tri-SM6.1-αvβ6-AD07475) | Day 43 |
| Group 11 (Tri-SM6.1-αvβ6-AD07475) | Day 57 |

Upon sacrifice on the respective date, total RNA was isolated from both lungs following collection and homogenization. Rat AGER mRNA expression was quantitated by probe-based quantitative PCR, normalized to rat GAPDH expression, and expressed as fraction of vehicle control group (geometric mean, +/−9500 confidence interval).

TABLE 19

Average Relative Rat RAGE mRNA Expression at Sacrifice in Example 5

| Group ID | Average Relative rAGER mRNA Expression (n = 5) | Low (error) | High (error) |
|---|---|---|---|
| Group 1 (isotonic saline; day 8 sacrifice) | 1.000 | 0.261 | 0.352 |
| Group 2 (0.5 mg/kg deposited dose Tri-SM6.1-αvβ6-AD07475; day 2 sacrifice) | 0.428 | 0.074 | 0.090 |
| Group 3 (0.5 mg/kg deposited dose Tri-SM6.1-αvβ6-AD07475; day 3 sacrifice) | 0.179 | 0.025 | 0.028 |
| Group 4 (0.5 mg/kg deposited dose Tri-SM6.1-αvβ6-AD07475; day 4 sacrifice) | 0.077 | 0.014 | 0.017 |
| Group 5 (0.5 mg/kg deposited dose Tri-SM6.1-αvβ6-AD07475; day 5 sacrifice) | 0.061 | 0.005 | 0.005 |
| Group 6 (0.5 mg/kg deposited dose Tri-SM6.1-αvβ6-AD07475; day 8 sacrifice) | 0.042 | 0.005 | 0.006 |
| Group 7 (0.5 mg/kg deposited dose Tri-SM6.1-αvβ6-AD07475; day 15 sacrifice) | 0.042 | 0.007 | 0.009 |
| Group 8 (0.5 mg/kg deposited dose Tri-SM6.1-αvβ6-AD07475; day 22 sacrifice) | 0.049 | 0.010 | 0.012 |
| Group 9 (0.5 mg/kg deposited dose Tri-SM6.1-αvβ6-AD07475; day 29 sacrifice) | 0.097 | 0.014 | 0.016 |
| Group 10 (0.5 mg/kg deposited dose Tri-SM6.1-αvβ6-AD07475; day 43 sacrifice) | 0.137 | 0.015 | 0.017 |
| Group 11 (0.5 mg/kg deposited dose Tri-SM6.1-αvβP6-AD07475; day 57 sacrifice) | 0.123 | 0.013 | 0.015 |

As shown in the data in Table 19 above, the RAGE RNAi agent AD07475 showed significant AGER gene inhibition at a dose of only 0.5 mg/kg, and the duration of knockdown was maintained through at least day 22 before slowly beginning to return to baseline levels, suggesting that monthly dosing (e.g., administration every 28 days) may be feasible.

Example 6. In Vivo Inhaled Aerosolized Administration of RAGE RNAi Agents in Rats and Targeting Ligand Effect On study day 1, male Sprague Dawley rats were administered a single dose at varying concentrations of the RAGE RNAi agent Tri-SM6.1-αvβ6-AD07475, or the RAGE RNAi agent AD7475 without the αvβ6 epithelial cell targeting ligand attached. Using a jet nebulizer (Misty Max 10), aerosol was delivered to a rodent single-tier flow-past nose-only inhalation exposure chamber (CH Technologies). One of the ports was equipped with a filter housing so that RNAi agent aerosol concentration could be assessed. Using an assumed respiratory minute volume allometrically scaled to rodent body weight, along with aerosol concentration determined from filter collection and RNAi agent quantification, exposure times were adjusted to target the reported PDD listed in Table 20. For the Groups that included the targeting ligand, the RAGE RNAi agent was conjugated to a tridentate small molecule αvβ6 epithelial cell targeting ligand (Tri-SM6.1, see FIG. 1) at the 5' terminal end of the sense strand, formulated in isotonic saline. The chemically modified sequences for RAGE RNAi agent AD07475 are shown in Table 7B (showing duplex), Table 3 (showing respective antisense strand), and Table 5 (showing respective sense strand with linker but without tridentate small molecule αvβ6 epithelial cell targeting ligand (Tri-SM6.1). The dosing groups were as follows:

TABLE 20

RAGE RNAi Agent and Dosing for Example 6

| Group ID | AC Duplex Number |
|---|---|
| Group 1 (isotonic saline) | N/A |
| Group 2 (0.24 mg/kg deposited dose Tri-SM6.1-αvβ6-AD07475) | AC000292 |
| Group 3 (0.12 mg/kg deposited dose Tri-SM6.1-αvβ6-AD07475) | AC000292 |
| Group 4 (0.06 mg/kg deposited dose Tri-SM6.1-αvβ6-AD07475) | AC000292 |
| Group 5 (0.03 mg/kg deposited dose Tri-SM6.1-αvβ6-AD07475) | AC000292 |
| Group 6 (0.015 mg/kg deposited dose Tri-SM6.1-αvβ6-AD07475) | AC000292 |
| Group 7 (0.24 mg/kg deposited dose AD07475) | N/A |
| Group 8 (0.12 mg/kg deposited dose AD07475) | N/A |
| Group 9 (0.06 mg/kg deposited dose AD07475) | N/A |
| Group 10 (0.03 mg/kg deposited dose AD07475) | N/A |
| Group 11 (0.015 mg/kg deposited dose AD07475) | N/A |

Five (5) rats were dosed per group. Rats were sacrificed on study day 8, and total RNA was isolated from both lungs following collection and homogenization. Rat AGER mRNA expression was quantitated by probe-based quantitative PCR, normalized to rat GAPDH expression, and expressed as fraction of vehicle control group (geometric mean, +/−95% confidence interval).

TABLE 21

Average Relative Rat RAGE mRNA Expression at Sacrifice in Example 6

| Group ID | Average Relative rAGER mRNA Expression (n = 5) | Low (error) | High (error) |
|---|---|---|---|
| Group 1 (isotonic saline) | 1.000 | 0.143 | 0.168 |
| Group 2 (0.24 mg/kg deposited dose Tri-SM6.1-αvβ6-AD07475) | 0.081 | 0.010 | 0.011 |
| Group 3 (0.12 mg/kg deposited dose Tri-SM6.1-αvβ6-AD07475) | 0.081 | 0.019 | 0.025 |
| Group 4 (0.06 mg/kg deposited dose Tri-SM6.1-αvβ6-AD07475) | 0.130 | 0.033 | 0.043 |
| Group 5 (0.03 mg/kg deposited dose Tri-SM6.1-αvβ6-AD07475) | 0.342 | 0.112 | 0.165 |
| Group 6 (0.015 mg/kg deposited dose Tri-SM6.1-αvβ6-AD07475) | 0.436 | 0.088 | 0.110 |
| Group 7 (0.24 mg/kg deposited dose AD07475) | 0.107 | 0.032 | 0.046 |
| Group 8 (0.12 mg/kg deposited dose AD07475) | 0.157 | 0.041 | 0.055 |
| Group 9 (0.06 mg/kg deposited dose AD07475) | 0.309 | 0.067 | 0.086 |
| Group 10 (0.03 mg/kg deposited dose AD07475) | 0.436 | 0.120 | 0.165 |
| Group 11 (0.015 mg/kg deposited dose AD07475) | 0.537 | 0.052 | 0.058 |

As shown in the data in Table 21 above, at each of the time points measured the RAGE RNAi agent AD07475 showed substantial inhibition compared to control both with and without a targeting ligand. Indeed, even at the lowest dose tested of 0.015 mg/kg deposited dose, inhibition levels approaching 50% (see Group 6 (with targeting ligand Tri-SM6.1-αvβ6; 56.4% gene inhibition) and Group 11 (no targeting ligand; 46.3% gene inhibition)). Further, at each of the respective dose levels measured, the RNAi agent conjugated to the targeting ligand numerically outperformed the RNAi agent without the targeting ligand (with the differences generally becoming more pronounced at lower dose levels), indicating the existence of a ligand effect that can provide increased inhibitory activity in vivo.

Example 7. In Vivo Intratracheal Administration of RAGE RNAi Agents in Rats

On study day 1, male Sprague Dawley rats were administered 200 microliters via a microsprayer device (Penn Century, Philadelphia, PA) suitable for intratracheal (IT) administration of isotonic saline or 0.25 mg/kg of one of the following RAGE RNAi agents:

TABLE 22

RAGE RNAi Agent and Dosing for Example 7

| Group ID | AC Duplex Number |
|---|---|
| Group 1 (isotonic saline) | AC000286 |
| Group 2 (0.25 mg/kg Tri-SM6.1-αvβ36-AD07474) | AC000292 |
| Group 3 (0.25 mg/kg Tri-SM6.1-αvβ36-AD07475) | AC000293 |
| Group 4 (0.25 mg/kg Tri-SM6.1-αvβ36-AD07972) | AC000294 |
| Group 5 (0.25 mg/kg Tri-SM6.1-αvβ36-AD07973) | AC000290 |
| Group 6 (0.25 mg/kg Tri-SM6.1-αvβ36-AD07974) | AC000291 |
| Group 7 (0.25 mg/kg Tri-SM6.1-αvβ36-AD07975) | AC000312 |
| Group 8 (0.25 mg/kg Tri-SM6.1-αvβ36-AD07976) | AC000286 |

As noted in Table 22, each of the RAGE RNAi agents were conjugated to a tridentate small molecule αvβ6 epithelial cell targeting ligand (Tri-SM6.1, see FIG. 1) at the 5' terminal end of the sense strand, formulated in isotonic saline.

The chemically modified sequences for RAGE RNAi agents AD07474, AD07475, AD07972, AD07973, AD07974, AD07975, and AD07976 are shown in Table 7B (showing duplex), Table 3 (showing respective antisense strand), and Table 5 (showing respective sense strand with linker but without tridentate small molecule αvβ36 epithelial cell targeting ligand (Tri-SM6.1).

Five (5) rats were dosed per group. Rats were sacrificed on study day 8, and total RNA was isolated from both lungs following collection and homogenization. Rat AGER mRNA expression was quantitated by probe-based quantitative PCR, normalized to rat GAPDH expression, and expressed as fraction of vehicle control group (geometric mean, +/−95% confidence interval).

TABLE 23

Average Relative Rat RAGE mRNA Expression at Sacrifice (Day 8) in Example 7

| Group ID | Average Relative rAGER mRNA Expression (n = 5) | Low (error) | High (error) |
|---|---|---|---|
| Group 1 (isotonic saline) | 1.000 | 0.132 | 0.152 |
| Group 2 (0.25 mg/kg Tri-SM6.1-αvβ-AD07474) | 0.210 | 0.038 | 0.047 |
| Group 3 (0.25 mg/kg Tri-SM6.1-αvβ-AD07475) | 0.150 | 0.038 | 0.052 |
| Group 4 (0.25 mg/kg Tri-SM6.1-αvβ-AD07972) | 0.118 | 0.020 | 0.024 |
| Group 5 (0.25 mg/kg Tri-SM6.1-αvβ-AD07973) | 0.145 | 0.038 | 0.052 |
| Group 6 (0.25 mg/kg Tri-SM6.1-αvβ-AD07974) | 0.338 | 0.041 | 0.046 |
| Group 7 (0.25 mg/kg Tri-SM6.1-αvβ-AD07975) | 0.194 | 0.051 | 0.070 |
| Group 8 (0.25 mg/kg Tri-SM6.1-αvβ-AD07976) | 0.244 | 0.046 | 0.057 |

As shown in the data in Table 23 above, each of the RAGE RNAi agents showed significant AGER gene inhibition at a dose of only 0.25 mg/kg. Each of the RAGE RNAi agents tested including different chemical modifications but all included underlying nucleotide sequences targeting position 177 of the AGER gene.

Example 8. In Vivo Intratracheal Administration of RAGE RNAi Agents in Rats

On study day 1, male Sprague Dawley rats were administered 200 microliters via a microsprayer device (Penn Century, Philadelphia, PA) suitable for intratracheal (IT) administration of isotonic saline or 0.25 mg/kg of one of the following RAGE RNAi agents:

TABLE 24

RAGE RNAi Agent and Dosing for Example 8

| Group ID | AC Duplex Number |
|---|---|
| Group 1 (isotonic saline) | N/A |
| Group 2 (0.1 mg/kg Tri-SM6.1-αvβ6-AD07475) | AC000292 |
| Group 3 (0.1 mg/kg Tri-SM6.1-αvβ6-AD07704) | AC000438 |
| Group 4 (0.1 mg/kg Tri-SM6.1-αvβ6-AD07708) | AC000439 |
| Group 5 (0.1 mg/kg Tri-SM6.1-αvβ6-AD08030) | AC000440 |
| Group 6 (0.1 mg/kg Tri-SM6.1-αvβ6-AD08031) | AC000441 |
| Group 7 (0.1 mg/kg Tri-SM6.1-αvβ6-AD08032) | AC000442 |
| Group 8 (0.1 mg/kg Tri-SM6.1-αvβ6-AD08033) | AC000414 |
| Group 9 (0.1 mg/kg Tri-SM6.1-αvβ6-AD08034) | AC000415 |
| Group 10 (0.1 mg/kg Tri-SM6.1-αvβ6-AD08035) | AC000416 |
| Group 11 (0.1 mg/kg Tri-SM6.1-αvβ6-AD08036) | AC000417 |
| Group 12 (0.1 mg/kg Tri-SM6.1-αvβ6-AD08037) | AC000418 |
| Group 13 (0.1 mg/kg Tri-SM6.1-αvβ6-AD08038) | AC000419 |
| Group 14 (0.1 mg/kg Tri-SM6.1-αvβ6-AD08039) | AC000420 |

As noted in Table 24, each of the RAGE RNAi agents were conjugated to a tridentate small molecule αvβ6 epithelial cell targeting ligand (Tri-SM6.1, see FIG. 1) at the 5' terminal end of the sense strand, formulated in isotonic saline.

The chemically modified sequences for the RAGE RNAi agents in Example 8 are shown in Table 7B (showing duplex), Table 3 (showing respective antisense strand), and Table 5 (showing respective sense strand with linker but without tridentate small molecule αvβ36 epithelial cell targeting ligand (Tri-SM6.1).

Five (5) rats were dosed per group. Rats were sacrificed on study day 8, and total RNA was isolated from both lungs following collection and homogenization. Rat AGER mRNA expression was quantitated by probe-based quantitative PCR, normalized to rat GAPDH expression, and expressed as fraction of vehicle control group (geometric mean, +/−95% confidence interval).

TABLE 25

Average Relative Rat RAGE mRNA Expression at Sacrifice (Day 8) in Example 8

| Group ID | Average Relative rAGER mRNA Expression (n = 5) | Low (error) | High (error) |
|---|---|---|---|
| Group 1 (isotonic saline) | 1.000 | 0.118 | 0.134 |
| Group 2 (0.1 mg/kg Tri-SM6.1-αvβ6-AD07475) | 0.232 | 0.030 | 0.034 |
| Group 3 (0.1 mg/kg Tri-SM6.1-αvβ6-AD07704) | 0.372 | 0.049 | 0.057 |
| Group 4 (0.1 mg/kg Tri-SM6.1-αvβ6-AD07708) | 0.382 | 0.102 | 0.139 |
| Group 5 (0.1 mg/kg Tri-SM6.1-αvβ6-AD08030) | 0.268 | 0.054 | 0.067 |
| Group 6 (0.1 mg/kg Tri-SM6.1-αvβ6-AD08031) | 0.215 | 0.065 | 0.093 |
| Group 7 (0.1 mg/kg Tri-SM6.1-αvβ6-AD08032) | 0.314 | 0.034 | 0.038 |
| Group 8 (0.1 mg/kg Tri-SM6.1-αvβ6-AD08033) | 0.244 | 0.075 | 0.108 |
| Group 9 (0.1 mg/kg Tri-SM6.1-αvβ6-AD08034) | 0.723 | 0.078 | 0.088 |
| Group 10 (0.1 mg/kg Tri-SM6.1-αvβ6-AD08035) | 0.281 | 0.076 | 0.104 |
| Group 11 (0.1 mg/kg Tri-SM6.1-αvβ6-AD08036) | 0.288 | 0.029 | 0.033 |
| Group 12 (0.1 mg/kg Tri-SM6.1-αvβ6-AD08037) | 0.253 | 0.056 | 0.071 |
| Group 13 (0.1 mg/kg Tri-SM6.1-αvβ6-AD08038) | 0.359 | 0.105 | 0.149 |
| Group 14 (0.1 mg/kg Tri-SM6.1-αvβ6-AD08039) | 0.317 | 0.125 | 0.206 |

As shown in the data in Table 25 above, each of the RAGE RNAi agents showed significant AGER gene inhibition at a dose of only 0.1 mg/kg. Each of the RAGE RNAi agents tested including different chemical modifications but all included underlying nucleotide sequences targeting position 177 of the AGER gene.

Example 9. In Vivo Inhaled Aerosolized Administration of RAGE RNAi Agents in Cynomolgus Monkeys On study day 1, female cynomolgus monkeys were administered a single dose at 1 mg/kg PDD of the RAGE RNAi agent Tri-SM6.1-αvβ6-AD09150, Tri-SM6.1-αvβ6-AD09151, or Tri-SM6.1-αvβ6-AD09152. Using a vibrating mesh nebulizer (Aeroneb® Solo), aerosol was delivered to restrained, anesthetized monkeys fitted with a primate inhalation helmet. One of the helmets was equipped with a filter housing so that RNAi agent aerosol concentration could be assessed. Using an assumed respiratory minute volume allometrically scaled to rodent body weight, along with aerosol concentration determined from filter collection and RNAi agent quantification, exposure times were adjusted to target the reported PDD listed in Table 26. The RAGE RNAi agent was conjugated to a tridentate small molecule αvβ6 integrin receptor targeting ligand (Tri-SM6.1, see FIG. 1) at the 5' terminal end of the sense strand, formulated in isotonic saline. The chemically modified sequences for RAGE RNAi agents are shown in Table 7B (showing duplex), Table 3 (showing respective antisense strand), and Table 5 (showing respective sense strand with linker but without tridentate small molecule αvβ6 integrin receptor targeting ligand (Tri-SM6.1). The dosing groups were as follows:

TABLE 26

RAGE RNAi Agent and Dosing for Example 9 (calculated with 25% deposited fraction).

| Group ID | AC Duplex Number |
|---|---|
| Group 1 (isotonic saline) | N/A |
| Group 2 (0.98 mg/kg deposited dose Tri-SM6.1-αvβ6-AD09150) | AC001266 |
| Group 3 (1.05 mg/kg deposited dose Tri-SM6.1-αvβ6-AD09151) | AC001267 |
| Group 4 (1.04 mg/kg deposited dose Tri-SM6.1-αvβ6-AD09152) | AC001268 |

Three (3) monkeys were dosed per group. Monkeys were sacrificed on study day 15, and total RNA was isolated from lung samples following collection and homogenization. The data in the following Table 27 shows mRNA expression sampled from the distal left caudal lobe. The data in the following Table 28 shows mRNA expression sampled from the distal right caudal lobe. Cynomolgus monkey AGER mRNA expression was quantitated by probe-based quantitative PCR, normalized to Cynomolgus monkey beta-actin expression, and expressed as fraction of vehicle control group (geometric mean, +/−95es confidence interval).

TABLE 27

Average Relative Cynomolgus Monkey RAGE mRNA Expression, Distal Left Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.342 | 0.520 |
| Group 2 (0.98 mg/kg deposited dose Tri-SM6.1-αvβ6-AD09150) | 0.113 | 0.069 | 0.178 |
| Group 3 (1.05 mg/kg deposited dose Tri-SM6.1-αvβ6-AD09151) | 0.081 | 0.040 | 0.079 |
| Group 4 (1.04 mg/kg deposited dose Tri-SM6.1-αvβ6-AD09152) | 0.708 | 0.437 | 1.142 |

TABLE 28

Average Relative Cynomolgus Monkey RAGE mRNA Expression, Distal Right Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.330 | 0.492 |
| Group 2 (0.98 mg/kg deposited dose Tri-SM6.1-αvβ6-AD09150) | 0.069 | 0.032 | 0.059 |
| Group 3 (1.05 mg/kg deposited dose Tri-SM6.1-αvβ6-AD09151) | 0.069 | 0.028 | 0.049 |
| Group 4 (1.04 mg/kg deposited dose Tri-SM6.1-αvβ6-AD09152) | 0.630 | 0.406 | 1.141 |

As shown in the data in Table 28 above, RNAi agent AD09150 and AD09151 showed substantial inhibition (93%) compared to control, demonstrating the ability to robustly silence AGER expression in non-human primates.

In a separate qPCR assay, cynomolgus monkey AGER mRNA expression was quantified. The data in the following Tables 29 through 42 show mRNA expression sampled from the cynomolgus lung samples. Cynomolgus monkey AGER mRNA expression was quantitated by probe-based quantitative PCR, normalized to Cynomolgus monkey beta-actin expression, and expressed as fraction of vehicle control group (geometric mean, +/−95% confidence interval). Some lung tissue was repeated with different tissue samples, when available, for example, Distal Left Caudal Lobe and Distal Left Cranial Lobe.

TABLE 29

Average Relative Cynomolgus Monkey RAGE mRNA Expression, Distal Left Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.272 | 0.373 |
| Group 2 (0.98 mg/kg deposited dose Tri-SM6.1-αvβ6-AD09150) | 0.138 | 0.097 | 0.330 |
| Group 3 (1.05 mg/kg deposited dose Tri-SM6.1-αvβ6-AD09151) | 0.065 | 0.031 | 0.059 |

TABLE 29-continued

Average Relative Cynomolgus Monkey RAGE mRNA Expression, Distal Left Caudal Lobe, at Sacrifice in Example 9.

| Group ID | Average Relative cAGER mRNA Expression (n = 3) | Low (error) | High (error) |
|---|---|---|---|
| Group 4 (1.04 mg/kg deposited dose Tri-SM6.1-αvβ6-AD09152) | 0.850 | 0.435 | 0.890 |

TABLE 30

Average Relative Cynomolgus Monkey RAGE mRNA Expression, Medial Left Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.433 | 0.762 |
| Group 2 (0.98 mg/kg deposited dose Tri-SM6.1-αvβ6-AD09150) | 0.122 | 0.086 | 0.298 |
| Group 3 (1.05 mg/kg deposited dose Tri-SM6.1-αvβ6-AD09151) | 0.133 | 0.039 | 0.054 |
| Group 4 (1.04 mg/kg deposited dose Tri-SM6.1-αvβ6-AD09152) | 0.877 | 0.528 | 1.329 |

TABLE 31

Average Relative Cynomolgus Monkey RAGE mRNA Expression, Proximal Left Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.297 | 0.422 |
| Group 2 (0.98 mg/kg deposited dose Tri-SM6.1-αvβ6-AD09150) | 0.152 | 0.094 | 0.246 |
| Group 3 (1.05 mg/kg deposited dose Tri-SM6.1-αvβ6-AD09151) | 0.084 | 0.032 | 0.053 |
| Group 4 (1.04 mg/kg deposited dose Tri-SM6.1-αvβ6-AD09152) | 0.781 | 0.446 | 1.038 |

TABLE 32

Average Relative Cynomolgus Monkey RAGE mRNA Expression, Distal Left Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.231 | 0.300 |
| Group 2 (0.98 mg/kg deposited dose Tri-SM6.1-αvβ6-AD09150) | 0.126 | 0.072 | 0.166 |
| Group 3 (1.05 mg/kg deposited dose Tri-SM6.1-αvβ6-AD09151) | 0.104 | 0.056 | 0.119 |

TABLE 32-continued

Average Relative Cynomolgus Monkey RAGE mRNA Expression, Distal Left Cranial Lobe, at Sacrifice in Example 9.

| Group ID | Average Relative cAGER mRNA Expression (n = 3) | Low (error) | High (error) |
|---|---|---|---|
| Group 4 (1.04 mg/kg deposited dose Tri-SM6.1-αvβ6-AD09152) | 0.549 | 0.370 | 1.134 |

TABLE 33

Average Relative Cynomolgus Monkey RAGE mRNA Expression, Distal Left Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.306 | 0.440 |
| Group 2 (0.98 mg/kg deposited dose Tri-SM6.1-αvβ6-AD09150) | 0.076 | 0.045 | 0.113 |
| Group 3 (1.05 mg/kg deposited dose Tri-SM6.1-αvβ6-AD09151) | 0.048 | 0.019 | 0.031 |
| Group 4 (1.04 mg/kg deposited dose Tri-SM6.1-αvβ6-AD09152) | 0.548 | 0.355 | 1.008 |

TABLE 34

Average Relative Cynomolgus Monkey RAGE mRNA Expression, Medial Left Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.383 | 0.620 |
| Group 2 (0.98 mg/kg deposited dose Tri-SM6.1-αvβ6-AD09150) | 0.157 | 0.116 | 0.447 |
| Group 3 (1.05 mg/kg deposited dose Tri-SM6.1-αvβ6-AD09151) | 0.054 | 0.028 | 0.059 |
| Group 4 (1.04 mg/kg deposited dose Tri-SM6.1-αvβ6-AD09152) | 0.826 | 0.485 | 1.175 |

TABLE 35

Average Relative Cynomolgus Monkey RAGE mRNA Expression, Proximal Left Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.174 | 0.211 |
| Group 2 (0.98 mg/kg deposited dose Tri-SM6.1-αvβ6-AD09150) | 0.106 | 0.074 | 0.242 |
| Group 3 (1.05 mg/kg deposited dose Tri-SM6.1-αvβ6-AD09151) | 0.106 | 0.053 | 0.104 |

TABLE 35-continued

Average Relative Cynomolgus Monkey RAGE mRNA Expression, Proximal Left Cranial Lobe, at Sacrifice in Example 9.

| Group ID | Average Relative cAGER mRNA Expression (n = 3) | Low (error) | High (error) |
|---|---|---|---|
| Group 4 (1.04 mg/kg deposited dose Tri-SM6.1-αvβ6-AD09152) | 0.404 | 0.275 | 0.864 |

TABLE 36

Average Relative Cynomolgus Monkey RAGE mRNA Expression, Distal Right Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.070 | 0.075 |
| Group 2 (0.98 mg/kg deposited dose Tri-SM6.1-αvβ6-AD09150) | 0.116 | 0.081 | 0.267 |
| Group 3 (1.05 mg/kg deposited dose Tri-SM6.1-αvβ6-AD09151) | 0.050 | 0.027 | 0.059 |
| Group 4 (1.04 mg/kg deposited dose Tri-SM6.1-αvβ6-AD09152) | 0.690 | 0.222 | 0.328 |

TABLE 37

Average Relative Cynomolgus Monkey RAGE mRNA Expression, Medial Right Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.493 | 0.972 |
| Group 2 (0.98 mg/kg deposited dose Tri-SM6.1-αvβ6-AD09150) | 0.243 | 0.145 | 0.359 |
| Group 3 (1.05 mg/kg deposited dose Tri-SM6.1-αvβ6-AD09151) | 0.124 | 0.057 | 0.105 |
| Group 4 (1.04 mg/kg deposited dose Tri-SM6.1-αvβ6-AD09152) | 0.549 | 0.184 | 0.277 |

TABLE 38

Average Relative Cynomolgus Monkey RAGE mRNA Expression, Proximal Right Caudal Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.451 | 0.821 |
| Group 2 (0.98 mg/kg deposited dose Tri-SM6.1-αvβ6-AD09150) | 0.160 | 0.088 | 0.198 |
| Group 3 (1.05 mg/kg deposited dose Tri-SM6.1-αvβ6-AD09151) | 0.122 | 0.078 | 0.216 |

TABLE 38-continued

Average Relative Cynomolgus Monkey RAGE mRNA Expression, Proximal Right Caudal Lobe, at Sacrifice in Example 9.

| Group ID | Average Relative cAGER mRNA Expression (n = 3) | Low (error) | High (error) |
|---|---|---|---|
| Group 4 (1.04 mg/kg deposited dose Tri-SM6.1-αvβ6-AD09152) | 0.262 | 0.175 | 0.522 |

TABLE 39

Average Relative Cynomolgus Monkey RAGE mRNA Expression, Distal Right Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.161 | 0.192 |
| Group 2 (0.98 mg/kg deposited dose Tri-SM6.1-αvβ6-AD09150) | 0.268 | 0.142 | 0.300 |
| Group 3 (1.05 mg/kg deposited dose Tri-SM6.1-αvβ6-AD09151) | 0.097 | 0.039 | 0.066 |
| Group 4 (1.04 mg/kg deposited dose Tri-SM6.1-αvβ6-AD09152) | 0.395 | 0.243 | 0.634 |

TABLE 40

Average Relative Cynomolgus Monkey RAGE mRNA Expression, Distal Right Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.362 | 0.568 |
| Group 2 (0.98 mg/kg deposited dose Tri-SM6.1-αvβ6-AD09150) | 0.172 | 0.112 | 0.320 |
| Group 3 (1.05 mg/kg deposited dose Tri-SM6.1-αvβ6-AD09151) | 0.156 | 0.034 | 0.044 |
| Group 4 (1.04 mg/kg deposited dose Tri-SM6.1-αvβ6-AD09152) | 0.923 | 0.613 | 1.820 |

TABLE 41

Average Relative Cynomolgus Monkey RAGE mRNA Expression, Medial Right Cranial Lobe, at Sacrifice in Example 9.

| Group ID | Average Relative cAGER mRNA Expression (n = 3) | Low (error) | High (error) |
|---|---|---|---|
| Group 1 (isotonic saline) | 1.000 | 0.496 | 0.984 |
| Group 2 (0.98 mg/kg deposited dose Tri-SM6.1-αvβ6-AD09150) | 0.301 | 0.154 | 0.315 |
| Group 3 (1.05 mg/kg deposited dose Tri-SM6.1-αvβ6-AD09151) | 0.098 | 0.050 | 0.100 |

TABLE 41-continued

| Average Relative Cynomolgus Monkey RAGE mRNA Expression, Medial Right Cranial Lobe, at Sacrifice in Example 9. | | | |
|---|---|---|---|
| Group ID | Average Relative cAGER mRNA Expression (n = 3) | Low (error) | High (error) |
| Group 4 (1.04 mg/kg deposited dose Tri-SM6.1-αvβ6-AD09152) | 0.303 | 0.233 | 1.007 |

TABLE 42

| Average Relative Cynomolgus Monkey RAGE mRNA Expression, Proximal Right Cranial Lobe, at Sacrifice in Example 9. | | | |
|---|---|---|---|
| Group ID | Average Relative cAGER mRNA Expression (n = 3) | Low (error) | High (error) |
| Group 1 (isotonic saline) | 1.000 | 0.098 | 0.108 |
| Group 2 (0.98 mg/kg deposited dose Tri-SM6.1-αvβ6-AD09150) | 0.156 | 0.075 | 0.146 |
| Group 3 (1.05 mg/kg deposited dose Tri-SM6.1-αvβ6-AD09151) | 0.080 | 0.047 | 0.114 |
| Group 4 (1.04 mg/kg deposited dose Tri-SM6.1-αvβ6-AD09152) | 0.445 | 0.198 | 0.358 |

As shown in the data in Tables 29 through 42 above, RNAi agent AD09150 and AD09151 showed substantial inhibition (up to 92%) compared to control, demonstrating the ability to robustly silence AGER expression in non-human primates.

Example 10. In Vivo Anti-Inflammatory Effect of RAGE Knock-Down in Rat Model of Airway Inflammation, Delivery Via Aerosol On study day 1 and again on study day 15, male Sprague Dawley rats were administered a 0.5 mg/kg deposited dose of the RAGE RNAi agent Tri-SM6.1-avo36-AD07475, or a vehicle control without an RNAi agent, in accordance with Table 43 below. Using a jet nebulizer (Misty Max 10), aerosol was delivered to a rodent single-tier flow-past nose-only inhalation exposure chamber (CH Technologies). One of the ports was equipped with a filter housing so that RNAi agent aerosol concentration could be assessed. Using an assumed respiratory minute volume allometrically scaled to rodent body weight, along with aerosol concentration determined from filter collection and RNAi agent quantification.

On day 40, rats in Group 4 and Group 5 were challenged with a single intra-tracheal dose of 400 ug/rat of *Alternaria alternata* (Alt) prepared in saline, and rats in Group 2 and 3 where administered a 400 ug/rat dose of saline control. Rats in Group N-1 were naive and had no treatment administered.

TABLE 43

| RAGE RNAi Agent and Dosing for Example 10. | | |
|---|---|---|
| Group ID | AC Duplex Number | Animals per Group |
| Group 1 (naïve: no treatment) | N/A | 3 |
| Group 2 (saline aerosol days 1 and 15)/(saline IT day 40) | N/A | 5 |

TABLE 43-continued

| RAGE RNAi Agent and Dosing for Example 10. | | |
|---|---|---|
| Group ID | AC Duplex Number | Animals per Group |
| Group 3 (0.5 mg/kg deposited dose Tri-SM6.1-αvβ6-AD07475 days 1 and 15)/(saline IT day 40) | AC000292 | 5 |
| Group 4 (saline aerosol days 1 and 15)/(*Alternaria* IT day 40) | N/A | 7 |
| Group 5 (0.5 mg/kg deposited dose Tri-SM6.1-αvβ6-AD07475)/(*Alternaria* IT day 40) | AC000292 | 7 |

After 48 hours post-administration of the Alternaria (i.e., Day 42), rats were anesthetized with isoflurane/02, had blood drawn, and were euthanized by exsanguination. Trachea was canulated and bronchoalveolar lavage (BAL) was collected after washing with 2×10 mL of ice-cold PBS. BAL samples were spun down, cells resuspended with 1 mL of ice-cold PBS, and aliquot was mixed with Turk's solution (ratio 1:1), and total cell counted via hemocytomers. Cytospins were prepared, stained and differential cell counting performed. Supernatant was used for soluble RAGE (sRAGE) and cytokines measurements. One lobe was used to determine AGER mRNA expression and tissue samples were analyzed to assess concentration of RAGE protein.

Granulocytes, both eosinophils and neutrophils, are well known markers for cellular inflammation. For the BAL samples, the total and differential cells were counted and the number of inflammatory cells were derived. Group 5 (in which RAGE RNAi agent was administered and the tissues were challenged by *Alternaria*) showed a reduction of inflammatory cells as compared to Group 4 (in which no RNAi agent was administered).

Further, VEGF is known to cause vascular remodeling and is induced by inflammation. The groups administered with RAGE RNAi agent (Groups 3 and 5) showed reductions in VEGF levels in the BAL samples examined.

Example 11. In Vivo Anti-Inflammatory Effect of RAGE Knock-Down in Rat Model of Airway Inflammation, Delivery Via Intra-Tracheal Microsprayer On study day 1, day 8, and day 29, male Brown-Norway rats were administered a dose of 3 mg/kg (1.5 mL/kg) of the RAGE RNAi agent Tri-SM6.1-αvβ6-AD07475 or vehicle. Volume calculated at 1.5 mL/kg was loaded into a syringe that was connected to a microsprayer device (Penn Century, Philadelphia, PA).

On day 43, rats in Group 3 and Group 4 were challenged with a single intra-tracheal dose of 400 ug/rat of *Alternaria alternata* prepared in saline, and rats in Group 1 and 2 were administered a 400 ug/rat dose of saline control. Rats in Group N-1 were naive and had no treatment administered.

TABLE 44

| RAGE RNAi Agent and Dosing for Example 11. | | |
|---|---|---|
| Group ID | AC Duplex Number | Animals per Group |
| Group N-1 (naïve: no treatment) | N/A | 4 |
| Group 1 (saline IT days 1, 8, and 29)/(saline IT day 43) | N/A | 6 |

TABLE 44-continued

RAGE RNAi Agent and Dosing for Example 11.

| Group ID | AC Duplex Number | Animals per Group |
|---|---|---|
| Group 2 (IT dose 3.0 mg/kg Tri-SM6.1-αvβ6-AD07475 on days 1, 8, and 29)/(*Alternaria* IT day 43) | AC000292 | 4 |
| Group 3 (saline IT days 1 and 15)/(saline day 43) | N/A | 8 |
| Group 4 (IT dose 3.0 mg/kg Tri-SM6.1-αvβ6-AD07475 on days 1, 8, and 29)/(*Alternaria* IT day 43) | AC000292 | 8 |

After 48 hours post-administration of the *Alternaria* (i.e. day 45), rats were anesthetized with isoflurane/02, blood was drawn, and were euthanized by exsanguination. Trachea was canulated and bronchoalveolar lavage (BAL) collected after washing with 2×10 mL of ice-cold PBS. BAL samples were spun down, cells resuspended with 1 mL of ice-cold PBS, and aliquot was mixed with Turk's solution (ratio 1:1), and total cell counted via hemocytomers. Cytospins were prepared, stained and differential cell counting performed. Supematant was used for soluble RAGE (sRAGE) and cytokines measurements. One lobe was used to determine AGER mRNA expression and part of tissue was used to determine tissue concentration of RAGE protein.

Soluble RAGE (sRAGE) was measured in the serum and bronchoalveolar lavage fluid (BALF) samples by ELISA. sRAGE was nearly completely reduced by administration of the RAGE RNAi agents (see Groups 2 and 4).

Further, as noted in the prior Example, granulocytes (both eosinophils and neutrophils) are well known markers for cellular inflammation. For the BAL samples, the total and differential cells were counted and the number of inflammatory cells were derived. The impact of RAGE inhibition by the RAGE RNAi agents disclosed herein on eosinophilic inflammation induced by *Alternaria* extract was assessed. Group 4 (treated with RAGE RNAi agent) showed a reduction in total granulocytes compared to Group 3 (no RAGE RNAi agent administered).

Other biomarkers, such as MIP1a, IL-13, IP-10 and VEGF, are also indicative of cellular inflammation. For the *Alternaria* challenged groups, administration of the RAGE RNAi agent (Group 4) resulted in a reductions of each of these pro-inflammatory biomarkers compared to the group in which no RAGE RNAi agent was administered (Group 3).

Example 12. Dose Response of In Vivo Inhaled Aerosolized Administration of RAGE RNAi Agents in Cynomolgus Monkeys Fifteen (15) female cynomolgus animals were randomly assigned to five (5) treatment groups. The animals were dosed according to as summarized in the following Table 45. Animals were fasted the night before study days requiring anesthesia, but given water ad libitum. Animals were anesthetized with ketamine hydrochloride (5-10 mg/kg, IM), followed by isoflurane inhalation. Animals were initially anesthetized with isoflurane (4-5%) using a mask until a properly sized cuffed endotracheal tube was inserted, just proximal to the carina to allow the insertion of a pediatric fiberoptic bronchoscope to perform bronchoalveolar lavage (BAL) and to allow exposure through the endotracheal tube. Anesthetized animals were moved to the exposure system and connected to the ventilator. Anaesthetized and ventilated animals received a single inhalation exposure with either isotonic saline or RAGE RNAi agent Tri-SM6.1-αvβ6-AD09151 (AC001267). Animals were ventilated during the duration of the exposure using a Harvard pump set to 10 to 15 mL/kg tidal volume, 30 breaths per minute and inspiratory volume of 35:65. After finishing the exposure, the anesthesia was removed and animal then covered with blankets or Bair Hugger at a recovery station and connected to a monitor device for continuous capture of heart rate and 02 saturation. The RAGE RNAi agent was conjugated to a tridentate small molecule αvβ6 epithelial cell targeting ligand (Tri-SM6.1, see FIG. 1) at the 5' terminal end of the sense strand, formulated in isotonic saline. The chemically modified sequences for RAGE RNAi agents are shown in Table 7B (showing duplex), Table 3 (showing respective antisense strand), and Table 5 (showing respective sense strand with linker but without tridentate small molecule αvβ6 epithelial cell targeting ligand (Tri-SM6.1).

TABLE 45

RAGE RNAi Agent and Dosing for Example 12.

| Group ID | AC Duplex Number | Animals per Group | Targeted Deposited Dose/Animal | Calculated Deposited Dose |
|---|---|---|---|---|
| Group 1 (isotonic saline) | N/A | 3 | (same exposure time as Groups 2 through 5) | N/A |
| Group 2 (Tri-SM6.1-αvβ6-AD09151) | AC001267 | 3 | 0.0625 mg/kg | 0.13 mg/kg |
| Group 3 (Tri-SM6.1-αvβ6-AD09151) | AC001267 | 3 | 0.125 mg/kg | 0.20 mg/kg |
| Group 4 (Tri-SM6.1-αvβ6-AD09151) | AC001267 | 3 | 0.25 mg/kg | 0.31 mg/kg |
| Group 5 (Tri-SM6.1-αvβ6-AD09151) | AC001267 | 3 | 0.5 mg/kg | 0.47 mg/kg |

Bronchoalveolar lavage (BAL) and blood (serum) were collected at −7 days prior to exposure and 2-4 weeks after inhalation exposure (Days −7, 15, 29). All animals were euthanized just before sample collection on Day 29 to collect lung tissue.

The left lung of each animal was harvested for histology. The right lung was obtained, lobes separated, individually weighted and snap frozen. Separate lobes were sectioned in three (3) approximately equal pieces sliced at a longitudinal plane, perpendicular to the airway. Namely, separate lobes were sectioned in three (3) approximately equal pieces at a longitudinal plane, perpendicular to the airway, namely the proximal, medial, and distal. For cranial and medial lobes, two to three equally divided samples were collected from proximal slice, and three from the other two slices. Approximately equal size tissue cubes were obtained with presence and absence of visible airways.

The data in the following Tables 47 through 71 show mRNA expression sampled from the cynomolgus lung samples. Cynomolgus monkey AGER mRNA expression was quantitated by probe-based quantitative PCR, normalized to Cynomolgus monkey GAPDH expression, and expressed as fraction of vehicle control group (geometric mean, +/−9500 confidence interval).

TABLE 47

Average Relative Cynomolgus Monkey RAGE mRNA Expression, Right Distal Cranial Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.111 | 0.125 |
| Group 2 (0.13 mg/kg deposited dose Tri-SM6.1-αvβ6-AD09151) | 0.406 | 0.113 | 0.156 |
| Group 3 (0.20 mg/kg deposited dose Tri-SM6.1-αvβ6-AD09151) | 0.589 | 0.165 | 0.229 |
| Group 4 (0.31 mg/kg deposited dose Tri-SM6.1-αvβ6-AD09151) | 0.353 | 0.076 | 0.096 |
| Group 5 (0.47 mg/kg deposited dose Tri-SM6.1-αvβ6-AD09151) | 0.358 | 0.139 | 0.227 |

TABLE 48

Average Relative Cynomolgus Monkey RAGE mRNA Expression, Right Distal Middle Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.156 | 0.185 |
| Group 2 (0.13 mg/kg deposited dose Tri-SM6.1-αvβ6-AD09151) | 0.373 | 0.106 | 0.149 |
| Group 3 (0.20 mg/kg deposited dose Tri-SM6.1-αvβ6-AD09151) | 0.468 | 0.126 | 0.172 |
| Group 4 (0.31 mg/kg deposited dose Tri-SM6.1-αvβ6-AD09151) | 0.226 | 0.047 | 0.061 |
| Group 5 (0.47 mg/kg deposited dose Tri-SM6.1-αvβ6-AD09151) | 0.208 | 0.068 | 0.101 |

TABLE 49

Average Relative Cynomolgus Monkey RAGE mRNA Expression, Right Distal Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.070 | 0.075 |
| Group 2 (0.13 mg/kg deposited dose Tri-SM6.1-αvβ6-AD09151) | 0.327 | 0.053 | 0.063 |
| Group 3 (0.20 mg/kg deposited dose Tri-SM6.1-αvβ6-AD09151) | 0.432 | 0.041 | 0.045 |
| Group 4 (0.31 mg/kg deposited dose Tri-SM6.1-αvβ6-AD09151) | 0.338 | 0.146 | 0.278 |
| Group 5 (0.47 mg/kg deposited dose Tri-SM6.1-αvβ6-AD09151) | 0.155 | 0.032 | 0.041 |

TABLE 50

Average Relative Cynomolgus Monkey RAGE mRNA Expression, Right Proximal Caudal Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.200 | 0.250 |
| Group 2 (0.13 mg/kg deposited dose Tri-SM6.1-αvβ6-AD09151) | 0.436 | 0.113 | 0.153 |
| Group 3 (0.20 mg/kg deposited dose Tri-SM6.1-αvβ6-AD09151) | 0.449 | 0.073 | 0.087 |
| Group 4 (0.31 mg/kg deposited dose Tri-SM6.1-αvβ6-AD09151) | 0.371 | 0.055 | 0.064 |
| Group 5 (0.47 mg/kg deposited dose Tri-SM6.1-αvβ6-AD09151) | 0.337 | 0.099 | 0.140 |

TABLE 51

Average Relative Cynomolgus Monkey RAGE mRNA Expression, Right Proximal Middle Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.090 | 0.098 |
| Group 2 (0.13 mg/kg deposited dose Tri-SM6.1-αvβ6-AD09151) | 0.491 | 0.128 | 0.172 |
| Group 3 (0.20 mg/kg deposited dose Tri-SM6.1-αvβ6-AD09151) | 0.597 | 0.090 | 0.106 |
| Group 4 (0.31 mg/kg deposited dose Tri-SM6.1-αvβ6-AD09151) | 0.450 | 0.034 | 0.033 |
| Group 5 (0.47 mg/kg deposited dose Tri-SM6.1-αvβ6-AD09151) | 0.345 | 0.038 | 0.043 |

TABLE 52

Average Relative Cynomolgus Monkey RAGE mRNA Expression, Right Proximal Caudal Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.083 | 0.090 |
| Group 2 (0.13 mg/kg deposited dose Tri-SM6.1-αvβ6-AD09151) | 0.419 | 0.074 | 0.090 |
| Group 3 (0.20 mg/kg deposited dose Tri-SM6.1-αvβ6-AD09151) | 0.569 | 0.093 | 0.111 |
| Group 4 (0.31 mg/kg deposited dose Tri-SM6.1-αvβ6-AD09151) | 0.273 | 0.056 | 0.078 |
| Group 5 (0.47 mg/kg deposited dose Tri-SM6.1-αvβ6-AD09151) | 0.308 | 0.080 | 0.108 |

TABLE 53

Average Relative Cynomolgus Monkey RAGE mRNA Expression, Right Distal Cranial Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.074 | 0.080 |
| Group 2 (0.13 mg/kg deposited dose Tri-SM6.1-αvβ6-AD09151) | 0.265 | 0.072 | 0.099 |
| Group 3 (0.20 mg/kg deposited dose Tri-SM6.1-αvβ6-AD09151) | 0.555 | 0.055 | 0.061 |
| Group 4 (0.31 mg/kg deposited dose Tri-SM6.1-αvβ6-AD09151) | 0.286 | 0.017 | 0.018 |
| Group 5 (0.47 mg/kg deposited dose Tri-SM6.1-αvβ6-AD09151) | 0.296 | 0.057 | 0.070 |

TABLE 54

Average Relative Cynomolgus Monkey RAGE mRNA Expression, Right Distal Middle Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.053 | 0.056 |
| Group 2 (0.13 mg/kg deposited dose Tri-SM6.1-αvβ6-AD09151) | 0.395 | 0.129 | 0.191 |

TABLE 54-continued

Average Relative Cynomolgus Monkey RAGE mRNA Expression, Right Distal Middle Lobe, at Sacrifice in Example 12.

| Group ID | Average Relative cAGER mRNA Expression (n = 3) | Low (error) | High (error) |
|---|---|---|---|
| Group 3 (0.20 mg/kg deposited dose Tri-SM6.1-αvβ6-AD09151) | 0.569 | 0.109 | 0.135 |
| Group 4 (0.31 mg/kg deposited dose Tri-SM6.1-αvβ6-AD09151) | 0.169 | 0.030 | 0.042 |
| Group 5 (0.47 mg/kg deposited dose Tri-SM6.1-αvβ6-AD09151) | 0.333 | 0.132 | 0.220 |

TABLE 55

Average Relative Cynomolgus Monkey RAGE mRNA Expression, Right Distal Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.395 | 0.652 |
| Group 2 (0.13 mg/kg deposited dose Tri-SM6.1-αvβ6-AD09151) | 0.567 | 0.070 | 0.080 |
| Group 3 (0.20 mg/kg deposited dose Tri-SM6.1-αvβ6-AD09151) | 0.713 | 0.096 | 0.111 |
| Group 4 (0.31 mg/kg deposited dose Tri-SM6.1-αvβ6-AD09151) | 0.442 | 0.133 | 0.204 |
| Group 5 (0.47 mg/kg deposited dose Tri-SM6.1-αvβ6-AD09151) | 0.285 | 0.084 | 0.120 |

TABLE 56

Average Relative Cynomolgus Monkey RAGE mRNA Expression, Right Proximal Cranial Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.269 | 0.368 |
| Group 2 (0.13 mg/kg deposited dose Tri-SM6.1-αvβ6-AD09151) | 0.451 | 0.127 | 0.176 |
| Group 3 (0.20 mg/kg deposited dose Tri-SM6.1-αvβ6-AD09151) | 0.513 | 0.134 | 0.181 |
| Group 4 (0.31 mg/kg deposited dose Tri-SM6.1-αvβ6-AD09151) | 0.355 | 0.053 | 0.062 |
| Group 5 (0.47 mg/kg deposited dose Tri-SM6.1-αvβ6-AD09151) | 0.307 | 0.106 | 0.161 |

TABLE 57

Average Relative Cynomolgus Monkey RAGE mRNA Expression, Right Medial Cranial Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.082 | 0.090 |
| Group 2 (0.13 mg/kg deposited dose Tri-SM6.1-αvβ6-AD09151) | 0.397 | 0.103 | 0.139 |
| Group 3 (0.20 mg/kg deposited dose Tri-SM6.1-αvβ6-AD09151) | 0.549 | 0.049 | 0.053 |

TABLE 57-continued

Average Relative Cynomolgus Monkey RAGE mRNA Expression, Right Medial Cranial Lobe, at Sacrifice in Example 12.

| Group ID | Average Relative cAGER mRNA Expression (n = 3) | Low (error) | High (error) |
|---|---|---|---|
| Group 4 (0.31 mg/kg deposited dose Tri-SM6.1-αvβ6-AD09151) | 0.278 | 0.071 | 0.095 |
| Group 5 (0.47 mg/kg deposited dose Tri-SM6.1-αvβ6-AD09151) | 0.280 | 0.091 | 0.135 |

TABLE 58

Average Relative Cynomolgus Monkey RAGE mRNA Expression, Right Medial Middle Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.058 | 0.061 |
| Group 2 (0.13 mg/kg deposited dose Tri-SM6.1-αvβ6-AD09151) | 0.396 | 0.072 | 0.088 |
| Group 3 (0.20 mg/kg deposited dose Tri-SM6.1-αvβ6-AD09151) | 0.577 | 0.124 | 0.157 |
| Group 4 (0.31 mg/kg deposited dose Tri-SM6.1-αvβ6-AD09151) | 0.375 | 0.074 | 0.093 |
| Group 5 (0.47 mg/kg deposited dose Tri-SM6.1-αvβ6-AD09151) | 0.307 | 0.039 | 0.045 |

TABLE 59

Average Relative Cynomolgus Monkey RAGE mRNA Expression, Right Medial Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.082 | 0.089 |
| Group 2 (0.13 mg/kg deposited dose Tri-SM6.1-αvβ6-AD09151) | 0.408 | 0.122 | 0.174 |
| Group 3 (0.20 mg/kg deposited dose Tri-SM6.1-αvβ6-AD09151) | 0.507 | 0.052 | 0.058 |
| Group 4 (0.31 mg/kg deposited dose Tri-SM6.1-αvβ6-AD09151) | 0.280 | 0.036 | 0.046 |
| Group 5 (0.47 mg/kg deposited dose Tri-SM6.1-αvβ6-AD09151) | 0.283 | 0.048 | 0.058 |

TABLE 60

Average Relative Cynomolgus Monkey RAGE mRNA Expression, Right Distal Cranial Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.088 | 0.096 |
| Group 2 (0.13 mg/kg deposited dose Tri-SM6.1-αvβ6-AD09151) | 0.351 | 0.066 | 0.082 |
| Group 3 (0.20 mg/kg deposited dose Tri-SM6.1-αvβ6-AD09151) | 0.509 | 0.077 | 0.090 |
| Group 4 (0.31 mg/kg deposited dose Tri-SM6.1-αvβ6-AD09151) | 0.316 | 0.064 | 0.081 |
| Group 5 (0.47 mg/kg deposited dose Tri-SM6.1-αvβ6-AD09151) | 0.311 | 0.085 | 0.117 |

TABLE 61

Average Relative Cynomolgus Monkey RAGE mRNA Expression, Right Distal Middle Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.227 | 0.294 |
| Group 2 (0.13 mg/kg deposited dose Tri-SM6.1-αvβ6-AD09151) | 0.195 | 0.086 | 0.154 |
| Group 3 (0.20 mg/kg deposited dose Tri-SM6.1-αvβ6-AD09151) | 0.429 | 0.119 | 0.165 |
| Group 4 (0.31 mg/kg deposited dose Tri-SM6.1-αvβ6-AD09151) | 0.289 | 0.028 | 0.040 |
| Group 5 (0.47 mg/kg deposited dose Tri-SM6.1-αvβ6-AD09151) | 0.242 | 0.069 | 0.096 |

TABLE 62

Average Relative Cynomolgus Monkey RAGE mRNA Expression, Right Distal Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.077 | 0.083 |
| Group 2 (0.13 mg/kg deposited dose Tri-SM6.1-αvβ6-AD09151) | 0.434 | 0.114 | 0.155 |
| Group 3 (0.20 mg/kg deposited dose Tri-SM6.1-αvβ6-AD09151) | 0.554 | 0.131 | 0.171 |
| Group 4 (0.31 mg/kg deposited dose Tri-SM6.1-αvβ6-AD09151) | 0.540 | 0.240 | 0.405 |
| Group 5 (0.47 mg/kg deposited dose Tri-SM6.1-αvβ6-AD09151) | 0.314 | 0.087 | 0.121 |

TABLE 63

Average Relative Cynomolgus Monkey RAGE mRNA Expression, Right Medial Cranial Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.131 | 0.151 |
| Group 2 (0.13 mg/kg deposited dose Tri-SM6.1-αvβ6-AD09151) | 0.499 | 0.169 | 0.256 |
| Group 3 (0.20 mg/kg deposited dose Tri-SM6.1-αvβ6-AD09151) | 0.545 | 0.116 | 0.147 |
| Group 4 (0.31 mg/kg deposited dose Tri-SM6.1-αvβ6-AD09151) | 0.332 | 0.020 | 0.021 |
| Group 5 (0.47 mg/kg deposited dose Tri-SM6.1-αvβ6-AD09151) | 0.360 | 0.100 | 0.138 |

TABLE 64

Average Relative Cynomolgus Monkey RAGE mRNA Expression, Right Medial Middle Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.071 | 0.076 |
| Group 2 (0.13 mg/kg deposited dose Tri-SM6.1-αvβ6-AD09151) | 0.571 | 0.130 | 0.169 |
| Group 3 (0.20 mg/kg deposited dose Tri-SM6.1-αvβ6-AD09151) | 0.708 | 0.131 | 0.161 |
| Group 4 (0.31 mg/kg deposited dose Tri-SM6.1-αvβ6-AD09151) | 0.306 | 0.035 | 0.039 |
| Group 5 (0.47 mg/kg deposited dose Tri-SM6.1-αvβ6-AD09151) | 0.258 | 0.074 | 0.103 |

TABLE 65

Average Relative Cynomolgus Monkey RAGE mRNA Expression, Right Medial Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.180 | 0.219 |
| Group 2 (0.13 mg/kg deposited dose Tri-SM6.1-αvβ6-AD09151) | 0.381 | 0.080 | 0.101 |
| Group 3 (0.20 mg/kg deposited dose Tri-SM6.1-αvβ6-AD09151) | 0.580 | 0.109 | 0.135 |
| Group 4 (0.31 mg/kg deposited dose Tri-SM6.1-αvβ6-AD09151) | 0.304 | 0.041 | 0.052 |
| Group 5 (0.47 mg/kg deposited dose Tri-SM6.1-αvβ6-AD09151) | 0.235 | 0.039 | 0.046 |

TABLE 66

Average Relative Cynomolgus Monkey RAGE mRNA Expression, Right Proximal Cranial Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.153 | 0.180 |
| Group 2 (0.13 mg/kg deposited dose Tri-SM6.1-αvβ6-AD09151) | 0.492 | 0.152 | 0.220 |
| Group 3 (0.20 mg/kg deposited dose Tri-SM6.1-αvβ6-AD09151) | 0.486 | 0.115 | 0.151 |
| Group 4 (0.31 mg/kg deposited dose Tri-SM6.1-αvβ6-AD09151) | 0.265 | 0.026 | 0.029 |
| Group 5 (0.47 mg/kg deposited dose Tri-SM6.1-αvβ6-AD09151) | 0.272 | 0.053 | 0.065 |

TABLE 67

Average Relative Cynomolgus Monkey RAGE mRNA Expression, Right Proximal Middle Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.124 | 0.141 |
| Group 2 (0.13 mg/kg deposited dose Tri-SM6.1-αvβ6-AD09151) | 0.537 | 0.121 | 0.157 |
| Group 3 (0.20 mg/kg deposited dose Tri-SM6.1-αvβ6-AD09151) | 0.509 | 0.156 | 0.226 |
| Group 4 (0.31 mg/kg deposited dose Tri-SM6.1-αvβ6-AD09151) | 0.247 | 0.064 | 0.077 |
| Group 5 (0.47 mg/kg deposited dose Tri-SM6.1-αvβ6-AD09151) | 0.322 | 0.090 | 0.125 |

TABLE 68

Average Relative Cynomolgus Monkey RAGE mRNA Expression, Right Proximal Caudal Hilar Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.088 | 0.097 |
| Group 2 (0.13 mg/kg deposited dose Tri-SM6.1-αvβ6-AD09151) | 0.310 | 0.067 | 0.086 |
| Group 3 (0.20 mg/kg deposited dose Tri-SM6.1-αvβ6-AD09151) | 0.502 | 0.105 | 0.133 |
| Group 4 (0.31 mg/kg deposited dose Tri-SM6.1-αvβ6-AD09151) | 0.248 | 0.043 | 0.054 |
| Group 5 (0.47 mg/kg deposited dose Tri-SM6.1-αvβ6-AD09151) | 0.219 | 0.050 | 0.065 |

TABLE 69

Average Relative Cynomolgus Monkey RAGE mRNA Expression, Right Medial Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.112 | 0.126 |
| Group 2 (0.13 mg/kg deposited dose Tri-SM6.1-αvβ6-AD09151) | 0.422 | 0.097 | 0.127 |
| Group 3 (0.20 mg/kg deposited dose Tri-SM6.1-αvβ6-AD09151) | 0.492 | 0.049 | 0.054 |
| Group 4 (0.31 mg/kg deposited dose Tri-SM6.1-αvβ6-AD09151) | 0.222 | 0.018 | 0.019 |
| Group 5 (0.47 mg/kg deposited dose Tri-SM6.1-αvβ6-AD09151) | 0.221 | 0.088 | 0.147 |

TABLE 70

Average Relative Cynomolgus Monkey RAGE mRNA Expression, Right Medial Middle Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.086 | 0.094 |
| Group 2 (0.13 mg/kg deposited dose Tri-SM6.1-αvβ6-AD09151) | 0.434 | 0.144 | 0.216 |
| Group 3 (0.20 mg/kg deposited dose Tri-SM6.1-αvβ6-AD09151) | 0.693 | 0.134 | 0.167 |
| Group 4 (0.31 mg/kg deposited dose Tri-SM6.1-αvβ6-AD09151) | 0.291 | 0.057 | 0.065 |
| Group 5 (0.47 mg/kg deposited dose Tri-SM6.1-αvβ6-AD09151) | 0.277 | 0.064 | 0.084 |

TABLE 71

Average Relative Cynomolgus Monkey RAGE mRNA Expression, Right Medial Caudal Lobe, at Sacrifice in Example 12.

| Group ID | Average Relative cAGER mRNA Expression (n = 3) | Low (error) | High (error) |
|---|---|---|---|
| Group 1 (isotonic saline) | 1.000 | 0.159 | 0.189 |
| Group 2 (0.13 mg/kg deposited dose Tri-SM6.1-αvβ6-AD09151) | 0.338 | 0.080 | 0.106 |
| Group 3 (0.20 mg/kg deposited dose Tri-SM6.1-αvβ6-AD09151) | 0.438 | 0.058 | 0.067 |
| Group 4 (0.31 mg/kg deposited dose Tri-SM6.1-αvβ6-AD09151) | 0.297 | 0.090 | 0.113 |
| Group 5 (0.47 mg/kg deposited dose Tri-SM6.1-αvβ6-AD09151) | 0.215 | 0.072 | 0.108 |

As shown in the data in Tables 47 through 71 above, RNAi agent AD09151 showed substantial inhibition (>70% inhibition observed with single inhaled dose at 0.31 mg/kg and 0.47 mg/kg) compared to control, demonstrating the ability to robustly silence AGER expression in non-human primates.

Tissue RAGE protein was analyzed via Western Blot. Pulverized lung tissue aliquot, based on availability of tissues, which included caudal distal lung tissue, and middle lobe tissue, was homogenized in radioimmunoprecipitation assay buffer (RIPA) using Qiagen bead-based homogenizer. Protein concentration was determined via bicinchoninic acid assay (BCA assay). The samples were prepared in Laemelli buffer and boiled. The gel was loaded with 10 μg total protein, and semi-dry transferred into a polyvinylidene difluoride (PVDF) membrane. The blot was assayed via Pierce Fast-western kit (30 min. primary antibody (ab216329) 1:1000 in proprietary blocking buffer, 15 min. HRP, 3×5 min. washes, 5 min. detection substrate West Pico). The resulting blot was imaged on iBright for RAGE and total protein stain, with the membrane treated with total protein normalization reagent. Densitometry of both bands of interest and for total protein minus background signal was quantified using iBright software.

Dose response of cynomolgus monkeys after administration of RAGE RNAi agent shows progressively higher RAGE protein inhibition in higher RAGE RNAi agent dose concentrations. This can be seen in both the middle and caudal lobes, with up to ~80-88% RAGE protein inhibition at 0.47 mg/kg.

Serum samples from cynomolgus monkeys at Day 15 and 29 after dosing with RAGE RNAi agent were collected, and Serum sRAGE levels were quantified via Gyros Protein Technologies assay. The following Table 72 shows the serum sRAGE levels at Day 15, normalized to baseline, along with standard deviation. The following Table 73 shows the serum sRAGE levels at Day 29, normalized to baseline, along with standard deviation.

TABLE 72

Serum sRAGE levels of cynomolgus monkeys after exposure to RAGE RNAi agent, Day 15.

| Group ID | Dose | Serum sRAGE (% BSL) | Standard Deviation |
|---|---|---|---|
| Group 1 (isotonic saline) | N/A | 92.710 | 0.014 |
| Group 2 Tri-SM6.1-αvβ6-AD09151 | 0.13 mg/kg | 63.293 | 16.806 |
| Group 3 Tri-SM6.1-αvβ6-AD09151 | 0.20 mg/kg | 57.873 | 7.367 |
| Group 4 Tri-SM6.1-αvβ6-AD09151 | 0.31 mg/kg | 47.710 | 15.971 |
| Group 5 Tri-SM6.1-αvβ6-AD09151 | 0.47 mg/kg | 43.377 | 4.487 |

TABLE 73

Serum sRAGE levels of cynomolgus monkeys after exposure to RAGE RNAi agent, Day 29.

| Group ID | Dose | Serum sRAGE (% BSL) | Standard Deviation |
|---|---|---|---|
| Group 1 (isotonic saline) | N/A | 100.470 | 28.206 |
| Group 2 Tri-SM6.1-αvβ6-AD09151 | 0.13 mg/kg | 79.750 | 17.336 |
| Group 3 Tri-SM6.1-αvβ6-AD09151 | 0.20 mg/kg | 66.523 | 5.243 |
| Group 4 Tri-SM6.1-αvβ6-AD09151 | 0.31 mg/kg | 46.873 | 25.249 |
| Group 5 Tri-SM6.1-αvβ6-AD09151 | 0.47 mg/kg | 39.833 | 13.811 |

After dosing with RAGE RNAi agents, cynomolgus monkeys showed significantly reduced serum sRAGE levels, compared to baseline levels. As shown in Tables 72 and 73, the dose response showed progressively more reduced sRAGE levels (higher sRAGE inhibition) at higher RAGE RNAi agent dosing concentrations, showing up to ~39-43% serum sRAGE levels (~57-61% inhibition) at Days 15 and 29 after exposure to RAGE RNAi agent.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. aralkyl groups, aralkenyl groups, or aralkynyl groups, each of which may be linear, branched, cyclic, and/or substituted or unsubstituted. In some embodiments, the location of attachment for these moieties is at the 5' or 3' end of the sense strand, at the 2' position of the ribose ring of any given nucleotide of the sense strand, and/or attached to the phosphate or phosphorothioate backbone at any position of the sense strand.

Any of the RAGE RNAi agent nucleotide sequences listed in Tables 2, 3, 4, 5, 6, and 10, whether modified or unmodified, can contain 3' and/or 5' targeting group(s), linking group(s), and/or PK/PD modulator(s). Any of the RAGE RNAi agent sequences listed in Tables 3, 4, 5, 6, and 10, or are otherwise described herein, which contain a 3' or 5' targeting group, linking group, and/or PK/PD modulator can alternatively contain no 3' or 5' targeting group, linking group, or PK/PD modulator, or can contain a different 3' or 5' targeting group, linking group, or pharmacokinetic modulator including, but not limited to, those depicted in Table 11. Any of the RAGE RNAi agent duplexes listed in Tables 7A, 7B, 8, 9A, 9B, and 10, whether modified or unmodified, can further comprise a targeting group or linking group, including, but not limited to, those depicted in Table 11, and the targeting group or linking group can be attached to the 3' or 5' terminus of either the sense strand or the antisense strand of the RAGE RNAi agent duplex.

Examples of certain modified nucleotides, capping moieties, and linking groups are provided in Table 11.

Alternatively, other linking groups known in the art may be used. In many instances, linking groups can be commercially acquired or alternatively, are incorporated into commercially available nucleotide phosphoramidites. (See, e.g., International Patent Application Publication No. WO 2019/161213, which is incorporated herein by reference in its entirety).

In some embodiments, a RAGE RNAi agent is delivered without being conjugated to a targeting ligand or pharmacokinetic/pharmacodynamic (PK/PD) modulator (referred to as being "naked" or a "naked RNAi agent").

The invention claimed is:

1. An RNAi agent for inhibiting expression of a Receptor for Advanced Glycation End-products gene, comprising:

an antisense strand wherein nucleotides 1 through 21 (5'→3') of the antisense strand comprise the nucleotide sequence UGAUGUUUUGAGCACCUACUC (SEQ ID NO:9) (5' →3'); and a sense strand comprising the modified nucleotide sequence:

gsaguagGfuGfcUfcaaaacauca (SEQ ID NO:14) (5'→3');

wherein a represents 2'-O-methyl adenosine, c represents 2'-O-methyl cytidine, g represents 2'-O-methyl guanosine, u represents 2'-O-methyl uridine; Gf represents 2'-fluoro guanosine, Uf represents 2'-fluoro uridine; and s represents a phosphorothioate linkage;

wherein at least one nucleotide of the antisense strand is a modified nucleotide or includes a modified internucleoside linkage.

2. The RNAi agent of claim 1, wherein the modified nucleotide is selected from the group consisting of: 2'-O-methyl nucleotide, 2'-fluoro nucleotide, 2'-deoxy nucleotide, 2',3'-seco nucleotide mimic, locked nucleotide, 2'-F-arabino nucleotide, 2'-methoxyethyl nucleotide, abasic nucleotide, ribitol, inverted nucleotide, inverted 2'-O-methyl nucleotide, inverted 2'-deoxy nucleotide, 2'-amino-modified nucleotide, 2'-alkyl-modified nucleotide, morpholino nucleotide, vinyl phosphonate-containing nucleotide, cyclopropyl phosphonate-containing nucleotide, and 3'-O-methyl nucleotide.

3. The RNAi agent of claim 1, wherein the sense strand comprises one or two inverted abasic residues.

4. The RNAi agent of claim 1, wherein the RNAi agent is comprised of a sense strand and an antisense strand that form a duplex having the nucleotide sequence pair selected from the group consisting of: SEQ ID NO: 609/14; SEQ ID NO: 5/14; SEQ ID NO: 6/14; SEQ ID NO: 616/14; SEQ ID NO: 617/14; SEQ ID NO: 618/14; SEQ ID NO: 5/11; SEQ ID NO: 6/11; and SEQ ID NO: 5/797.

5. The RNAi agent of claim 1, comprising an antisense strand that comprises, consists of, or consists essentially of the modified nucleotide sequence (5'→3'):

cPrpusGfsasuguuuugaGfcAfcCfuacusc (SEQ ID NO:6);

wherein a represents 2'-O-methyl adenosine, c represents 2'-O-methyl cytidine, g represents 2'-O-methyl guanosine, u represents 2'-O-methyl uridine; Af represents 2'-fluoro adenosine, Cf represents 2'-fluoro cytidine, Gf represents 2'-fluoro guanosine, cPrpu represents 5'-cyclopropyl phosphonate-2'-O-methyl uridine; s represents a phosphorothioate linkage; and wherein all or substantially all of the nucleotides on the sense strand are modified nucleotides.

6. The RNAi agent of claim 1, wherein the sense strand comprises the nucleotide sequence (5'→3'):

Tri-SM6.1-αvβ6-(TA14)gsaguagGfuGfcUfcaaaacaucas (invAb) (SEQ ID NO:11); wherein a represents 2'-O-methyl adenosine, c represents 2'-O-methyl cytidine, g represents 2'-O-methyl guanosine, u represents 2'-O-methyl uridine; Gf represents 2'-fluoro guanosine, Uf represents 2'-fluoro uridine; s represents a phosphorothioate linkage; invAb represents inverted abasic deoxyribonucleotide; and wherein Tri-SM6.1-αvβ6-(TA14) is of the formula:

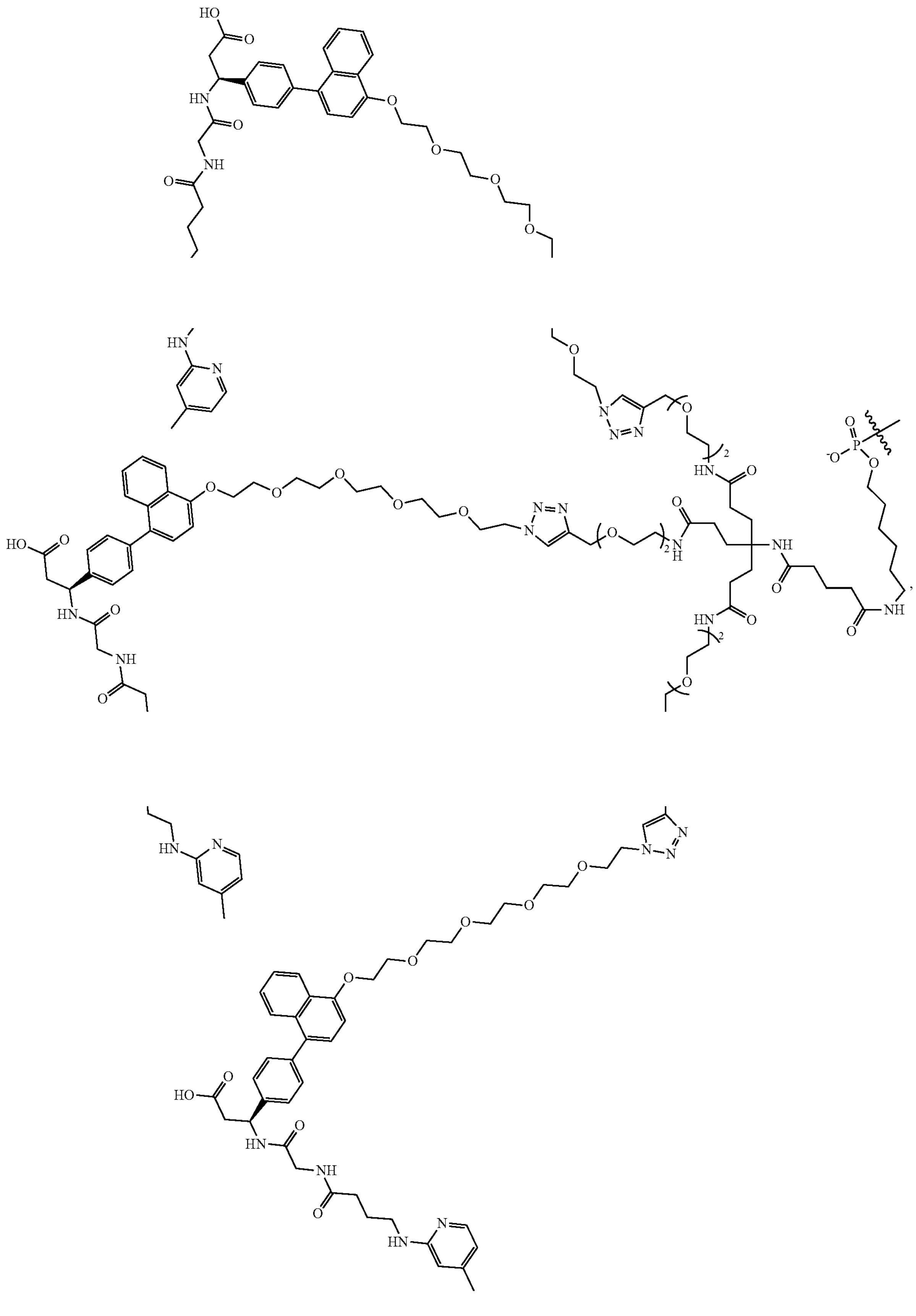

wherein ⌇ indicates the point of attachment to the RNAi agent.

7. The RNAi agent of claim 1, wherein the RNAi agent is linked to a targeting ligand.

8. The RNAi agent of claim 7, wherein the targeting ligand comprises the structure:

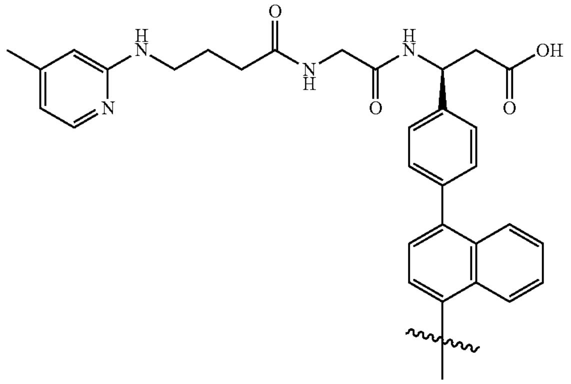 [SMILES: *c1ccc(-c2ccc([C@H](CC(=O)O)NC(=O)CNC(=O)CCCNc3cc(C)ccn3)cc2)c2ccccc12]

or a pharmaceutically acceptable salt thereof, or

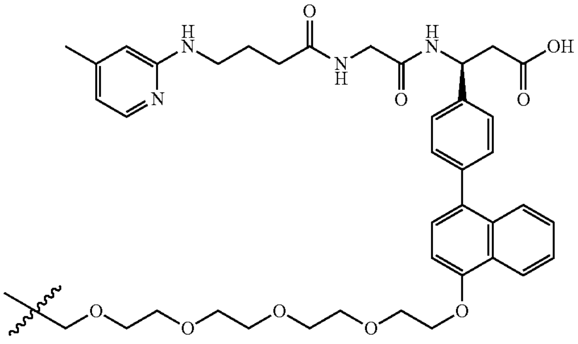 [SMILES: *COCCOCCOCCOCCOc1ccc(-c2ccc([C@H](CC(=O)O)NC(=O)CNC(=O)CCCNc3cc(C)ccn3)cc2)c2ccccc12]

or a pharmaceutically acceptable salt thereof, wherein ⌇ indicates the point of connection to the RNAi agent.

9. The RNAi agent of claim 7, wherein the targeting ligand has a structure selected from the group consisting of:

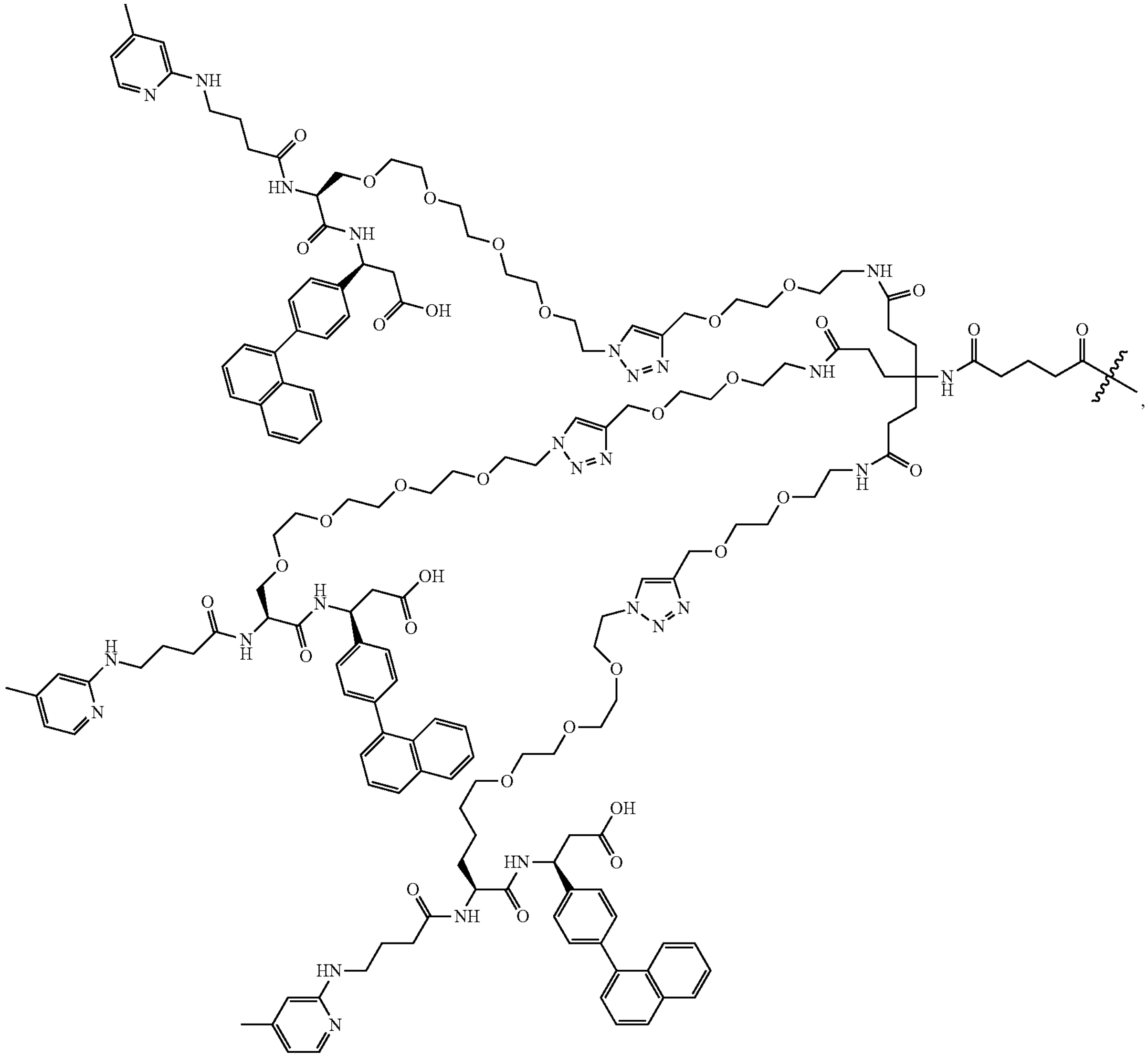 [SMILES: *C(=O)CCCC(=O)NC(CCC(=O)NCCOCCOCc1cn(CCOCCOCCOCCCC[C@H](NC(=O)CCCNc2cc(C)ccn2)C(=O)N[C@@H](CC(=O)O)c2ccc(-c3cccc4ccccc34)cc2)nn1)(CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1)CCC(=O)NCCOCCOCc1cn(CCOCCOCCOCCOC[C@H](NC(=O)CCCNc2cc(C)ccn2)C(=O)N[C@@H](CC(=O)O)c2ccc(-c3cccc4ccccc34)cc2)nn1]

,

-continued
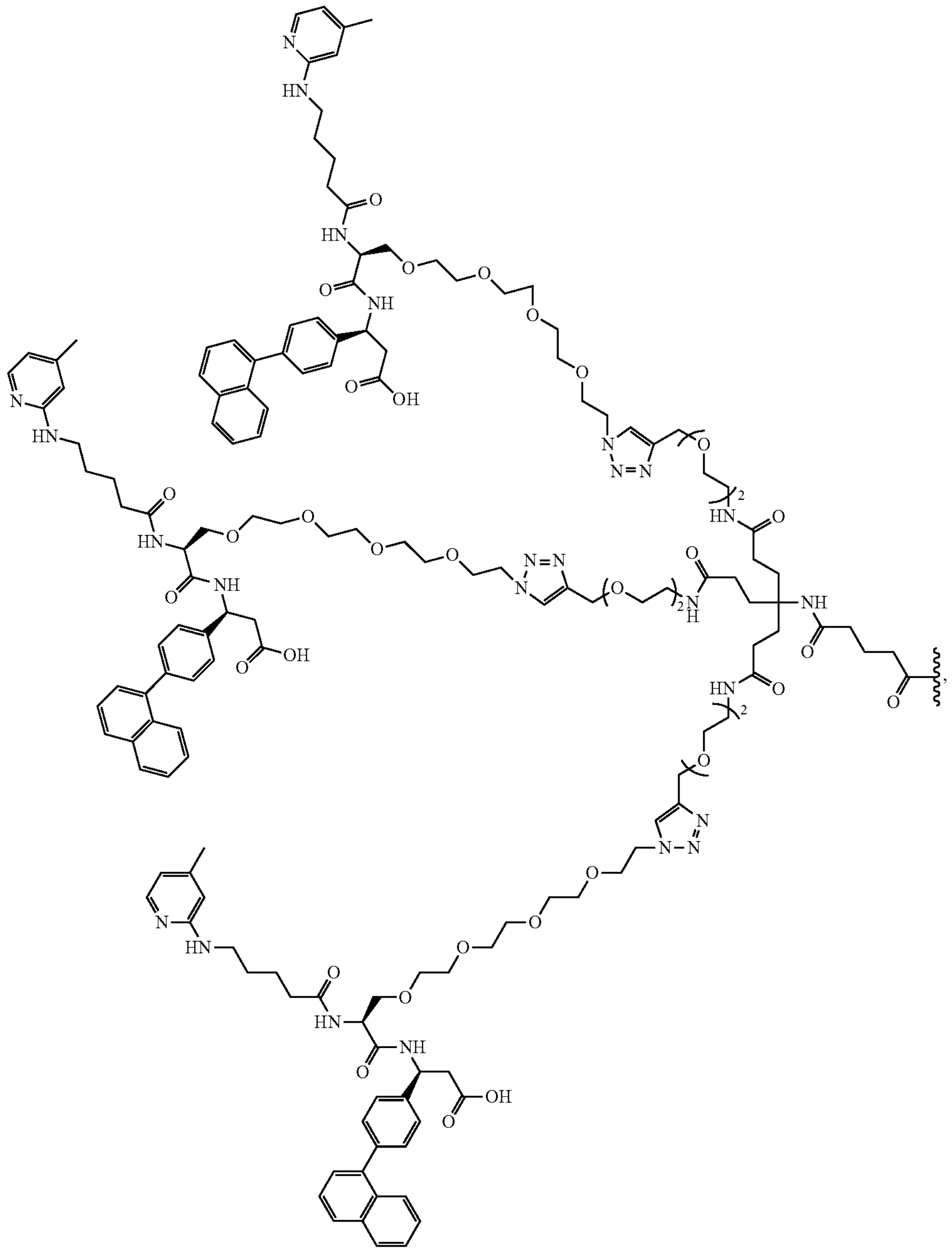

-continued
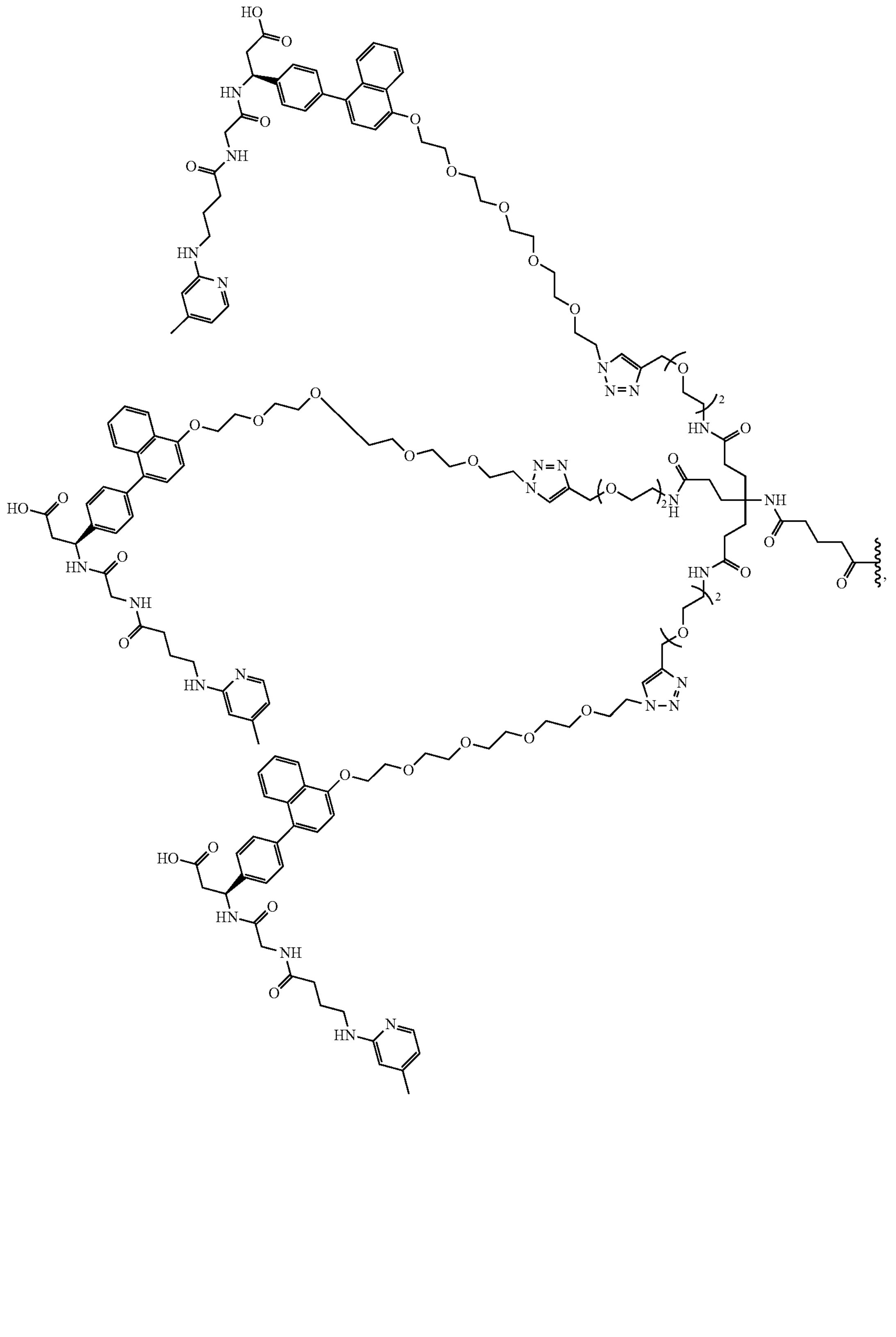

-continued
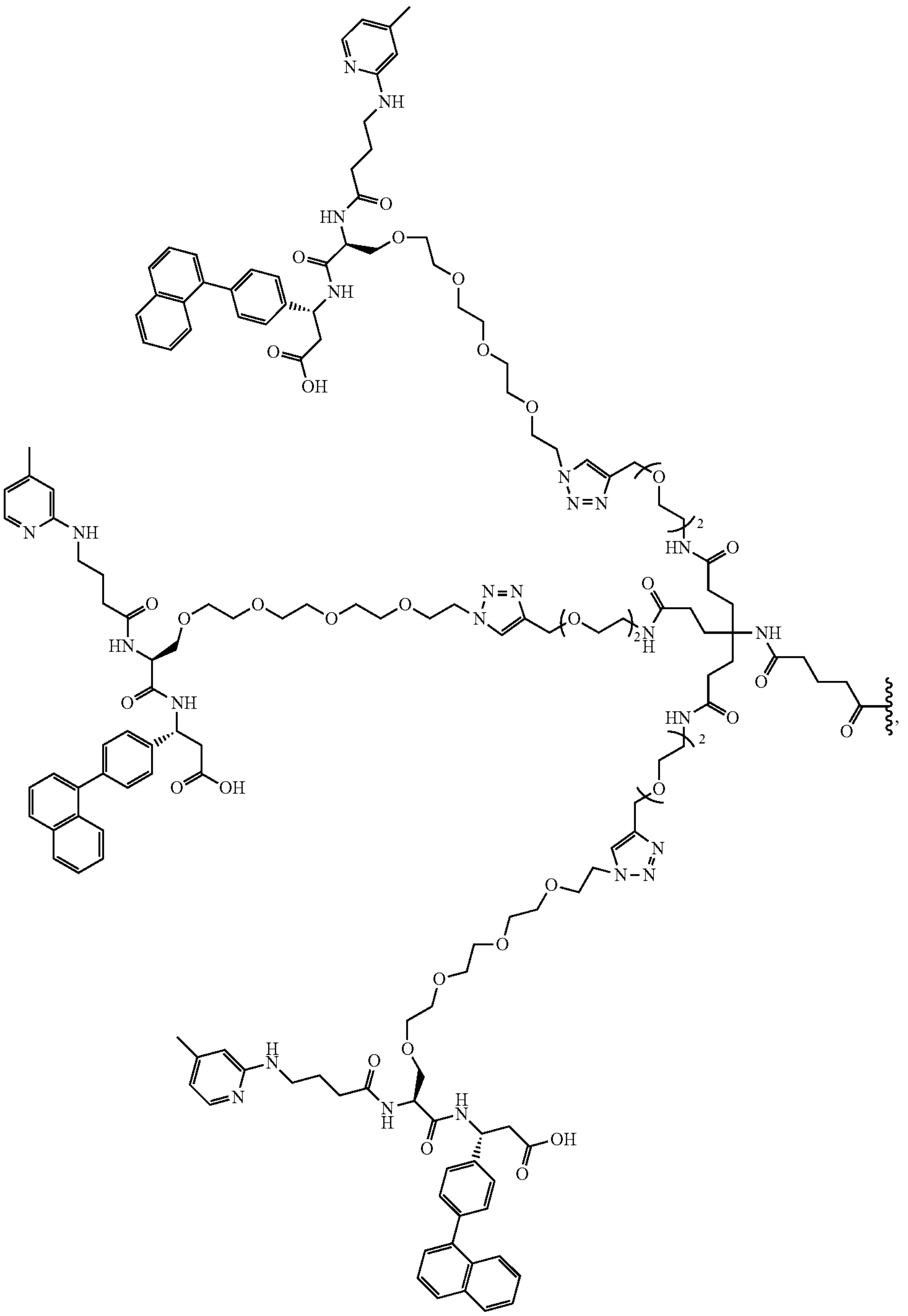

-continued
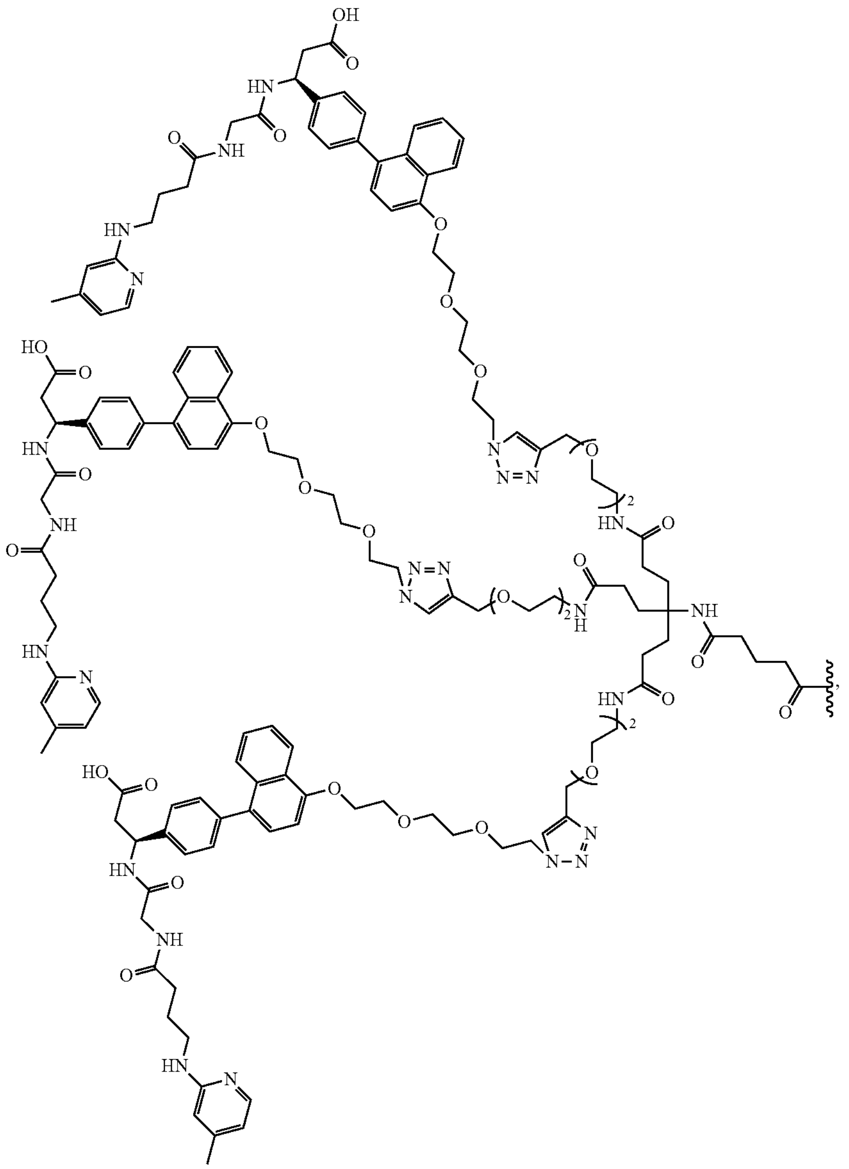

-continued
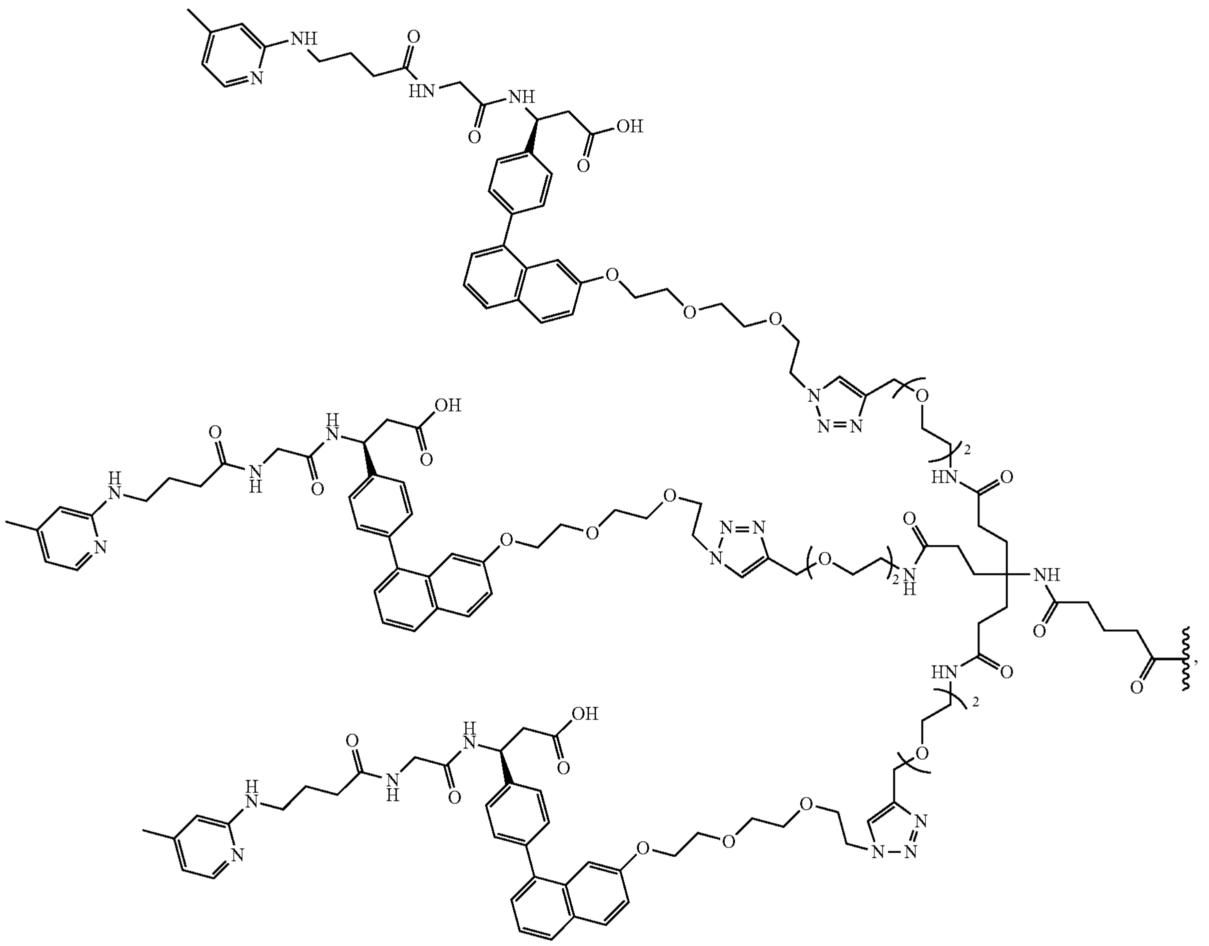

-continued
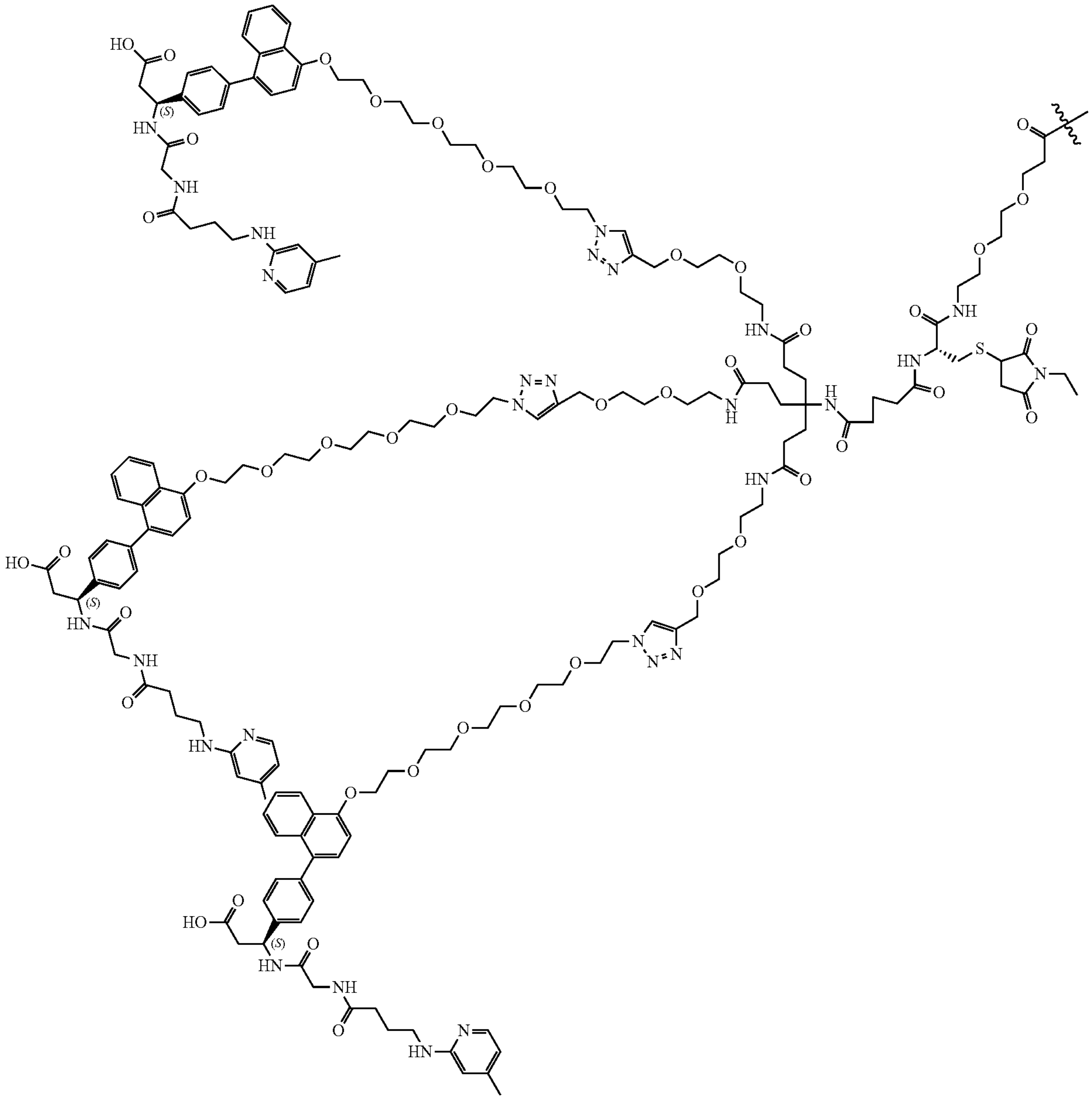
,

-continued
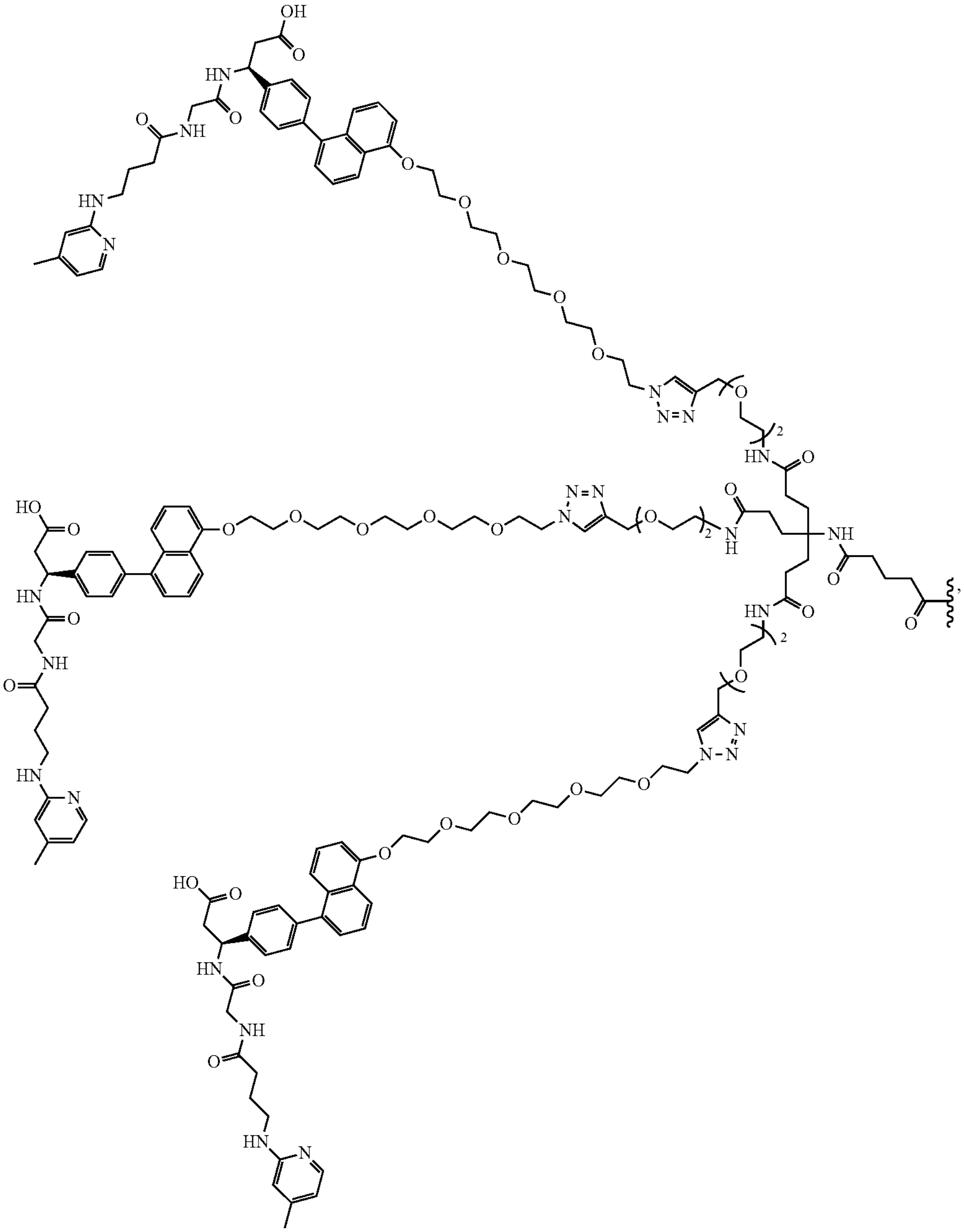
, and

-continued
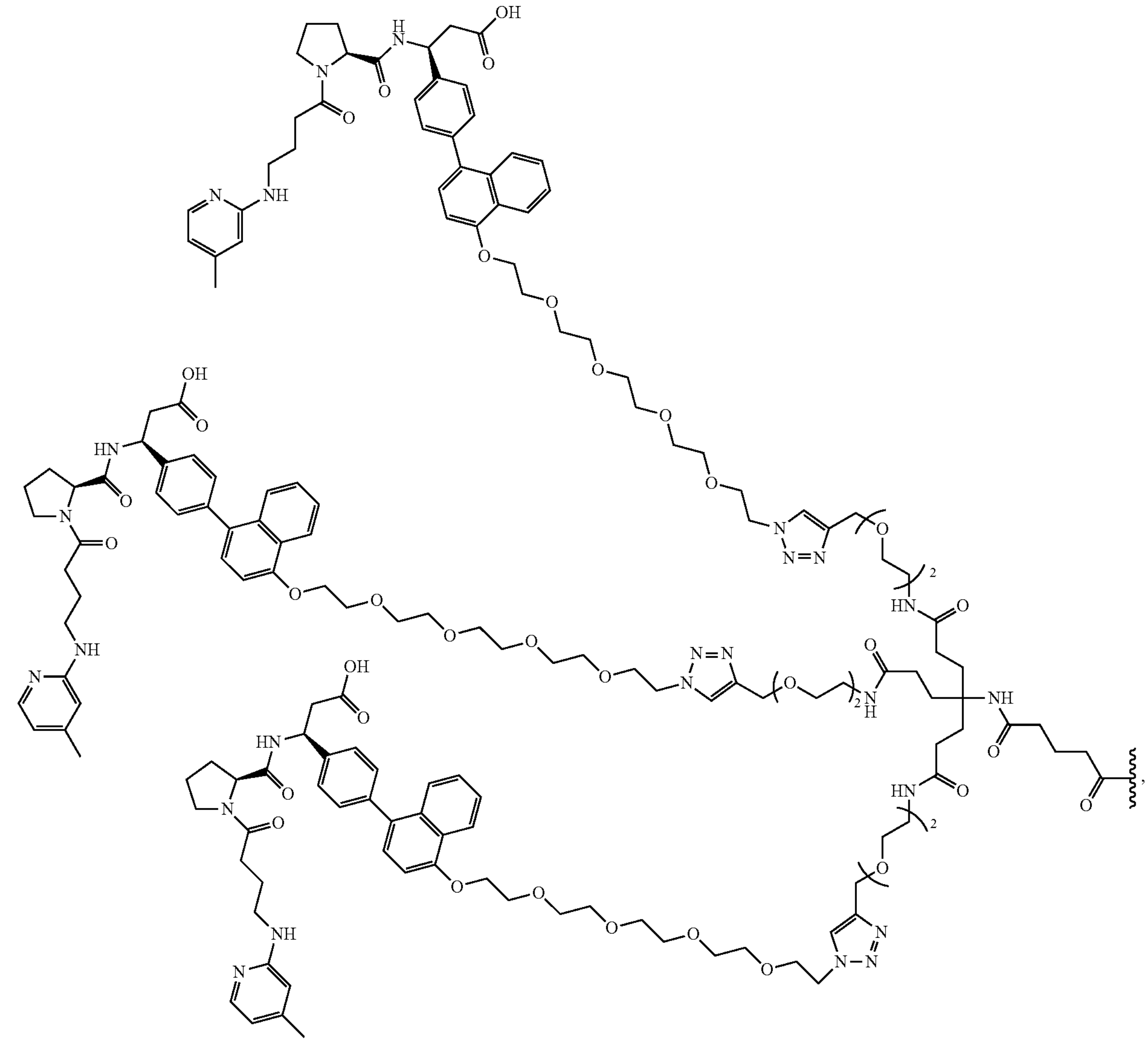
, wherein ⌇ indicates the point of connection to the RNAi agent.

10. The RNAi agent of claim 9, wherein the targeting ligand is of the formula:

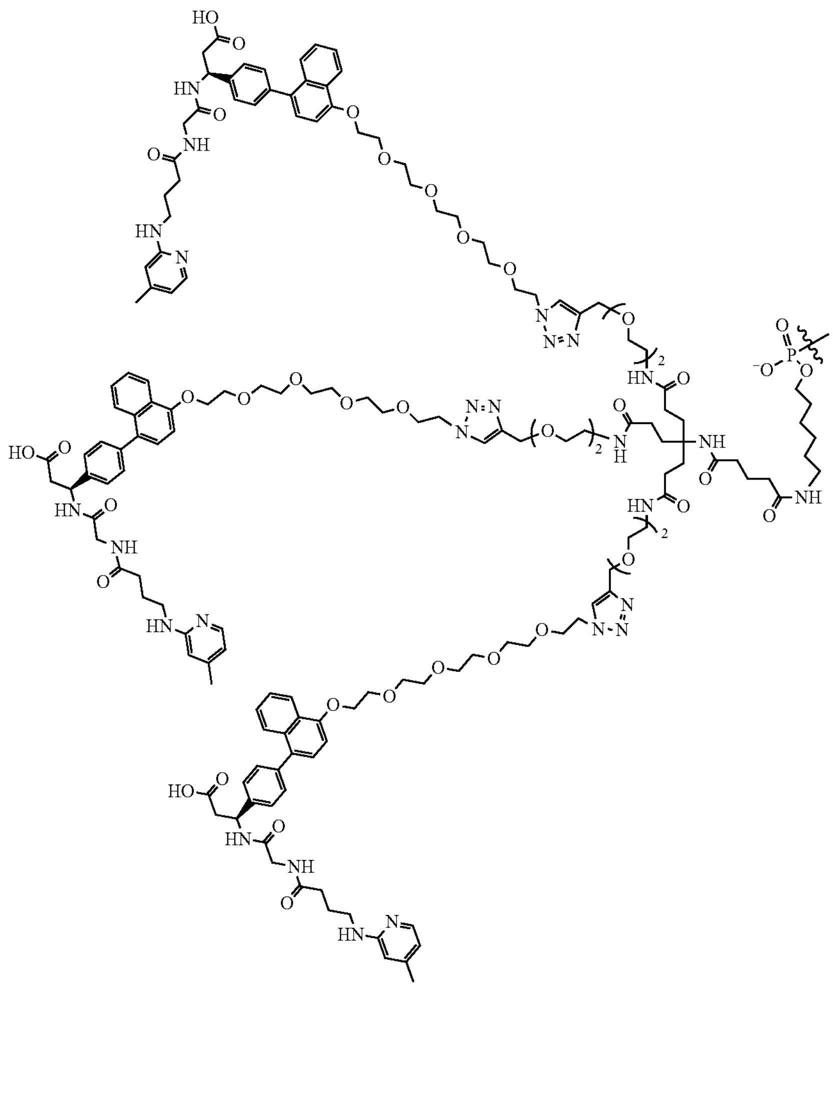

wherein ⌇ indicates the point of connection to the RNAi agent.

11. A method for inhibiting expression of a Receptor for Advanced Glycation End-products gene in a cell, the method comprising introducing into a cell an effective amount of an RNAi agent of claim 1.

12. The method of claim 11, wherein the cell is within a subject.

13. An RNAi agent for inhibiting expression of a Receptor for Advanced Glycation End-products gene, comprising:

an antisense strand that comprises, consists of, or consists essentially of the modified nucleotide sequence (5'→3'):

cPrpusGfsasuguuuugaGfcAfcCfuacusc (SEQ ID NO:6); and a sense strand that comprises, consists of, or consists essentially of the modified nucleotide sequence (5'→3'):

Tri-SM6.1-αvβ6-(TA14)gsaguagGfuGfcUfcaaaacaucas(invAb) (SEQ ID NO:11);

wherein a represents 2'-O-methyl adenosine, c represents 2'-O-methyl cytidine, g represents 2'-O-methyl guanosine, u represents 2'-O-methyl uridine; Af represents 2'-fluoro adenosine, Cf represents 2'-fluoro cytidine, Gf represents 2'-fluoro guanosine, Uf represents 2'-fluoro uridine; cPrpu represents 5'-cyclopropyl phosphonate-2'-O-methyl uridine; s represents a phosphorothioate linkage; invAb represents inverted abasic deoxyribonucleotide; wherein all or substantially all of the nucleotides on the sense strand are modified nucleotides; and wherein Tri-SM6.1-αvβ6-(TA14) is of the formula:

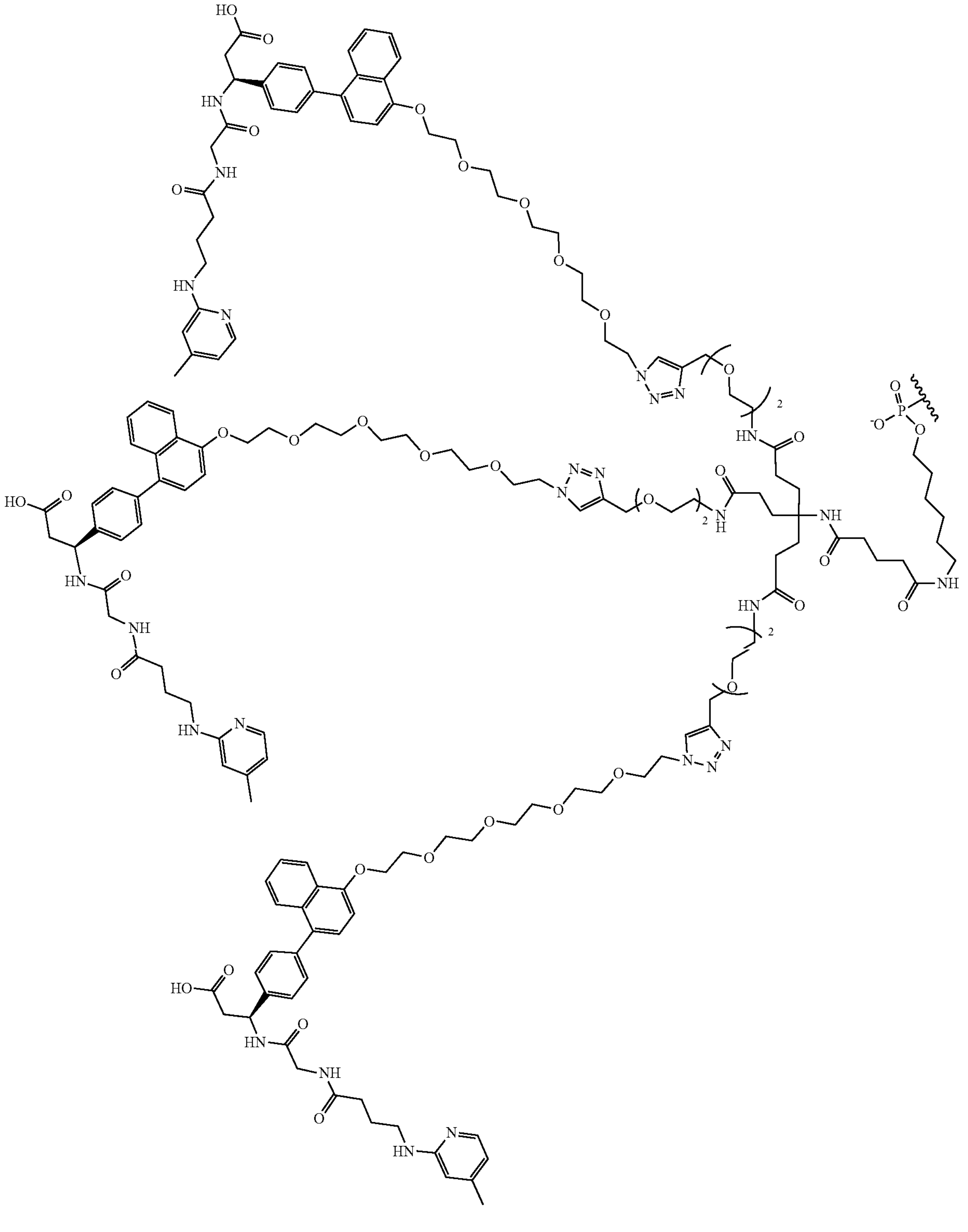
wherein ⌇ indicates the point of attachment to the RNAi agent.
* * * * *